US010960087B2

(12) United States Patent
Burnier et al.

(10) Patent No.: US 10,960,087 B2
(45) Date of Patent: Mar. 30, 2021

(54) COMPOSITIONS AND METHODS FOR TREATMENT OF DIABETIC RETINOPATHY

(71) Applicant: NOVARTIS AG, Basel (CH)

(72) Inventors: John Burnier, Pacifica, CA (US);
Thomas Gadek, Oakland, CA (US);
Charles Semba, Palo Alto, CA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/659,789

(22) Filed: Mar. 17, 2015

(65) Prior Publication Data
US 2016/0220702 A1  Aug. 4, 2016

Related U.S. Application Data

(63) Continuation of application No. 12/288,330, filed on Oct. 17, 2008, now abandoned.

(60) Provisional application No. 60/999,571, filed on Oct. 19, 2007.

(51) Int. Cl.
| *A61K 49/00* | (2006.01) |
| *A61K 9/00* | (2006.01) |
| *A61K 31/277* | (2006.01) |
| *A61K 31/472* | (2006.01) |
| *A61K 31/4725* | (2006.01) |
| *A61K 31/517* | (2006.01) |
| *A61K 45/06* | (2006.01) |
| *A61K 31/343* | (2006.01) |
| *A61K 31/198* | (2006.01) |
| *A61K 31/341* | (2006.01) |
| *A61K 31/66* | (2006.01) |
| *A61K 31/496* | (2006.01) |
| *A61K 31/4025* | (2006.01) |
| *A61K 31/14* | (2006.01) |
| *A61K 31/381* | (2006.01) |
| *A61K 31/502* | (2006.01) |
| *A61F 9/00* | (2006.01) |
| *A61K 9/06* | (2006.01) |
| *A61K 9/08* | (2006.01) |
| *A61K 39/395* | (2006.01) |
| *C07K 16/28* | (2006.01) |
| *G01N 33/68* | (2006.01) |
| *A61K 39/00* | (2006.01) |

(52) U.S. Cl.
CPC ............ *A61K 49/00* (2013.01); *A61F 9/0017* (2013.01); *A61K 9/0014* (2013.01); *A61K 9/0048* (2013.01); *A61K 9/06* (2013.01); *A61K 9/08* (2013.01); *A61K 31/14* (2013.01); *A61K 31/198* (2013.01); *A61K 31/277* (2013.01); *A61K 31/341* (2013.01); *A61K 31/343* (2013.01); *A61K 31/381* (2013.01); *A61K 31/4025* (2013.01); *A61K 31/472* (2013.01); *A61K 31/4725* (2013.01); *A61K 31/496* (2013.01); *A61K 31/502* (2013.01); *A61K 31/517* (2013.01); *A61K 31/66* (2013.01); *A61K 39/39533* (2013.01); *A61K 45/06* (2013.01); *C07K 16/2821* (2013.01); *G01N 33/6893* (2013.01); *A61K 2039/505* (2013.01); *A61K 2039/507* (2013.01); *C07K 2317/92* (2013.01); *G01N 2333/70503* (2013.01); *G01N 2333/70525* (2013.01); *G01N 2800/042* (2013.01); *G01N 2800/164* (2013.01)

(58) Field of Classification Search
None
See application file for complete search history.

(56) References Cited

U.S. PATENT DOCUMENTS

| 3,773,919 A | 11/1973 | Boswell |
| 3,989,816 A | 11/1976 | Rajadhyaksha |
| 4,316,893 A | 2/1982 | Rajadhyaksha |
| 4,405,616 A | 9/1983 | Rajadhyaksha |
| 4,557,934 A | 12/1985 | Cooper |
| 4,568,343 A | 2/1986 | Leeper et al. |
| 4,668,506 A | 5/1987 | Bawa |
| 4,713,244 A | 12/1987 | Bawa et al. |
| 4,767,628 A | 8/1988 | Hutchinson |
| 4,908,202 A | 3/1990 | Schulz |
| 4,931,279 A | 6/1990 | Bawa et al. |
| 4,992,445 A | 2/1991 | Lawter et al. |
| 5,001,139 A | 3/1991 | Lawter et al. |
| 5,023,252 A | 6/1991 | Hseih |
| 5,134,122 A | 7/1992 | Orsolini |
| 5,135,916 A | 8/1992 | Sims et al. |
| 5,149,780 A | 9/1992 | Plow et al. |

(Continued)

FOREIGN PATENT DOCUMENTS

| CN | 1511151 A | 7/2004 |
| CN | 1914195 A | 2/2007 |

(Continued)

OTHER PUBLICATIONS

Fong et al (Diabetes Care 27(Suppl 1):S84-S87, 2004).*

(Continued)

*Primary Examiner* — Craig D Ricci
(74) *Attorney, Agent, or Firm* — Troutman Pepper Hamilton Sanders LLP

(57) ABSTRACT

The present invention provides compounds and methods for the treatment of diabetic retinopathy. In particular, LFA-1 antagonists are described herein to be used in the treatment of diabetic retinopathy. One aspect of the invention provides for diagnosis of diabetic retinopathy and administration of a LFA-1 antagonist, after the patient is diagnosed with diabetic retinopathy.

18 Claims, 12 Drawing Sheets

Specification includes a Sequence Listing.

(56) References Cited

U.S. PATENT DOCUMENTS

| | | |
|---|---|---|
| 5,192,741 A | 3/1993 | Orsolini et al. |
| 5,236,704 A | 8/1993 | Fujioka et al. |
| 5,288,854 A | 2/1994 | Diamond et al. |
| 5,298,492 A | 3/1994 | Neustadt et al. |
| 5,340,800 A | 8/1994 | Liu et al. |
| 5,397,791 A | 3/1995 | Hartman et al. |
| 5,424,289 A | 6/1995 | Yang et al. |
| 5,424,399 A | 6/1995 | Arnaout |
| 5,445,832 A | 8/1995 | Orsolini et al. |
| 5,470,953 A | 11/1995 | Gallatin et al. |
| 5,585,359 A | 12/1996 | Breslin et al. |
| 5,597,567 A | 1/1997 | Whitcup et al. |
| 5,612,052 A | 3/1997 | Shalaby |
| 5,622,700 A | 4/1997 | Jardieu et al. |
| 5,624,837 A | 4/1997 | Fodor et al. |
| 5,672,659 A | 9/1997 | Shalaby et al. |
| 5,747,035 A | 5/1998 | Presta et al. |
| 5,840,332 A | 11/1998 | Lerner et al. |
| 5,843,884 A | 12/1998 | Sims |
| 5,843,885 A | 12/1998 | Benedict et al. |
| 5,849,327 A | 12/1998 | Berliner et al. |
| 5,863,910 A | 1/1999 | Bolonick et al. |
| 5,877,224 A | 3/1999 | Brocchini et al. |
| 5,893,985 A | 4/1999 | Luo et al. |
| 5,922,356 A | 7/1999 | Koseki et al. |
| 5,936,089 A | 8/1999 | Carpino et al. |
| 5,968,895 A | 10/1999 | Gefter et al. |
| 5,973,188 A | 10/1999 | Alig et al. |
| 5,980,945 A | 11/1999 | Ruiz |
| 6,011,011 A | 1/2000 | Hageman |
| 6,162,432 A | 12/2000 | Wanner et al. |
| 6,180,608 B1 | 1/2001 | Gefter et al. |
| 6,203,793 B1 | 3/2001 | Lipsky et al. |
| 6,204,280 B1 | 3/2001 | Gante et al. |
| 6,294,522 B1 | 9/2001 | Zablocki et al. |
| 6,319,897 B1 | 11/2001 | Lambris et al. |
| 6,331,640 B1 | 12/2001 | Fotouhi et al. |
| 6,340,679 B1 | 1/2002 | Peyman et al. |
| 6,358,976 B1 | 3/2002 | Wityak et al. |
| 6,488,916 B1 | 12/2002 | Fowler |
| 6,515,124 B2 | 2/2003 | Fotouhi et al. |
| 6,521,619 B2 | 2/2003 | Link et al. |
| 6,524,581 B1 | 2/2003 | Adamis |
| 6,605,597 B1 | 8/2003 | Zablocki et al. |
| 6,620,422 B1 | 9/2003 | Maquin et al. |
| 6,630,447 B2 | 10/2003 | Larson |
| 6,630,492 B1 | 10/2003 | Bauer et al. |
| 6,642,225 B2 | 11/2003 | Albert et al. |
| 6,653,478 B2 | 11/2003 | Urbanski et al. |
| 6,667,060 B1 | 12/2003 | Vandecruys et al. |
| 6,667,318 B2 | 12/2003 | Burdick et al. |
| 6,670,321 B1 | 12/2003 | Adamis |
| 6,710,064 B2 | 3/2004 | Launay et al. |
| 6,764,681 B2 | 7/2004 | Wanner et al. |
| 6,773,916 B1 | 8/2004 | Thiel et al. |
| 6,787,542 B2 | 9/2004 | Wang et al. |
| 6,803,384 B2 | 10/2004 | Fotouhi et al. |
| 6,818,638 B2 | 11/2004 | Baenteli et al. |
| 6,867,203 B2 | 3/2005 | Gunawardana |
| 6,872,382 B1 | 3/2005 | Gamache et al. |
| 6,872,735 B2 | 3/2005 | Burdick et al. |
| 6,977,267 B2 | 12/2005 | Dhar et al. |
| 7,078,420 B2 | 7/2006 | Dhar et al. |
| 7,097,851 B1 | 8/2006 | Takada |
| 7,129,247 B2 | 10/2006 | Wang et al. |
| 7,166,568 B1 | 1/2007 | Sims |
| 7,186,727 B2 | 3/2007 | Dhar et al. |
| 7,199,125 B2 | 4/2007 | Dhar et al. |
| 7,211,586 B2 | 5/2007 | Fenton et al. |
| 7,217,728 B2 | 5/2007 | Fotouhi et al. |
| 7,314,938 B2 | 1/2008 | Shen et al. |
| 7,323,171 B2 | 1/2008 | Wanner et al. |
| 7,375,237 B2 | 5/2008 | Dhar et al. |
| 7,396,530 B2 | 7/2008 | Goffe |
| 7,785,578 B2 | 8/2010 | Miller et al. |
| 7,790,743 B2 | 9/2010 | Shen et al. |
| 7,858,095 B2 | 12/2010 | Vaishnaw |
| 7,928,122 B2 | 4/2011 | Shen et al. |
| 7,989,626 B2 | 8/2011 | Shen et al. |
| 8,080,562 B2 | 12/2011 | Burnier et al. |
| 8,084,047 B2 | 12/2011 | Shen et al. |
| 8,168,655 B2 | 5/2012 | Gadek et al. |
| 8,592,450 B2 | 11/2013 | Gadek et al. |
| 2001/0006656 A1 | 7/2001 | Harlan et al. |
| 2001/0031260 A1 | 10/2001 | Lee et al. |
| 2002/0019446 A1 | 2/2002 | Brocchini et al. |
| 2002/0045582 A1 | 4/2002 | Margolin et al. |
| 2002/0115692 A1 | 8/2002 | Archibald et al. |
| 2002/0119994 A1 | 8/2002 | Burdick et al. |
| 2002/0132807 A1 | 9/2002 | Wang et al. |
| 2002/0143035 A1 | 10/2002 | Launay et al. |
| 2002/0176841 A1 | 11/2002 | Barker et al. |
| 2002/0177591 A1 | 11/2002 | O'Donnell et al. |
| 2003/0044406 A1 | 3/2003 | Dingivan |
| 2003/0064105 A1 | 4/2003 | Kim et al. |
| 2003/0068320 A1 | 4/2003 | Dingivan |
| 2003/0068384 A1 | 4/2003 | Brocchini et al. |
| 2003/0069560 A1 | 4/2003 | Adamis et al. |
| 2003/0138488 A1 | 7/2003 | Kohn et al. |
| 2003/0166630 A1 | 9/2003 | Auvin et al. |
| 2003/0171296 A1 | 9/2003 | Gefter et al. |
| 2003/0216307 A1 | 11/2003 | Kohn et al. |
| 2004/0006236 A1 | 1/2004 | Fotouhi et al. |
| 2004/0009998 A1 | 1/2004 | Dhar et al. |
| 2004/0028648 A1 | 2/2004 | Adamis |
| 2004/0038973 A1 | 2/2004 | Nahra et al. |
| 2004/0058968 A1 | 3/2004 | Burdick et al. |
| 2004/0120960 A1 | 6/2004 | Jardieu et al. |
| 2004/0122047 A1 | 6/2004 | Fenton et al. |
| 2004/0248920 A1 | 12/2004 | Dhar et al. |
| 2004/0259897 A1 | 12/2004 | Dhar et al. |
| 2005/0004153 A1 | 1/2005 | Dhar et al. |
| 2005/0080119 A1 | 4/2005 | Fotouhi et al. |
| 2005/0090498 A1 | 4/2005 | Samizu et al. |
| 2005/0107399 A1 | 5/2005 | Boman et al. |
| 2005/0119279 A1 | 6/2005 | Dhar et al. |
| 2005/0142066 A1 | 6/2005 | Mentzer |
| 2005/0148588 A1 | 7/2005 | Burdick et al. |
| 2005/0203135 A1 | 9/2005 | Burdick et al. |
| 2005/0267098 A1 | 12/2005 | Shen et al. |
| 2006/0052434 A1 | 3/2006 | Dhar et al. |
| 2006/0074099 A1 | 4/2006 | DelMonte et al. |
| 2006/0142319 A1 | 6/2006 | Chen et al. |
| 2006/0148836 A1 | 7/2006 | Dhar et al. |
| 2006/0229588 A1 | 10/2006 | Demopulos et al. |
| 2006/0281739 A1 | 12/2006 | Gadek et al. |
| 2006/0281820 A1 | 12/2006 | Soda |
| 2006/0286108 A1 | 12/2006 | Bell |
| 2007/0025990 A1 | 2/2007 | Dingivan |
| 2007/0027101 A1 | 2/2007 | Guyer et al. |
| 2007/0048216 A1 | 3/2007 | Norenberg |
| 2007/0066585 A1 | 3/2007 | Wang et al. |
| 2007/0090205 A1 | 4/2007 | Kunze et al. |
| 2007/0105824 A1 | 5/2007 | Erickson-Miller et al. |
| 2007/0142317 A1 | 6/2007 | Warren et al. |
| 2007/0149593 A1 | 6/2007 | Ghosh et al. |
| 2007/0155671 A1 | 7/2007 | Fotouhi et al. |
| 2007/0256685 A1 | 11/2007 | Mueller-walz |
| 2008/0019977 A1 | 1/2008 | Adamis |
| 2008/0108677 A1 | 5/2008 | Bjorklund et al. |
| 2008/0176896 A1 | 7/2008 | Shen et al. |
| 2008/0182839 A1 | 7/2008 | Shen et al. |
| 2008/0234271 A1 | 9/2008 | Guckian et al. |
| 2008/0242710 A1 | 10/2008 | Baumann |
| 2008/0249157 A1 | 10/2008 | Cossio Mora et al. |
| 2009/0155176 A1 | 6/2009 | Burnier et al. |
| 2009/0258069 A1 | 10/2009 | Burnier et al. |
| 2009/0258070 A1 | 10/2009 | Burnier et al. |
| 2009/0298869 A1 | 12/2009 | Burnier et al. |
| 2010/0092541 A1 | 4/2010 | Burnier et al. |
| 2010/0092542 A1 | 4/2010 | Burnier et al. |
| 2010/0093693 A1 | 4/2010 | Shen et al. |
| 2011/0092707 A1 | 4/2011 | Burnier |
| 2011/0124669 A1 | 5/2011 | Shen et al. |

(56) References Cited

U.S. PATENT DOCUMENTS

| | | |
|---|---|---|
| 2011/0165228 A1 | 7/2011 | Burnier et al. |
| 2011/0165229 A1 | 7/2011 | Burnier et al. |
| 2012/0107404 A1 | 5/2012 | Burnier et al. |
| 2012/0232019 A1 | 9/2012 | Gadek et al. |
| 2013/0144063 A1 | 6/2013 | Burnier et al. |
| 2013/0150585 A1 | 6/2013 | Burnier |

FOREIGN PATENT DOCUMENTS

| | | | |
|---|---|---|---|
| EP | 0314863 A2 | 5/1989 | |
| EP | 0314863 A3 | 4/1990 | |
| EP | 0362526 A2 | 4/1990 | |
| EP | 0362531 A1 | 4/1990 | |
| EP | 0362526 A3 | 7/1990 | |
| EP | 0326151 B1 | 6/1993 | |
| EP | 0656789 B1 | 12/1997 | |
| EP | 0467389 B1 | 10/1999 | |
| EP | 1396490 A1 | 3/2004 | |
| EP | 1392306 B1 | 1/2008 | |
| JP | 2007099641 A | 4/2007 | |
| WO | 199003400 A1 | 4/1990 | |
| WO | 199010652 A1 | 9/1990 | |
| WO | 199013316 A1 | 11/1990 | |
| WO | 199119511 A1 | 12/1991 | |
| WO | 199203473 A1 | 3/1992 | |
| WO | 9316702 A1 | 9/1993 | |
| WO | 9324150 A1 | 12/1993 | |
| WO | 199403481 A1 | 2/1994 | |
| WO | 9406452 A1 | 3/1994 | |
| WO | 199411400 A1 | 5/1994 | |
| WO | 9415587 A2 | 7/1994 | |
| WO | 9415587 A3 | 9/1994 | |
| WO | 199504531 A1 | 2/1995 | |
| WO | 199528170 A1 | 10/1995 | |
| WO | 199609836 A1 | 4/1996 | |
| WO | 9704744 A1 | 2/1997 | |
| WO | 9726015 A1 | 7/1997 | |
| WO | 9740085 A2 | 10/1997 | |
| WO | 9740085 A3 | 1/1998 | |
| WO | 9813029 A1 | 4/1998 | |
| WO | 9825642 A2 | 6/1998 | |
| WO | 9825642 A3 | 7/1998 | |
| WO | 9846599 A1 | 10/1998 | |
| WO | 199846599 A1 | 10/1998 | |
| WO | 199949856 A2 | 10/1999 | |
| WO | 199949856 A3 | 11/1999 | |
| WO | 0021920 A1 | 4/2000 | |
| WO | 0038714 A1 | 7/2000 | |
| WO | 0044731 A1 | 8/2000 | |
| WO | 0072883 A2 | 12/2000 | |
| WO | 0101964 A1 | 1/2001 | |
| WO | 0112233 A2 | 2/2001 | |
| WO | 0127102 A1 | 4/2001 | |
| WO | 0101964 A3 | 6/2001 | |
| WO | 0149249 A2 | 7/2001 | |
| WO | 0149311 A1 | 7/2001 | |
| WO | 0158853 A1 | 8/2001 | |
| WO | 0112233 A3 | 11/2001 | |
| WO | 0187840 A1 | 11/2001 | |
| WO | 0149249 A3 | 1/2002 | |
| WO | 0230398 A2 | 4/2002 | |
| WO | 0238129 A2 | 5/2002 | |
| WO | 200250080 A1 | 6/2002 | |
| WO | 02058672 A2 | 8/2002 | |
| WO | 02059114 A1 | 8/2002 | |
| WO | 02074247 A2 | 9/2002 | |
| WO | 02058672 A3 | 12/2002 | |
| WO | 02074247 A3 | 12/2002 | |
| WO | 02098426 A1 | 12/2002 | |
| WO | 0238129 A3 | 2/2003 | |
| WO | 0230398 A3 | 3/2003 | |
| WO | 03053401 A2 | 7/2003 | |
| WO | 03075887 A1 | 9/2003 | |
| WO | 03053401 A3 | 1/2004 | |
| WO | 2004026406 A1 | 4/2004 | |
| WO | 2005010024 A2 | 2/2005 | |
| WO | 2005014532 A1 | 2/2005 | |
| WO | 2005014533 A2 | 2/2005 | |
| WO | 2005042710 A1 | 5/2005 | |
| WO | 2005044817 A1 | 5/2005 | |
| WO | 2005080373 A1 | 9/2005 | |
| WO | 2005123706 A1 | 12/2005 | |
| WO | 06047788 A2 | 5/2006 | |
| WO | 2006125119 A1 | 11/2006 | |
| WO | WO 2006/125119 * | 11/2006 | ........... A61K 31/166 |
| WO | 2007039286 A1 | 4/2007 | |
| WO | 2009054914 A1 | 4/2009 | |
| WO | 0647788 A3 | 5/2009 | |
| WO | 09139817 A2 | 11/2009 | |
| WO | 09139817 A3 | 1/2010 | |

OTHER PUBLICATIONS

Heidenkummer et al (Graefe's Arch Clin Exp Ophthalmol 230:483-487, 1992) (Year: 1992).*
Adamis AP. Is diabetic retinopathy an inflammatory disease? Br J Opthalmol. Apr. 2002; 86(4):363-5.
Zhong, et al. Discovery and Development of Potent LFA-1/ICAM-1 Antagonist SAR 1118 as an Ophthalmic Solution for Treating Dry Eye. ACS Med. Chem. Lett. DOI: 10.1021/ml2002482. Publication Date (web): Jan. 31, 2012.
Genentech. Voluntary U.S. Market withdrawal of Raptiva® (Efalizumab). Apr. 8, 2009. (to patient).
Ayalasomayajula, et al. Celecoxib, a selective cyclooxygenase-2 inhibitor, inhibits retinal vascular endothelial growth factor expression and vascular leakage in a streptozotocin—induced diabetic rat model. European Journal of Pharmacology. 2003; 458: 283-289.
Bacon et al. "Tear and conjunctival changes during the allergin-induced early- and late- phase responses", J Allergy Clin Immunol. 2000, 106(5):948-954.
Barouch, F.C. et al, Integrin-mediated neutrophil adhesion and retinal leukostasis in diabetes, Invest Ophthalmol Vis Sci, 2000, vol. 41, No. 5, p. 1153-8.
Berge, et al. Pharmaceutical salts. J Pharmaceutical Sciences. 1977; 66: 1-19.
Boschelli, et al. 3-Alkoxybenzo[b]thiophene-2-carboxamides as inhibitors of neutrophil-endothelial cell adhesion. J Med Chem. 1994; 37(6): 717-8.
Boschelli, et al. Inhibition of E-Selectin-, ICAM-1-, and VCAM-1-mediated cell adhesion by benzo[b]thiophene-, benzufuran-, indole-, and naphthalene-2-carboxamides: Identification of PD 144795 as an antiinflammatory agent. J Med Chem. 1995; 38: 4597-614.
Brill et al. "Induction of mast cell interactions with blood vessel wall components by direct contact with intact T cells or T cell membranes in vitro", Clin Exp Allergy 2004, 34(11):1725-1731.
Burdick, et al. N-Benzoyl amino acids as ICAM/LFA-1 inhibitors. Part 2: Structure-activity relationship of the benzoyl moiety. Bioorganic & Medicinal Chemistry Letters. 2004; 14(9): 2055-9.
Burdick, et al. N-Benzoyl amino acids as LFA-1/ICAM inhibitors 1: amino acid structure-activity relationship. Bioorganic & Medicinal Chemistry Letters. 2004; 13(6): 1015-8.
Callen, J.P. Complications and adverse reactions in the use of newer biologic agents. Semin Cutan Med Surg. Mar. 2007; 26 (1):6-14.
Genentech. Voluntary U.S. Market withdrawal of Raptiva® (Efalizumab). Apr. 8, 2009. (to professional).
Chang, et al. Effects of pharmacologic agents on the reversed passive Arthus reaction in the rat. Eur J Pharmacol. 1981; 69(2): 155-64.
Chavanpatil, et al. Novel sustained release, swellable and bioadhesive gastroretentive drug delivery system for ofloxacin. Int J Pharm. 2006; 316(1-2): 86-92.
Chibber, et al., Leukocytes in Diabetic Retinopathy, Current Diabetes Reviews, Feb. 2007;3:(1):3-14.
Gennaro et al., "Remington: The Science and Practice of Pharmacy, 1995, 19th Edition", Mack Publishing Company, pp. xiv-xvi, 1496-1503, 1562-1567, 1588-1589, 1598-1599, 1672-1677.
Choi et al. "Late-phase reaction in ocular allergy" Current Opinion in Allergy & Clinical Immunology 2008, 8 (5):438-444.

(56) References Cited

OTHER PUBLICATIONS

Ciprandi, et al. "Allergic subjects express intercellular adhesion molecule—1 (ICAM-1 or CD54) on epithelial cells of conjunctiva after allergen challenge" J Allergy Clin Immunol. 1993, 91(3):783-792.

Coleman, et al. Chemoselective Cleavage of Benzyl Ethers, Esters, and Carbamates in the Presence of Other Easily Reducible Groups. Synthesis. 1999;1399-1400.

Cosimi, et al. In vivo effects of monoclonal antibody to ICAM-1 (CD54) in nonhuman primates with renal allografts. J Immunol. 1990; 144(12): 4604-12.

Crocker, et al. The role of fluorine substitution in the structure-activity relationships (SAR) of classical cannabinoids. Bioorg med chem lett. 2007; 17(6):1504-1507.

Cunhas-Vaz. Characterization and relevance of different diabetic retinopathy phenotypes. Dev. Ophthal. 2007; 39: 13-30.

Davies et al. "Physiological Parameters in Laboratory Animals and Humans", Pharmaceutical Research 1993, 10 (7):1093-1095.

Devine L, Lightman SL, Greenwood J. Role of LFA-1, ICAM-1, VLA-4 and VCAM-1 in lymphocyte migration across retinal pigment epithelial monolayers in vitro. Immunology. Jul. 1996;88(3):456-62.

Diamond, et al. The dynamic regulation of integrin adhesiveness. Current Biology. 1994; 4(6): 506-32.

Drugs.com. Genentech Announces Voluntary Withdrawal of Raptiva from the U.S. Market. Apr. 2009.

Earle et al. "A Simplified Clinical Procedure for Measurement of Glomerular Filtration Rate and Renal Plasma Flow", Proc. Soc. Exp. Biol. Med. 1946, 62:262-269.

EMA. Press Release. European Medicines Agency recommends suspension of the marketing authorisation of Raptiva (efalizumab). Feb. 19, 2009.

European Extended Search Report dated Oct. 6, 2011, issued in corresponding European Application No. 08842113.6.

European Office Action dated Nov. 9, 2010 for Application No. 6770607.7.

European office action dated Mar. 28, 2012 for Application No. 11181066.9.

European search report and search opinion dated Nov. 30, 2011 for Application No. 9732599.7.

European search report dated May 20, 2009 for Application No. 06770607.7.

FDA. FDA Advises Public of Serious Adverse Event with Psoriasis Drug Raptiva. Feb. 19, 2009.

FDA. FDA Public Health Advisory Updated Safety Information about Raptiva (efalizumab). Feb. 19, 2009.

FDA. FDA Statement on the Voluntary Withdrawal of Raptiva From the U.S. Market. Apr. 8, 2009.

Fischer, et al. Prevention of graft failure by an anti-HLFA-1 monoclonal antibody in HLA-mismatched bone-marrow transplantation. The Lancet. 1986; 2: 1058-60.

Fischer, et al. Role of the LFA-1 molecule in cellular interactions required for antibody production in humans. J Immunol. May 1, 1986;136(9):3198-203.

Fox. Systemic diseases associated with dry eye. Int Ophthalmol Clin, 1994; 34(1):71-87.

Frenette. Locking a leukocyte integrin with statins. N. Engl. J. Med. 2001; 345: 1419-1421.

Frishberg, et al. Cyclosporine A regulates T cell-epithelial cell adhesion by altering LFA-1 and ICAM-1 expression. Kidney Int. Jul. 1996; 50(1):45-53.

Gadek, et al. Generation of an LFA-1 antagonist by the transfer of the ICAM-1 immunoregulatory epitope to a small molecule. Science. 2002; 295: 1086-9.

Gao, et al. ICAM-1 expression predisposes ocular tissues to immune-based inflammation in dry eye patients and Sjogrens syndrome-like MRL/lpr mice. Exp Eye Res. Apr. 2004;78(4):823-35.

Genentech. Genentech Issue Dear Healthcare Provider Letter Regarding a 2nd Case of PML in a Raptiva Patient. Nov. 17, 2008.

Genentech. Genentech Issues Dear Healthcare Provider Letter Regarding a Reported Case of PML in a Raptiva Patient. Oct. 2, 2008.

Goodman, et al. "Amino acid active esters. III. Base-catalyzed racemization of peptide active ester". Journal of Organic Chemistry, 1962; 27:3409-3416.

Gorski, A. The role of cell adhesion molecules in immunopathology. Immunology Today. 1994; 15: 251-5.

Green et al. "Dynamic shifts in LFA-1 affinity regulate neutrophil rolling, arrest, and transmigration on inflamed endothelium" Blood 2006, 107(5):2101-2111.

Guan, et al. Retinal hemodynamics in early diabetic macular edema. Diabetes. 2006; 55(3):813-8.

Hecht, et al. Effects of methyl and fluorine substitution on the metabolic activation and tumorigenicity of polycyclic aromatic hydrocarbons. ACS Symposium series. 1985; 283(5):85-105. Abstract only.

Higuchi et al. Pro-drugs as Novel Delivery Systems. A. C. S. Symposium Series, and in Edward B. Roche, ed., Bioreversible Carriers in Drug Design, American Pharmaceutical Association and Pergamon Press. vol. 14. 1987.

Hildreth, et al. Monoclonal antibodies against porcine LFA-1: Species cross-reactivity and functional effects of 0-subunit-specific antibodies. Molecular Immunology. 1989; 26(9): 883-95.

Hoffman, et al. Pharmacokinetic and pharmacodynamic aspects of gastroretentive dosage forms. Int J Pharm. 2004; 277(1-2): 141-53.

Huang, et al. A binding interface of the I domain of lymphocyte function-associated antigen-1 (LFA-1) required for specific interaction with intercellular adhesion molecule 1 (ICAM-1). J Biological Chemistry. 1995; 270(32): 19008-16.

Hughes, et al. Vascular leucocyte adhesion molecules unaltered in the human retina in diabetes. Br J Ophthalmol. Apr. 2004;88(4):566-72.

International search report and written opinion dated Sep. 24, 2009 for PCT Application No. US2009/02391.

International search report dated Mar. 17, 2009 for PCT Application No. US2008/011878.

International search report dated Sep. 19, 2006 for PCT Application No. PCT/US2006/19327.

Musza, et al. Potent new cell adhesion inhibitory compounds from the root of *Trichilia rubra*. Tetrahedron. 1994; 50 (39): 11369-78.

Joussen, et al. Leukocyte- Mediated Endothelial Cell Injury and Death in the Diabetic Retina. J. Pathol. 2001; 158(1): 147-162.

Kaiser, et al. "Hydrolysis-induced racemization of amino acids", Limnol. Oceanogr. Methods. 2005, 3:318-325.

Kallen, et al. Structural basis for LFA-1 inhibition upon lovastatin binding to the CD1 1 a I-domain. J. Mol. Biol. 1999; 292: 1-9.

Kavanaugh, et al. Treatment of refractory rheumatoid arthritis with a monoclonal antibody to intercellular adhesion molecule 1. Arthritis Rheum. 1994; 37(7): 992-1004.

Keating, et al. Competition between intercellular adhesion molecule-1 and a small-molecule antagonist for a common binding site on the alphal subunit of lymphocyte function-associated antigen-1. Protein Sci. 2006; 15 (2):290-303. (Epub Dec. 29, 2005).

Keating, et al. Putting the pieces together : Contribution of fluorescence polarization assays to small molecule lead optimization. Proc. SPIE. 2000; vol. 3913, p. 128-137. (Online Publication Date: Jul. 2, 2003).

Kelly, et al. Cutting edge: a small molecule antagonist of LFA-1-mediated cell adhesion. J. Immunol. 1999; 163: 5173-5177.

King, F.D. (Ed.), "Bioisosteres, conformational restriction and pro-drugs—case history: an example of a conformational restriction approach," Medical Chemistry: Principles and Practice, 1994, Chapter 14, 206-209.

Kishimoto, et al. Integrins, ICAMs, and selectins: Role and regulation of adhesion molecules in neutrophil recruitment to inflammatory sites. Adv Pharmacol. 1994; 25: 117-69.

Klausner, et al. Novel gastroretentive dosage forms: evaluation of gastroretentivity and its effect on levodopa absorption in humans. Pharm Res. 2003; 20(9): 1466-73.

Kristina Fiore.FDA Issues Boxed Warning for Efalizumab. MedPage Today. Published: Oct. 16, 2008.

(56) References Cited

OTHER PUBLICATIONS

Kunert, et al. Analysis of Topical Cyclosporine Treatment of Patients with Dry Eye Syndrome. Arch Ophthalmol, vol. 118, Nov. 2000, 1489-1496.

Kunert, et al. Goblet cell numbers and epithelial proliferation in the conjunctiva of patients with dry eye syndrome treated with cyclosporine. Arch Ophthalmol. Mar. 2002;120(3):330-7.

Kuypers, et al. Leukocyte membrane adhesion proteins LFA-1, CR3 and p150,95: a review of functional and regulatory aspects. Res. Immunol. 1989; 140:461-486.

Landegren. Measurement of cell numbers by means of the endogenous enzyme hexosaminidase. Applications to detection of lymphokines and cell surface antigens. J. Immunol. Methods 1984; 57, 379-388.

Lang, "Ocular drug delivery conventional ocular formulations", Advanced Drug Delivery Reviews 1995, 16:39-43.

Le Mauff, et al. Effect of anti-LFA1 (CD11a) monoclonal antibodies in acute rejection of human kidney transplantation. Transplantation. 1991; 52(2): 291-5.

Legarreta Eye Center, Dry Eye, Jan 2002, printed from <http://www.legarretaeyecenter.com/dry-eye.html> with Google date entry, 3 pages.

Ley, et al. Getting to the site of inflammation: the leukocyte adhesion cascade updated. Nat Rev Immunol Sep. 2007;7 (9):678-689.

Li et al. "Lymphocyte Function-Associated Antigen-1-Dependent Inhibition of Corneal Wound Healing" Am J Pathol. 2006, 169(5):1590-1600.

Liu, et al. Discovery of novel p-arylthio cinnamides as antagonists of leukocyte function-associated antigen-1/ intracellular adhesion molecule-1 interaction. 1. Identification of an additional binding pocket based on an anilino diaryl sulfide lead. J. Med. Chem. 2000; 43, 4025-4040.

Liu, et al. Novel p-arylthio cinnamides as antagonists of leukocyte function-associated antigen-1/intracellular adhesion molecule-1 interaction. 2. Mechanism of inhibition and structure-based improvement of pharmaceutical properties. J Med Chem. Apr. 12, 2001;44(8):1202-1210.

Liu, G. Inhibitors of LFA-1/ICAM-1 interaction: from monoclonal antibodies to small molecules. Drugs of the Future. 2001; 26: 767-78.

Liu, G. Small molecule antagonists of the LFA-1/ICAM-1 interaction as potential therapeutic agents. Expert Opin Ther Patents. 2001; 11: 1383-93.

Lo, et al. Two leukocyte receptors (CD11a/CD18 and CD1 lb/CD18) mediate transient adhesion to endothelium by binding to different ligands. J Immunol. Nov. 15, 1989;143(10):3325-9.

Lu, et al. The binding sites for competitive antagonistic, allosteric antagonistic, and agonistic antibodies to the I domain of the integrin LFA-1. J Immunol. 2004; 173: 3972-8.

Mekori et al. "Mast cell-T cell interactions". J Allergy Clin Immunol. 1999, 104(3):517-523.

Meleth AD, Agrón E, Chan CC, Reed GF, Arora K, Byrnes G, Csaky KG, Ferris FL 3rd, Chew EY. Serum inflammatory markers Diabetologia. Dec. 2002; 45(12):1617-34. In diabetic retinopathy. Invest Ophthalmol Vis Sci. Nov. 2005; 46 (11):4295-301.

Mentzer, et al. LFA-1 membrane molecule in the regulation of homotypic adhesions of human B lymphocytes. J Immunol Jul. 1985;135(1):9-11.

Mingxia Yuan, et al., "A Preliminary Study on the Relationship Between Adhesion Molecules and Diabetic Retinopathy in Diabetic Rats," Chinese Journal of Endocrinology and Metabolism, vol. 15, (4), pp. 207-211, Aug. 1999 (No English Translation).

Mingxia Yuan, et al., "A Preliminary Study on the Relationship Between Adhesion Molecules and Diabetic Retinopathy in Diabetic Rats," Chinese Journal of Endocrinology and Metabolism, vol. 15, (4), pp. 207-211, Aug. 1999 (English Translation).

Miyamoto et al. "In vivo quantification of leukocyte behavior in the retina during endotoxin-induced uveitis" Investigative Opthalmology & Visual Science 1996, 37(13):2708-2715.

Miyamoto, et al. "In vivo demonstration of increased leukocyte entrapment in retinal microcirculation of diabetic rats", Investigative Opthalmology & Visual Science 1998, 39(11):2190-2194.

Miyamoto, K. et al, Prevention of leukostasis and vascular leakage in streptozotocin-induced diabetic retinopathy via intercellular adhesion molecule-1 inhibition, Proc Natl Acad Sci USA, 1999, vol. 96, No. 19, p. 10836-41

Murphy, et al. The Pharmacologic Assessment of a Novel Lymphocyte Function-Associated Antigen-1 Antagonist (SAR 1118) for the Treatment of Keratoconjunctivitis Sicca in Dogs. Invest Ophthalmol Vis Sci. May 16, 2011;52 (6):3174-80.

Nam KO, Maiorov V, Feuston B, Kearsley S. Dynamic control of allosteric antagonism of leukocyte function antigen-1 and intercellular adhesion molecule-1 interaction. Proteins. Aug. 1, 2006;64(2):376-84.

Nishiwaki et al. "Visualization and quantitative analysis of leukocyte dynamics in retinal microcirculation of rats" Investigative Opthalmology & Visual Science 1996, 37(7):1341-1347.

Notice of Allowance dated Mar. 5, 2010, for U.S. Appl. No. 11/978,388.

Notice of Allowance dated Mar. 9, 2010, for U.S. Appl. No. 11/934,049.

Office action dated Jun. 7, 2011 for U.S. Appl. No. 11/436,906.

Office Action dated Jun. 8, 2011 for U.S. Appl. No. 12/508,367.

Office Action dated Sep. 28, 2010 for U.S. Appl. No. 12/508,311.

Office Action dated Sep. 28, 2010 for U.S. Appl. No. 12/508,367.

Office Action dated Dec. 21, 2010 for U.S. Appl. No. 11/436,906.

Office action dated Oct. 5, 2011 for U.S. Appl. No. 13/011,775.

Office action dated Sep. 15, 2011 for U.S. Appl. No. 13/011760.

Park, et al. Effects of fluorine substitution on drug metabolism: pharmacological and toxicological implications. Drug Metab Rev. 1994;26(3):605-43.

Park, et al. Metabolism of fluorine-containing drugs. Annu Rev Pharmacol Toxicol. 2001;41:443-70.

Patani, et al. Bioisosterism: A rational approach in drug design. Chem. Rev. 1996; 96:3147-3176.

Plobeck, et al. New diarylmethylpiperazines as potent and selective nonpeptidic (5 opioid receptor agonists with increased in vitro metabolic stability. J Med Chem. 2000; 43: 3878-94.

Porta M, Bandello F. Diabetic retinopathy a Clinical update. Diabetologia. Dec. 2002; 45(12):1617-34.

Rao, et al. Delivery of SAR 1118 to the retina via ophthalmic drops and its effectiveness in a rat streptozotocin (STZ) model of diabetic retinopathy (DR). Invest Ophthalmol Vis Sci. Oct. 2010; 51 (10):5198-204. Epub May 5, 2010.

Remington: The Science and Practice of Pharmacy, 21st edition, 2005, Philip Gerbino (Editor), p. 1158.

Rothlein, et al. 1. Leukocyte adhesion in inflammation: From discovery to the clinic. Adhesion Molecules. Wegner, C.D., Ed.; 1994: 1-8.

Salas, et al. Rolling adhesion through an extended conformation of integrin aLi32 and relation to a I and 0 I-like domain interaction. Immunity. 2004; 20(4): 393-406.

Sanders, et al. Characterization of the physical interaction between antigen-specific B and T cells. J. Immunol. 1986; 137:2395-2404.

Sanfilippo, et al. Novel thiazole based heterocycles as inhibitors of LFA-1/ICAM-1 mediated cell adhesion. J Med Chem. 1995; 38: 1057-9.

Sapirstein et al. "Volumes of Distribution and Clearances of Intravenously Injected Creatinine in the Dog" American Journal of Physiology 1955, 181:330-336.

Shimaoka, et al. Reversibly locking a protein fold in an active conformation with a disulfide bond: Integrin alpha L I domains with high affinity and antagonist activity in vivo. PNAS. 2001; 98(11): 6009-14.

Shimaoka, et al. Small molecule integrin antagonists that bind to the 62 subunit I-like domain and-activate signals in one direction and block them in the other. Immunity. 2003; 19(3): 391-402.

Shimaoka, et al. Structures of the aL I domain and its complex with ICAM-1 reveal a shape-shifting pathway for integrin regulation. Cell. 2003; 112(1): 99-111.

(56) References Cited

OTHER PUBLICATIONS

Shimaoka, et al. Therapeutic antagonists and the conformational regulation of the (32 integrins. Curr Topics Med Chem. 2004; 4: 1485-95.
Shulman, et al. Lymphocyte crawling and transendothelial migration require chemokine triggering of high-affinity LFA-1 integrin. Immunity. Mar. 20, 2009;30(3):384-396.
Skelly, et al. FDA and AAPS Report of the Workshop on Principles and Practices of In-Vitro Percutaneous Penetration Studies: Relevance to Bioavailability and Bioequivalence. Pharmaceutical Research 1987 4(3): 265-267.
Solomans. Fundamentals of Organic Chemistry. 5th ed. 1982; 630.
Springer, T. Adhesion receptors of the immune system. Nature. 1990; 346: 425-34.
Stern, et al. Conjunctival T-cell subpopulations in Sjogren's and non-Sjogren's patients with dry eye. Invest Ophthalmol Vis Sci. Aug. 2002;43(8):2609-14.
Streubel, et al. Gastroretentive drug delivery systems. Expert Opin Drug Deliv. 2006; 3(2): 217-33.
The Eye Digest, Eye Exam for Dry Eyes, Mar. 2003, printed from <http://www.agingeye.net/dryeyes/dryeeyeseyeexam.php> and google date entry, 4 pages.
Thomson Scientific. Database WPI. Week 200746. London, GB. 2007.
U.S Office action dated Jan. 22, 2010, for U.S. Appl. No. 11/436,906.
U.S Office action dated Jul. 22, 2010, for U.S. Appl. No. 11/436,906.
U.S Office action dated Jun. 25, 2012, for U.S. Appl. No. 12/909,241.
U.S. Office Action dated Apr. 25, 2012, for U.S. Appl. No. 13/011,775.
U.S. Office Action dated Jan. 16, 2013, for U.S. Appl. No. 13/011,760.
U.S. Office Action dated Jan. 16, 2013, for U.S. Appl. No. 13/011,775.
U.S. Office Action dated Mar. 13, 2012, for U.S. Appl. No. 13/011,760.
U.S. Office action dated Nov. 9, 2012, for U.S. Appl. No. 13/289,172.
U.S. Office Action dated Oct. 28, 2013, for U.S. Appl. No. 13/011,775.
U.S. Office action dated Sep. 8, 2011, for U.S. Appl. No. 12/386,361.
Ward, S. Millipede-like lymphocyte crawling: feeling the way with filopodia. Immunity. Mar. 20, 2009;30(3):315-317.
Weitz-Schmidt, et al. Statins selectively inhibit leukocyte function antigen-1 by binding to a novel regulatory integrin site. Nature Med. 2001; 7: 687-692.
Welzenbach, et al. Small molecule inhibitors induce conformational changes in the I domain and the I-like domain of lymphocyte function-associated antigen-1. J Biological Chemistry. 2002; 277(12): 10590-8.
Wermuth. The practice of medicinal chemistry-molecular variations based on isosteric replacements. Academic Press Limited. 1996; 226-228.
Whitcup et al. "Blocking ICAM-1 (CD54) and LFA-1 (CD11a) inhibits experimental allergic conjunctivitis". Clin Immunol. 1999, 93(2):107-13.
Australian Office Action dated Apr. 2, 2013, issued in corresponding Australian Application No. 2008317473.
Australian Office Action dated Nov. 6, 2015, issued in corresponding Australian Application No. 2014208186.
Canadian Office Action dated Feb. 12, 2016, issued in corresponding Canadian Application No. 2,702,984.
Chinese Office Action dated Jan. 28, 2014, issued in the corresponding Chinese Application No. 200880117716.2.
Japanese Office Action dated Aug. 19, 2015, issued in corresponding Japanese Application No. 2014144595.

\* cited by examiner

Interaction of LFA-1 Immunological Synapse Formation

Immunological Synapse Formation

Inhibition of Proper Immunological
Synapse Formation via LFA-1 Inhibition

Interaction of LFA-1 with ICAM Costimulation

LFA-1:ICAM-1 'Costimulation'

Costimulation

Decreased or Absent LFA-1 Mediated Costimulation

Compound 1, R = (C=S)NH-Fluorescein  Compound 2A, R = H
Compound 2B, R = (C=S)NH-Fluorescein

Compound 3  Compound 4

A-286982  Compound 5

```
                        SEQUENCE LISTING

<160> NUMBER OF SEQ ID NOS: 9

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Tyr Asn Leu Asp Val Arg Gly Ala Arg Ser Phe Ser
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Val Ile Val Gly Ala Pro Gly Glu Gly Asn Ser Thr
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Gly Phe Asp Met Pro Cys
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Meta-Tyr

<400> SEQUENCE: 4

Cys Gly Tyr Asp Met Pro Cys
1               5
```

```
<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Arg Ile Pro Arg Gly Asp Met Pro Asp Asp Arg Cys
1               5                   10

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: N'-3-phenylpropyl Asn

<400> SEQUENCE: 6

Cys Asn Pro Cys
1

<210> SEQ ID NO 7
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cactgtggcg ccctggtttt caggaaggta gtggatcagg cacaagcaaa caggacctga      60
cttc                                                                  64

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ser Gly Ser Gly
1               5

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tctgagccat gtgctggtat cgaggggc                                        28
```

COMPOSITIONS AND METHODS FOR TREATMENT OF DIABETIC RETINOPATHY

CROSS-REFERENCE

This application is a continuation of U.S. application Ser. No. 12/288,330, filed on Oct. 17, 2008, which claims the benefit of U.S. Provisional Application Ser. No. 60/999,571, filed Oct. 19, 2007, the entire disclosures of which are incorporated herein by reference in their entirety.

BACKGROUND OF THE INVENTION

Worldwide, one of the most significant causes of blindness is diabetic retinopathy (DR) which often includes an associated disorder, diabetic macular edema (DME), which is one of the complications of diabetes resulting in microvasculature insult, injury and degeneration in the body, and in particular, the eye. The loss of workplace and personal function subsequent to such loss of visual function can have devastating impact upon the individual and on the community surrounding that individual as a whole. Nearly all individuals with diabetes demonstrate some degree of diabetic retinopathy, and the numbers of diabetic patients are increasing, therefore there is need for more effective treatments for vision loss and the symptoms of DR and associated macular edema.

SUMMARY OF THE INVENTION

In one aspect, the present invention provides methods of treating a subject suffering from diabetic retinopathy comprising administering to said subject in need thereof a therapeutically effective amount of a therapeutic agent which inhibits the interaction of LFA-1 and an ICAM.

In a second aspect a method is provided of treating a subject suffering from macular edema comprising administering to said subject in need thereof a therapeutically effective amount of a therapeutic agent which inhibits the interaction of LFA-1 and an ICAM, thereby reducing and/or preventing macular edema in an eye of said subject.

In an third aspect of the invention, a method is provided to treat diabetic retinopathy in a subject comprising performing a diabetic retinopathy diagnostic test on said subject; determining whether said subject suffers from diabetic retinopathy based on the results of said diagnostic test; and upon diagnosis of said diabetic retinopathy, administering to said subject an effective amount of a (LFA-1) antagonist in a pharmaceutically acceptable formulation.

In a fourth aspect of the invention, a method is provided for reducing and/or preventing post-operative ocular inflammation in a subject suffering from diabetes comprising administering to said subject in need thereof a therapeutically effective amount of a LFA-1 antagonist, thereby reducing and/or preventing post-operative inflammation in an eye of said subject.

In some embodiments, post-operative inflammation is the result of vitrectomy, laser photocoagulation therapy, photodynamic therapy, or LASIK. In other embodiments, the diagnostic step is performed by imaging an eye of said subject or analysis of a biological sample of an eye of said subject.

In some of the embodiments of the invention, the ICAM is ICAM-1, ICAM-2, or ICAM-3. In some embodiments, the ICAM is ICAM-1. In some embodiments of the invention, the therapeutic agent is an LFA-1 antagonist. In some of the embodiments of the invention, the LFA-1 antagonist binds to a high affinity binding site in the aL subunit of LFA-1 overlapping the ICAM-1 binding site. In other embodiments of the invention, the LFA-1 antagonist is directly competitive vith the binding of ICAM-1 at the aL subunit of LFA-1. In some embodiments of the invention, the LFA-1 antagonist is a competive inhibitor of the interaction between LFA-1 and ICAM-1. In some embodiments of the invention, the LFA-1 antagonist is an allosteric antagonist of the binding of ICAM-1 at the αL subunit of LFA-1.

In some of the embodiments of the invention, the diabetic retinopathy is non-proliferative. In some of the inventions, the diabetic retinopathy is proliferative. In some embodiments of the invention, damage resulting from diabetic retinopathy is macular edema, retinal neovascularization, fibrovascular growth over a retina, loss of vision, basement membrane thickening, retinal edema, or retinal ischemia.

In some of the embodiments of the invention, an LFA antagonist is provided which is an antibody. In some of the embodiments of the invention, an LFA antagonist is provided which is a compound of Formula I, II, III, IV, V or VI.

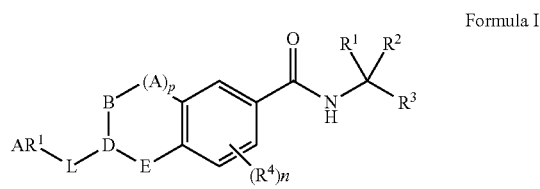

Formula I

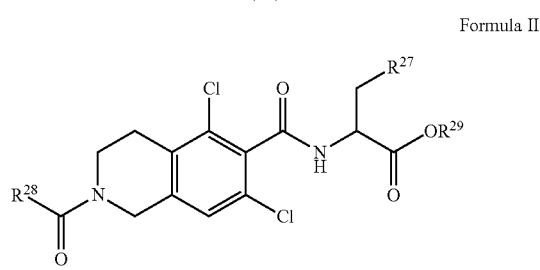

Formula II

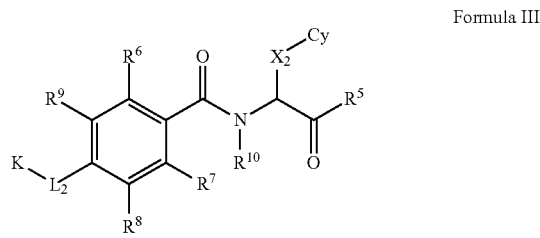

Formula III

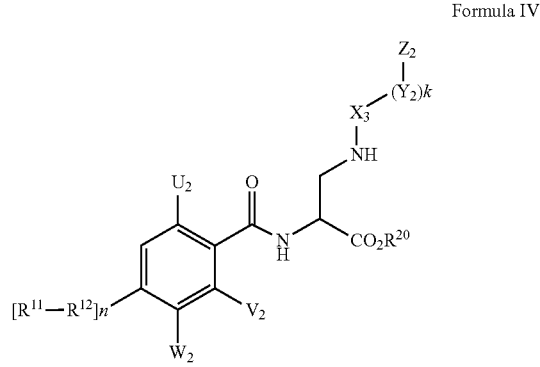

Formula IV

-continued

Formula V

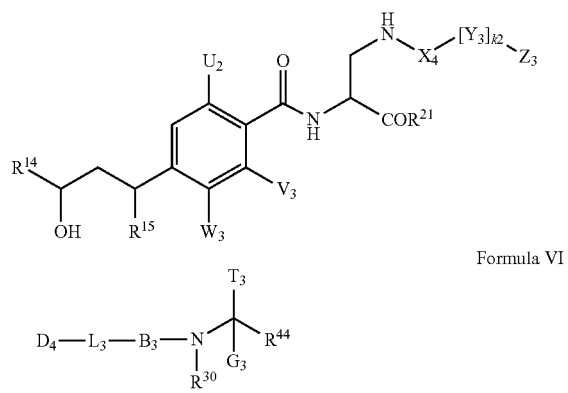

Formula VI

In some of the embodiments of the invention, an LFA antagonist is provided which is a compound of Formula IA, IIA or IIB.

Formula IA

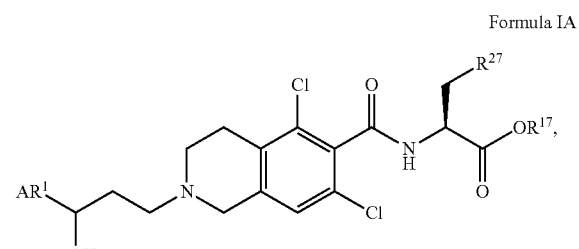

In some embodiments, the compound of Formula II is provided which contains a stereochemistry as in Formula II'.

Formula II'

Formula IIA

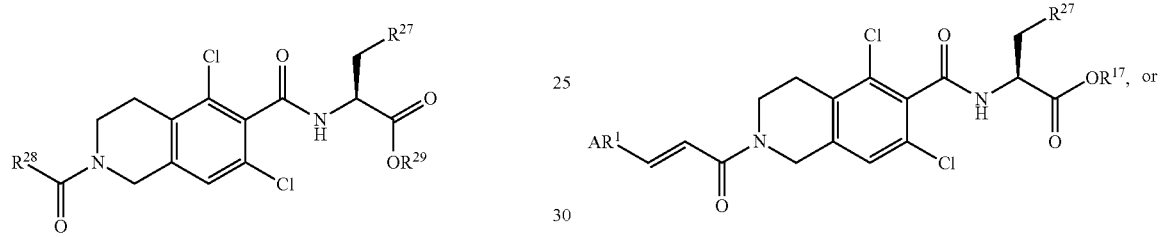

In some of the embodiments of the invention, the compound of Formula III is provided which contains a stereochemistry as in Formula III'.

Formula III'

Formula IIB

In some of the embodiments of the invention, the LFA-1 antagonist is a compound with one of the following structures:

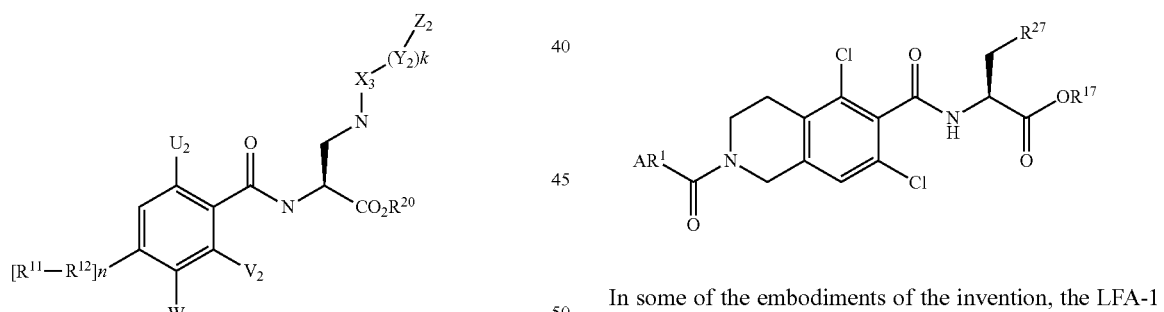

5
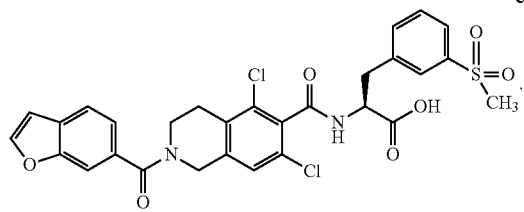
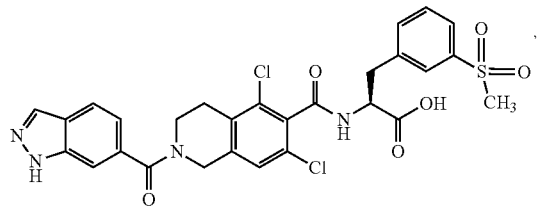
6
-continued
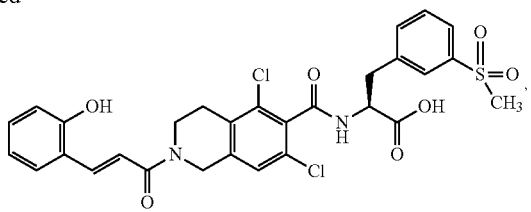
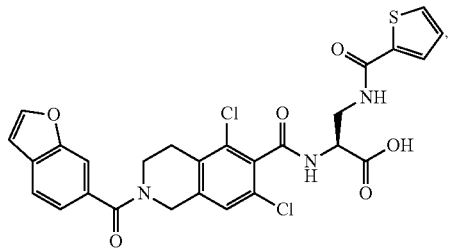
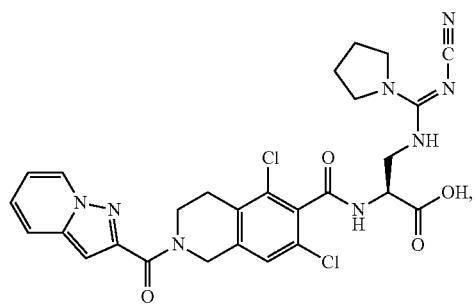
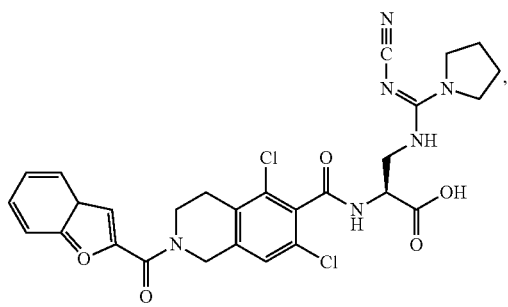
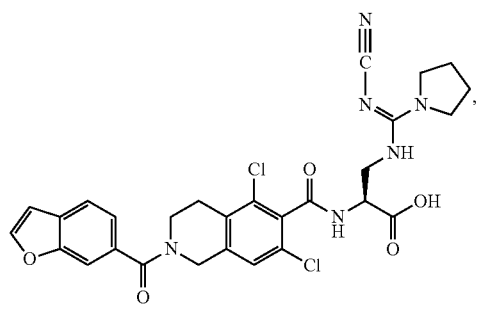
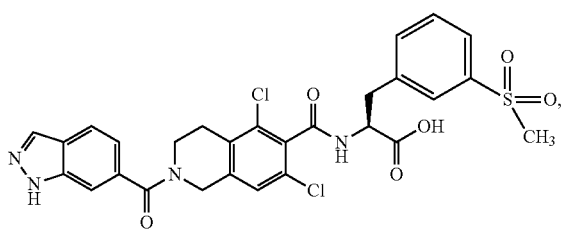
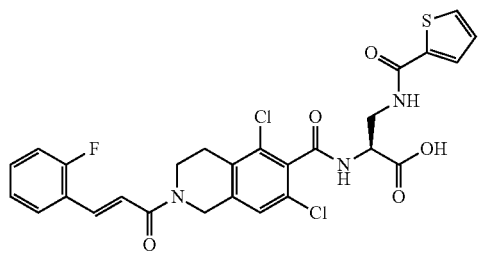
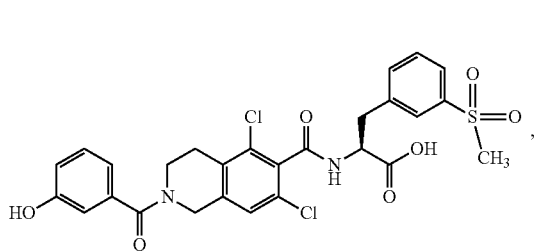
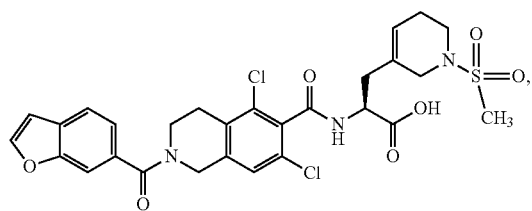
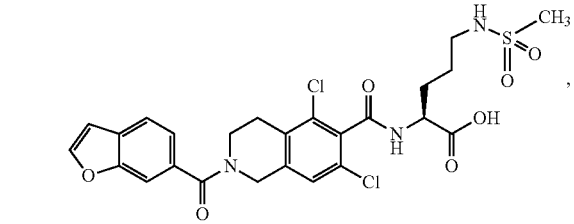

-continued
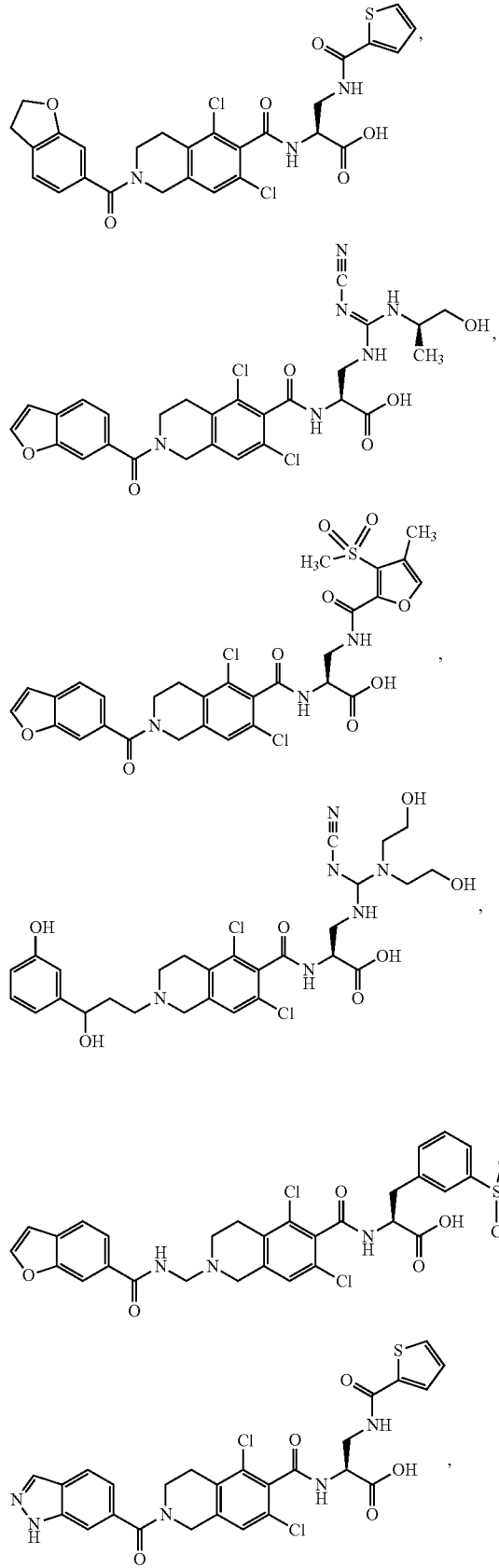

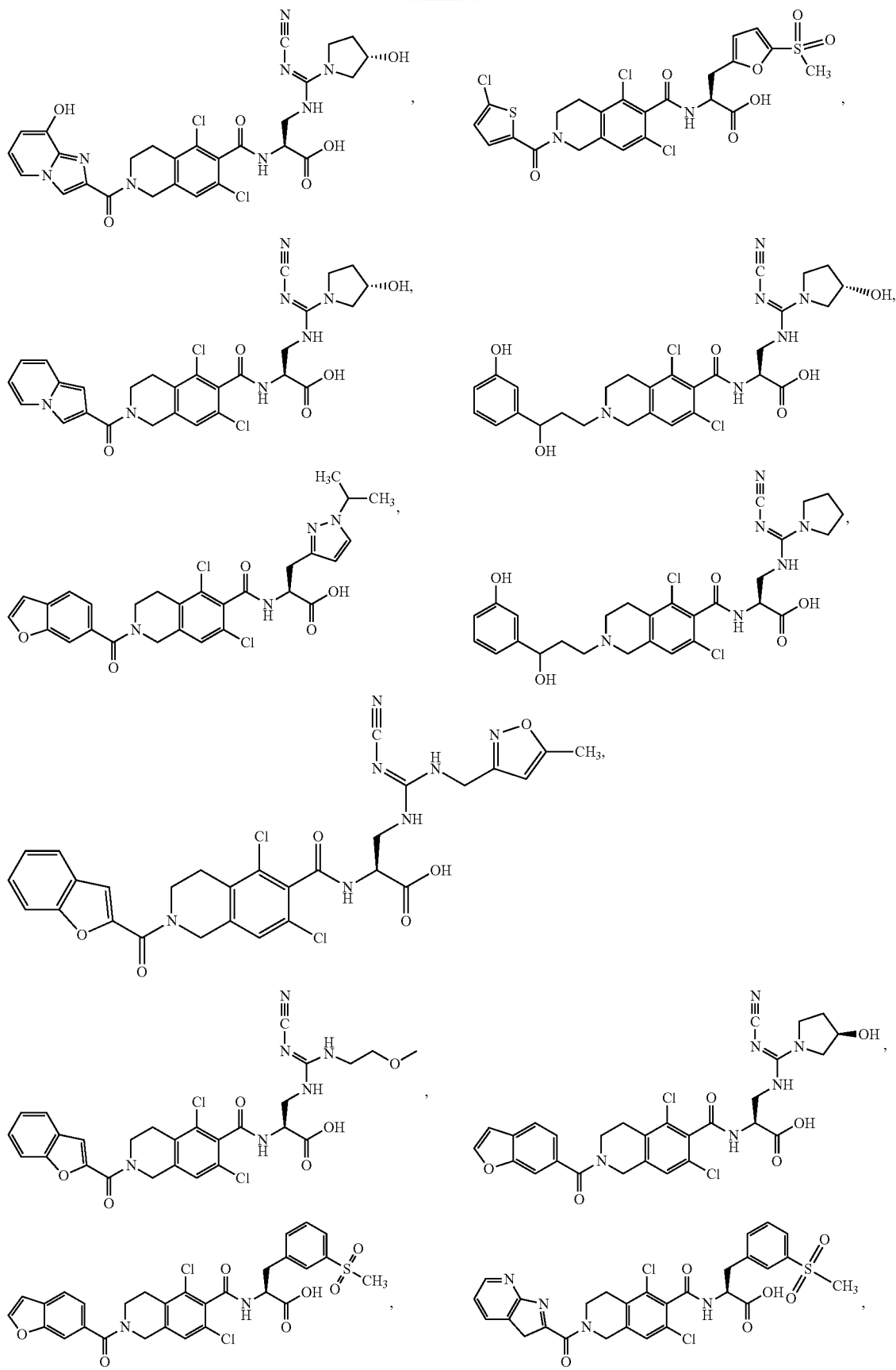

11
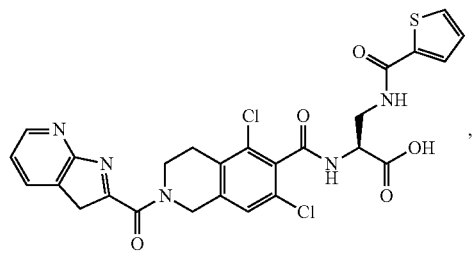
12
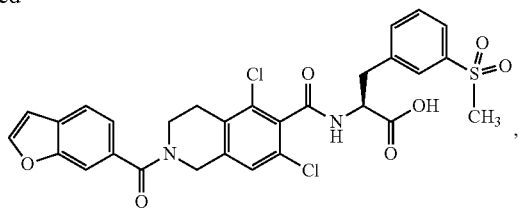
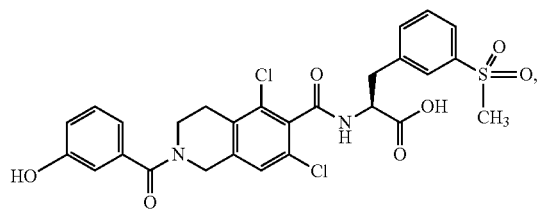
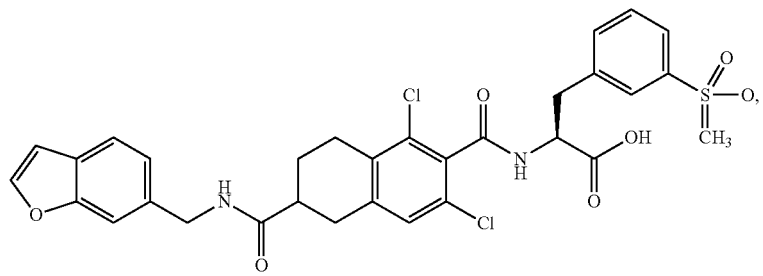
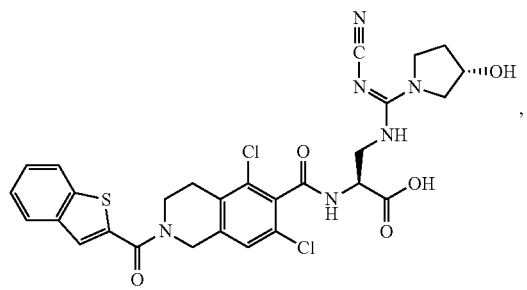
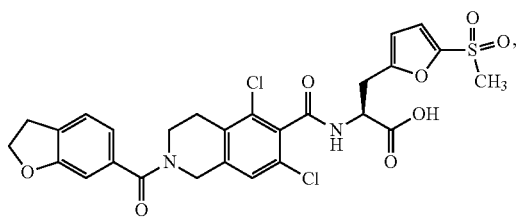
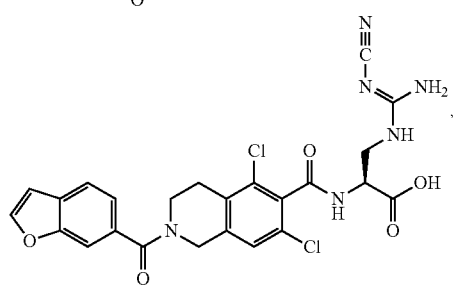
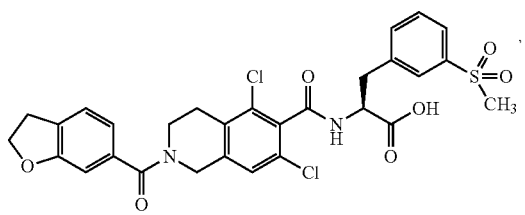
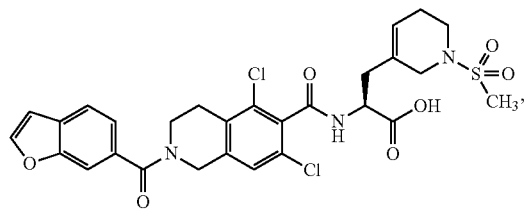
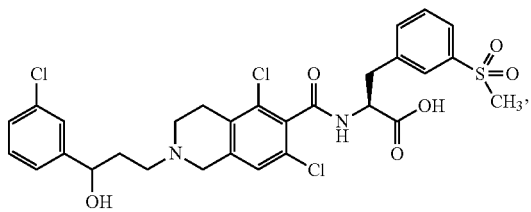
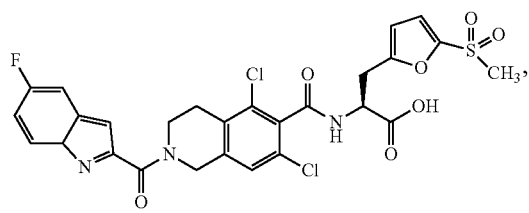
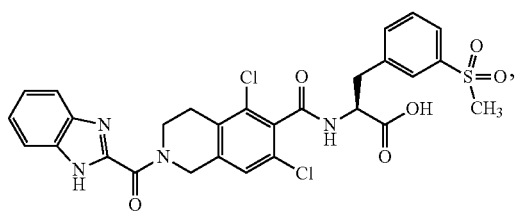

-continued
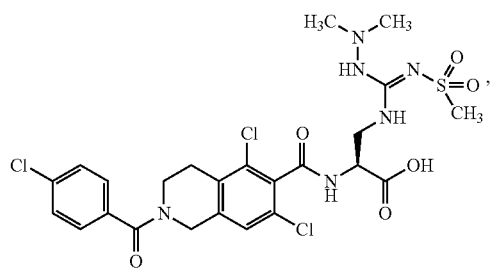
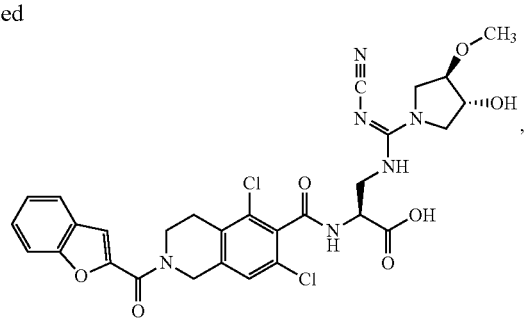
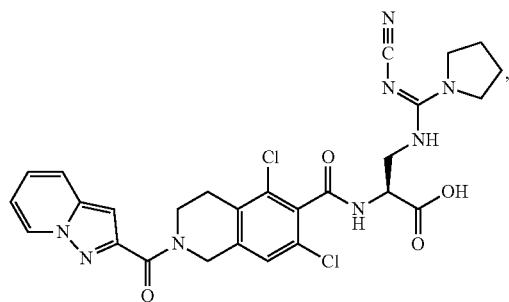
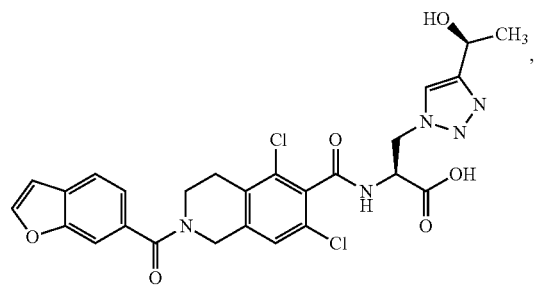
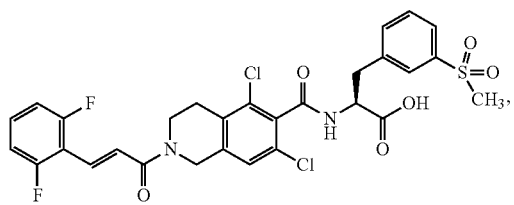
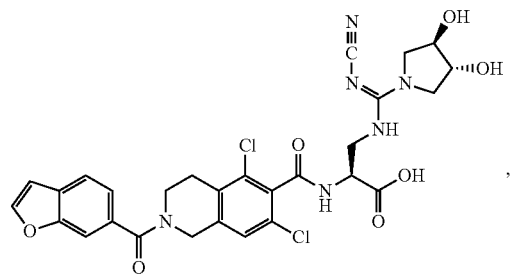
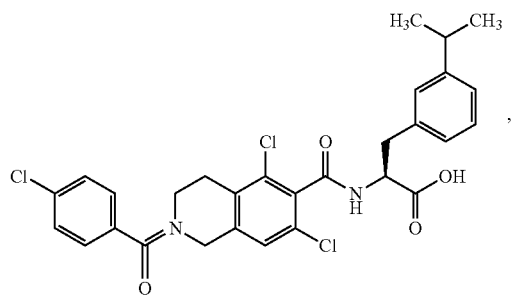
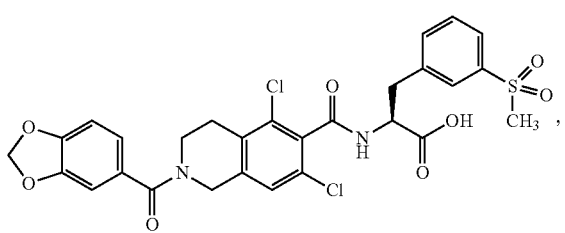
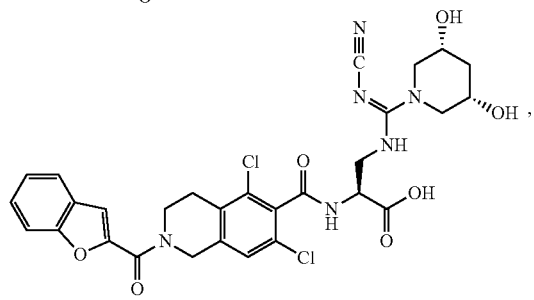

-continued
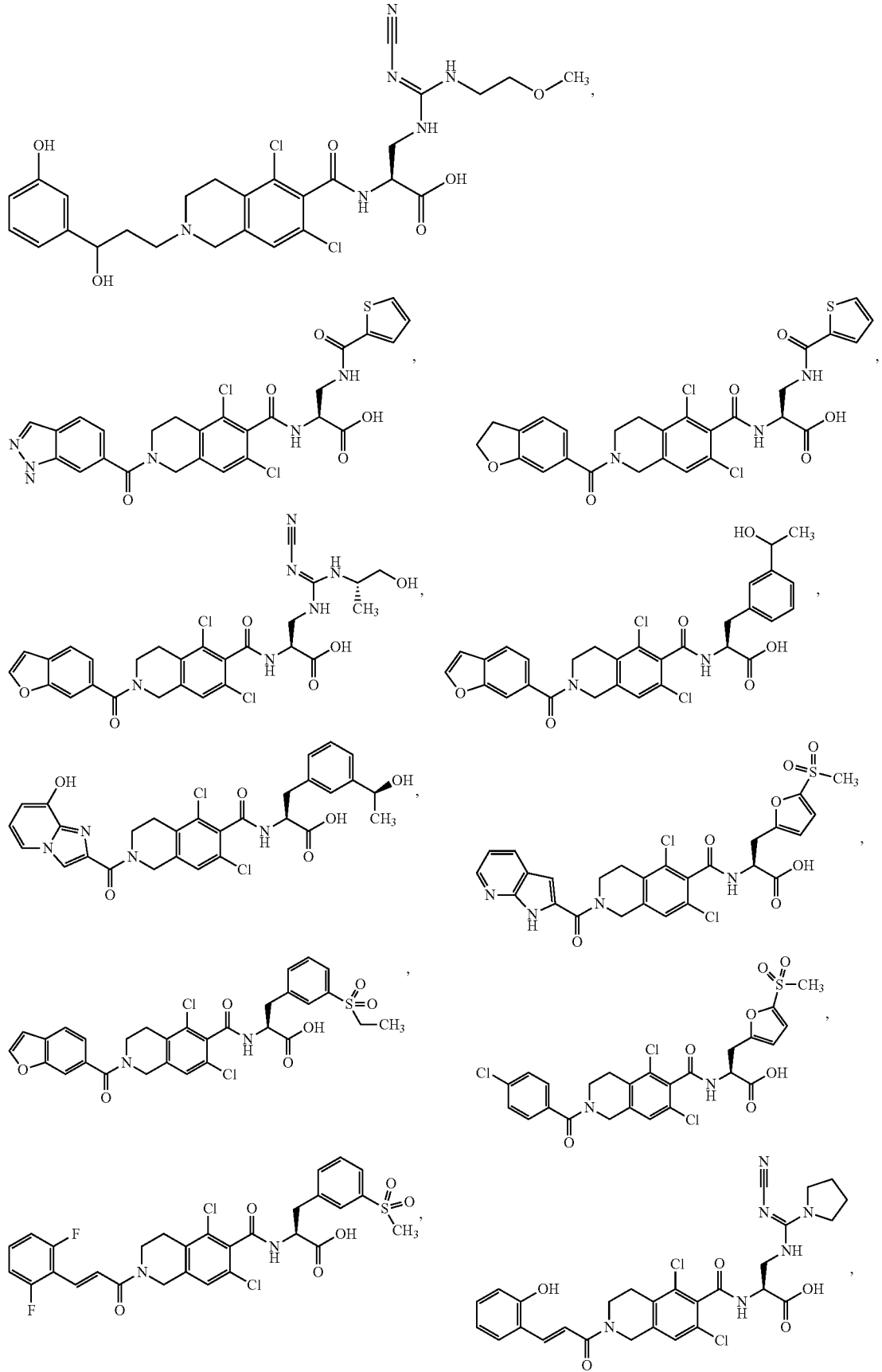

-continued
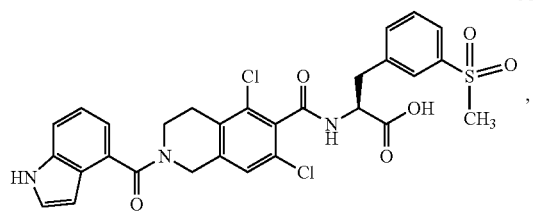
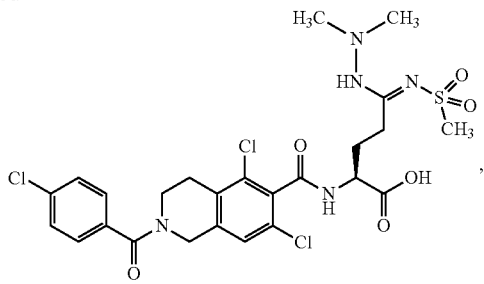
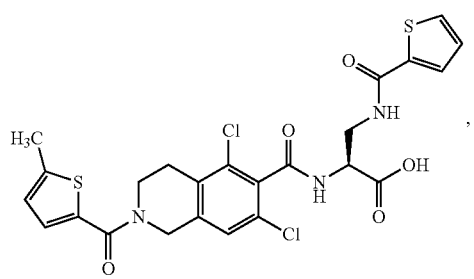
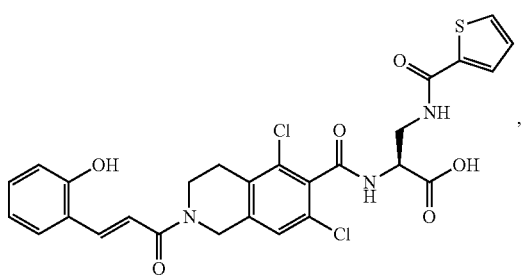
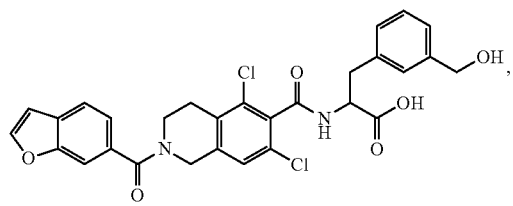
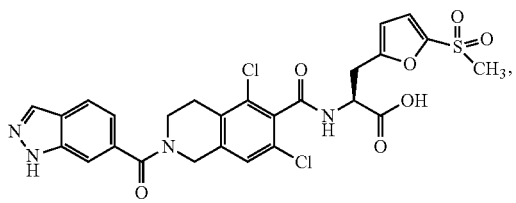
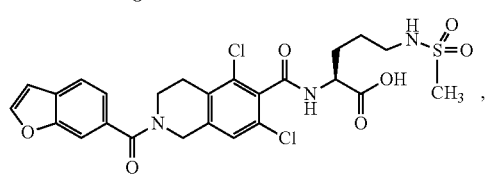
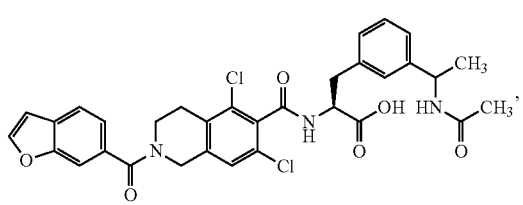
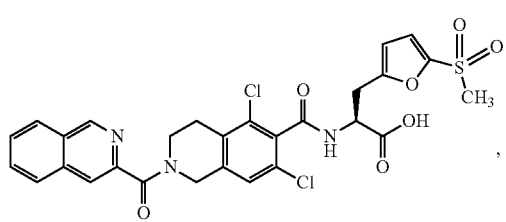
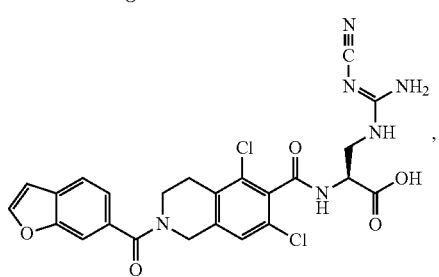
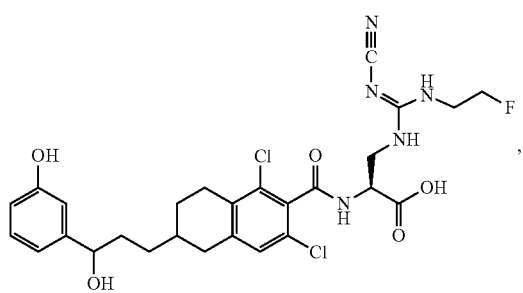
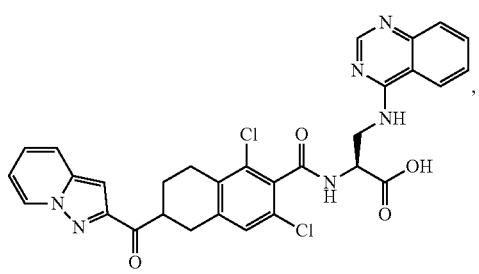

-continued
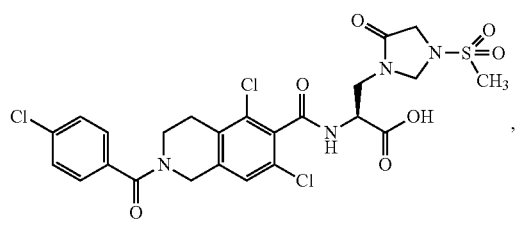
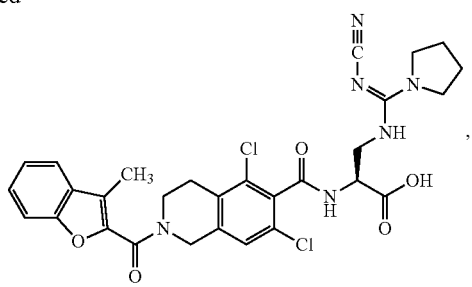
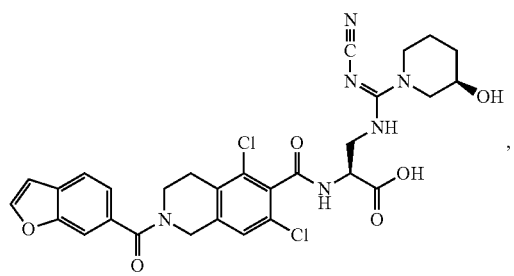
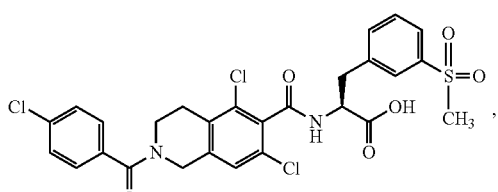
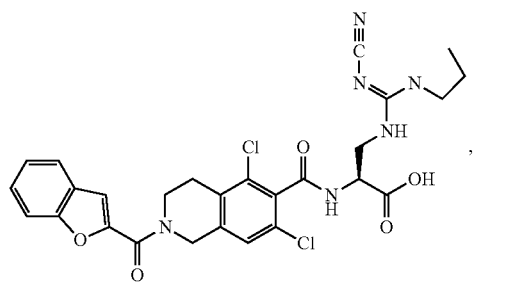
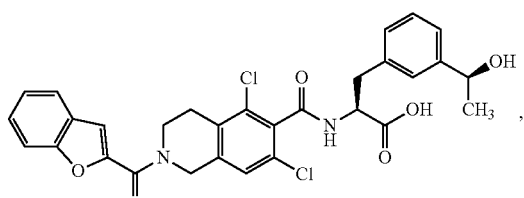
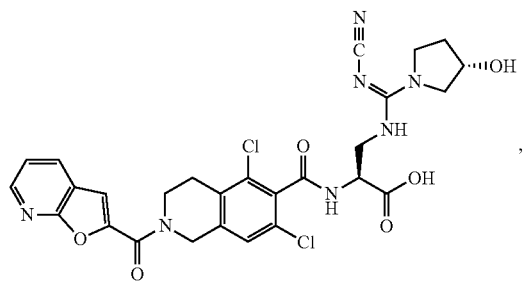
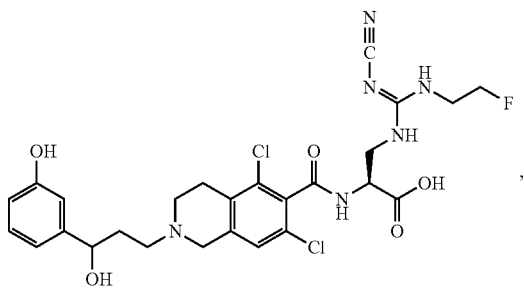
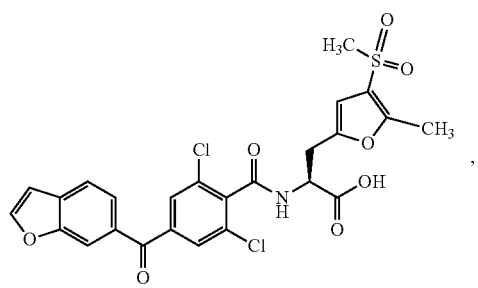
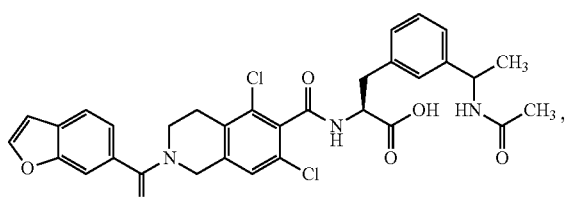
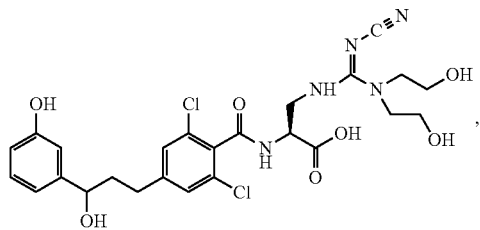
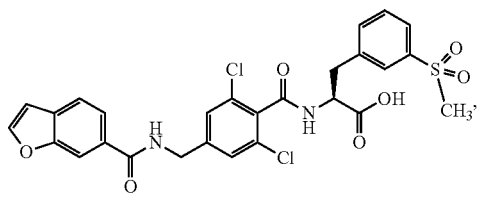

-continued
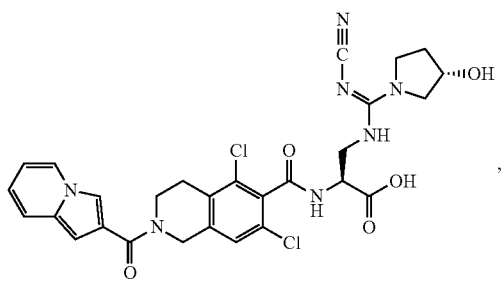
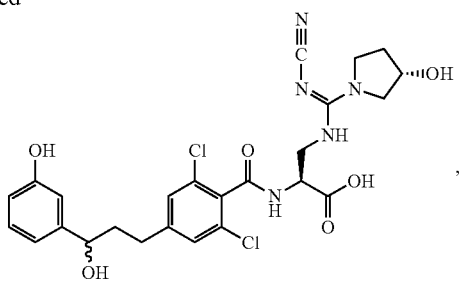
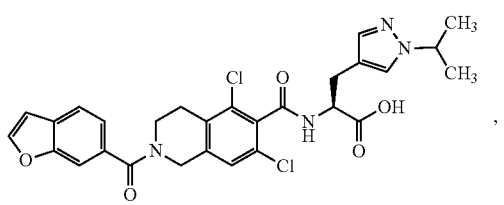
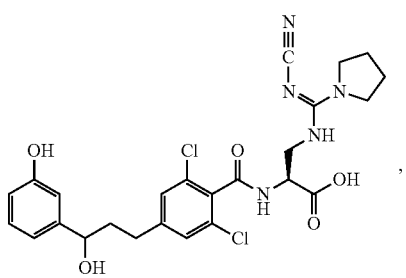
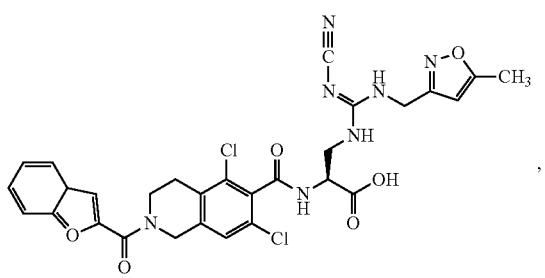
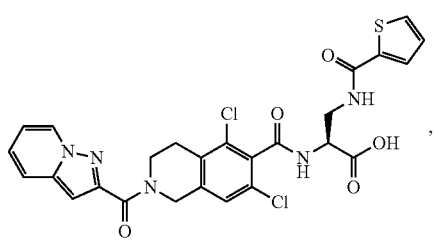
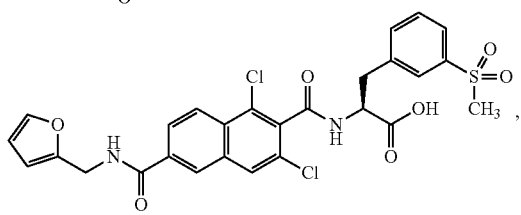
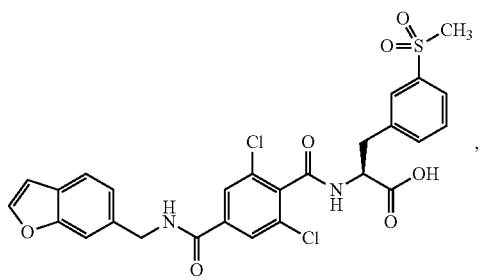
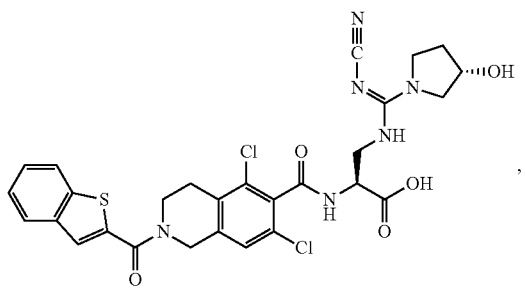
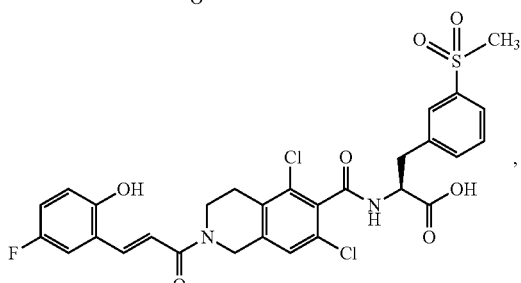
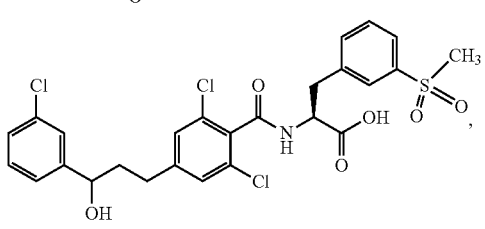
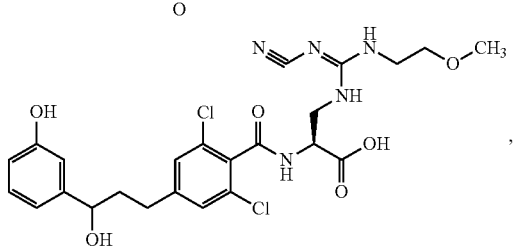

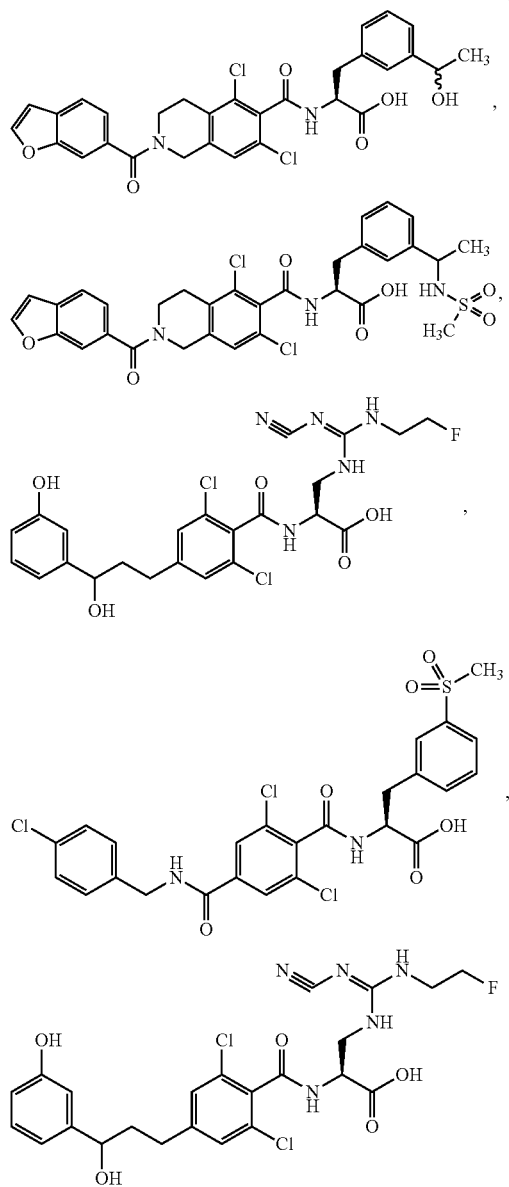
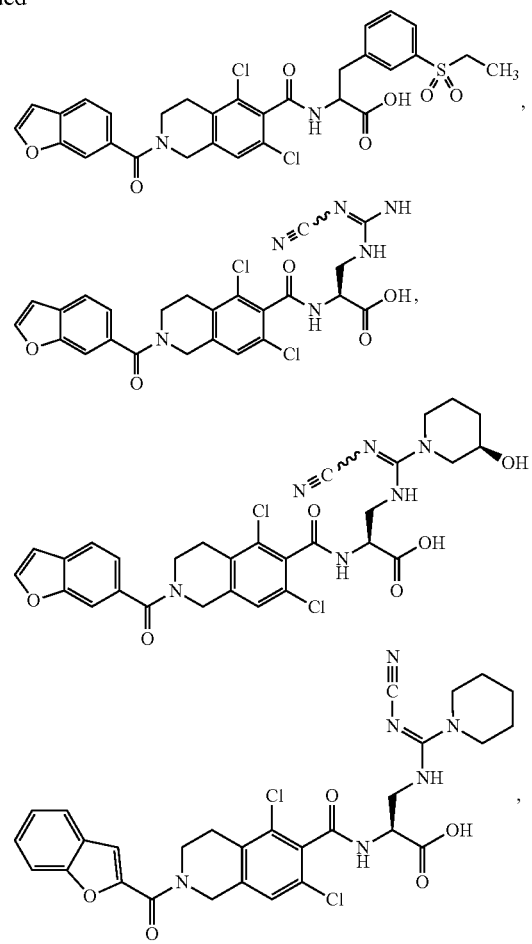
and their pharmaceutically acceptable salts and esters.
and their pharmaceutically acceptable salts and esters.
In some of the embodiments of the invention, the LFA-1 antagonist is a compound of Formula VII, VIII, IX, X, or XI or enantiomers, pharmaceutically-acceptable salts, or solvates, thereof.
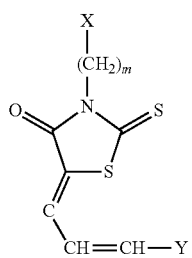
Formula VII
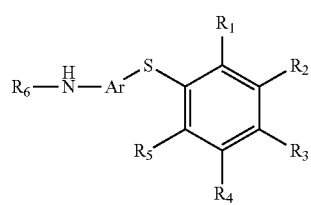
Formula VIII
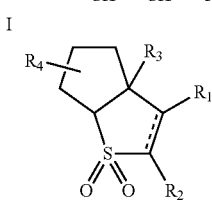
Formula IX Formula XI

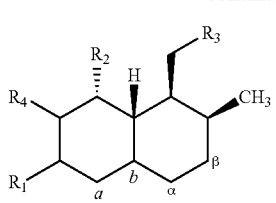

Formula X

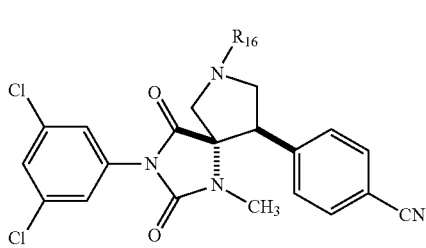

In some of the embodiments of the invention, the therapeutic agent is administered topically, orally, periocularly, intraocularly, via injection, nasally, via an aerosol, via an insert, via an implanted device, or via a drop. In other of the embodiments of the invention, the therapeutic agent is administered in a carrier vehicle which is liquid drops, liquid wash, nebulized liquid, gel, ointment, aerosol, spray, polymer micro and nanoparticles, solution, suspension, solid, biodegradable matrix, powder, crystals, foam, or liposomes. In some of the embodiments of the invention, a therapeutically effective amount of said therapeutic agent is delivered to an eye of said subject via local or systemic delivery. In some of the embodiments of the invention an injectable administration is performed intraocularly or periocularly. In some embodiments of the invention, administration is accomplished by administering an intra-ocular instillation of a gel, cream, powder, foam, crystals, liposomes, spray, polymer micro or nanospheres, or liquid suspension form of said compound. In some of the embodiments, polymer micro or nanospheres are used to deliver the therapeutic agent via periocular or intraocular injection or implantation.

In some of the embodiments, a therapeutically effective amount of the therapeutic agent is delivered to an eye of the subject via local or systemic delivery.

In some of the embodiments of the invention, the therapeutic agent is administered in a carrier vehicle which is liquid drops, liquid wash, nebulized liquid, gel, ointment, aerosol, spray, polymer micro and nanoparticles, solution, suspension, solid, biodegradable matrix, powder, crystals, foam, or liposomes. In some of the embodiments of the invention, topical administration comprises infusion of said compound to said eyes via a device selected from the group consisting of a pump-catheter system, an insert, a continuous or selective release device, a bioabsorbable implant, a continuous or sustained release formulation, and a contact lens. In some of the embodiments of the invention, injectable administration is performed intraocularly, intravitreally, periocularly, subcutaneously, subconjunctivally, retrobulbarly, or intracamerally. Controlled release formulations are also provided for in some embodiments of the invention. In some embodiments of the invention, the compounds of the invention are formulated as prodrugs. In some embodiments of the invention the formulation of the therapeutic agent includes no preservative. In some embodiments of the invention the formulation of the therapeutic agent includes at least one preservative. In some embodiments of the invention the the formulation of the therapeutic agent includes a thickening agent. In other embodiments of the invention, the formulation of the therapeutic agent uses PLGA micro- or nanoparticles.

In some embodiments of the invention, the compound is administered to the subject in an amount sufficient to achieve intraocular or retinal concentrations of from about $1 \times 10^{-8}$ to about $1 \times 10^{-1}$ moles/liter. In some embodiments of the invention, the compound is administered at least once a year. In other embodiments of the invention, the compound is administered at least once a day. In other embodiments of the invention, the compound is administered at least once a week. In some embodiments of the invention, the compound is administered at least once a month.

In some embodiments of the invention, a second therapeutic agent is administered prior to, in combination with, at the same time, or after administration of the LFA-1 antagonist. In some embodiments, the second therapeutic agent is selected from the group consisting of antioxidants, antiinflammatory agents, antimicrobials, steroids, protein kinase C inhibitors, angiotensin converting enzyme inhibitors, anti-angiogenic agents, complement inhibitors, and anti-apoptotic agents. In some embodiments of the invention, the second therapeutic agent is an anti-adhesion therapeutic agent that binds to an allosteric binding site on LFA-1. In some embodiments of the invention, the second therapeutic agent is an anti-adhesion therapeutic antibody or antibody fragment.

In some embodiments of the invention a diagnostic test is included in a method of treatment with an LFA-1 antagonist. In one embodiment, a diagnostic test for diabetic retinopathy is performed and after a diagnosis of the disease is made, the subject is administered an LFA-1 antagonist as described herein. In some embodiments of the invention, the diagnostic test is performed by imaging an eye of the subject or analysis of a biological sample of an eye of the subject.

In another aspect, the invention provides a pharmaceutical composition formulated for ocular delivery comprising a therapeutic agent which inhibits the interaction of LFA-1 and an ICAM and a pharmaceutically acceptable carrier. In some embodiments, the pharmaceutical composition comprises a therapeutic agent which inhibits the interaction of LFA-1 and an ICAM, which is a compound of Formula I, II, III, IV, V, VI, VII, VIII, IX, X, or XI. In some embodiments, the pharmaceutical composition is suitable for topical administration. In some embodiments, the pharmaceutical composition is suitable for administration via injection. In some embodiments, the pharmaceutical composition is suitable for administration suitable for administration as an implant.

In another aspect, compounds are provided for use in the methods of the invention. Compounds that are useful in the methods of the invention include antibodies, fragments of antibodies, polypeptides, peptides, polymers, and organic small molecules. In another an embodiment of the method of the present invention, the antibody Raptiva is used in an ocular formulation to treat diabetic retinopathy.

INCORPORATION BY REFERENCE

All publications and patent applications mentioned in this specification are herein incorporated in its entirety by reference to the same extent as if each individual publication or patent application was specifically and individually indicated to be incorporated in its entirety by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
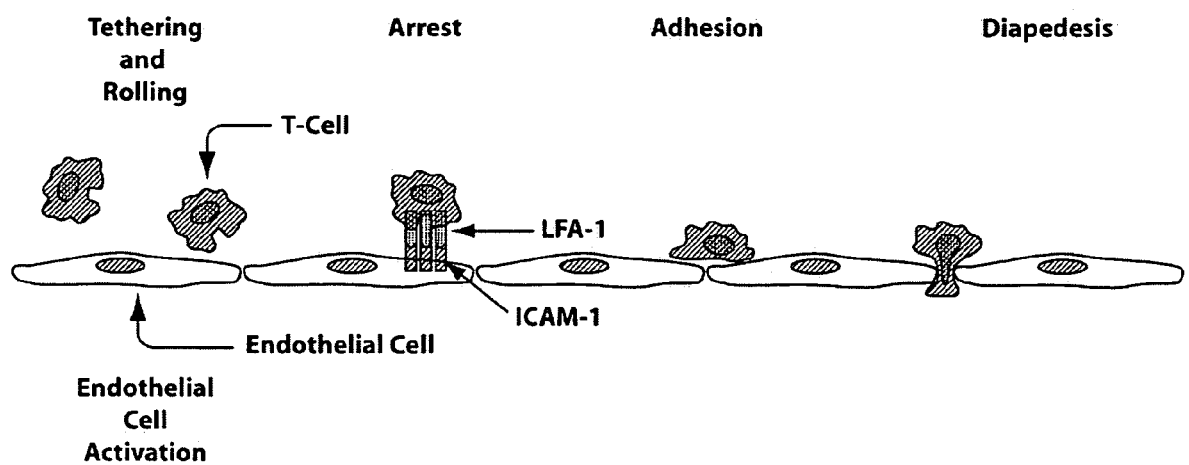
FIG. 1 depicts rolling, adhesion of leukocytes and transendothelial migration resulting from LFA-1:ICAM-1 interaction.

I. Biology and Disease: Diabetic Retinopathy (DR) and the Use of LFA-1 Antagonists in Treatments for DR Diabetes is often described as a global disease leading to deleterious effects observed throughout the body of an individual suffering from this disease, which may increase significantly as the individual ages. Ocular complications of diabetes is a leading cause of visual loss and blindness worldwide.

One overall effect is the development of alterations in the retinal microvasculature that leads to loss of microcapillary autoregulation, a condition known as diabetic retinopathy (DR).

Diabetic retinopathy is often divided into two categories for clinical disease management: non-proliferative (or background stage) and a later, proliferative stage.

Non-proliferative diabetic retinopathy (NPDR) demonstrates, at its outset, abnormalities of the normal microvascular architecture characterized by degeneration of retinal capillaries, formation of saccular capillary microaneurysms, pericyte deficient capillaries, and capillary occlusion and obliteration. Mechanisms of action include diabetes-induced vascular inflammation leading to occlusion of the vascular lumen by leukocytes and platelets followed by the eventual death of both pericytes and endothelial cells. Attraction and adhesion of leukocytes to the vascular wall by the inflammatory process cause leukocytes to adhere temporarily to the endothelium (leukostasis), release cytotoxic factors, and injure or kill the endothelial cell. The damaged endothelial surface initiates platelet adherence, aggregation, microthrombi formation, vascular occlusion and ischemia. Another consequence of endothelial injury is alteration in the Blood-Retinal Barrier (BRB) causing increased vascular permeability. This can be evidenced by fluorescein leakage during fluorescein angiography or retinal thickening assessed by optical coherence tomography (OCT). Consequences of this leakage can be clinically significant macular edema and deposition of lipoproteins in the retina (hard exudates) contributing to retinal thickening. As the process continues, retinal ganglion cells are lost leading towards visual loss or blindness. The disrupted autoregulation and decreased retinal blood flow resulting from the changes in vasculature in endothelial cells, pericyte death, and capillary obliteration are markers for progression of DR, and leads to development of retinal ischemia, which enables development of the more severe, proliferative stage of DR.

Proliferative DR involves neovascularization or angiogenesis, induced by retinal ischemia of the disc or other locations of the retina. This new vasculature can cause hemorrhage of the vitreous humour and retinal detachments from accompanying contractile fibrous tissue.

At any point during this progression of diabetic retinopathy, macular edema or diabetic macular edema (DME) can develop, with severe impact on vision function. Progression of this associated disorder is predicted by retinal vascular leakage and leads to photocoagulation treatment in order to reduce the risk of vision loss. Since a large proportion of patients with diabetic retinopathy suffer from this disorder as well, it is a relevant clinical intervention target. All of these injuries or degenerative insults may lead to impairment or even complete loss of visual acuity and offer targets for therapeutic intervention. No efficient therapeutic options currently are available. Laser photocoagulation involves administering laser burns to various areas of the eye and is used in the treatment of many neovascularization-linked disorders. Neovascularization, in particular, is commonly treated with scatter or panretinal photocoagulation. However, laser treatment may cause permanent blind spots corresponding to the treated areas. Laser treatment may also cause persistent or recurrent hemorrhage, increase the risk of retinal detachment, or induce neovascularization or fibrosis. Other treatment options for ocular-related disorders include thermotherapy, vitrectomy, photodynamic therapy, radiation therapy, surgery, e.g., removal of excess ocular tissue, and the like. However, in most cases, all available treatment options have limited therapeutic effect, require repeated, costly procedures, and/or are associated with dangerous side-effects.

Hyperglycemic control has not proved to be sufficient to end this progression. A number of processes have been identified as contributing to retinal capillary occlusion and capillary obliteration in DR, including microthrombosis, apoptosis, and proinflammatory changes, which may be useful intervention points to prevent progression of DR and/or reverse damage already incurred. Further, an early event in initiation of the breakdown of the BRB and capillary nonperfusion, appears to be leukocyte adhesion to the diabetic retinal vasculature.

Adherent leukocytes are temporally and spatially associated with retinal endothelial cell injury and death within one week of streptozotocin-induced experimental diabetes in rats. Antibody based neutralization of ICAM-1 and CD18 has been shown to prevent both leukocyte adhesion and retinal endothelial cell imjury and death. (A. M. Joussen, T. Murata, A. Tsujikawa, B. Kirchof, S-E. Bursell, A. P. Adamis "Leukocyte-Mediated Endothelial Cell Injury and Death in the Diabetic Retina" (2001) A, J. Pathol. 158(1): 147-162.)

Inhibiting adhesion events, disrupting proinflammatory response cycles, and preventing formation of a cellular capillaries in ischemic tissues, all of which arise in this disease state, may be advantageous strategies for therapy. Lymphocyte function-associated antigen-1 (LFA-1)/Intracellular adhesion molecule-1 (ICAM-1) interactions mediate each of these molecular events. Hence, the LFA-1 antagonists of the invention may be useful in therapies against one or more of the pathological symptoms observed in this disease.

Not intending to limit the mechanism of action, the methods of the present invention involve the inhibition of initiation and progression of diabetic retinopathy (DR) by inhibiting the interaction between LFA-1 and ICAM-1. LFA-1 and ICAM-1 are molecules with extracellular receptor domains which are involved in the process of lymphocyte/leukocyte adhesion, migration and proliferation, leading to a cascade of inflammatory responses. In preferred embodiments, such methods provide anti-inflammatory effects in-vitro and in-vivo, e.g., as described in more detail below, and are useful in the treatment of DR.

Human blood contains white blood cells (leukocytes) which are further classified as neutrophils, lymphocytes (with B- and T-subtypes), monocytes, eosinophils, and basophils. Several of these classes of leukocytes, neutrophils, eosinophils, basophils and lymphocytes, are involved in inflammatory disorders. LFA-1 is one of a group of leucointegrins which are expressed on most leucocytes, and is considered to be the lymphoid integrin which interacts with a number of ICAMs as ligands. Disrupting these interactions, and thus the immune/inflammatory response provides for reduction of inflammation, in particular, inflammation of the eye.

For example, ICAM-1 (CD54) is a member of the ICAM family of adhesion receptors (ICAM-1, ICAM-2, ICAM-3, ICAM-4) in the immunoglobulin protein super family, and is expressed on activated leucocytes, dermal fibroblasts, and endothelial cells. It is normally expressed on the endothelial cells lining the vasculature, and is upregulated upon exposure to cytokines such as IL-1, LPS and TNF during immune/inflammatory initiation.

Research conducted over the last decade has helped elucidate the molecular events involved in the movement and activation of cells in the immune system, focusing on cell-to-cell triggering interactions within the cascade. The interaction of Intercellular Adhesion Molecules (ICAMs) with leukointegrins plays a role in the functioning of the immune system. Immune processes such as antigen presentation, leukocyte mediated cytotoxicity, T-cell mediated cytotoxicity and leukocyte transendothelial migration (diapedesis) may require cellular adhesion mediated by ICAMs interacting with leukointegrins.

The interaction of ICAM-1 and LFA-1 (LFA-1 is also referred to as $\alpha_L\beta_2$ and CD11a/CD18) has been shown to be involved in the processes of adhesion, leukocyte transendothelial migration, migration to sites of injury, and proliferation of lymphocytes at the activated target site, as shown in FIG. 1. For example, it is presently believed that prior to leukocyte adhesion and transendothelial migration, components of the inflammatory response, the presence of cytokines/chemokines activate integrins constitutively expressed on leukocytes. Blood vessel endothelial cells also upregulate ICAM-1 in response to the presence of the same cytokines/chemokines. As rolling leukocytes approach activated endothelial cells, their progress is first slowed by these upregulated ICAM-1 receptors. This is followed by a ligand/receptor interaction between LFA-1 and ICAM-1, expressed on blood vessel endothelial cell surfaces, which arrests the lymphocyte from rolling further. The lymphocyte then flattens, and transmigration takes place. This process is of importance both in lymphocyte transmigration through vascular endothelium as well as lymphocyte trafficking from peripheral blood to lymph nodes. However, in Diabetic Retinopathy (DR), as discussed above, leukostasis is the initial trigger for cytotoxic factor release which damages and/or kills endothelial cells in the local area. This damage leads to vessel leakiness and inflammation, which continues and/or amplifies the injurious response.

Figure 2:
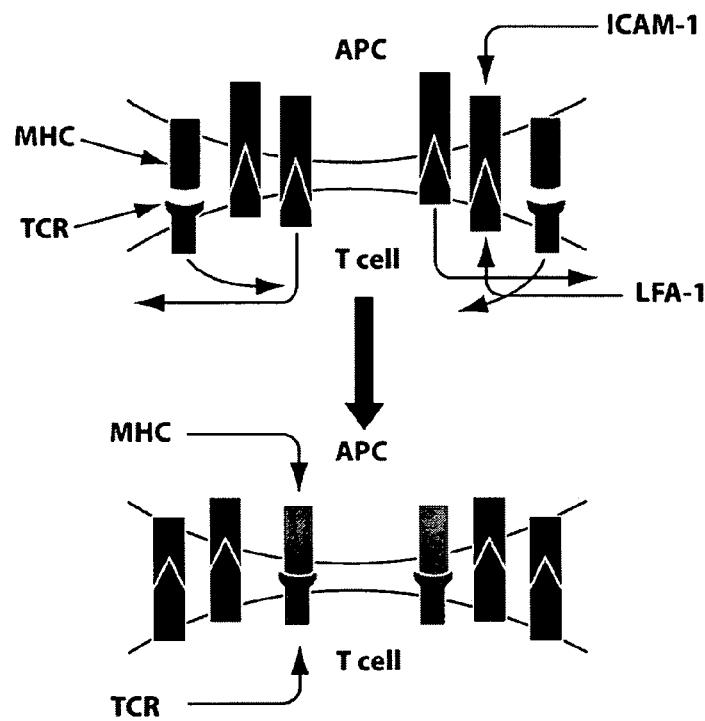
FIG. 2 depicts antigen activation of the LFA-1:ICAM-1 interaction.
Figure 2:
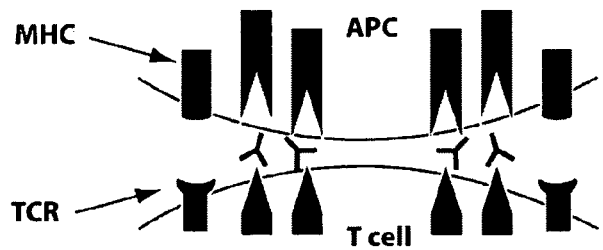
Figure 3:
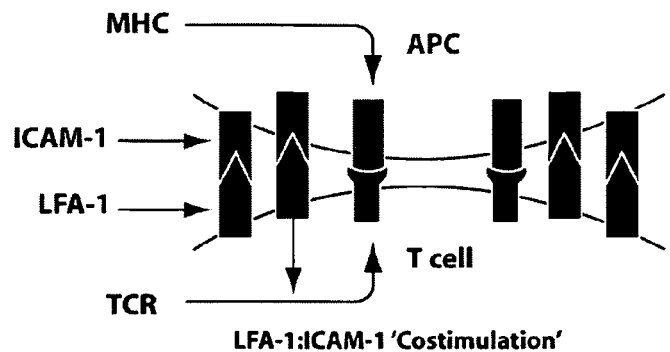
FIG. 3 depicts co-stimulatory function of the LFA-1:ICAM-1 interaction.
Figure 3:
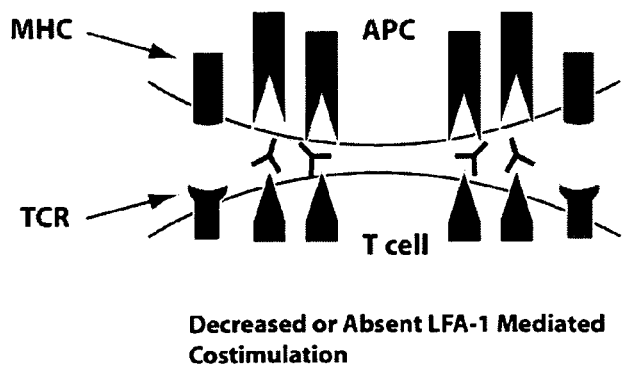

LFA-1 plays a role in creating and maintaining the immunological synapse, which may be defined as the physical structure of the interacting surfaces of T cells and Antigen Presenting Cells (APCs), as shown in FIG. 2. LFA-1 stabilizes T-cell engagement with the APC, and thus leads to activation of T cells. The interaction of LFA-1 and ICAM-1 also appears to provide co-stimulatory signals to resting T cells, as shown in FIG. 3. CD4+ T-cell proliferation and cytokine synthesis are mediated by this interaction as part of the inflammatory response.

Given the role that the interaction of ICAM-1 and LFA-1 plays in immune/inflammatory response, it is desirable to modulate these interactions to achieve a desired therapeutic result (e.g., inhibition of the interaction in the event of an overactive inflammatory response). Also, since LFA-1 has several ligand partners within the ICAM family (ICAM-1, ICAM-2 and ICAM-3), involving a number of signaling pathways, in some embodiments of the invention, it is desirable to modulate these interactions selectively. In some embodiments of the invention, therapeutic agents are provided that will interfere with the association of LFA-1 with ICAM-1, ICAM-2, and/or ICAM-3 to thus modulate the respective signaling pathways for each pair of interactions.

The methods and compositions described herein can modulate one or more components of the pathways described herein. In addition to inhibiting interaction between LFA-1 and ICAM-1, the methods and compositions of the present invention may also intervene in either earlier or later portions of the inflammatory process as well. For example, upregulation of ICAM-1 or LFA-1 (activation) on endothelial cells or leukocytes, prior to tethering and transendothelial migration, may be modulated by the methods and compositions described herein. The present invention may be useful in modulating the expression of cytokines or chemokines that activate ICAM-1 and LFA-1 in the course of leukocyte trafficking, in modulating the transport of the cytokines or chemokines, in preventing transmigration of the arrested leukocyte, in modulating signaling via other mechanisms that are involved in leukocyte proliferation at the site of injury or inflammation, and the like.

The invention provides therapeutic agents that interfere with the association of LFA-1 with ICAM-1, which can block the adhesion, migration, proliferation, and release of inflammatory signals to surrounding tissue by immune system cells. In some embodiments, the invention provides methods of administering a therapeutic agent which inhibits the interaction between LFA-1 and an ICAM. In one example, the therapeutic agent binds to either LFA-1 or binds to an ICAM. More specifically, the invention provides therapeutic agents that bind to LFA-1 to inhibit the association of LFA-1 with ICAM-1, ICAM-2, and/or ICAM-3 thus acting as LFA-1 antagonists. In some embodiments, the therapeutic agent provided by the invention binds at the high affinity binding site in the aL subunit overlapping the ICAM-1 binding site, which is a directly competitive antagonist of LFA-1. In some embodiments, the therapeutic agent provided by the invention inhibits the interaction between LFA-1 and ICAM-1 but does not completely block the high affinity binding site in the αL subunit overlapping the ICAM-1 binding site, and is a competitive but not a directly competitive antagonist of LFA-1. In some embodiments, the therapeutic agent provided by the invention binds at a site outside the high affinity binding site in the αL subunit overlapping the ICAM-1 binding site, and is an allosteric antagonist. In some of the embodiments, the therapeutic agent provided by the invention is an allosteric antagonist and is a competitive but not directly competitive antagonist of LFA-1. In some embodiments of the invention, the therapeutic agents are useful in treating diabetic retinopathy and disorders associated with that condition.

II. Compounds Useful in the Method

The term "aliphatic", as used herein, includes both saturated and unsaturated, straight chain (unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like.

Furthermore, as used herein, the terms "alkyl", "alkenyl", "alkynyl", and the like encompass both substituted and unsubstituted groups. In certain embodiments, as used herein, "lower alkyl" is used to indicate those alkyl groups (substituted, unsubstituted, branched or unbranched) having about 1-6 carbon atoms.

In certain embodiments, the alkyl, alkenyl and alkynyl groups employed in the invention contain about 1-20 aliphatic carbon atoms. In certain other embodiments, the alkyl, alkenyl, and alkynyl groups employed in the invention contain about 1-10 aliphatic carbon atoms. In yet other embodiments, the alkyl, alkenyl, and alkynyl groups employed in the invention contain about 1-8 aliphatic carbon atoms. In still other embodiments, the alkyl, alkenyl, and alkynyl groups employed in the invention contain about 1-6 aliphatic carbon atoms. In yet other embodiments, the alkyl, alkenyl, and alkynyl groups employed in the invention contain about 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents.

Alkenyl groups include, but are not limited to, for example, ethenyl, propenyl, butenyl, and the like. Representative alkynyl groups include, but are not limited to, ethynyl, 2-propynyl and the like.

The term "lower alkylene" as used herein refers to a hydrocarbon chain which links together two other groups, i.e. is bonded to another group at either end, for example methylene, ethylene, butylene and the like. Such a substituent is preferably from 1 to 10 carbons and more preferably from 1 to 5 carbons. Such groups may be substituted, preferably with an amino, acetylamino (a lower alkylcarbonyl group bonded via a nitrogen atom), or cyclo lower alkyl group. By the latter is meant a saturated hydrocarbon ring group, preferably with a total of 3 to 10 methylenes (inclusive of the attachment carbons), more preferably 3 to 6.

The term "alicyclic", as used herein, refers to compounds which combine the properties of aliphatic and cyclic compounds and include but are not limited to monocyclic, or polycyclic aliphatic hydrocarbons and bridged cycloalkyl compounds, which are optionally substituted with one or more functional groups.

As will be appreciated by one of ordinary skill in the art, "alicyclic" is intended herein to include, but is not limited to, cycloalkyl, cycloalkenyl, and cycloalkynyl moieties, which are optionally substituted with one or more functional groups.

Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl, cyclohexyl, —$CH_2$-cyclohexyl, cyclohexenylethyl, cyclohexanylethyl, norbornyl moieties and the like, which again, may bear one or more substituents.

The term "alkoxy" or "alkyloxy", as used herein refers to a saturated or unsaturated parent molecular moiety through an oxygen atom. In certain embodiments, the alkyl group contains about 1-20 aliphatic carbon atoms. In certain other embodiments, the alkyl group contains about 1-10 aliphatic carbon atoms. In yet other embodiments, the alkyl group employed in the invention contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkoxy, include but are not limited to, methoxy, ethoxy, isopropoxy, n-butoxy, i-butoxy, sec-butoxy, tert-butoxy, neopentoxy, n-hexloxy and the like.

The term "lower alkoxy" as used herein refers to a lower alkyl as defined above which may be branched or unbranched as also defined above and which is bonded by an oxygen to another group (i.e. alkyl ethers).

The term "thioalkyl" as used herein refers to a saturated or unsaturated (i.e., S-alkenyl and S-alkynyl) group attached to the parent molecular moiety through a sulfur atom. In certain embodiments, the alkyl group contains about 1-20 aliphatic carbon atoms. In certain other embodiments, the alkyl group contains about 1-10 aliphatic carbon atoms. In yet other embodiments, the alkyl group employed in the invention contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of thioalkyl include, but are not limited to, methylthio, ethylthio, propylthio, isopropylthio, n-butylthio, and the like.

The term "lower alkylthio" as used herein refers to a lower alkyl group bonded through a divalent sulfur atom, for example, a methylmercapto or an isopropylmercapto group. By lower alkylenethio is meant such a group which is bonded at each end.

The term "alkylamino" refers to a group having the structure-NHR' wherein R' is alkyl, as defined herein. The term "aminoalkyl" refers to a group having the structure $NH_2R'$—, wherein as defined herein. In certain embodiments, the alkyl group contains about 1-20 aliphatic carbon atoms. In certain other embodiments, the alkyl group contains about 1-10 aliphatic carbon atoms. In yet other embodiments, the alkyl group employed in the invention contains about aliphatic carbon atoms. In still other embodiments, the alkyl group contains about 1-6 aliphatic carbon atoms. In yet other embodiments, the alkyl group contains about 1-4 aliphatic carbon atoms. Examples of alkylamino include, but are not limited to, methylamino, and the like.

Some examples of substituents of the above-described aliphatic (and other) moieties of compounds of the invention include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; $R_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aryl or heteroaryl substituents described above and herein may be substituted or unsubstituted. Additional examples of generally applicable substituents are illustrated by the specific embodiments shown in the Examples that are described herein.

In general, the term "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaromatic moiety", as used herein, refers to a stable mono- or polycyclic, unsaturated moiety having preferably 3-14 carbon atoms, each of which may be substituted or unsubstituted; and comprising at least one heteroatom selected from O, S, and N within the ring in place of a ring carbon atom). In certain embodiments, the term "heteroaromatic moiety" refers to a planar ring comprising at least one heteroatom, having p-orbitals perpendicular to the plane of the ring at each ring atom, and satisfying the Huckel rule where the number of pi electrons in the ring is (4n+2) wherein n is an integer.

It will also be appreciated that aromatic and heteroaromatic moieties, as defined herein may be attached via an alkyl or heteroalkyl moiety and thus also include -(alkyl) aromatic, -(heteroalkyl) aromatic, -(heteroalkyl) heteroaromatic, and -(heteroalkyl) heteroaromatic moieties. Thus, as used herein, the phrases "aromatic or heteroaromatic moieties" and "aromatic, (heteroalkyl) aromatic, -(heteroalkyl) heteroaromatic, and (heteroalkyl) heteroaromatic" are interchangeable. Substituents include, but are not limited to, any of the previously mentioned substituents, e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to, phenyl, naphthyl, tetrahydronaphthyl, indanyl, indenyl and the like.

The term "heteroaryl" as used herein, does not differ significantly from the common meaning of the term in the art, and refers to a cyclic aromatic radical having from five to ten ring atoms of which one ring atom is selected from S, and N; zero, one or two ring atoms are additional heteroatoms independently selected from S, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —C(=O)N(R$_x$)$_2$; —OC(=O)R$_x$; —OCO$_2$R$_x$; —OC(=O)N(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl) aryl or -(alkyl) heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —C(=O)N(R$_x$)$_2$; —OC(=O)R$_x$; —OCO$_2$R$_x$; —OC(=O)N(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e. place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —C(=O)N(R$_x$)$_2$; —OC(=O)R$_x$; —OCO$_2$R$_x$; —OC(=O)N(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from S and N (wherein the nitrogen and sulfur heteroatoms may be optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6- or 7-membered ring or a polycyclic group wherein at least one ring atom heteroatom selected from S and N (wherein the nitrogen and sulfur heteroatoms may be optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, pyranyl, pyrrolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —C(=O)N(R$_x$)$_2$; —OC(=O)R$_x$; —OCO$_2$R$_x$; —OC(=O)N(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl described above and herein may be substituted or unsubstituted. Additionally, it will be appreciated that any of the alicyclic or heterocyclic moieties described above and herein may comprise an aryl or heteroaryl moiety fused thereto.

The terms "halo" and "halogen" used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino" as used herein, refers to a primary (—NH$_2$), secondary (—NHR$_x$), tertiary (—NR$_x$R$_y$), or quaternary amine (—N$^+$R$_x$R$_y$R$_z$), where R$_y$ and R$_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, iso-propylamino, piperidino, trimethylamino, and propylamino.

The term "acyl", as used herein, refers to a group having the general formula —C(=O)R, where R is an aliphatic, alicyclic, heteroaliphatic, heterocyclic, aromatic or heteroaromatic moiety, as defined herein.

The term "sulfonamido" as used herein, refers to a group of the general formula —SO2NRxRy where Rx and Ry are independently hydrogen, or an aliphatic, alicyclic, heteroaliphatic, heterocyclic, aromatic, heteroaromatic or acyl moiety, as defined herein.

The term "benzamido", as used herein, refers to a group of the general formula PhNRx, where Rx is hydrogen, or an aliphatic, alicyclic, heteroaliphatic, heterocyclic, aromatic, heteroaromatic or acyl moiety, as defined herein.

The term "$C_{1-6}$ alkylidene" as used herein, refers to a substituted or unsubstituted, linear or branched saturated divalent radical consisting solely of carbon and hydrogen atoms, having from one to six carbon atoms, having a free valence "-" at both ends of the radical.

The term "C$_{2-6}$ alkylidene" as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms, "alicyclic", "heterocyclic", heterocycloalkyl", "heterocycle" and the like, encompass substituted and unsubstituted, and saturated and unsaturated groups. Additionally, the terms "cycloalkyl", cycloalkenyl", cycloalkynyl", "heterocycloalkyl" "heterocycloalkenyl", "heterocycloalkynyl", "aromatic", "heteroaromatic", "aryl", "heteroaryl" and the like encompass both substituted and unsubstituted groups.

The term "natural amino acid" as used herein refers to any one of the common, naturally occurring L-amino acids found in naturally occurring proteins: glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met).

The term "unnatural amino acid" as used herein refers to all amino acids which are not natural amino acids. This includes, for example, α-, β-, D-, L-amino acid residues, and compounds of the general formula:

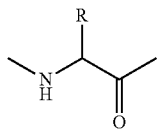

wherein the side chain R is other than the amino acid side chains occurring in nature.

More generally, the term "amino acid", as used herein, encompasses natural amino acids and unnatural amino acids.

The term "bioisosteres", as used herein, generally refers to two or more compounds or moieties that possess similar molecular shapes and/or volumes. In certain embodiments, bioisosteres have approximately the same distribution of electrons. In certain other embodiments, bioisosteres exhibit similar biological properties. In preferred embodiments, bioisosteres possess similar molecular shapes and volumes; have approximately the same distribution of electrons; and exhibit similar biological properties.

The term "pharmaceutically acceptable derivative", as used herein, denotes any pharmaceutically acceptable salt, ester, or salt of such ester, of such compound, or any other adduct or derivative which, upon administration to a subject, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

As used herein, the term pharmaceutically acceptable salt" refers to those salts which are suitable for pharmaceutical use, preferably for use in the tissues of humans and lower animals without undue irritation, allergic response and the like. Pharmaceutically acceptable salts of amines, carboxylic acids, and other types of compounds, are well known in the art. For example, S. M. Berge, et al., describe pharmaceutically acceptable salts in detail in J Pharmaceutical Sciences, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzoate, bisulfate, borate, butyrate, camphorate, camphorsulfonate, citrate, cyclopentanepropionate, digluconate, dodecylsulfate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, nicotinate, nitrate, oleate, oxalate, palmitate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, sulfonate and aryl sulfonate.

As used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic alcohol compounds, particularly alkanes, alkenes, ehtylene glycol, cycloalkanes, and the like in which each alkyl or alkenyl moiety advantageously has not more than 6 carbon atoms. These are exemplary only and in no way limit the possibilities of esters known in the art.

As used herein, the term "pharmaceutically acceptable prodrugs" refers to those prodrugs of the compounds of the present invention which are suitable for pharmaceutical use, preferably for use with the tissues of humans and lower animals with undue toxicity, irritation, allergic response, and the like, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A. C. S. Symposium Series, and in Edward B. Roche, ed., Bioreversible Carriers in Drug Design, American Pharmaceutical Association and Pergamon Press, 1987, both of which are incorporated herein by reference.

C. Compounds Useful in the Invention which are Directly Competitive Antagonists or Allosteric Antagonists of LFA-1 interaction with ICAM-1.

Antagonists which are directly competitive antagonists of the LFA-1 interaction with ICAM-1, at a high affinity binding site in the αL subunit of LFA-1 overlapping the ICAM-1 binding site can be identified, for example, by performing competitive binding experiments as described in S. M. Keating, K. R. Clark, L. D. Stepanich, F. Arellano, C. P. Edwards, S. C. Bodary, S. A. Spencer, T. R. Gadek, J. C, Marsters Jr., M. H. Beresini, "Competition between intercellualr adhesion molecule-1 and a small molecule antagonist for a common binding site on the αl subunit of lymphocyte function-associated antigen-1." (2006) Protein Science, 15:290-303. This high affinity site on LFA-1 that overlaps with the ICAM-1 binding site has been shown to include the MIDAS motif of the I domain in the αL subunit of LFA-1. Allosteric antagonism, which may be competitive but not directly competitive, can also be identified using this experimental design.

1. Identification of the Binding Site of Directly Competitive Antagonists of the LFA-1: ICAM Interaction.

a. Crosslinking of Compound 5 to the αL Subunit of LFA-1.

Figure 4:
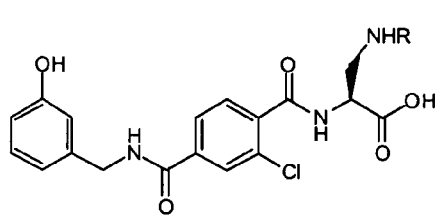
FIG. 4 depicts small molecule antagonists useful in the methods of identification.
Figure 4:
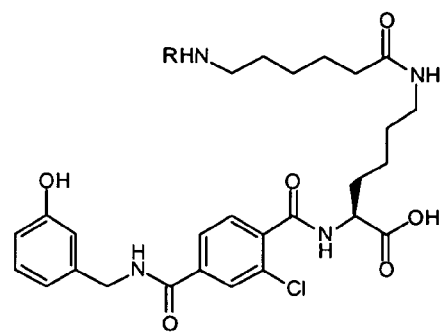
Figure 4:
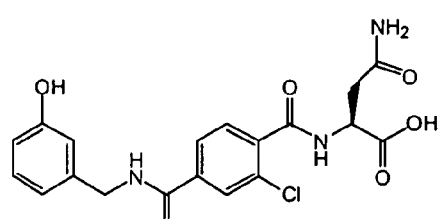
Figure 4:
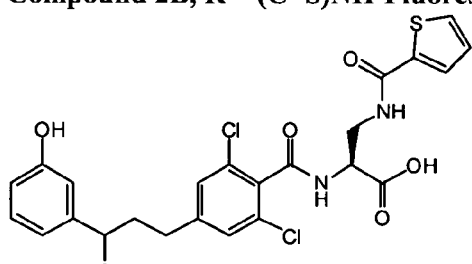
Figure 4:
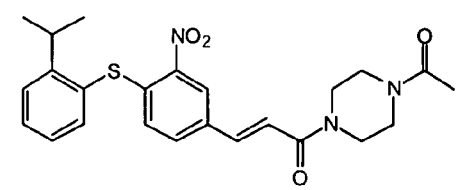
Figure 4:
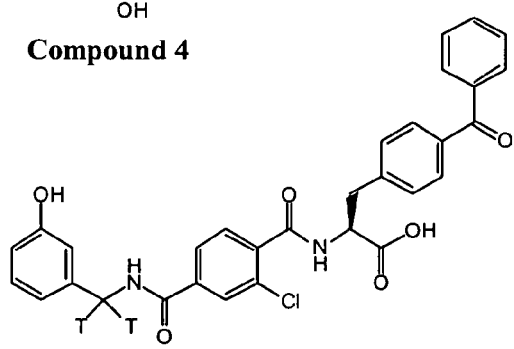
Figure 5:
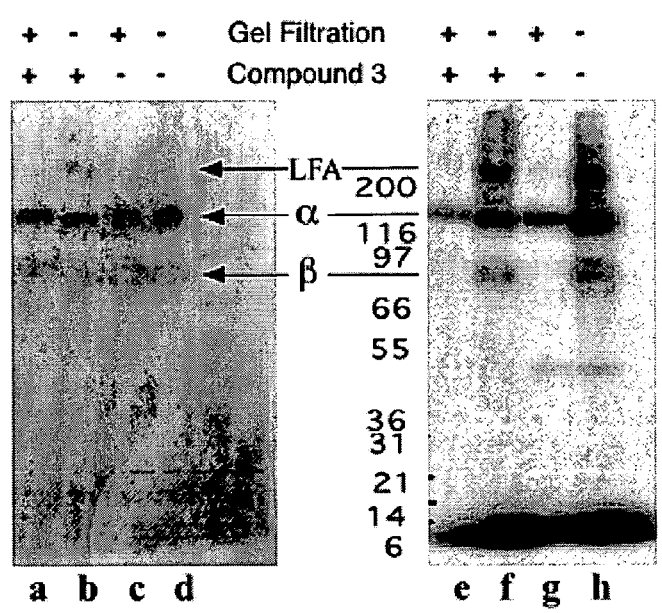
FIG. 5 depicts SDS-PAGE analysis of compound 5 cross-linked LFA-1.

The binding site of small molecule antagonists of this class was identified by binding compound 5, a tritium-labeled, photoactivatable analogue of compound 3 to LFA-1 and then photocrosslinking (FIG. 4). To maximize specific, high affinity crosslinking, it was necessary to gel filter the samples to remove unbound or weakly bound compound 5 prior to irradiation (FIG. 5, lanes e vs. f and g vs. h). In the absence of gel filtration, there was significant crosslinking of compound 5 to LFA-1 α subunit, β subunit, and heterodimer (the band at approximately 200,000), whereas nonspecific crosslinking was not observed in the gel filtered samples (data not shown). Under gel filtration conditions, compound 5 specifically crosslinked only to the αL subunit (FIG. 5, lanes c and g). Moreover, the presence of compound 3 during the incubation substantially reduced the incorporation of tritium into the αL subunit (FIG. 5, lane e vs. g). Similarly, in the presence of compound 3, there was a slight reduction of tritium incorporation into the αL subunit, β2 subunit and heterodimer in the absence of gel filtration (FIG. 5, lane f vs. h). No crosslinking of compound 5 occurred when gel filtered samples of the isolated, structurally intact αL or β2 subunits were used (data not shown). Thus, the high affinity binding site necessary to crosslink after gel filtration is provided by the intact LFA-1 heterodimer.

The site of crosslinking was further defined by fragmenting the affinity-labeled αL subunit with hydroxylamine, electrophoretically separating the fragments, and then performing N-terminal sequencing on the radiolabeled fragments to determine their locations within the protein sequence. Two sequences were identified, the first starting with residue 1 (sequence found: YNLDVRGARSFS (SEQ ID NO 1)) and the second with residue 30 (sequence found: GVIVGAPGEGNST (SEQ ID NO 2)). Both peptides were approximately 500 amino acids long as judged by their sizes on SDS-PAGE (50-60 kDa); this fragment size is consistent with the next two predicted cleavage sites (N-G) for hydroxylamine, N507 and N530. No label was incorporated into the C-terminal half of the subunit.

b. Lack of Binding of Compound 2B to LFA-1 Lacking the I Domain.

Figure 6:
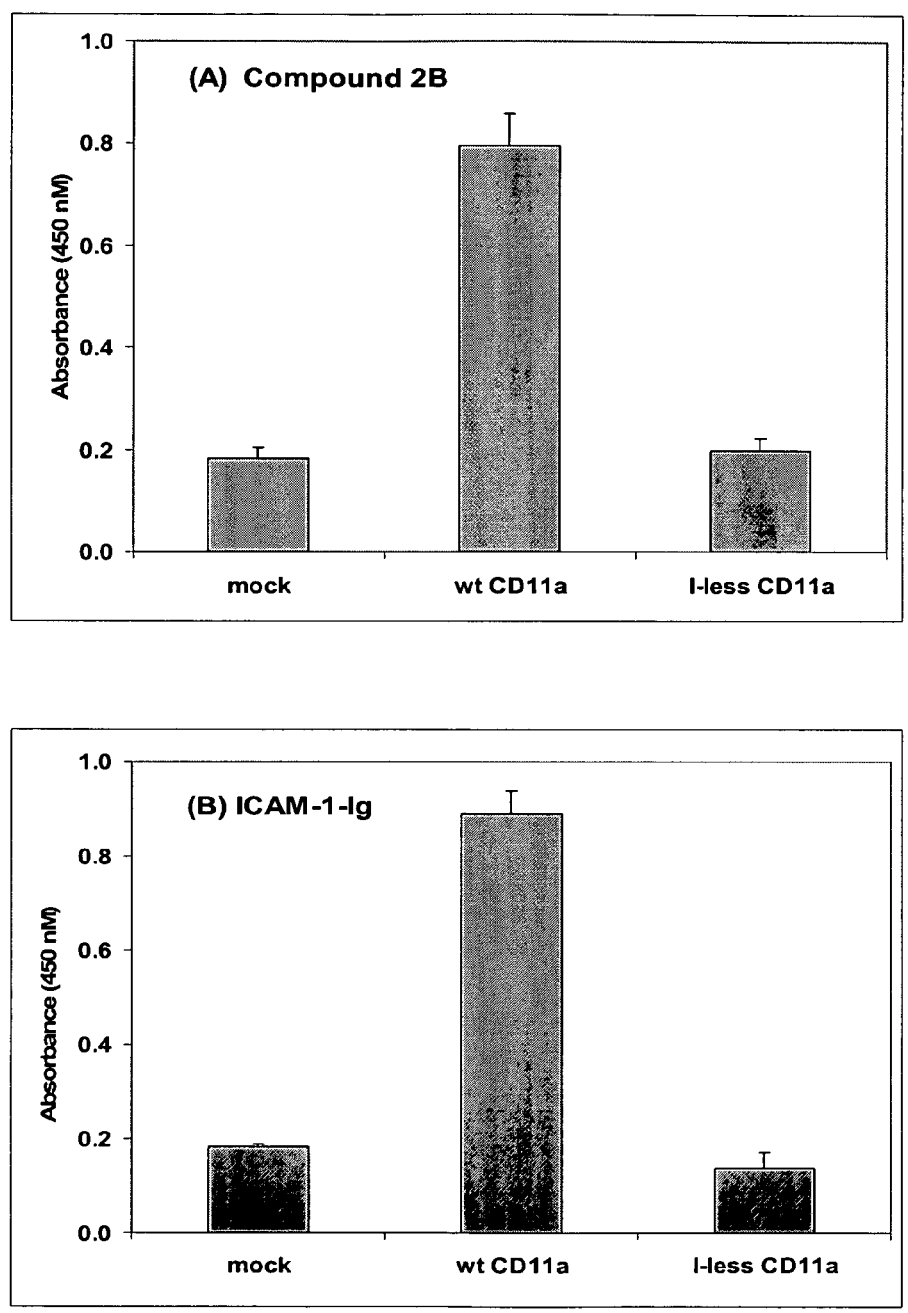
FIG. 6 depicts binding of compound 2B and ICAM-1-Ig to 293 cells expressing wild type LFA-1 or LFA-1 lacking the I domain.

The role of the I domain in the binding of compound 2B and related analogs to LFA-1 was demonstrated by preparing a construct of the αL subunit lacking the I domain. The 82 construct alone (mock) or together with the construct lacking the I domain or wild type αL was transfected into 293 cells, and the binding of compound 2B to the transfected cells was examined (FIG. 6). Compound 2B showed substantial binding to the wild type αL transfected cells but demonstrated no significant binding to the cells transfected with αL lacking the I domain relative to binding to mock (β2) transfected cells. Transfectants were also tested for their ability to adhere to ICAM-1.-Ig, and as expected, the LFA-1 transfected cells lacking the I domain and mock transfectants showed indistinguishable background levels of binding, while the wild type αL transfected cells showed robust adhesion (FIG. 6B). Evaluation of the binding of a panel of LFA-1 antibodies to the transfected cells indicated that, apart from loss of binding by antibodies that mapped to the I domain, the LFA-1 heterodimer appeared to be intact in the transfected cells lacking the αL I domain (data not shown).

The data support the conclusion that compound 3 and related molecules bind to a high affinity site on LFA-1 that overlaps with the ICAM-1 binding site which has previously been shown to include the MIDAS motif of the I domain in the αL subunit of LFA-1.

Corroborating evidence for the close proximity of the ICAM-1 and small molecule antagonist binding sites on LFA-1 can be seen in the common effect of the deletion of the I domain on the binding of both ICAM-1-Ig and compound 2B. Both compound 2B and ICAM-1 were unable to bind to LFA-1 lacking the I domain, the domain in which the ICAM-1 binding site is located. Moreover, the ability of A-286982 to allosterically modify the binding of both ICAM-1-Ig and compound 2B is consistent with a close proximity of their binding sites to the A-286982 binding site in the IDAS motif in the I domain of the LFA-1 α subunit. The selective photochemical crosslinking of compound 5 to the α chain of LFA-1 localizes its binding site to within residues 30-507 of this subunit. All of the findings noted above are consistent with a single high affinity small molecule binding site located in the I domain of the α chain of LFA-1.

Close examination of the photochemical crosslinking study performed with a relatively high concentration of compound 5 (4.1 µM, FIG. 5) affords direct evidence for an additional low affinity small molecule binding site on LFA-1. Dramatically different protein and crosslinking patterns are observed in the presence and absence of gel filtration. When samples are gel filtered to remove unbound and weakly bound molecules prior to irradiation, only high affinity labeling of the α subunit is observed. However, in the absence of the gel filtration step, irradiation of the complex of compound 5 with LFA-1 results in high intensity crosslinking to the a subunit and lower intensity crosslinking to a low affinity binding site in the 3 subunit whose complex with compound 5 is too weak to survive gel filtration. Under both conditions, the observed crosslinking is partially inhibited by a large excess (290 µM) of compound 3 (FIG. 5, lanes e and g, f and h), demonstrating the specific nature of the binding to both sites. Attempts to crosslink compound 5 to either of the isolated α or β subunits failed to afford high affinity complexes capable of surviving the gel filtration process. Consequently, it appears that the high affinity competitive binding of the class of compounds represented by compound 3 requires the presence of an intact full length LFA-1 heterodimer. Attempts to capture this binding site in constructs of either of the LFA-1 subunits or the isolated I domain results in diminished affinity of LFA-1 for ICAM-1 and small molecule analogs of compound 3 (e.g. XVA143). It is particularly interesting to note the presence of a minor LFA-1 heterodimer band that appears in the absence of gel filtration (FIG. 5, band at >200,000 daltons.) The intensity of the LFA-1 band as judged by both Coomassie blue staining and autoradiography is consistent with low affinity binding to a second site on the β chain that stabilizes the heterodimer.

The binding site responsible for the stabilization of LFA-1 to SDS-PAGE may reside in the I-like domain of the β subunit. As shown above, this β subunit binding site is not related to the high affinity binding site in the a subunit which is responsible for the direct competitive inhibition of ICAM-1 binding. However, the β subunit binding site responsible for LFA-1 stabilization by compound 3 may be the same as the low affinity β subunit crosslinking site.

There are two distinct binding sites for the class of LFA-1 small molecule antagonist probes used herein. The first is a high affinity binding site in the αL subunit of LFA-1 through which the small molecule and LFA-1 form a complex which is stable enough (e.g. $K_d$<25 nM) to survive the gel filtration process. It is this small molecule binding site that has been characterized in the binding experiments reported here as overlapping the ICAM-1 binding site and that correlates with: the potent inhibition of LFA-1/ICAM-1 binding by compounds 3 and 4 (compound 4 $IC_{50}$=1.4 nM); their potent inhibition of LFA-1 induced lymphocyte proliferation (compound 4 $IC_{50}$=3 nM) in vitro; and their inhibition of the immune system's response in vivo. The second site is a lower affinity binding site (e.g. $K_d$>1 µM) in the β subunit which is involved with stabilization of the LFA-1 heterodimer under SDS-PAGE. This site is more dynamic by nature (i.e. faster off rate) and does not survive the gel filtration/photolysis process. The characteristics of this second low affinity site are consistent with those of an α/β I-like allosteric antagonist binding site in the I-like domain of the β subunit. The low affinity binding of the ICAM-1 mimetics described herein to the β subunit of LFA-1, presumably to the I-like domain, is likely due to the sequence homology between the I and I-like domains, particularly with regard to similarities in MIDAS motifs and their affinities for the carboxylic acid moiety common to this class of antagonists. Given that the β2 family of integrins, including MAC-1, share this subunit, the affinity of compounds for the I-like domain in the β2 subunit must be attenuated in order to select antagonists which are specific to LFA-1.

The experiments described above substantiate the high affinity binding of compounds 3 and 4 to LFA-1 in a manner that is similar to that of ICAM-1, at a site overlapping the ICAM-1 binding site involving the MIDAS motif within the I domain of the LFA-1 α subunit. This is consistent with their proposed mimicry of the ICAM-1 epitope, and inconsistent with any conclusion that they function as α/β I-like allosteric antagonists of LFA-1/ICAM-1. The binding of these ICAM-1 mimetics to the 32 integrin subunit, albeit with lower affinity, raises the question of whether ICAM-1 itself binds to a second site in the I-like domain as part of a feedback mechanism.

It has been shown, supra, that small molecules can bind with high affinity to the α-L subunit, which is unique to LFA-1. Consequently these compounds can be selective for LFA-1 (αLβ2) over Mac-1(αMβ2). One preferred embodiment of the invention is to utilize selective inhibitors of LFA-1, which may confer advantages in therapeutic safety.

2. Competitive Binding Experiments.

a. Antagonist Competition in the LFA-1/ICAM-1 and LFA-1/Small Molecule ELISA.

Compounds 2A and 3, A-286982, and sICAM-1 were used to illustrate competitive inhibition of binding of ICAM-1-Ig to LFA-1, by titration into the LFA-1/ICAM-1 ELISA. The format and results from this form of the LFA-1/ICAM-1 assay are more robust due to antibody capture of the LFA-1 rather than direct coating onto the ELISA plate. The experiment was performed by the addition of 1/5 serial dilutions of compound 3 (-●-), compound 2A (-▲-), A-286982 (-♦-) and sICAM-1 (-▼-) followed by incubation with either ICAM-1-Ig (A) or compound 2B (B) on plates containing captured LFA-1. The data shown are the average of two plates from a single experiment and are representative of several independent measurements. The solid lines are the fits of the data. The $IC_{50}$ values (nM) are provided in the legends.

Figure 7:
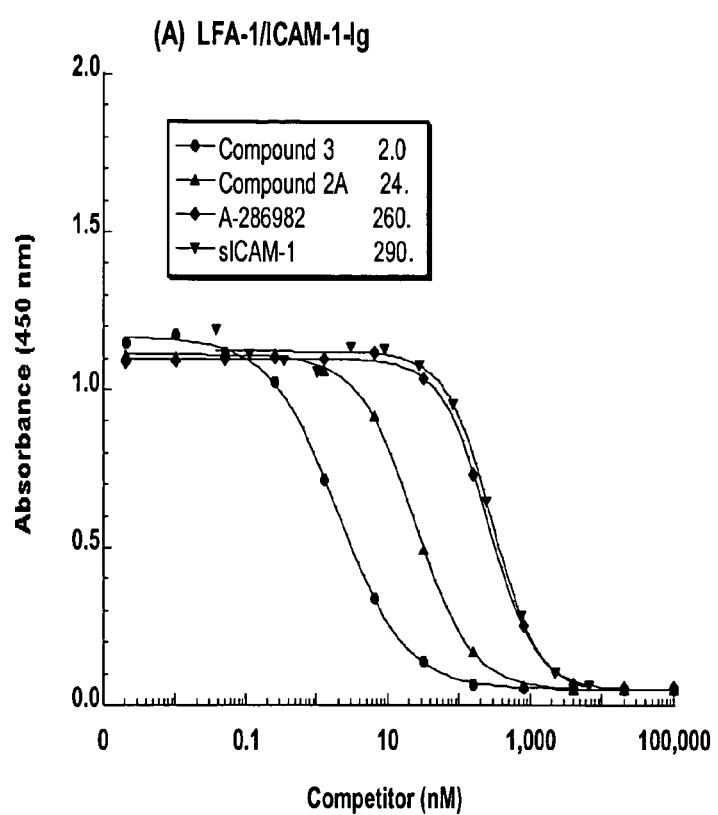
FIG. 7 depicts antagonist competition by compounds 2A, 3, A-286982 and sICAM-1 in the LFA-1/ICAM-1 and LFA-1/small molecule ELISAs.

Typical competition curves for these inhibitors in the ELISA are shown in FIG. 7A. Compound 3 potently inhibited the binding of ICAM-1-Ig to LFA-1 with a 2 nM $IC_{50}$. Compound 2A, an analogue of compound 3, inhibited binding but with an approximately 10-fold higher $IC_{50}$ value. A-286982 and sICAM-1 inhibited ICAM-1-Ig binding to LFA-1 but with $IC_{50}$ values that were more than 100-fold that of compound 3.

The ability of these same compounds to inhibit the binding of a FITC labeled small molecule antagonist, compound 2B, to LFA-1 was also demonstrated (FIG. 7B). The potencies of compounds 2A and 3 and soluble ICAM-1 as inhibitors of compound 2B binding paralleled their potencies as inhibitors of ICAM-1-Ig binding. Compound 3, compound 2A and sICAM-1 inhibited the binding of compound 2B to LFA-1 with $IC_{50}$ values of 3, 56, and 1200 nM, respectively. A-286982 did not inhibit but rather enhanced the binding of compound 2B to LFA-1 as indicated by the transient increase in the absorbance values, reaching a maximal effect at approximately 4 µM before decreasing.

Figure 8:
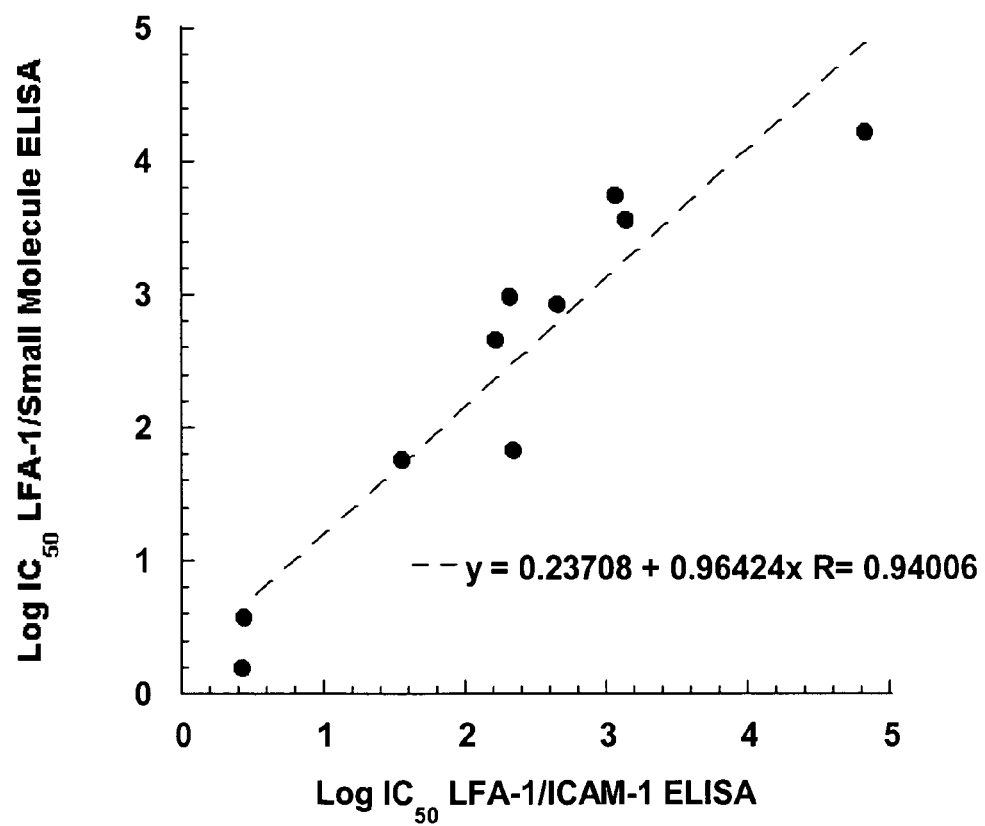
FIG. 8 depicts correlation of IC50 values from antagonist competition in the LFA-1/ICAM-1 and LFA-1/small molecule ELISAs.

The evaluation of $IC_{50}$ values in the LFA-1/small molecule and LFA-1/ICAM-1 ELISAs was extended to a larger set of compounds including a group of kistrin-derived peptides and small molecules representing the evolution of this class of LFA-1 small molecule antagonists. As shown in FIG. 8 (Correlation of $IC_{50}$ values from antagonist competition in the LFA-1: ICAM-1 and LFA-1: small molecules ELISAs. The $IC_{50}$ values of a diverse group of compounds (4 peptides, 5 small molecules and sICAM-1) in competition with compound 2B are plotted against the $IC_{50}$ values determined in competition with ICAM-1-Ig for binding to LFA-1. The slope of the plot is 0.964, y-intercept, 0.237 and R=0.940. Each data point is the average of $IC_{50}$ values from two plates), there is a good correlation (R=0.94) between the $IC_{50}$ values for competition in each of the two ligand binding assays for this diverse set of compounds, including sICAM-1, compounds 2A and 3, across five log units of potency. The common trend in potencies between the two antagonist competition ELISAs with ICAM-1-Ig and compound 2B as ligands reveals that each compound disrupts the binding of both ICAM-1 and small molecule ligands in a mechanistically similar fashion. This parallel in potency of inhibition demonstrates that ICAM-1-Ig and compound 2B are binding to the same site on LFA-1. Hence, the compounds of the invention are competitive antagonists of LFA-1.

b. Antagonist Modulation of Ligand Binding in LFA-1/ICAM-1 and LFA-1/Small Molecule ELISAs.

Figure 9:
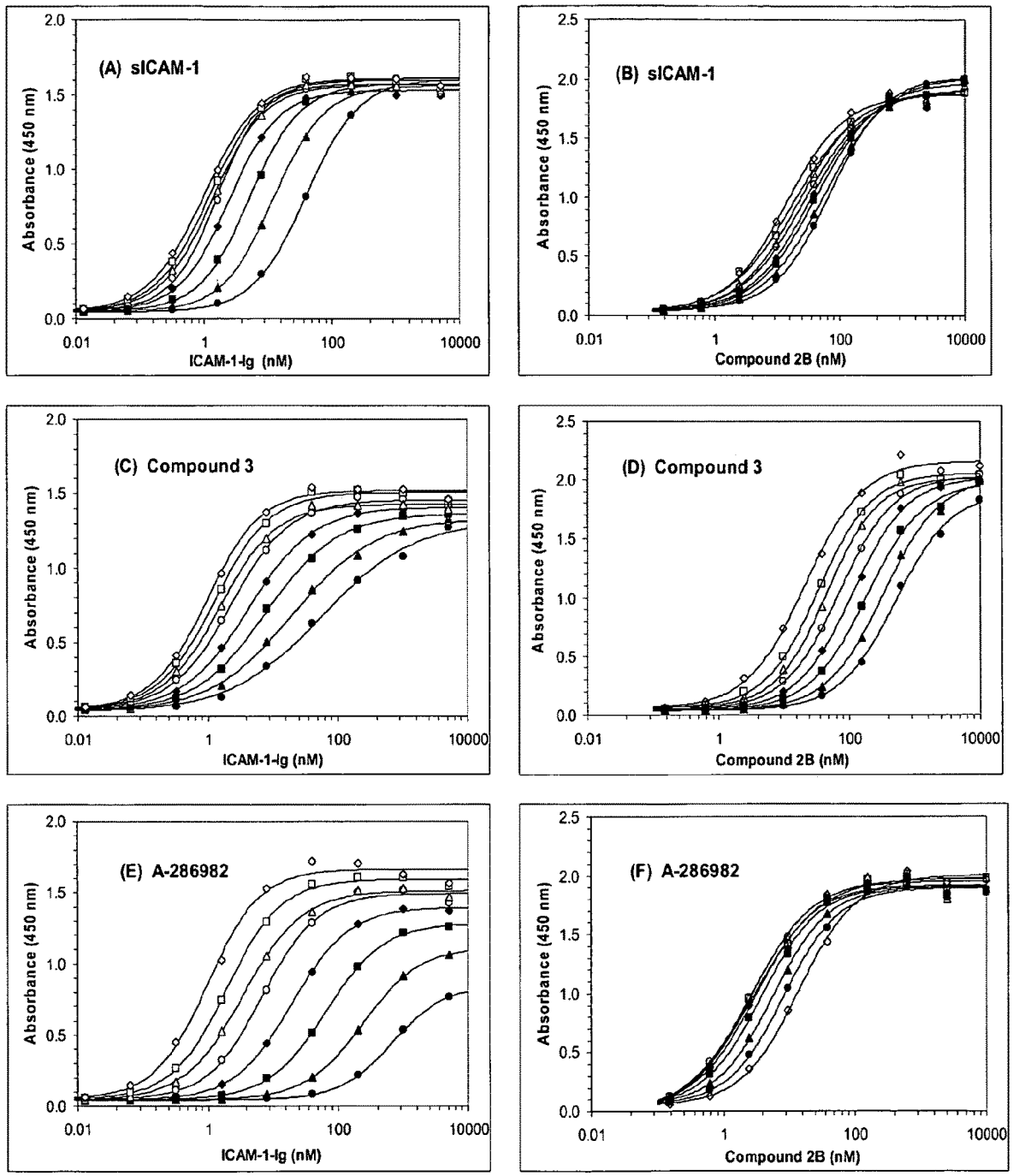
FIG. 9 depicts the effect of antagonists on ligand binding in the LFA-1/ICAM-1 and LFA-1/small molecule ELISAs.

An antagonist, which inhibits through direct competition with the ligand of interest, exhibits a non-saturable rightward shift of the ligand binding curves to higher apparent $EC_{50}$ values with increasing antagonist concentration and no reduction in the maximal binding of the ligand. Inhibition will be surmountable but will require increasing amounts of ligand in the presence of increasing concentrations of a direct competitive inhibitor. The effects of directly competitive compound 3, an allosteric antagonist A-286982 and sICAM-1 on the binding curves of ICAM-1-Ig and compound 2B to LFA-1 are shown in FIG. 9 as examples of antagonists displaying direct competition. Titration of ICAM-1-Ig (A, C, E) or compound 2B (B, D, F) in the absence (-◇-) or presence of antagonist in the LFA-1/ICAM-1 and LFA-1/small molecule ELISAs. The antagonists were added in two-fold dilutions starting at 2.4 (A) and 2.7 (B) M sICAM-1, 0.040 (C) and 0.10 (D) M compound 3 and 20 (E) and 50 (F) M A-286982. The order of antagonist concentrations was, -□- (lowest added antagonist concentration), -△-, -○-, -◆-, -■-, -▲- to -●- (highest antagonist concentration). The fits of the data are shown as the solid lines. The data shown are from one plate and are representative of a minimum of two experiments. (Note that A-286982 (F) resulted in increased binding of compound 2B to LFA-1.) In contrast, an allosteric inhibitor may alter the ligand binding curves by causing a reduction in maximal binding or saturation in the rightward shifts of the curves. As shown in FIG. 9A, the presence of increasing concentrations of sICAM-1 clearly shifted the ICAM-1-Ig binding curves rightward to higher $EC_{50}$ values. Additionally, the same maximal extent of binding of ICAM-1-Ig to LFA-1 was observed in the presence and absence of sICAM-1 as expected when two molecular forms of the same natural ligand are competing directly for binding to one site on a receptor. Similarly, increasing concentrations of compound 3 also shifted the binding of ICAM-1-Ig to higher $EC_{50}$ values with minimal variation in maximal ICAM-1-Ig binding (FIG. 9C). Although the rightward shifts in the ligand binding curves in the presence of a competitive antagonist are typically parallel, this is not always the case. The nonparallel slopes for the LFA-1/ICAM-1-Ig binding curves in the presence and absence of compound 3 may be due to an inability to attain complete equilibrium under the heterogeneous ligand binding ELISA conditions with this compound. In the LFA-1/compound 2B format of the ligand binding ELISA, increasing concentrations of compound 3 also clearly shifted the compound 2B binding curves to higher $EC_{50}$ values with no reduction in maximal binding (FIG. 9D). Increasing concentrations of sICAM-1 also showed a similar effect (FIG. 9B), although the extent of the shift in the curves was limited by the maximum achievable concentration of sICAM-1 at 2.7 µM. Thus, the effects of both sICAM-1 and compound 3 on ICAM-1-Ig and compound 2B binding to LFA-1 are characteristic of direct competition as described above.

The effect of A-286982 on ICAM-1-Ig and compound 2B binding to the receptor was clearly different (FIGS. 9E and 9F). In the LFA-1/ICAM-1 ELISA, the ICAM-1-Ig curves were shifted rightward to higher $EC_{50}$ values; however, the maximum binding of ICAM-1-Ig to LFA-1 decreased considerably with increasing concentrations of A-286982. The reduction in maximal binding and rightward shift of the ligand binding curves with increasing A-286982 concentration are reflective of allosteric inhibition as described above. A-286982 causes reductions in both ligand affinity and binding capacity; this demonstrates that A-286982 is an insurmountable antagonist of ICAM-1-Ig binding. In contrast, in the LFA/small molecule ELISA, the presence of A-286982 at micromolar concentrations shifted the compound 2B binding curves to lower $EC_{50}$ values and appeared to enhance the binding of compound 2B to LFA-1 (FIG. 9F). The contrasting effects of A-286982 on compound 2B and ICAM-1-Ig binding may be due to the known allosteric effect of the compound binding to the IDAS site on LFA-1. The A-286982 binding data serve as an illustration for allosteric inhibition for small molecule and protein ligand binding to LFA-1 in the binding experiments demonstrated in this method.

Figure 10:
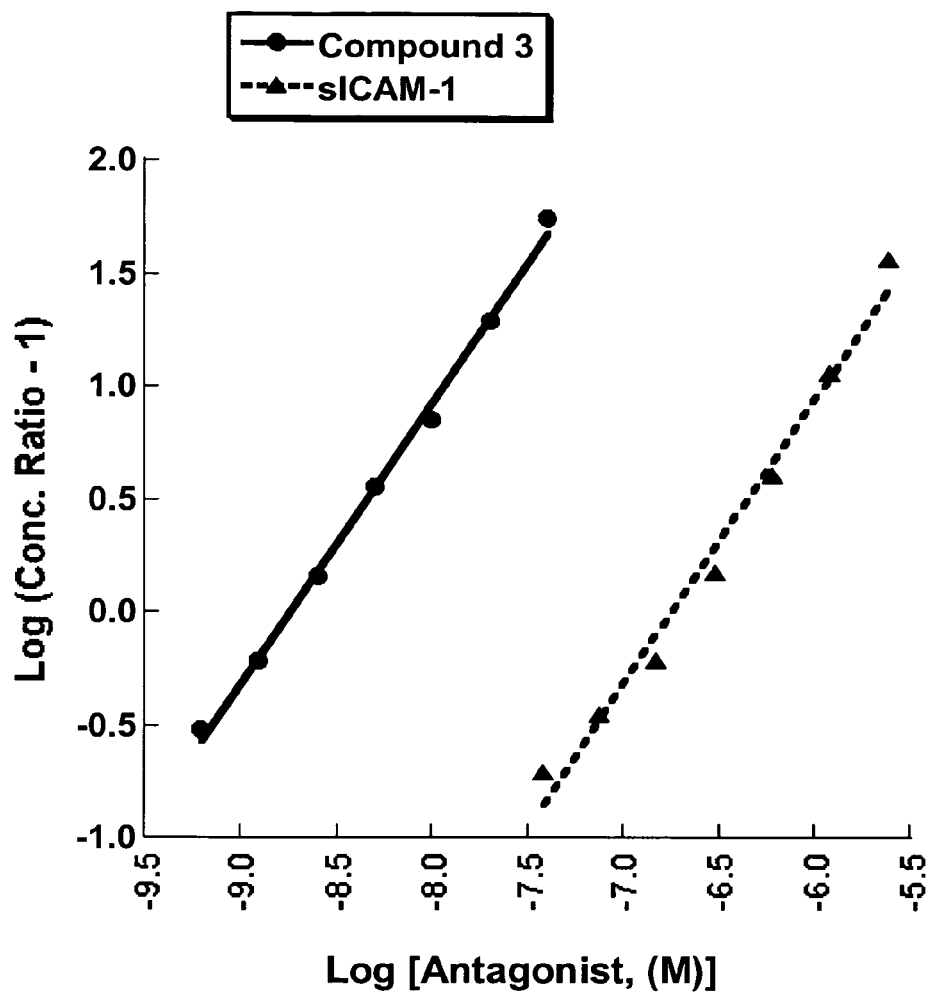
FIG. 10 depicts Schild regressions of sICAM-1 and compound 3 antagonism.

Schild analysis can be also used to investigate whether a compound inhibits ligand binding through direct competition for a single binding site. This model is based upon the assumptions that equiactive responses in an assay are the result of equivalent occupancy of receptor by ligand and that maximal binding is unchanged by the presence of antagonist. In a Schild analysis, the dose ratio is the ratio of the $EC_{50}$ values in the presence and absence of antagonist and is a measure of the ligand concentrations leading to equiactive responses. This dose ratio was determined for each concentration of antagonist and the Schild regressions were plotted as shown in FIG. 10. A linear response with a slope of 1 in a Schild regression indicates that inhibition by an antagonist is directly competitive and reversible. The Schild analysis would yield a nonlinear relationship and/or a slope that deviates significantly from 1 in the case of an allosteric inhibitor that does not result in a reduction of maximal binding. The Schild regressions for both sICAM-1 and compound 3 are shown in FIG. 10 with comparable slopes of 1.26 and 1.24, respectively. Schild regressions of s-ICAM-1 (-▲-) and compound 3 (-●-) antagonism in the LFA-1/ICAM-1 ligand binding ELISA are plotted from the data in FIGS. 5 (A) and (C), respectively. The slope of the plot for compound 3 is 1.24 with a y-intercept of 10.9 and R=0.99832. The slope of the sICAM-1 plot is 1.26, y-intercept, 8.51 and R=0.99131. Although the Schild analysis requires a linear regression with a slope close to 1 to demonstrate direct competitive inhibition, there is no guidance in the extensive literature as to what range of Schild values are acceptable. Slopes of 1.24 and 1.26 fall within the bounds of many published Schild values used to support competitive binding conclusions, and therefore, these slope values are not considered significantly different than 1. The linearity of the regression plots and the similarity in slopes of the relationships are consistent with binding of ligand (ICAM-1-Ig) and both antagonists (sICAM-1 and compound 3) to the same site in a similar manner.

A. Antibodies

Several suitable antibodies are known in the art. Blocking of the ICAMs, such as for example ICAM-1, or the leukointegrins, such as for example, LFA-1, by antibodies directed against either or both of these molecules can inhibit inflammatory response. Previous studies have investigated the effects of anti-CD11a MAbs on many T-cell-dependent immune functions in vitro and a number of immune responses in vivo. In vitro, anti-CD11a MAbs inhibit T-cell activation (See Kuypers T. W., Roos D. 1989 "Leukocyte membrane adhesion proteins LFA-1, CR3 and p150,95: a review of functional and regulatory aspects" Res. Immunol., 140:461-465; Fischer A, Durandy A, Sterkers G, Griscelli C. 1986 "Role of the LFA-1 molecule in cellular interactions required for antibody production in humans" J. Immunol., 136, 3198; target cell lysis by cytotoxic T-lymphocytes (Krensky et al., supra), formation of immune conjugates (Sanders V M, Snyder J M, Uhr J W, Vitetta E S., "Characterization of the physical interaction between antigen-specific B and T cells". J. Immunol., 137:2395 (1986); Mentzer S J, Gromkowski S H, Krensky A M, Burakoff S J, Martz E. 1985 "LFA-1 membrane molecule in the regulation of homotypic adhesions of human B lymphocytesn" J. Immunol., 135:9), and the adhesion of T-cells to vascular endothelium (Lo S K, Van Seventer G A, Levin S M, Wright S D., Two leukocyte receptors (CD11a/CD18 and CD11b/CD18) mediate transient adhesion to endothelium by binding to different ligands., J. Immunol., 143:3325 (1989)). Two anti-CD11a MAbs, HI 111, and G43-25B are available from PharmingenBD Biosciences. Additionally, a study including F8.8, CBR LFA 1/9, BL5, May.035, TS1/11, TS1/12, TS 1/22, TS2/14, 25-3-1, MHM2 and efalizumab evaluated the range of binding sites on LFA-1 these antibodies occupied. See Lu, C; Shimaoka, M.; Salas, A.; Springer, T. A. 2004, "The Binding Sites for Competitive Antagonistic, Allosteric Antagonistic, and Agonistic Antibodies to the I Domain of Integrin LFA-1" J. Immun. 173: 3972-3978 and references therein. It was shown that efalizumab, amongst other antibodies directed against LFA-1, is a directly competitive antagonist of LFA-1.

Thus, a number of antibodies which are directed against LFA-1, may be used to treat diabetic retinopathy, including efalizumab (Raptiva).

B. Small Molecules.

1. Peptides.

Peptides have been investigated for use in reducing the interaction of LFA-1 with ICAM-1. Polypeptides that do not contain an Fc region of an IgG are described in U.S. Pat. No. 5,747,035, which can be used to treat LFA-1 mediated disorders, in particular diabetic retinopathy. Use of dual peptides, the first a modulator of ICAM-1 and the second a blocking peptide with a sequence obtained from LFA-1 is described in U.S. Pat. No. 5,843,885 to reduce the interactions between LFA-1 and ICAM-1. Cyclic peptides have been described in U.S. Pat. No. 6,630,447 as inhibitors of the LFA-1: ICAM-1 interaction.

2. Small Organic Molecules.

a. Exemplary Compounds which are Directly Competitive Antagonists of LFA-1.

"Small organic molecule" generally is used to refer to organic molecules of a size comparable to those organic molecules generally used in pharmaceuticals. The term typically excludes organic biopolymers (e.g., proteins, nucleic acids, etc.). Small organic molecules most often range in size up to about 5000 Da, in some embodiments, up to about 2000 Da, or in other embodiments, up to about 1000 Da.

i. In one embodiment, compounds useful in the methods of the present invention include compounds of Formula I:

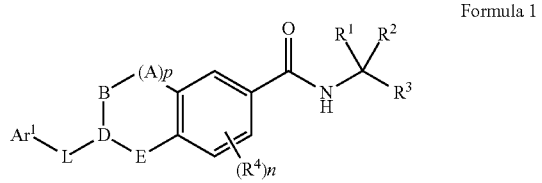

Formula 1 where $R^1$ and $R^2$ are each independently hydrogen, an amino acid side chain, $-(CH_2)_mOH$, $-(CH2)_m$aryl, $-(CH2)_m$heteroaryl, wherein m is 0-6, $-CH(R^{1A})(OR^{1B})$, $-CH(R^{1A})(NHR^{1B})$, U-T-Q, or an aliphatic, alicyclic, heteroaliphatic or heteroalicyclic moiety optionally substituted with U-T-Q; wherein U may be absent or one of the following: $-O-$, $-S(O)_{0-2}-$, $-SO_2N(R^{1A})$, $-N(R^{1A})-$, $-N(R^{1A})C(=O)-$, $-N(R^{1A})\overset{.}{C}(=O)-O-$, $-N(R^{1A})C(=O)-N(R^{1B})-$, $-N(R^{1A})-SO_2-$, $-C(=O)-$, $-C(=O)-O-$, $-O-C(=O)-$, aryl, heteroaryl, alkylaryl, alkylheteroaryl, $-C(=O)-N(R^{1A})-$, $-OC(=O)N(R^{1A})-$, $-C(=N-R^{1E})-$, $-C(=N-R^{1E})-O-$, $-C(=N-R^{1E})-N(R^{1A})-$, $-O-C(=N-R^{1E})-N(R^{1A})-$, $-N(R^{1A})C(=N-R^{1E})-$, $-N(R^{1A})C(=N-R^{1E})-O-$, $-N(R^{1A})C(=N-R^{1E})-N(R^{1B})-$, $-P(=O)(OR^{1A})-O-$, or $-P(=O)(R^{1A})-O-$; wherein T is absent or, an aliphatic, heteroaliphatic, aryl, heteroaryl, alkylaryl or alkylheteroaryl moiety; and Q is hydrogen, halogen, cyano, isocyanate, $-OR^{1B}$, $-SR^{1B}$, $-N(R^{1B})_2$, $-NHC(=O)OR^{1B}$, $-NHC(=O)N(R^{1B})_2$, $-NHC(=O)R^{1B}$, $-NHSO_2R^{1B}$, $NHSO_2N(R^{1B})_2$, $-NHSO_2NHC(=O)OR^{1B}$, $-NHC(=O)NHSO_2R^{1B}$, $-C(=O)NHC(=O)OR^{1B}$, $C(=O)NHC(=O)R^{1B}$, $-C(=O)NHC(=O)N(R^{1B})_2$, $-C(=O)NHSO_2R^{1B}$, $-C(=O)NHSO_2N(R^{1B})_2$, $C(=S)N(R^{1B})_2$, $-SO_2R^{1B}$, $-SO_2OR^{1B}$, $-SO_2N(R^{1B})_2$, $-SO_2-NHC(=O)OR^{1B}$, $-OC(=O)-N(R^{1B})_2$, $-OC(=O)R^{1B}$, $-OC(=O)NHC(=O)OR^{1B}$, $-OC(=O)NHSO_2R^{1B}$, $-OSO_2R^{1B}$, or an aliphatic heteroaliphatic, aryl or heteroaryl moiety, or wherein $R^1$ and $R^2$ taken together are an alicyclic or heterocyclic moiety, or together are

wherein each occurrence of $R^{1A}$ and $R^{1B}$ is independently hydrogen, an aliphatic, alicyclic, heteroaliphatic, heterocyclic, aryl, heteroaryl, alkylaryl or alkylheteroaryl moiety, $-C(=O)R^{1C}$, or $-C(=O)NR^{1C}R^{1D}$; wherein each occurrence of $R^{1C}$ and $R^{1D}$ is independently hydrogen, hydroxyl, or an aliphatic, heteroaliphatic, aryl, heteroaryl, alkylaryl or alkylheteroaryl moiety; and $R^{1E}$ is hydrogen, an aliphatic, alicyclic, heteroaliphatic, heterocyclic, aryl, heteroaryl, alkylaryl or alkylheteroaryl moiety, $-CN$, $-OR^{1C}$, $-NR^{1C}R^{1D}$ or $-SO2R^{1C}$;

where $R^3$ is $-C(=O)OR^{3A}$, $-C(=O)H$, $-CH_2OR^{3A}$, $-CH_2OC(=O)$-alkyl, $-C(=O)NH(R^{3A})$, $-CH_2X$; wherein each occurrence of $R^{3A}$ is independently hydrogen, a protecting group, an aliphatic, alicyclic, heteroaliphatic, heteroalicyclic, aryl, heteroaryl, alkylaryl, alkylheteroaryl, heteroalkylaryl, heteroalkylheteroaryl moiety, or a pharmaceutically acceptable salt or ester, or $R^{3A}$, taken together with $R^1$ and $R^2$, forms a heterocyclic moiety; wherein $X^0$ is a halogen selected from F, Br or I;

$R^4$ for each occurrence, is independently hydrogen, halogen, $-CN$, $-NO_2$, an aliphatic, alicyclic, heteroaliphatic, heteroalicyclic, aryl, heteroaryl, alkylaryl or alkylheteroaryl moiety, or is GRG1 wherein G is $-O-$, $-S-$, $NR^{G2}-$, $-CO-$, $-SO-$, $-SO_2-$, $C(=O)O-$, $-C(=O)NR^{G2}-$, $C(=O)-$, $-NR^{G2}C(=O)-$ or $-SO_2NR^{G2}-$, and $R^{G1}$ and $R^{G2}$ are independently hydrogen, an aliphatic, alicyclic, heteroaliphatic, heteroalicyclic, aryl, heteroaryl, alkylaryl or alkylheteroaryl moiety;

n is an integer from 0-4;

$AR^1$ is a monocyclic or polycyclic aryl, heteroaryl, alkylaryl, alkylheteroaryl, alicyclic or heterocyclic moiety;

A, B, D and E are connected by either a single or double bond, as valency permits; wherein each occurrence of A, B, D and E is independently C=O, $CR^iR^{ii}$, $NR^i$, $CR^i$, N, O, S, —S(=O) or SO$_2$; wherein each occurrence of R$^i$ and R$^{ii}$ are independently hydrogen, halogen, —CN, —NO2, an aliphatic, alicyclic, heteroaliphatic, heteroalicyclic, aryl, heteroaryl, alkylaryl or alkylheteroaryl moiety, or is -GR$^{G1}$ wherein G is —O—, —S—, —NR$^{G2}$, —CO—, —SO—, —C(=O)O—, —C(=O)NR$^{G2}$—, —OC(=O)—, —NR$^{G2}$C(=O)— or —SO$_2$NR$^{G2}$—, and R$^{G1}$ and R$^{G2}$ are independently hydrogen, an aliphatic, alicyclic, heteroaliphatic, heteroalicyclic, aryl, heteroaryl, alkylaryl or alkylheteroaryl moiety, or any two adjacent occurrences of taken together, represent an alicyclic, heteroalicyclic, aryl, or heteroaryl moiety;

p is an integer from 0-4; and,

L is absent or is V-W—X—Y—Z, wherein each occurrence of V, W, X, Y and Z is independently absent, C=O, NR$^{L1}$, —O—, —C(R$^{L1}$)=, =C(R$^{L1}$)—, —C(R$^{L1}$)(R$^{L2}$), C(=N—OR$^{L1}$), C(=NR$^{L1}$), —N=, S(O)$_{0-2}$; a substituted or unsubstituted C$_{1-6}$ alkenylidene or C$_{2-6}$ alkenylidine chain wherein up to two non-adjacent methylene units are independently optionally replaced by —C(=O)—, —CO$_2$—, —C(=O)C(=O)—, —C(C=O)NR$^{L3}$—, —OC(=O)—, —OC(=O)NR$^{L3}$—, —NR$^{L3}$NR$^{L4}$—, —NR$^{L3}$NR$^{L4}$C(=O)—, —NR$^{L3}$C(=O)—, NR$^{L3}$CO$_2$—, NR$^{L3}$C(=O)NR$^{L4}$—, —S(=O)—, —SO$_2$—, —NR$^{L3}$SO$_2$—, —SO$_2$NR$^{L3}$, —NR$^{L3}$SO$_2$NR$^{L4}$, —O—, —S—, or —NR$^{L3}$—; wherein each occurrence of R$^{L3}$ and R$^{L4}$ is independently hydrogen, alkyl, heteroalkyl, aryl, heteroaryl or acyl; or an aliphatic, alicyclic, heteroaliphatic, heteroalicyclic, aryl, heteroaryl, alkylaryl or alkylheteroaryl moiety; and each occurrence of R$^{L1}$ and R$^{L2}$ is independently hydrogen, hydroxyl, protected hydroxyl, amino, protected amino, thio, protected thio, halogen, cyano, isocyanate, carboxy, carboxyalkyl, formyl, formyloxy, azido, nitro, ureido, thioureido, thiocyanato, alkoxy, aryloxy, mercapto, sulfonamido, benzamido, tosyl, or an aliphatic, alicyclic, heteroaliphatic, heteroalicyclic, aryl, heteroaryl, alkylaryl or alkylheteroaryl moiety, or wherein one or more occurrences of R$^{L1}$ and R$^{L2}$, taken together, or taken together with one of V, W, X, Y or Z form an alicyclic or heterocyclic moiety or form an aryl or heteroaryl moiety.

Some preferred embodiments of the method of the present invention are of Formula II:

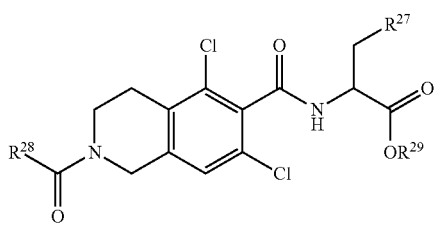

where R$^{28}$ is one of the following groups:

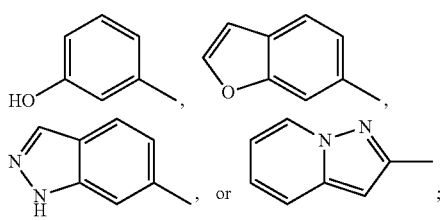

and R$^{27}$ is one of the following groups:

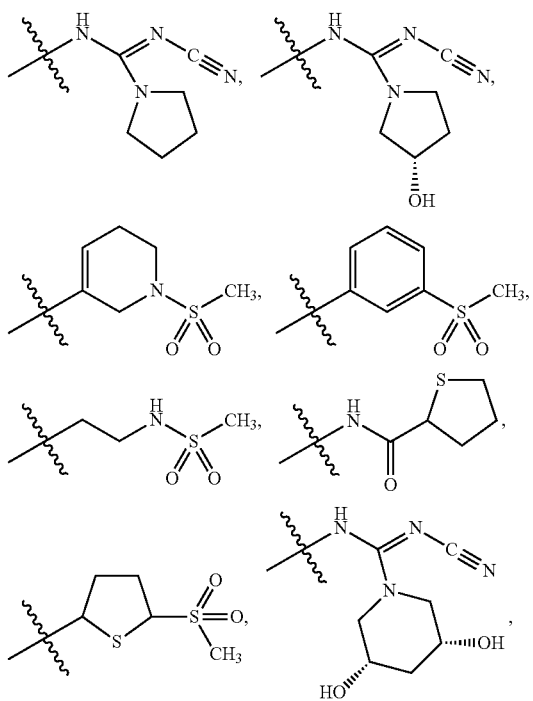

and R$^{29}$ is hydrogen, a pharmaceutically acceptable salt or ester.

Some preferred embodiments of the invention are compounds of the Formula II'

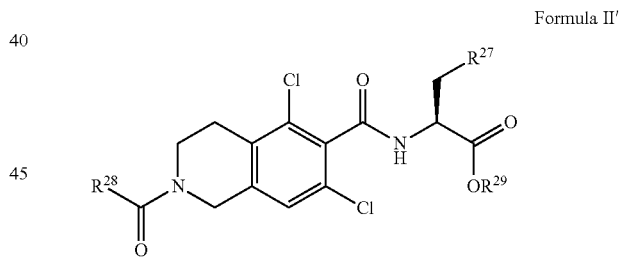

where the substitution is as in Formula II.

Some particularly preferred embodiments of compounds of the method of the present invention are compounds of Formulae IA, IIA and IIB:

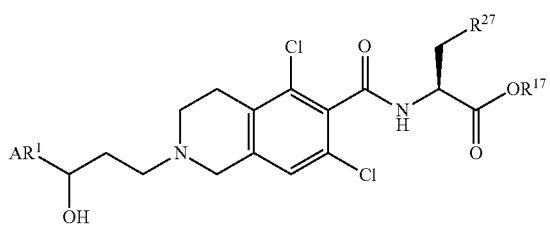

-continued

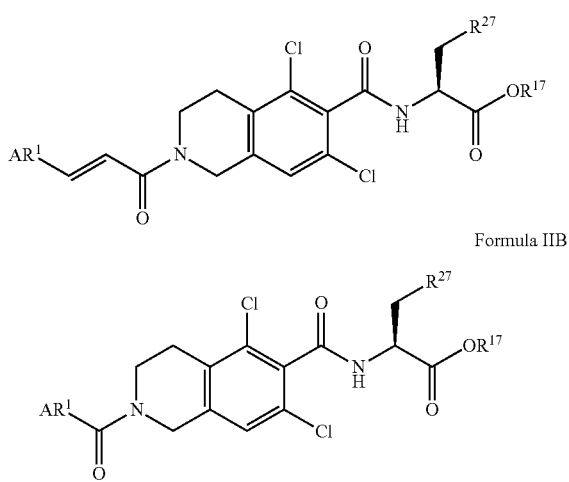

Formula IIA

Formula IIB where $R^{17}$ is hydrogen, pharmaceutically acceptable salts or esters, and $R^{27}$ is as in Formula II. Compounds of this class are disclosed in U.S. Pat. No. 7,314,938.

ii. Another set of preferred embodiments of compounds of the method of the invention are compounds of the Formula III:

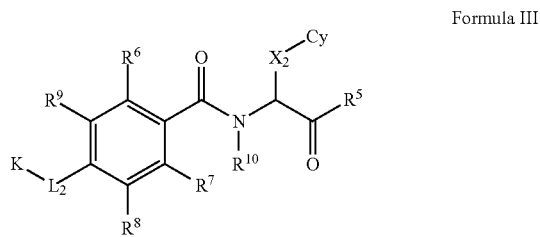

Formula III where Cy is an aromatic carbocycle, aromatic heterocycle or a non-aromatic carbocycle or heterocycle optionally substituted with hydroxyl (—OH), mercapto (—SH), thioalkyl, halogen (e.g. F, Cl, Br, I), oxo (═O), thio (═S), amino, aminoalkyl, amidine (—C(NH)—NH₂), guanidine (—NH₂—C(NH)—NH₂), nitro, alkyl or alkoxy. In a particular embodiment, Cy is a 3-5 member ring. In a preferred embodiment, Cy is a 5- or 6-member non-aromatic heterocycle optionally substituted with hydroxyl, mercapto, halogen (preferably F or Cl), oxo (═O), thio (═S), amino, amidine, guanidine, nitro, alkyl or alkoxy. In a more preferred embodiment, Cy is a 5-member non-aromatic heterocycle optionally substituted with hydroxyl, oxo, thio, Cl, $C_{1-4}$ alkyl (preferably methyl), or $C_{1-4}$ alkanoyl (preferably acetyl, propanoyl or butanoyl). More preferably the non-aromatic heterocycle comprises one or heteroatoms (N, O or S) and is optionally substituted with hydroxyl, oxo, mercapto, thio, methyl, acetyl, propanoyl or butyl. In particular embodiments the non-aromatic heterocycle comprises at least one nitrogen atom that is optionally substituted with methyl or acetyl. In a particularly preferred embodiment, the non-aromatic heterocycle is selected from the group consisting of piperidine, piperazine, morpholine, tetrahydrofuran, tetrahydrothiophene, oxazolidine, thiazolidine optionally substituted with hydroxy, oxo, mercapto, thio, alkyl or alkanoyl. In a most preferred embodiment Cy is a non-aromatic heterocycle selected from the group consisting of tetrahydrofuran-2-yl, thiazolidin-5-yl, thiazolidin-2-one-5-yl, and thiazolidin-2-thione-5-yl and pyrrolidine. In a preferred embodiment, Cy is a 5- or 6-member aromatic carbocycle or heterocycle optionally substituted with hydroxyl, mercapto, halogen (preferably F or Cl), oxo (═O), thio (═S), amino, amidine, guanidine, nitro, alkyl or alkoxy. In a more preferred embodiment, Cy is a 5-member aromatic carbocycle or heterocycle optionally substituted with hydroxyl, ox6, thio, Cl, $C_{1-4}$ alkyl (preferably methyl), or $C_{1-4}$ alkanoyl (preferably acetyl, propanoyl or butanoyl). More preferably the aromatic or heterocycle comprises one or heteroatoms (N, O or S) and is optionally substituted with hydroxyl, oxo, mercapto, thio, methyl, acetyl, propanoyl or butyl.

In another preferred embodiment Cy is a 3-6 member carbocycle optionally substituted with hydroxyl, mercapto, halogen, oxo, thio, amino, amidine, guanidine, alkyl, alkoxy or acyl. In a particular embodiment the carbocycle is saturated or partially unsaturated. In particular embodiments Cy is a carbocycle selected from the group consisting of cyclopropyl, cyclopropenyl, cyclobutyl, cyclobutenyl, cyclopentyl, cyclopentenyl, cyclohexyl or cyclohexenyl.

$X_2$ is a $C_{1-5}$ divalent hydrocarbon linker optionally having one or more carbon atoms replaced with N, O, S, SO or $SO_2$ and optionally being substituted with hydroxyl, mercapto, halogen, amino, aminoalkyl, nitro, oxo or thio. In a preferred embodiment $X_2$ will have at least one carbon atom. Replacements and substitutions may form an amide moiety (—NRC(═O)— or —C(═O)NR—) within the hydrocarbon chain or at either or both ends. X is also sulfonamide (—NRSO₂— or —SO₂NR), acyl, ether, thioether or amine. In a particularly preferred embodiment $X_2$ is the group —CH₂—NR¹⁰—C(O)— wherein the carbonyl —C(O)— portion thereof is adjacent (i.e. covalently bound) to Cy and $R^{10}$ is alkyl i.e. methyl or more preferably H.

K is a carbocycle or heterocycle optionally substituted with hydroxyl, mercapto, halogen, oxo, thio, a hydrocarbon, a halo-substituted hydrocarbon, amino, amidine, guanidine, cyano, nitro, alkoxy or acyl. In particular embodiment, K is aryl or heteroaryl optionally substituted with halogen or hydroxyl. In a particularly preferred embodiment, K is phenyl, furan-2-yl, thiophene-2-yl, phenyl substituted with a halogen (preferably Cl) or hydroxyl, preferably at the meta position.

$L_2$ is a divalent hydrocarbon optionally having one or more carbon atoms replaced with N, O, S, SO or $SO_2$ and optionally being substituted with hydroxyl, halogen oxo, or thio; or three carbon atoms of the hydrocarbon are replaced with an amino acid residue. Preferably $L_2$ is less than 10 atoms in length and more preferably 5 or less and most preferably 5 or 3 atoms in length. In particular embodiments, $L_2$ is —CH═CH—C(O)—NR¹⁰—CH₂—, —CH₂—NR¹⁰—C(O)—, —C(O)—NR¹⁰—CH₂—, —CH(OH)—(CH₂)₂—, —(CH₂)₂—CH(OH)—, —(CH₂)₃—, —C(O)—NR¹⁰—CH (R₇)—C(O)—NR¹⁰—, —NR¹⁰—C(O)—CH(R¹⁶)—NR¹⁰—C(O)—, —CH(OH)—CH₂—O— or —CH(OH)—CF₂—CH₂— wherein each $R^{10}$ is independently H or alkyl and $R^{16}$ is an amino acid side chain. Preferred amino acid side chains include non-naturally occurring side chains such as phenyl or naturally occurring side chains. Preferred side chains are those from Phe, Tyr, Ala, Gln and Asn. In a preferred embodiments $L_2$ is —CH═CH—C(O)—NR¹⁰—CH₂— wherein the —CH═CH— moiety thereof is adjacent (i.e. covalently bound) to K. In another preferred embodiment, $L_2$ is —CH₂—NR¹⁰—C(O)— wherein the methylene moiety (—CH₂—) thereof is adjacent to K. $R^5$ is H, OH, amino, O-carbocycle or alkoxy optionally substituted with amino, a carbocycle, a heterocycle, or a pharmaceutically acceptable salt or ester. In a preferred embodiment, $R^5$ is H, phenyl or $C_{1-4}$ alkoxy optionally substituted with a carbocycle such as phenyl. In a particular embodiment $R^5$ is H. In another particular embodiment $R^5$ is methoxy, ethoxy, propyloxy, butyloxy, isobutyloxy, s-butyloxy, t-butyloxy, phenoxy or benzyloxy. In yet another particular embodiment $R^5$ is $NH_2$. In a particularly preferred embodiment $R^5$ is ethoxy. In another particularly preferred embodiment $R^5$ is isobutyloxy. In another particularly preferred embodiment $R^5$ is alkoxy substituted with amino, for example 2-aminoethoxy, N-morpholinoethoxy, N,N-dialkyaminoethoxy, quaternary ammonium hydroxy alkoxy (e.g. trimethylammoniumhydroxyethoxy).

$R^{6-9}$ are independently H, hydroxyl, mercapto, halogen, cyano, amino, amidine, guanidine, nitro or alkoxy; or $R^7$ and $R^8$ together form a fused carbocycle or heterocycle optionally substituted with hydroxyl, halogen, oxo, thio, amino, amidine, guanidine or alkoxy. In a particular embodiment $R^6$ and $R^7$ are independently H, F, Cl, Br or I. In another particular embodiment, $R^8$ and $R^9$ are both H. In another particular embodiment, one of $R^6$ and $R^7$ is a halogen while the other is hydrogen or a halogen. In a particularly preferred embodiment, $R^7$ is Cl while $R^6$, $R^8$ and $R^9$ are each H. In another particularly preferred embodiment, $R^6$ and $R^7$ are both Cl while $R^8$ and $R^9$ are both H.

$R^{10}$ is H or a hydrocarbon chain optionally substituted with a carbocycle or a heterocycle. In a preferred embodiment, $R^{10}$ is H or alkyl i.e. methyl, ethyl, propyl, butyl, i-butyl, s-butyl or t-butyl. In a particular embodiment $R^{10}$ is H.

Compounds of the class of Formula III are disclosed in U.S. Pat. Nos. 6,667,318, 6,872,735, and 6,803,384.

iii. Further preferred embodiments of the method of the present invention are compounds of the Formula IV:

Formula IV

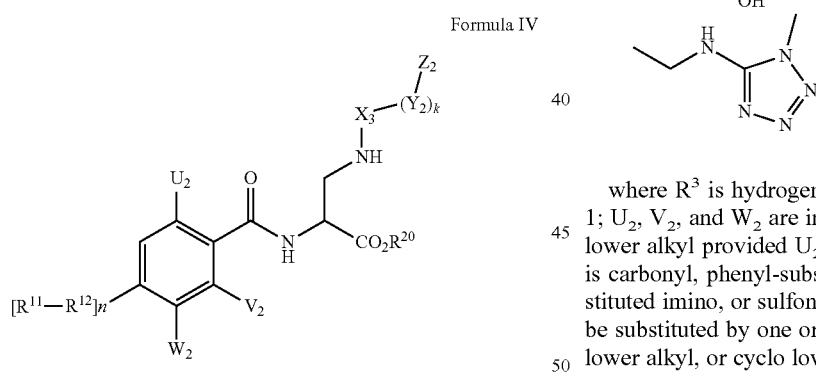

where $R^{11}$ is a group of the formula

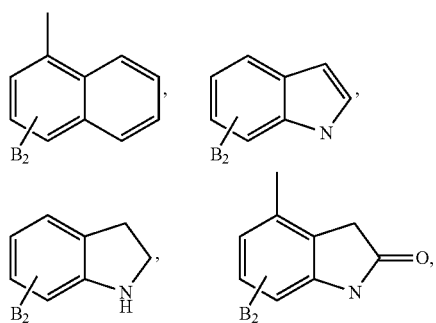

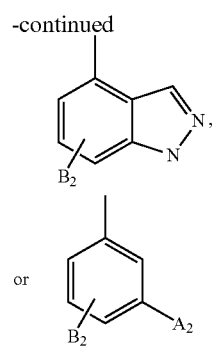

where A is hydrogen, hydroxy, amino, or halogen and B is amino, carboxy, hydrogen, hydroxy, cyano, trifluoromethyl, halogen, lower alkyl, or lower alkoxy;

$R^{12}$ is a group of the formula:

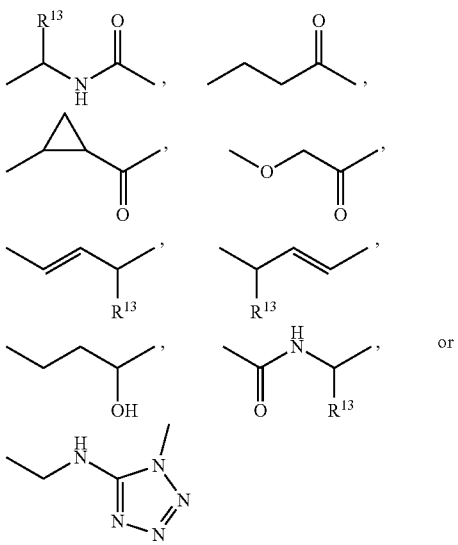

where $R^3$ is hydrogen, carboxy, or lower alkyl; n is 0 or 1; $U_2$, $V_2$, and $W_2$ are independently hydrogen, halogen, or lower alkyl provided $U_2$ and $V_2$ are not both hydrogen; $X_3$ is carbonyl, phenyl-substituted lower alkylene, imino, substituted imino, or sulfonyl; $Y_2$ is lower alkylene which may be substituted by one or more of amino, substituted amino, lower alkyl, or cyclo lower alkyl, or $Y_2$ is lower alkenylene or lower alkylenethio;

k is 0 or 1; when k is 1, $Z_2$ is hydrogen, lower alkylthio, —COOH, —$CONH_2$, amino; and when k is 0 or 1, $Z_2$ is 1-adamantyl, diphenylmethyl, 3-[[(5-chloropyridin-2-yl) amino]carbonyl]pyrazin-2-yl, hydroxy, phenylmethoxy, 2-chloro-4-[[[(3-hydroxyphenyl) methyl]amino]carbonyl] phenyl, [2,6-dichlorophenyl) methoxy]phenyl; further when k is 0 or 1, $Z_2$ may be cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, lower alkanesulfonyl, lower alkylthio, acetyl, aminocarbonyl, hydrazino, carboxy, alkoxycarbonyl, acetoxy, or also in addition with amino lower alkyl; and $R^{20}$ is hydrogen, a pharmaceutically acceptable salt or ester.

One embodiment of compounds of Formula IV has stereochemistry as indicated in Formula IV':

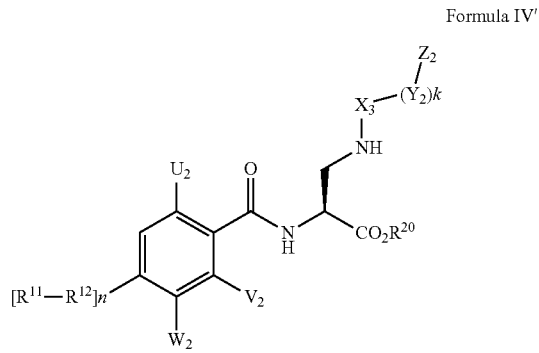

Formula IV' iv. Another set of preferred embodiments of the compounds of the method of the present invention are compounds of Formula V:

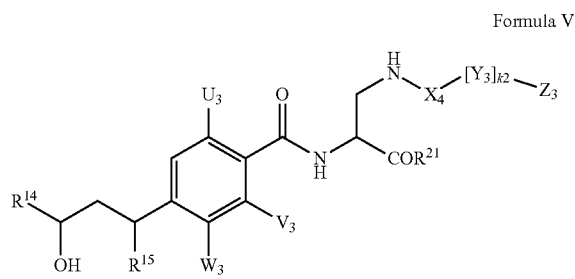

Formula V where $R^{14}$ is a group of the formula:

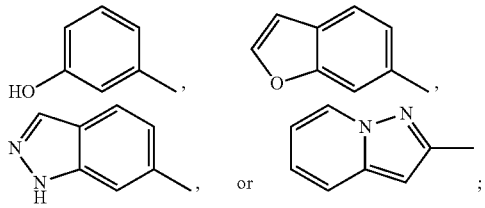

where $R^{15}$ is hydrogen, carboxy, or lower alkyl; $U_3$, $V_3$, and $W_3$ are independently hydrogen, halogen; or $U_3$, $V_3$, and $W_3$ are lower alkyl provided that $U_3$ and $V_3$ are not both hydrogen; $X_4$ is carbonyl, phenyl-substituted lower alkylene, imino, substituted imino which includes cyano, or sulfonyl; $Y_3$ is lower alkenylene, lower alkylenethio, or is lower alkylene which may be substituted by amino, acetylamino, or cyclo-lower alkyl;

$k_2$ is 0 or 1; when $k_2$ is 1, Z is hydrogen, lower alkylthio, —COOH, —CONH$_2$—, or amino; when $k_2$ is 0 or 1, $Z_3$ is 1-adamantyl, diphenylmethyl, 3-[[(5-chloropyridin-2-yl)amino]carbonyl]pyrazin-2-yl; and when $k_2$ is 0 or 1, Z may be cycloalkyl or aryl containing 0 to 3 heteroatoms which may be the same or different, or a fused ring system containing two or three rings which rings are independently cycloalkyl or aryl containing 0 to 3 heteroatoms which may be the same or different, any of which rings may be unsubstituted, or substituted with at least one of halogen, cyano, amino, substituted amino, aminosulfonyl, nitro, oxo, hydroxy, aryl, aryloxy, unsubstituted lower alkyl, halogen-substituted lower alkyl, lower alkoxy-substituted lower alkyl, lower alkoxy, carboxy, alkoxycarbonyl, or acetoxy; and, $R^{21}$ is hydrogen, pharmaceutically acceptable salts or esters thereof.

A preferred embodiment of compounds of Formula V has the stereochemistry as indicated in Formula V':

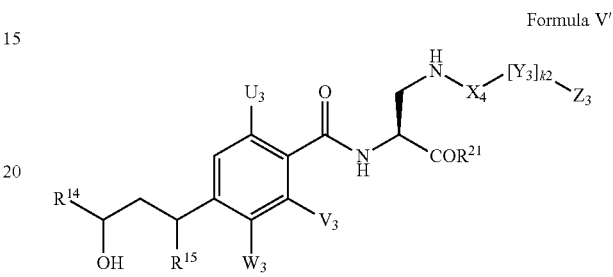

Formula V'

Other compounds of the class of Formula IV and V are disclosed in U.S. Pat. Nos. 7,217,728, 6,331,640, 6,515,124, and 6,803,384.

v. Another class of preferred compounds of the method are represented by Formula VI

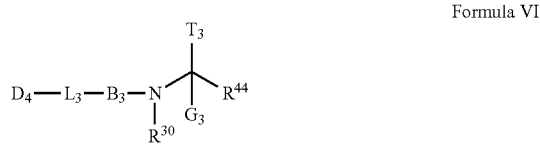

Formula VI where $D_4$ is a mono-, bi-, or tricyclic saturated, unsaturated, or aromatic ring, each ring having 5-, 6- or 7 atoms in the ring where the atoms in the ring are carbon or from one to four heteroatoms selected from the group nitrogen, oxygen, and sulfur, where any carbon or sulfur ring atom may optionally be oxidized, each ring substituted with 0-3 $R^{31}$;

$L_3$ is a bivalent linking group having one of the following structures;
-$L^3$-$L^2$-$L^1$-,
-$L^4$-$L^3$-$L^2$-$L^1$- or
-$L^5$-$L^4$-$L^3$-$L^2$-$L^1$-,
where $L^1$ is oxo (—O—), S(O)$_s$, C(=O), CR$^{32}$, R$^{32}$, CR$^{32}$ het, NR$^{30}$ or N, $L^2$ is oxo (—O—), S(O)$_s$, C(=O), C(=N—O—R$^{33}$), CR$^{34}$R$^{34'}$, CR$^{34}$, het NR$^{30}$ or N, $L^3$ is oxo (—O—), S(O)$_s$, C(=O), C(=N—O—R$^{33}$), CR$^{35}$R$^{35'}$, CR$^{35}$, het NR$^{30}$ or N, $L^4$ is absent, is oxo (—O—), S(O)$_s$, C(=O), C(=N—O—R$^{33}$), CR$^{36}$R$^{36'}$, CR$^{36}$, NR$^{30}$ or N, $L^5$ is absent, oxo (—O—), S(O)$_s$, C(=O), CR$^{37}$R$^{37'}$, CR$^{37}$, NR$^{30}$ or N, provided that only one of $L^1$-$L^3$ may be het and that when one of $L^1$-$L^3$ is het the other $L^1$-$L^5$ may be absent, where
$R^{32}$, $R^{32'}$, $R^{34}$, $R^{34'}$, $R^{35}$, $R^{35'}$, $R^{36}$, $R^{36'}$, $R^{37}$ and $R^{37'}$ each are independently $R^{38}$, $R^{39}$ or U-Q-V-W, optionally, $R^{24}$ and $R^{34'}$ separately or together may form a saturated, unsaturated or aromatic fused ring with $B_3$ through a substituent RP on B, the fused ring containing 5, 6 or 7 atoms in the ring and optionally containing 1-3 heteroatoms selected from the group O, S and N, where any S or N may optionally be oxidized;

optionally, $R^{35}$ and $R^{35}$ separately or together and $R^{36}$ and $R^{36'}$ separately or together may form a saturated, unsaturated or aromatic fused ring with $D_3$ through a substituent $R^{31}$ on $D_3$, the fused ring containing 5, 6 or 7 atoms in the ring and optionally containing 1-3 heteroatoms selected from the group O, S and N, where any S or N may optionally be oxidized;

also optionally, each $R^{32}$-$R^{37}$, $NR^{30}$ or N in $L^1$-$L^5$ together with any other $R^{32}$-$R^{37}$, $NR^{30}$ or N in $L^1$-$L^5$ may form a 5, 6 or 7 member homo- or heterocycle either saturated, unsaturated or aromatic optionally containing 1-3 additional heteroatoms selected from N, O and S, where any carbon or sulfur ring atom may optionally be oxidized, each cycle substituted with 0-3 $R^{31}$; and where s is 0-2; B is selected from the group:

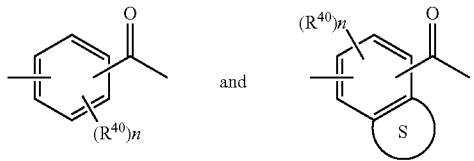

wherein

is a fused hetero- or homocyclic ring containing 5, 6 or 7 atoms, the ring being unsaturated, partially saturated or aromatic, the heteroatoms selected from 1-3 O, S and N, $Y_3$ is CH or $NR^{30}$; n is 0, 1, 3, or 3:

$G_3$ is hydrogen or $C_1$-$C_6$alkyl, optionally G taken together with T may form a $C_3$-$C_6$cycloalkyl optionally substituted with —V—W;

$T_3$ is one of the following
a naturally occurring α-amino-acid side chain,
and $U_4$-$Q_4$-$V_4$-$W_4$;

$U_4$ is an optionally substituted bivalent radical having one of the following structures:

$C_1$-$C_6$alkyl, $C_0$-$C_6$alkyl-Q, $C_2$-$C_6$alkenyl-Q, and$C_2$-$C_6$alkynyl-Q, where the substituents on any alkyl, alkenyl or alkynyl are 1-3 $R^{38}$;

$Q_4$ is absent or is —O—, —S(O)$_s$—, —SO$_2$—N(R$^{30}$)—, —N(R$^{30}$)—, —N(R$^{30}$)—C(=O)—, —N(R$^{30}$)—C(=O)—N(R$^{30}$)—,
—N(R$^{30}$)—C(=O)—O—, —N(R$^{30}$)—SO$_2$—, —C(=O)—, —C(=O)—O—,-het-, —C(O)—N(R$^{30}$)—,
—O—C(=O)—N(R30)-,-PO(OR30)O— or -P(O)O—;
where
s is 0-2 and
het is a mono- or bicyclic 5, 6, 7, 9 or 10 member heterocyclic ring, each ring containing 1-4 heteroatoms selected from N, O and S, where the heterocyclic ring may be saturated, partially saturated, or aromatic and any N or S being optionally oxidized, the heterocyclic ring being substituted with 0-3 $R^{41}$;

$V_4$ is absent or is an optionally substituted bivalent group with one of the following structures $C_1$-$C_6$alkyl, $C_3$-$C_8$cycloalkyl, $C_0$-$C_6$alkyl-$C_6$-$C_{10}$aryl, and $C_0$-$C_6$alky-het;

where the substituents on any alkyl are 1-3 $R^{38}$ and the substituents on any aryl or het are 1-3 $R^{31}$;

$W_4$ is hydrogen, $OR^{33}$, $SR^{42}$, $NR^{30}R^{30}$, NH—C(=O)—O—$R^{43}$, NH—C(=O)—NR"R", NH—C(=O)—$R^{43}$, NH—SO$_2$—$R^{37}$, NH—SO$_2$—$NR^{30}R^{30}$, NH—SO$_2$—NH—C(=O)—$R^{43}$, NH—C(=O)—NH—SO$_2$—$R^{37}$, C(=O)—NH—C(=O)—O—$R^{43}$, C(=O)—NH—C(=O—$R^{43}$, C(=O)—NH—C(=O)—$NR^{30}R^{30'}$, C(=O)—NH—SO$_2$—$R^{37}$, C(O)—NH—SO$_2$—$NR^{30}R^{30}$, C(=S)—$NR^{30}R^{30}$, $SO^2$—$R^{37}$, SO$_2$—O—$R^{37}$, $SO^2$—$NR^{37}R^{37'}$, SO$_2$—NH—C(=O)—O—$R^{43}$, SO$_2$—NH—C(=O)—$NR^{30}R^{30'}$, SO$_2$—NH—C(=O)—$R^{43}$, O—C(=O—$NR^{30}R^{30'}$, O—C(=O)—$R^{43}$, O—C(=O)—NH—C(=O)—$R^{43}$, O—C(=O)—NH—SO$_2$R$^{46}$ r O—SO$_2$—$R^{37}$;

$R^{44}$ is C(=O)—$R^{45}$, C(=O)—H, CH$_2$(OH), or CH$_2$O—C(=O)—$C_1$-$C_6$alkyl;

$R^{38}$ is $R^{38'}$ or $R^{38''}$ substituted with 1-3 $R^{38'}$; where $R^{38'}$ is hydrogen, halo (F, Cl, Br, I), cyano, isocyanate, carboxy, carboxy-$C_1$-$C_{11}$alkyl, amino, amino-$C_1$-$C_8$alkyl, aminocarbonyl, carboxamido, carbamoyl, carbamoyloxy, formyl, formyloxy, azido, nitro, imidazoyl, ureido, thioureido, thiocyanato, hydroxy, $C_1$-$C_6$alkoxy, mercapto, sulfonamido, het, phenoxy, phenyl, benzamido, tosyl, morpholino, morpholinyl, piperazinyl, piperidinyl, pyrrolinyl, imidazolyl, or indolyl;

$R^{38''}$ is $C_0$-$C_{10}$alkyl-Q-$C_0$-$C_6$alkyl, $C_0$-$C_{10}$alkenyl-Q-$C_0$-$C_6$alkyl, $C_0$-$C_{10}$alkynyl-Q-$C_0$-$C_6$alkyl, $C_3$-$C_{11}$cycloalkyl-Q-$C_0$-$C_6$alkyl, $C_3$-$C_{10}$cycloalkenyl-Q-$C_0$-$C_6$alkyl, $C_1$-$C_6$alkyl-$C_6$-$C_{12}$aryl-Q-$C_0$-$C_6$alkyl, $C_6$-$C_{10}$ aryl-$C_1$-$C_6$alkyl-Q-$C_0$-$C_6$alkyl, $C_0$-$C_6$alkyl-het-Q-$C_0$-$C_6$alkyl, $C_0$-$C_6$alkyl-Q-het-$C_0$-$C_6$alkyl, het-$C_0$-$C_6$alkyl-Q-$C_0$-$C_6$alkyl, $C_0$-$C_6$alkyl-Q-$C_6$-$C_{12}$aryl, or -Q-$C_1$-$C_6$alky;

$R^{43}$ is hydrogen and substituted or unsubstituted $C_1$-$C_{10}$alkyl, $C_2$-$C_{10}$alkenyl, $C_2$-$C_{10}$alkynyl, $C_3$-$C_{11}$cycloalkyl, $C_3$-$C_{10}$cycloalkenyl, $C_1$-$C_6$alkyl-$C_6$-$C_{12}$aryl, $C_6$-$C_{10}$aryl-$C_1$-$C_6$alkyl, $C_1$-$C_6$alkyl-het, het-$C_1$-$C_6$alkyl, $C_6$-$C_{12}$aryl or het, where the substituents on any alkyl, alkenyl or alkynyl are 1-3 $R^{38}$ and the substituents on any aryl or het are 1-3 $R^{31}$; $R^{31}$ is $R^{40}$ or $R^{41}$;

$R^{41}$ is OH, OCF$_3$, OR$^{43}$, SR$^{42}$, halo(F, Cl, Br, I), CN, isocyanate, NO$_2$, CF$_3$, $C_0$-$C_6$alkyl-$NR^{30}R^{30'}$, $C_0$-$C_6$alkyl-C(=O)—$NR^{30}R^{30'}$, $C_0$-$C_6$alkyl-C(=O)—$R^{38}$, $C_1$-$C_8$alkyl, $C_1$-$C_8$alkoxy, $C_2$-$C_8$alkenyl, $C_2$-$C_8$alkynyl, $C_3$-$C_6$cycloalkyl, $C_3$-$C_6$cycloalkenyl, $C_1$-$C_6$alkyl-phenyl, phenyl-$C_1$-$C_6$alkyl, $C_1$-$C_6$alkyloxycarbonyl, phenyl-$C_0$-$C_6$alkyloxy, $C_1$-$C_6$alkyl-het, het-$C_1$-$C_6$alkyl, SO$_2$-het, —O—$C_6$-$C_{12}$aryl, —SO$_2$—$C_6$-$C_6$-$C_{12}$aryl, —SO$_2$—$C_1$-$C_6$alkyl or het, where any alkyl, alkenyl or alkynyl may optionally be substituted with 1-3 groups selected from OH, halo(F, Cl, Br, I), nitro, amino and aminocarbonyl and the substituents on any aryl or het are 1-2 hydroxy, halo(F, Cl, Br, I), CF$_3$, $C_1$-$C_6$alkyl, $C_1$-$C_6$alkoxy, nitro and amino;

$R^{42}$ is S—$C_1$-$C_6$alkyl, C(=O)—$C_1$-$C_6$alkyl, C(=O)—$NR^{30}R^{30'}$, $C_1$-$C_6$alkyl, halo(F, Cl, Br, I)—$C_1$-$C_6$alkyl, benzyl or phenyl;

$R^{30}$ is $R^{43}$, NH—C(=O)—O—$R^{43}$, NH—C(=O)—$R^{43}$, NH—C(=O)—$NHR^{43}$, NH—SO$_2$—$R^{46}$, NH—SO$_2$—NH—C(=O)—$R^{43}$, NH—C(=O)—NH—SO$_2$—$R^{37}$, C(=O)—O—$R^{43}$, C(=O)—$R^{43}$, C(=O)—$NHR^{43}$, C(=O)—NH—C(=O)—O—$R^{43}$, C(=O)—NH—C(=O)—$R^{43}$, C(=O)—NH—SO$_2$—$R^{46}$, C(=O)—NH—SO$_2$—$NHR^{37}$, SO$_2$—$R^{37}$, SO$_2$—O—$R^{37}$, SO$_2$—N(R$^{43}$)$_2$, SO$_2$—NH—C(=O)—O—$R^{43}$, SO$_2$—NH—C(=O)—O—$R^{43'}$ or SO$_2$—NH—C(=)—$R^{43}$;

$R^{30'}$ is hydrogen, hydroxy and substituted or unsubstituted $C_1$-$C_{11}$alkyl, $C_1$-$C_{11}$alkoxy, $C_2$-$C_{10}$alkenyl, $C_2$-$C_{10}$alkynyl, $C_3$-$C_{11}$cycloalkyl, $C_3$-$C_{10}$cycloalkenyl, $C_1$-$C_6$alkyl-$C_6$-

$C_{12}$aryl, $C_6$-$C_{10}$aryl-$C_1$-$C_6$ alkyl, $C_6$-$C_{10}$aryl-$C_0$-$C_6$alkyloxy, $C_1$-$C_6$alkyl-het, het-$C_1$-$C_6$alkyl, $C_6$-$C_{12}$aryl, het, $C_1$-$C_6$alkylcarbonyl, $C_1$-$C_8$alkoxycarbonyl, $C_3$-$C_8$cycloalkylcarbonyl, $C_3$-$C_8$cycloalkoxycarbonyl, $C_6$-$C_{11}$aryloxycarbonyl, $C_7$-$C_{11}$arylalkoxycarbonyl, heteroarylalkoxycarbonyl, heteroarylalkylcarbonyl, heteroarylcarbonyl, heteroarylalkylsulfonyl, heteroarylsulfonyl, $C_1$-$C_6$alkylsulfonyl, or $C_6$-$C_{10}$ arylsulfonyl, where the substituents on any alkyl, alkenyl or alkynyl are 1-3 $R^{38}$ and the substituents on any aryl, het or heteroaryl are 1-3 $R^{31}$;

$R^{30}$ and $R^{30'}$ taken together with the common nitrogen to which they are attached may from an optionally substituted heterocycle having one of the following structures morpholinyl, piperazinyl, thiamorpholinyl, pyrrolidinyl, imidazolidinyl, indolinyl, isoindolinyl, 1,2,3,4-tetrahydro-quinolinyl, 1,2,3,4-tetrahydro-isoquinolinyl, thiazolidinyl or azabicyclononyl, where the substituents are 1-3 $R^{38}$;

$R^{33}$ is hydrogen and substituted or unsubstituted $C_1$-$C_6$alkyl, $C_1$-$C_6$alkylcarbonyl, $C_2$-$C_6$alkenyl, $C_2$-$C_6$alkynyl, $C_3$-$C_8$cycloalkyl or benzoyl, where the substituents on any alkyl are 1-3 $R^{38}$ and the substituents on any aryl are 1-3 $R^{40}$; $R^{40}$ is OH, halo(F, Cl, Br, I), CN, isocyanate, $OR^{43}$, $SR^{42}$, $SOR^{43}$, $NO_2$, $CF_3$, $R^{43}$, $NR^{30}R^{30'}$, $NR^{30}C(=O)$—O—$R^{43}$, $NRC(=O)$—$R^{43}$, $C_0$-$C_6$alkyl-$SO_2$—$R^{43}$, $C_0$-$C_6$alkyl-$SO_2$—$NR^{30}R^{30'}$, $C(=O)$—$R^{43}$, O—$C(=O)$—$R^{43}$, $C(=O)$—O—$R^{43}$, or $C(=O)$—$NR^{30}R^{30'}$, where the substituents on any alkyl, alkenyl or alkynyl are 1-3 $R^{38}$ and the substituents on any aryl or het are 1-3 $R^{31}$;

$R^{46}$ is a substituted or unsubstituted $C_1$-$C_8$alkyl, $C_2$-$C_8$alkenyl, $C_2$-$C_8$alkynyl, $C_3$-$C_8$cycloalkyl, $C_3$-$C_6$cycloalkenyl, $C_0$-$C_6$alkyl-phenyl, phenyl-$C_0$-$C_6$alkyl, $C_0$-$C_6$alkyl-het or het-$C_0$-$C_6$alkyl, where the substituents on any alkyl, alkenyl or alkynyl are 1-3 $R^{38}$ and the substituents on any aryl or het are 1-3 $R^{31}$;

$R^{45}$ is a substituted or unsubstituted hydroxy, $C_1$-$C_{11}$alkoxy, $C_3$-$C_{12}$cycloalkoxy, $C_8$-$C_{12}$aralkoxy, $C_8$-$C_{12}$arcycloalkoxy, $C_6$-$C_{10}$aryloxy, $C_3$-$C_{10}$ alkylcarbonyloxyalkyloxy, $C_3$-$C_{10}$ alkoxycarbonyloxyalkyloxy, $C_3$-$C_{10}$alkoxycarbonylalkyloxy, $C_5$-$C_{10}$cycloalkylcarbonyloxyalkyloxy, $C_5$-$C_{10}$cycloalkoxycarbonyloxyalkyloxy, $C_5$-$C_{10}$cycloalkoxycarbonylalkyloxy, $C_8$-$C_{12}$aryloxycarbonylalkyloxy, $C_8$-$C_{12}$aryloxycarbonyloxyalkyloxy, $C_8$-$C_{12}$arylcarbonyloxyalkyloxy, $C_5$-$C_{10}$alkoxyalkylcarbonyloxyalkyloxy, $(R^{30})(R^{30})N(C_1$-$C_{10}$alkoxy)-,

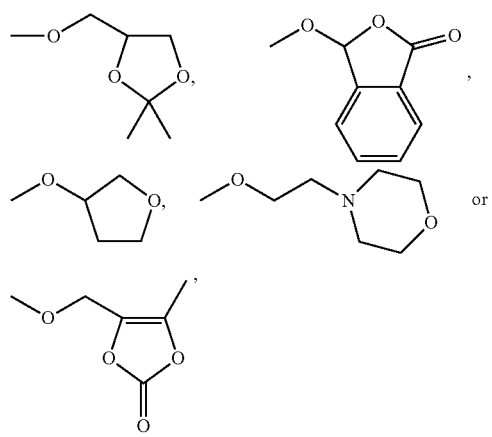

where the substituents on any alkyl, alkenyl or alkynyl are 1-3 $R^{38}$ and the substituents on any aryl or het are 1-3 $R^{31}$ and pharmaceutically acceptable salts thereof.

Compounds of Formulas I-VI also include pharmaceutically acceptable salts, and esters including pro-drug compounds of Formula I-VI, where $R^{34}$, $R^5$ $R^{10}$, $R^{17}$, $R^{18}$, $R^{19}$, $R^{20}$, $R^{21}$, $R^{29}$, and a carboxylic ester at $R^{44}$ may be lower alkyl or —$CH_2CH_2$—$R^{22}$ where $R^{22}$ is one of the following:

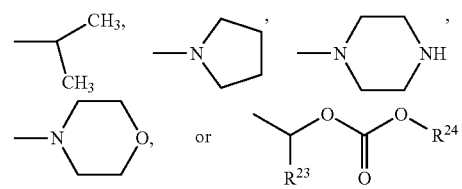

where $R^{23}$ is hydrogen or methyl and $R^{24}$ is lower alkyl or lower cycloalkyl.

A preferred embodiment of compounds of Formula VI has the stereochemistry indicated in Formula VI'.

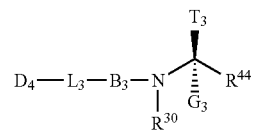

Formula VI'

Compounds of the class of Formula VI are disclosed in U.S. Patent Application Publication No. 20050203135.

Some of the compounds described herein may comprise one or more asymmetric centers, and thus may comprise individual stereoisomers, individual diastereomers and any mixtures therein. Further, compounds of the invention may contain geometric isomers of double bonds, comprising Z and E isomers, and may be present as pure geometric isomers or mixtures thereof.

In some preferred embodiments, the methods of the present invention are performed with the following compounds:

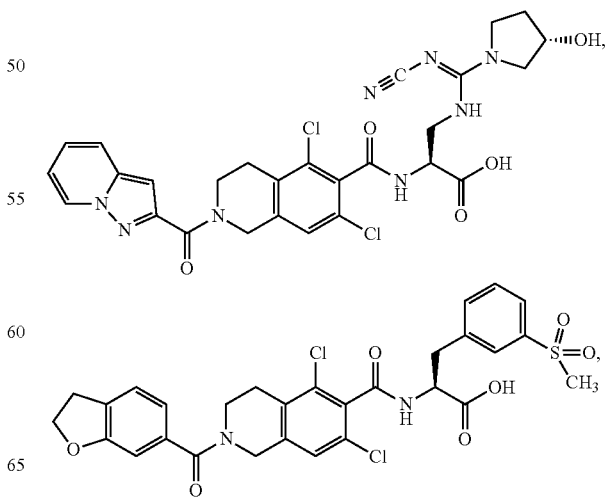

59
-continued
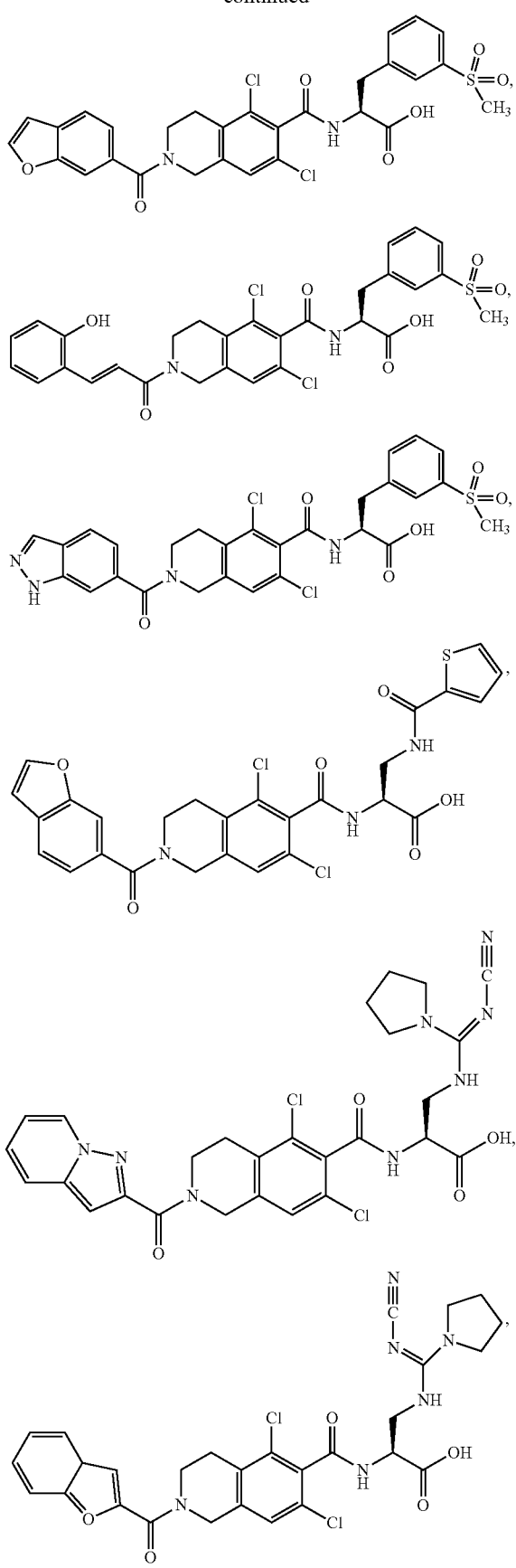
60
-continued
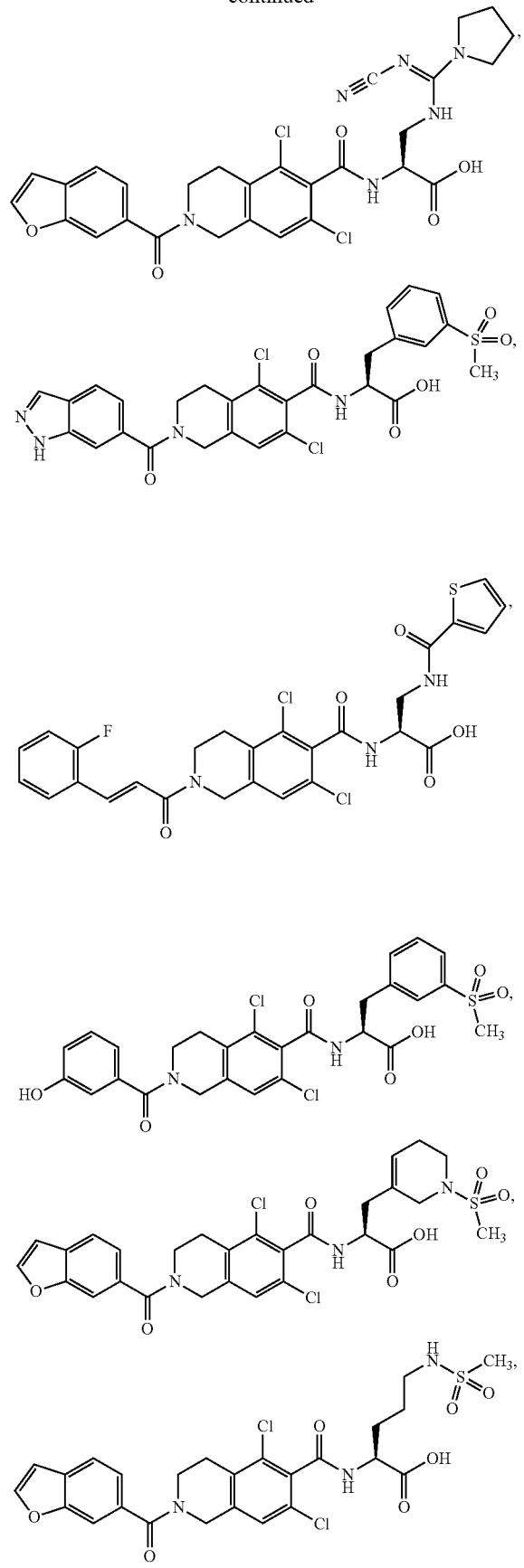

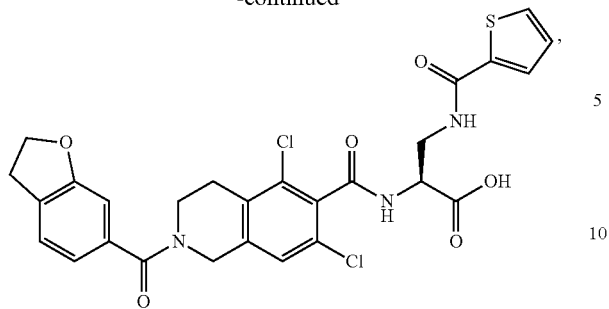
and their pharmaceutically acceptable salts and esters.
Compounds of the present invention include the following compounds:
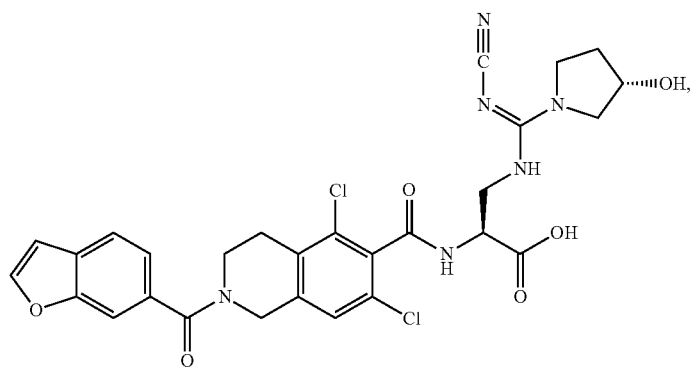
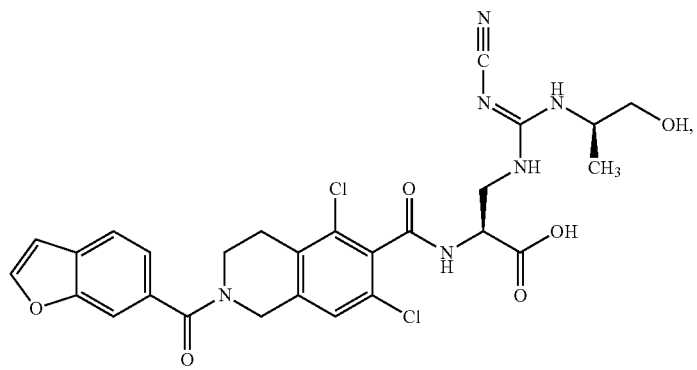
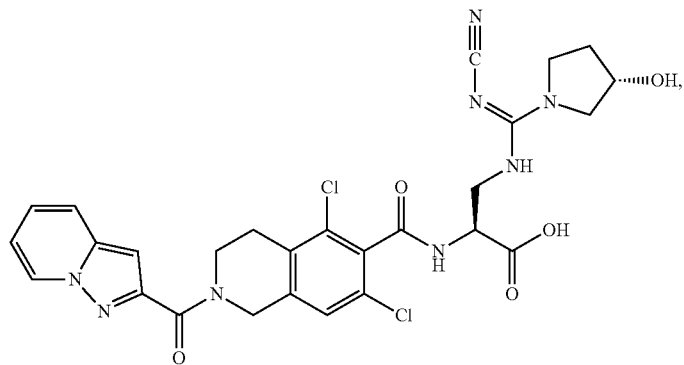

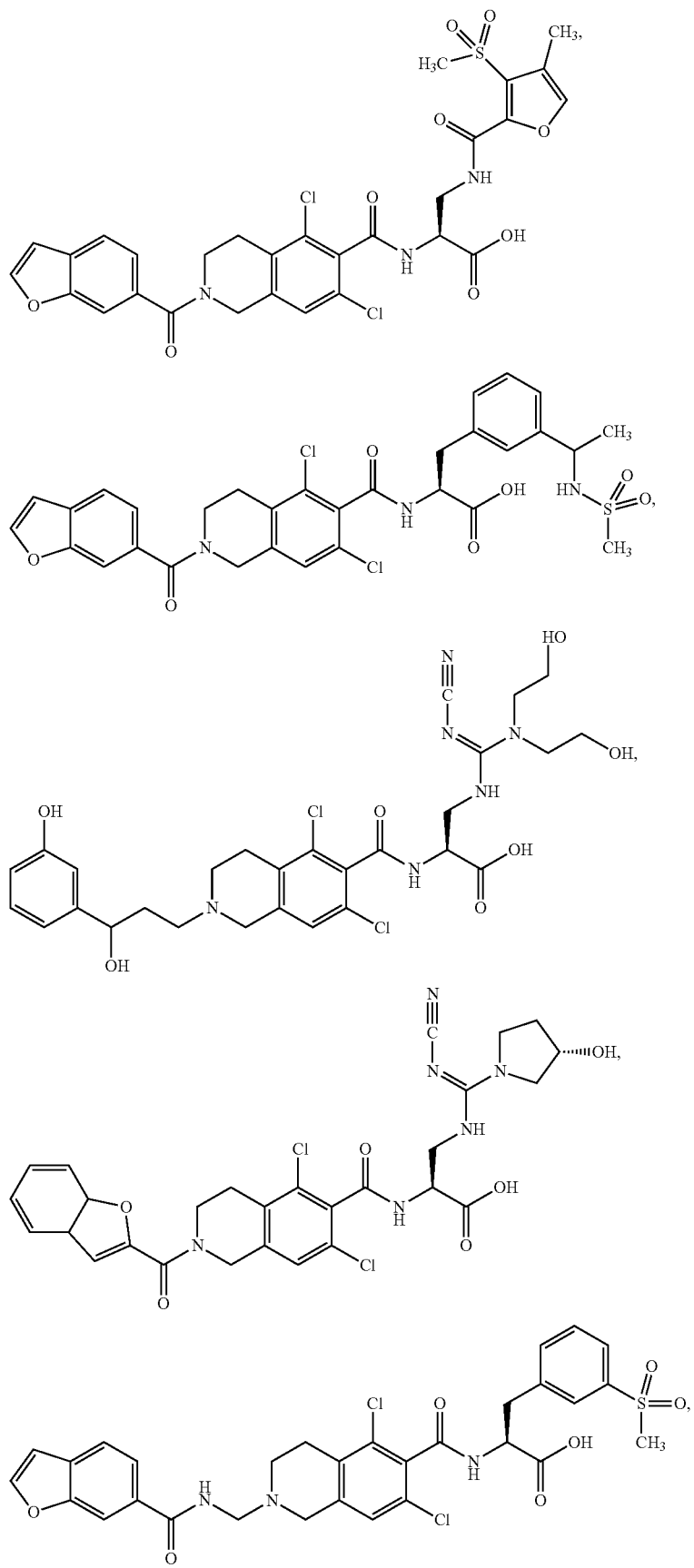

-continued
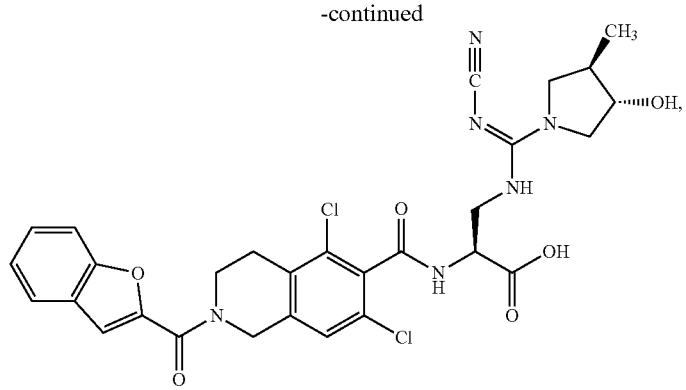
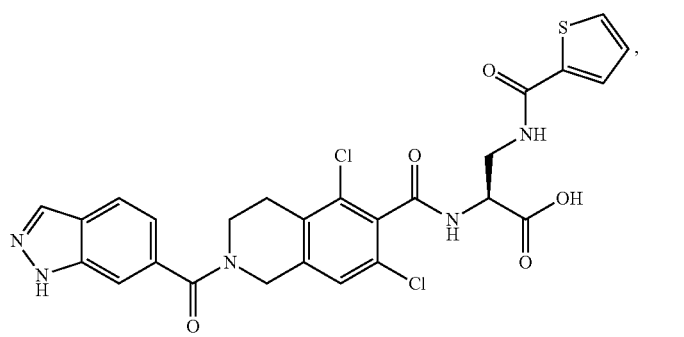
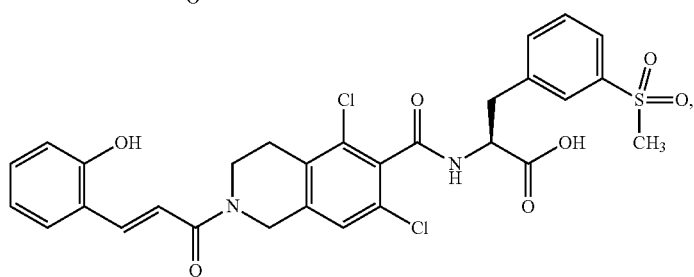
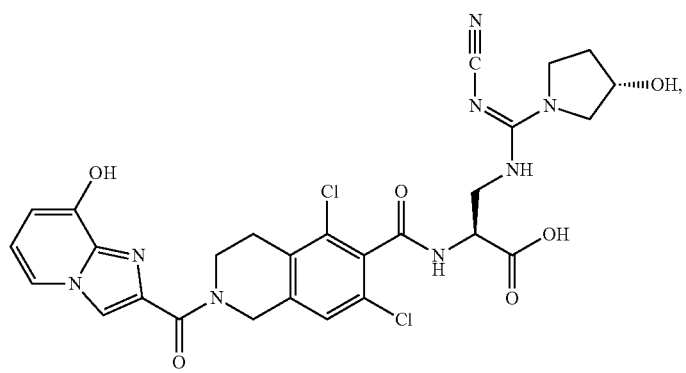
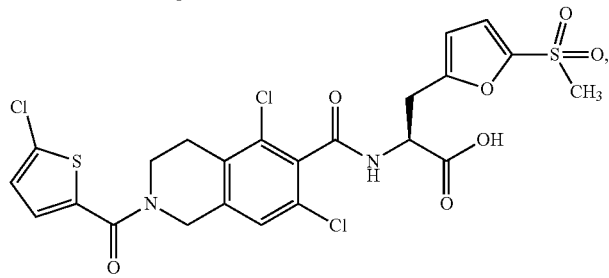

-continued
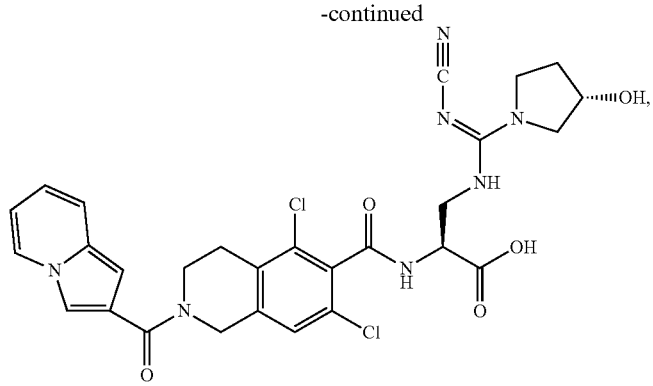
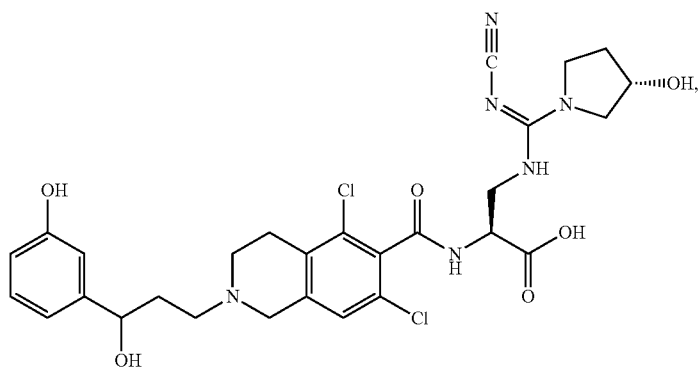
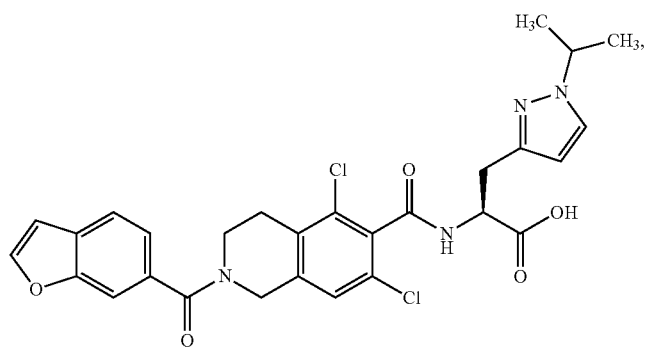
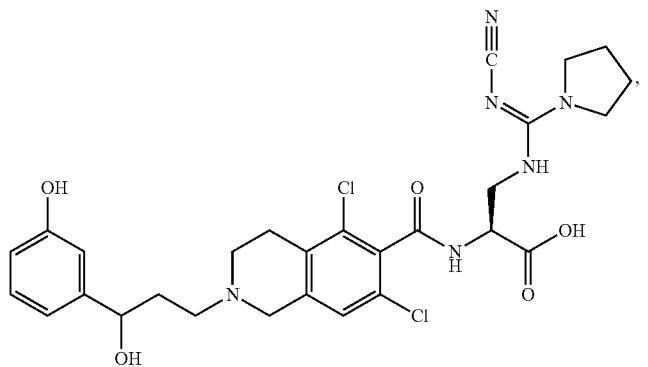

-continued
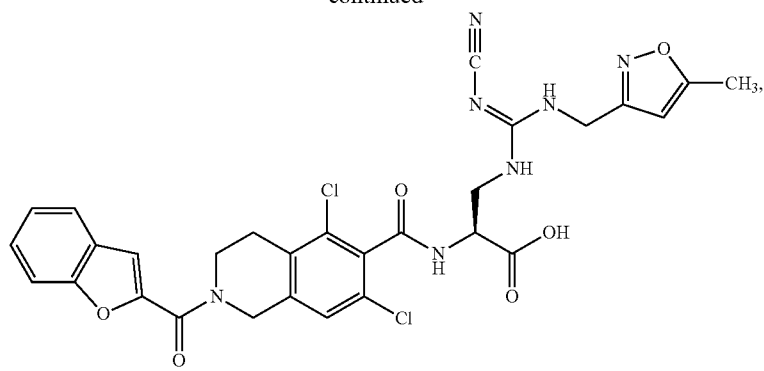
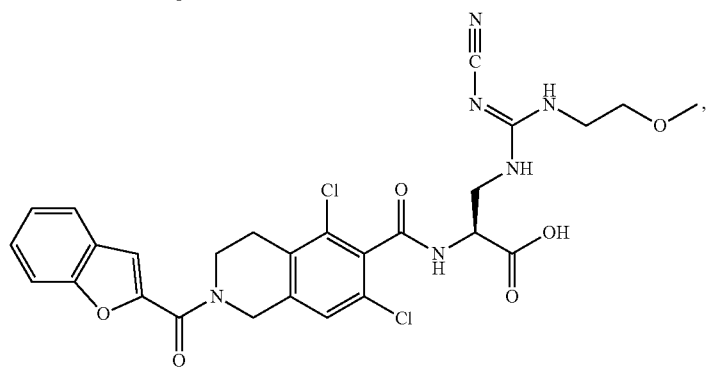
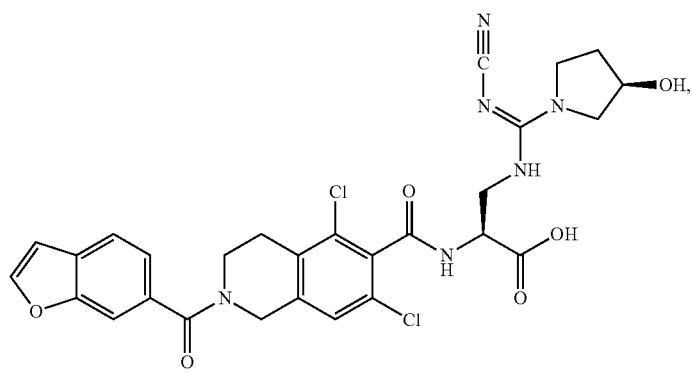
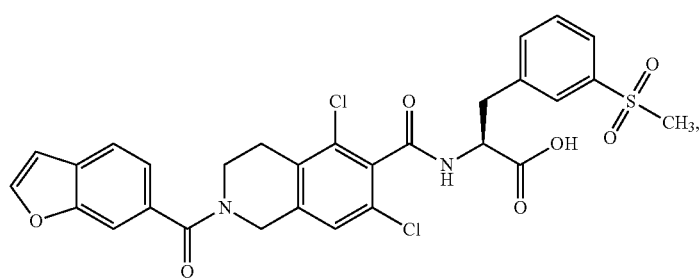
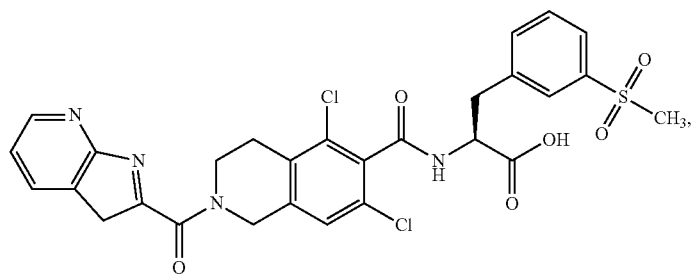

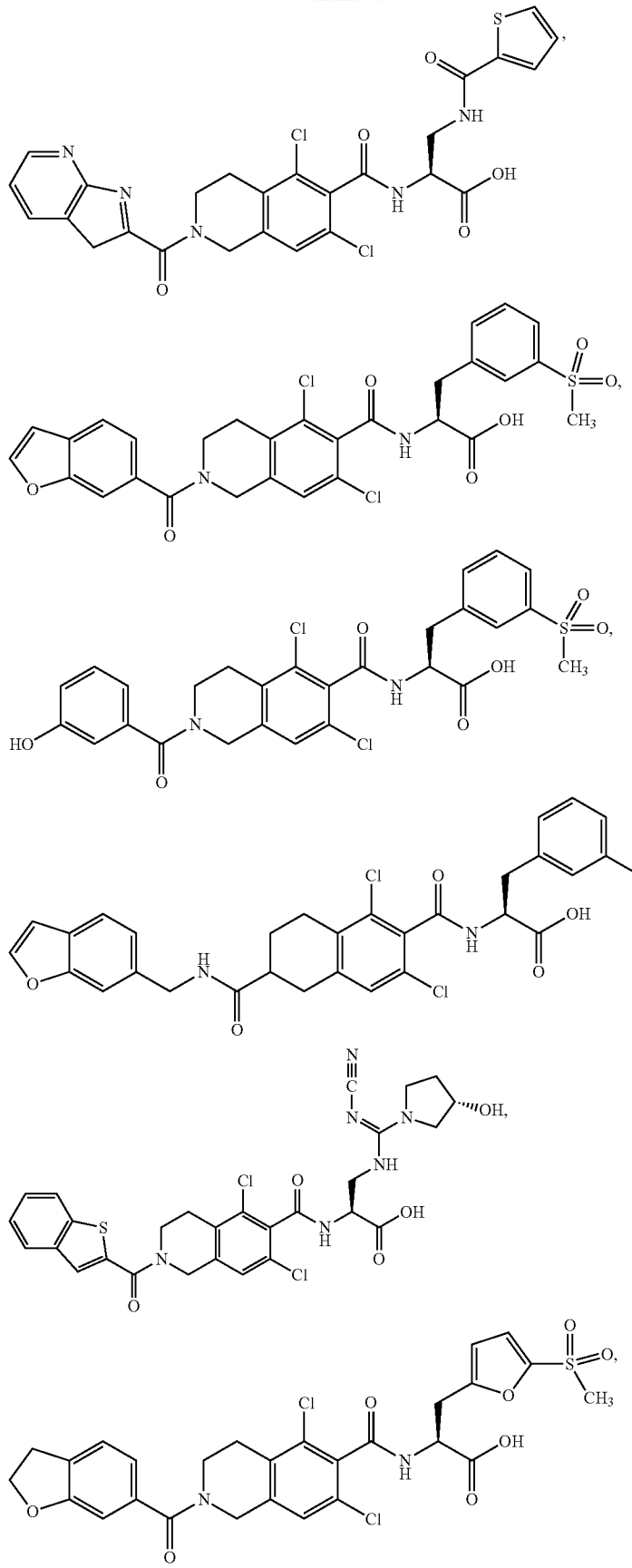

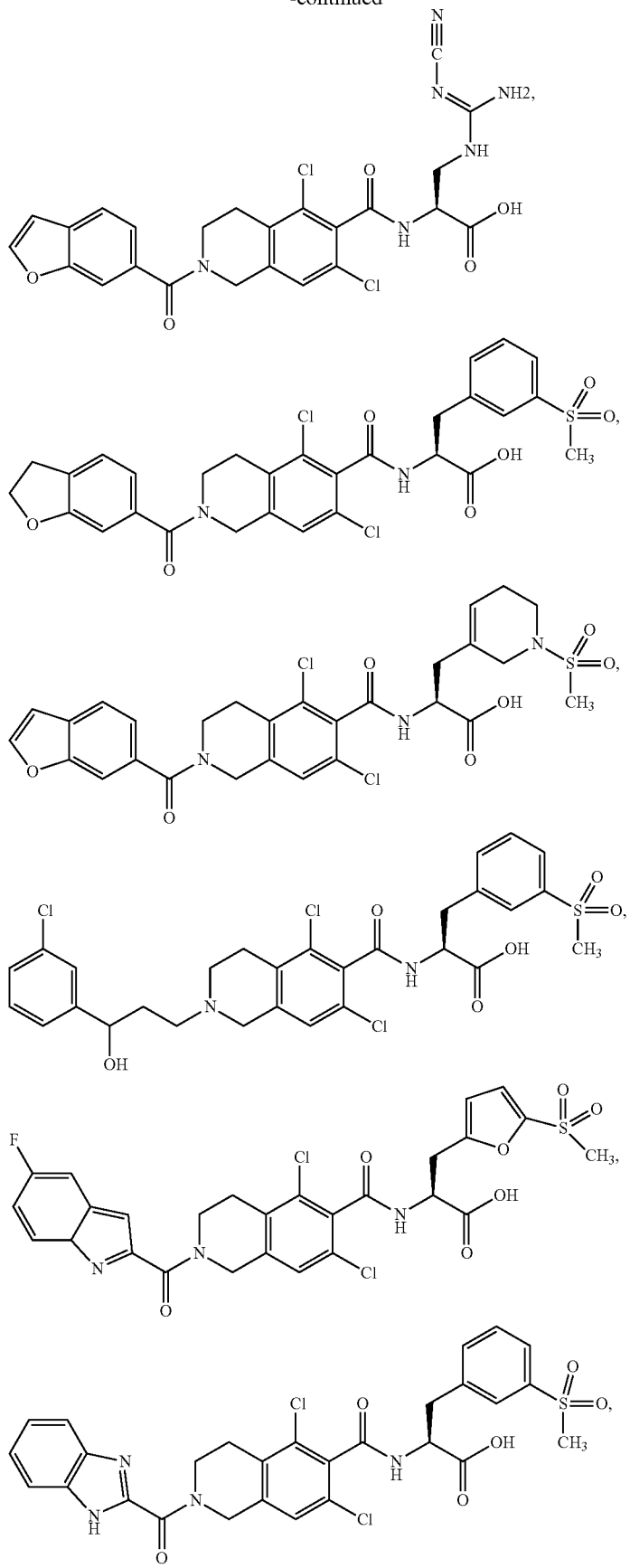

-continued
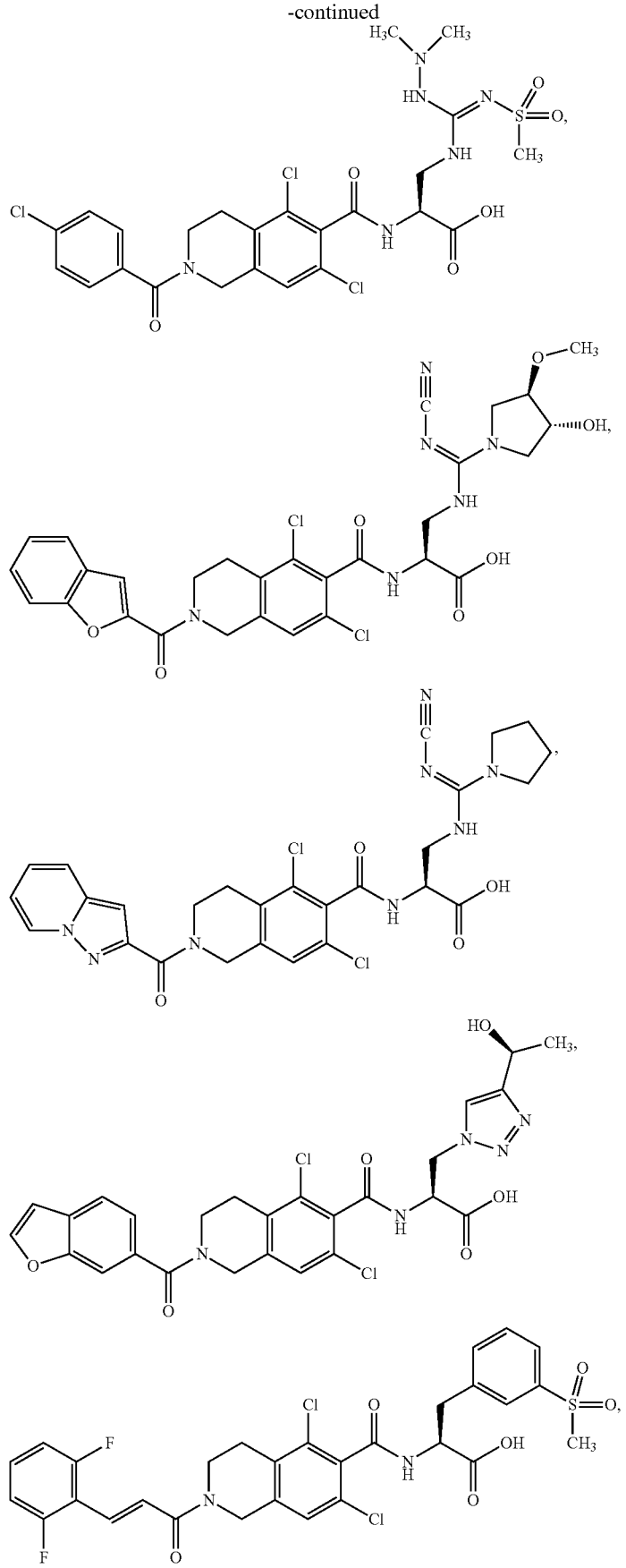

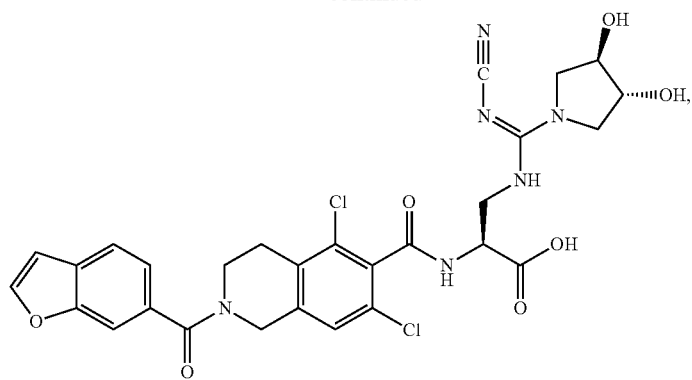
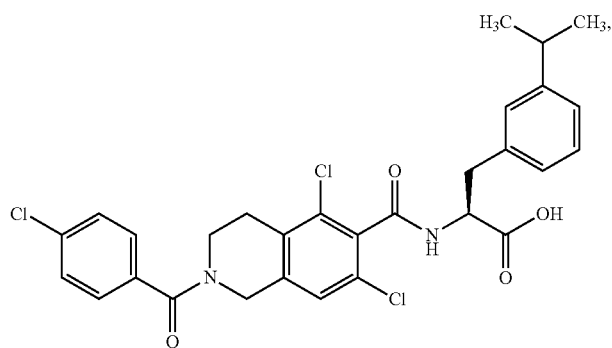
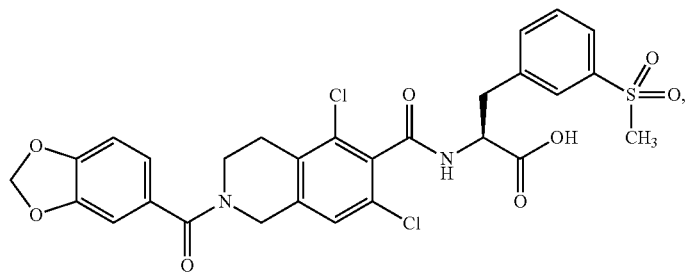
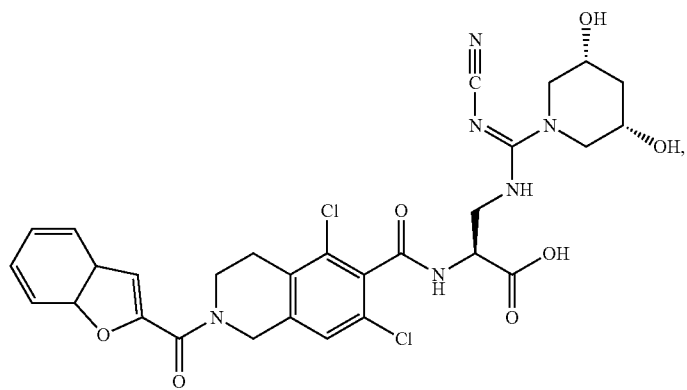

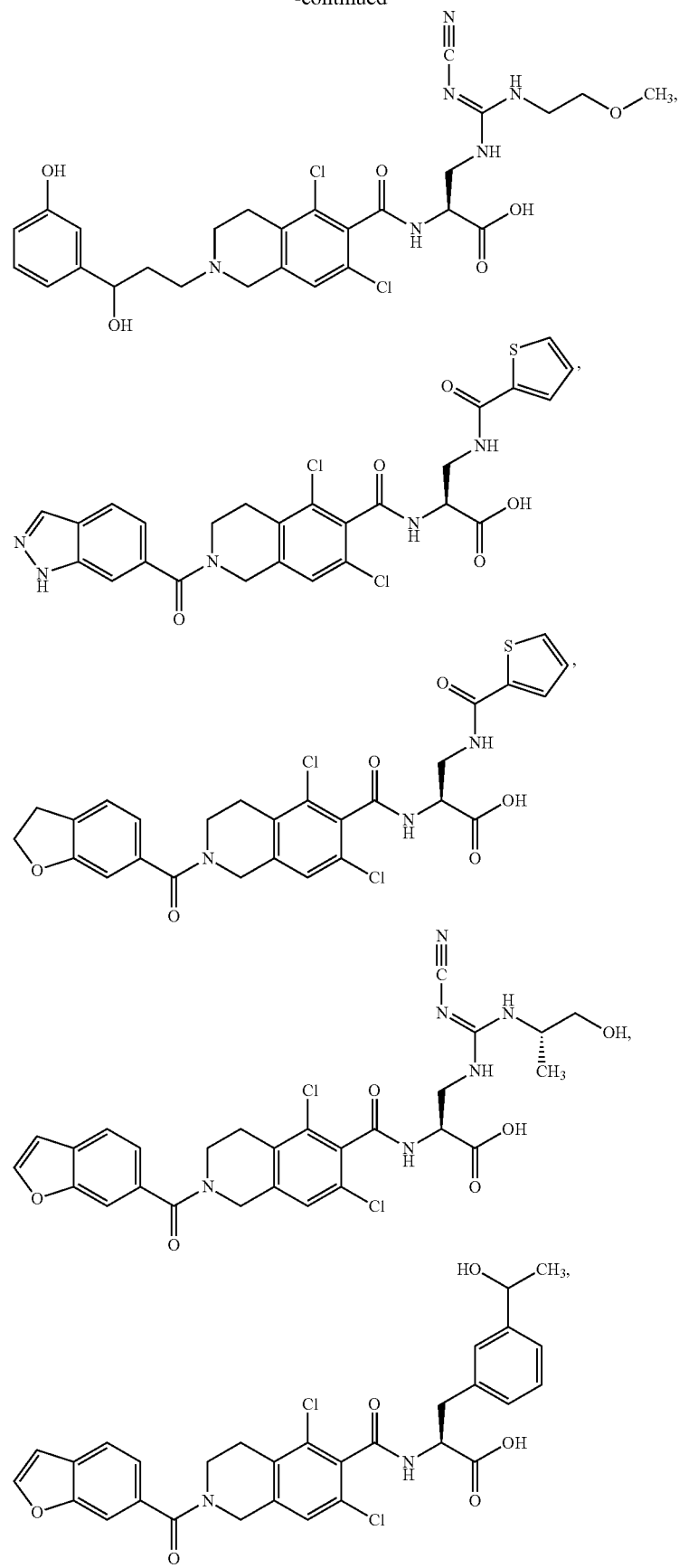

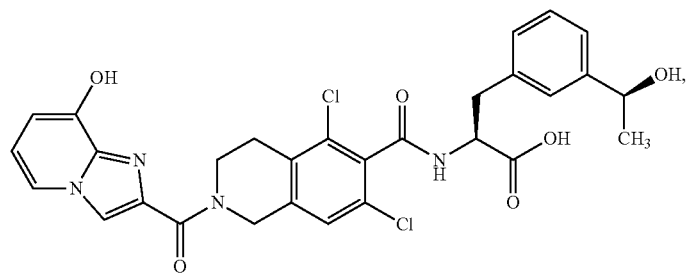
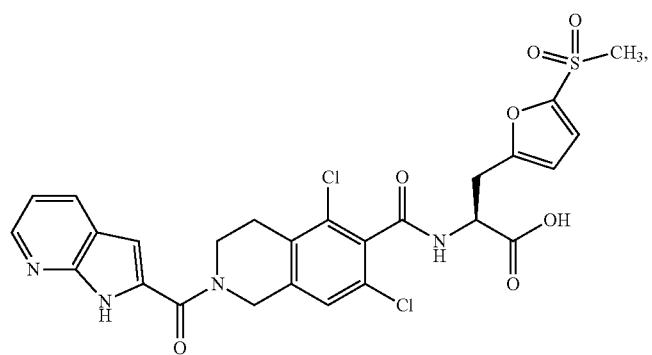
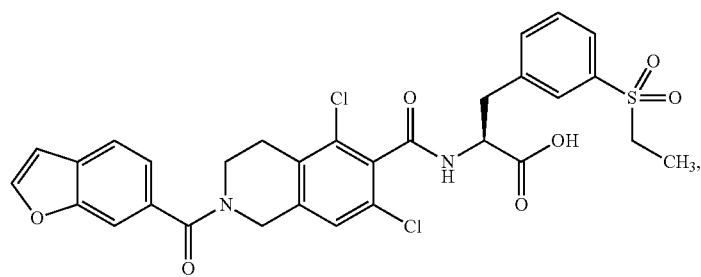
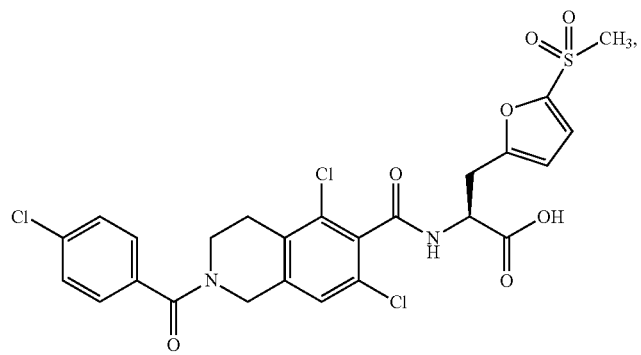
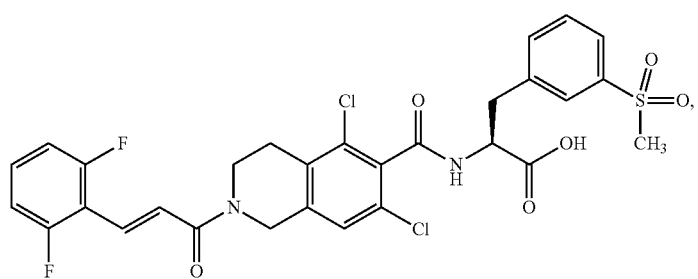

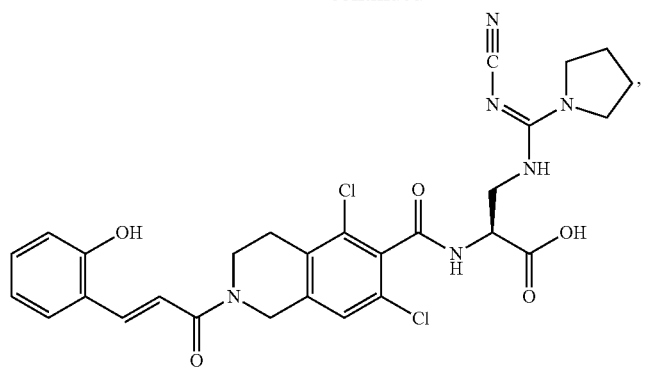
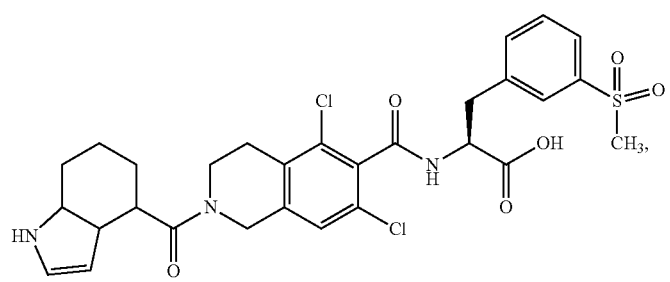
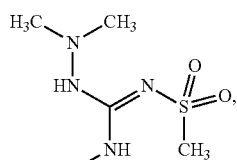
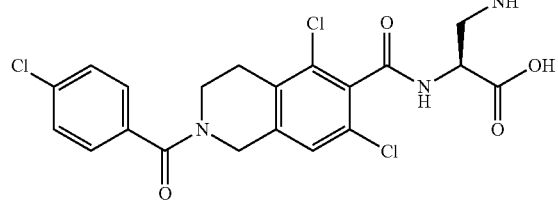
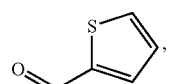
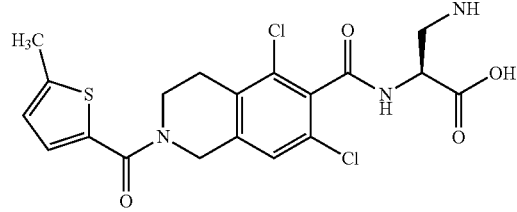
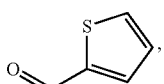
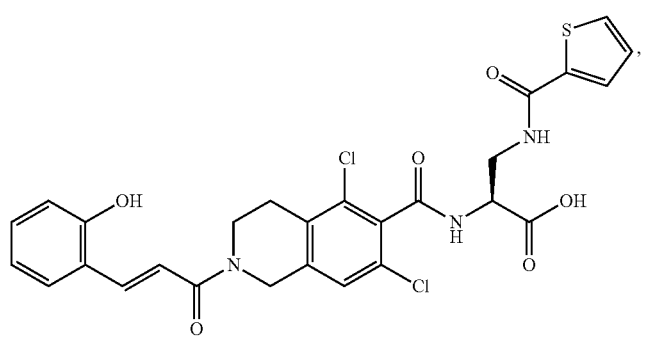

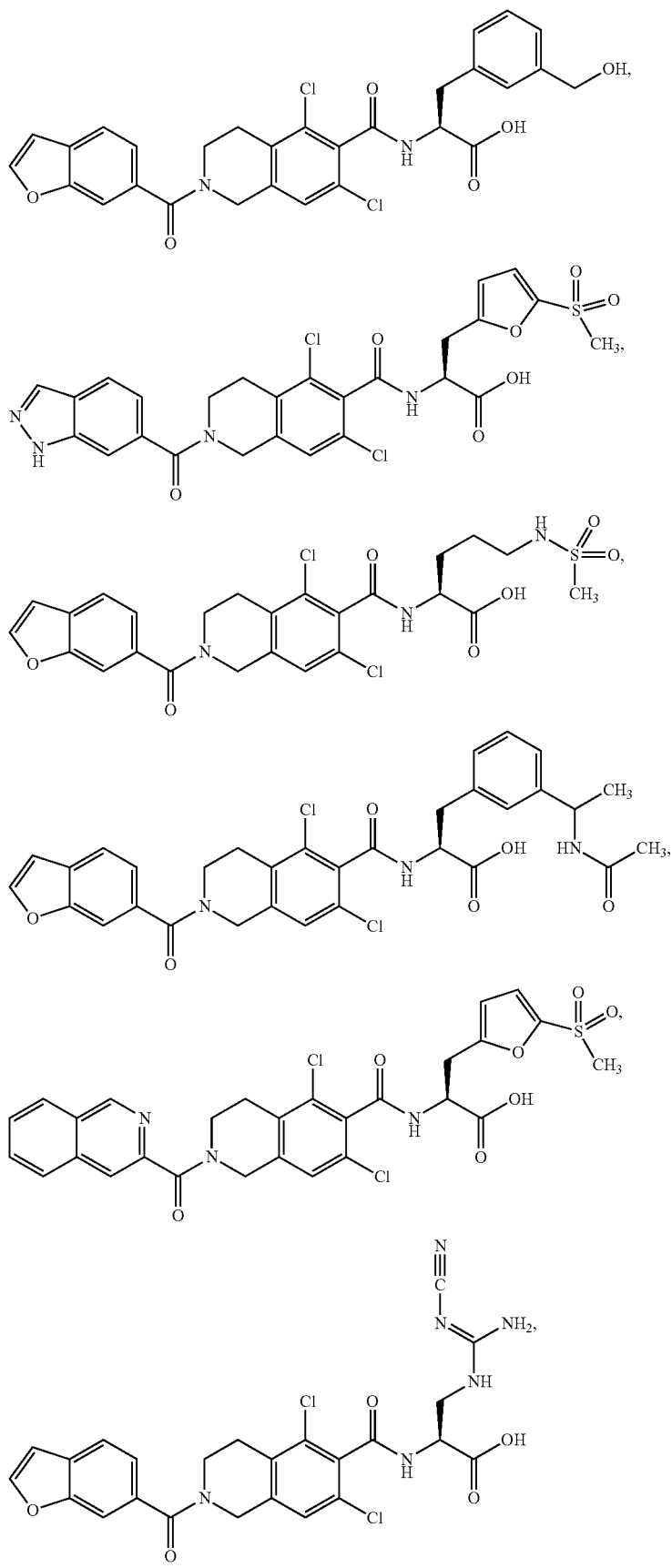

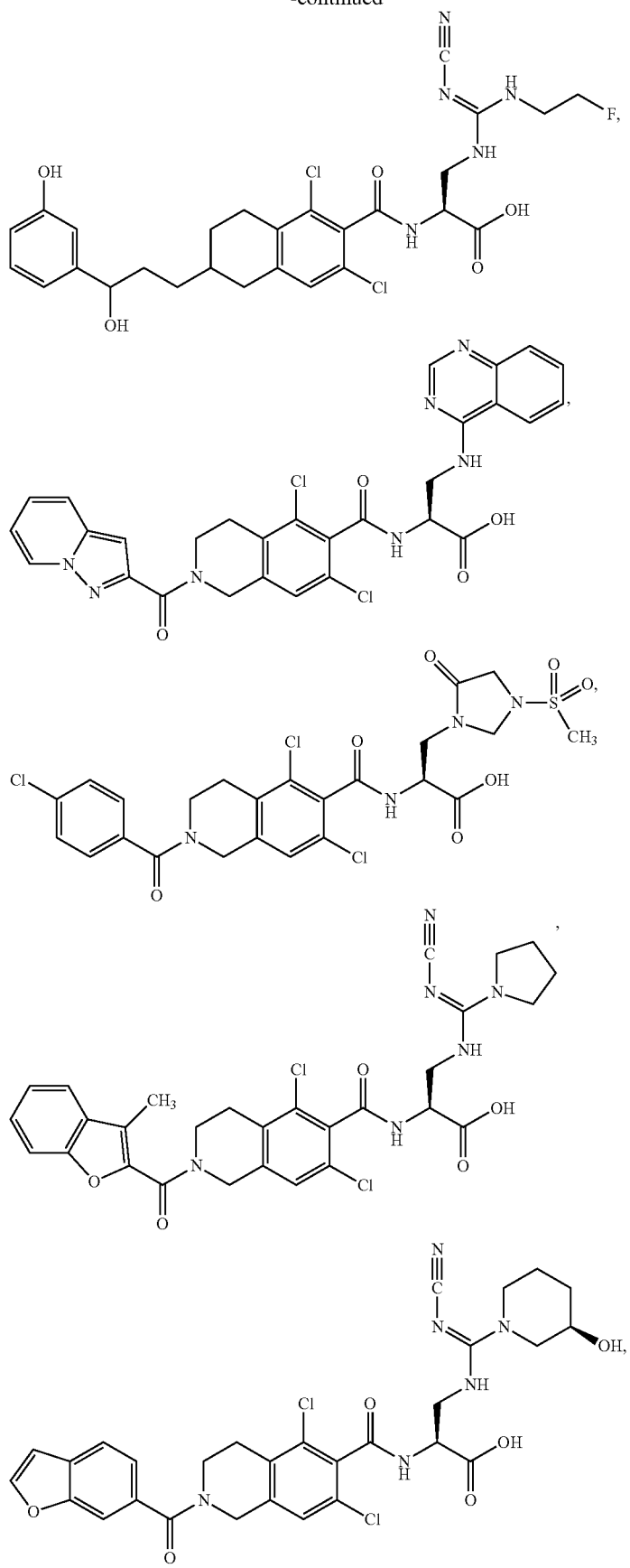

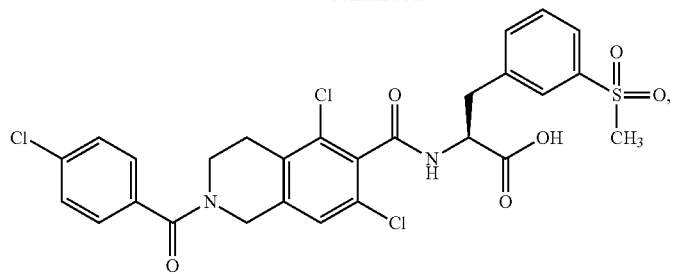
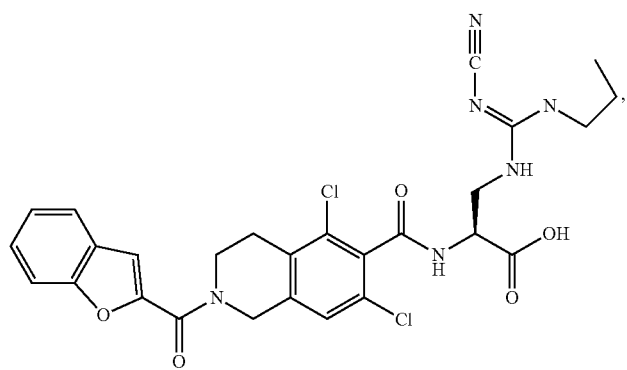
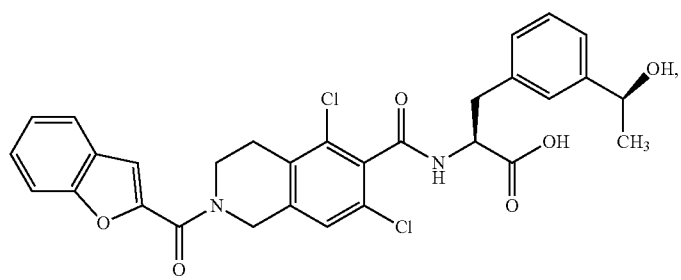
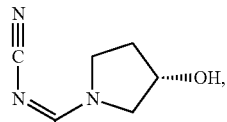
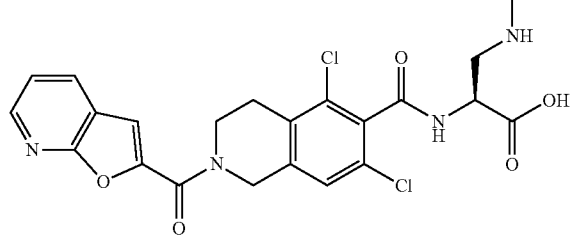
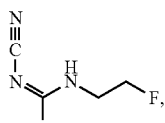
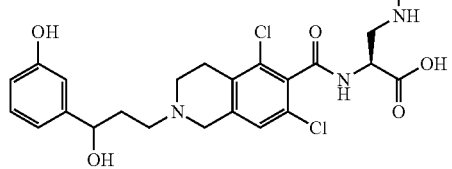

-continued
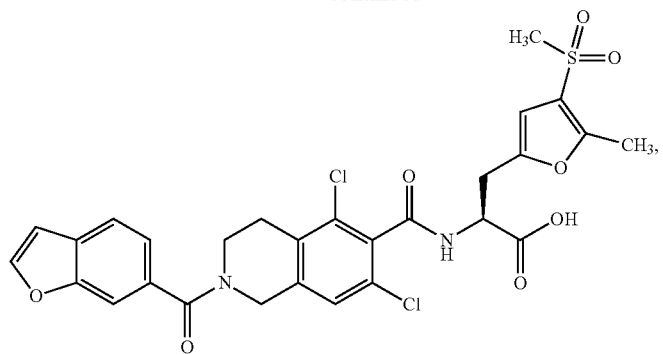
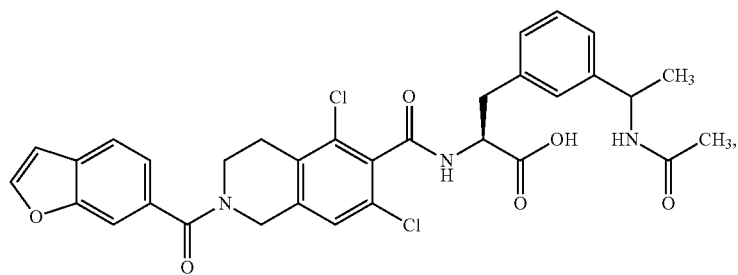
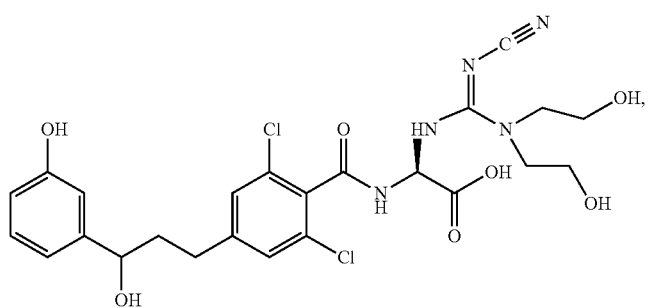
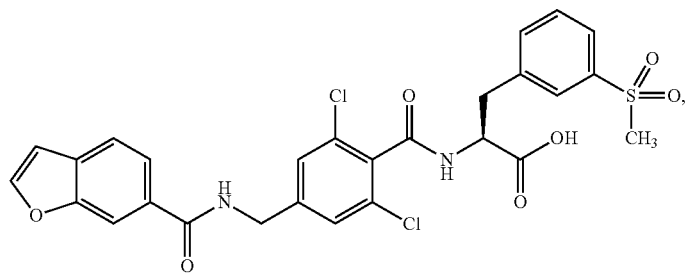
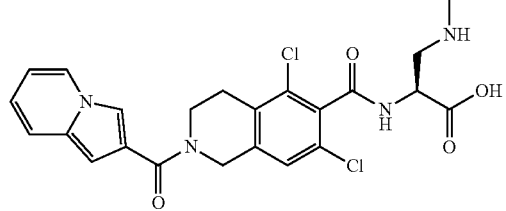

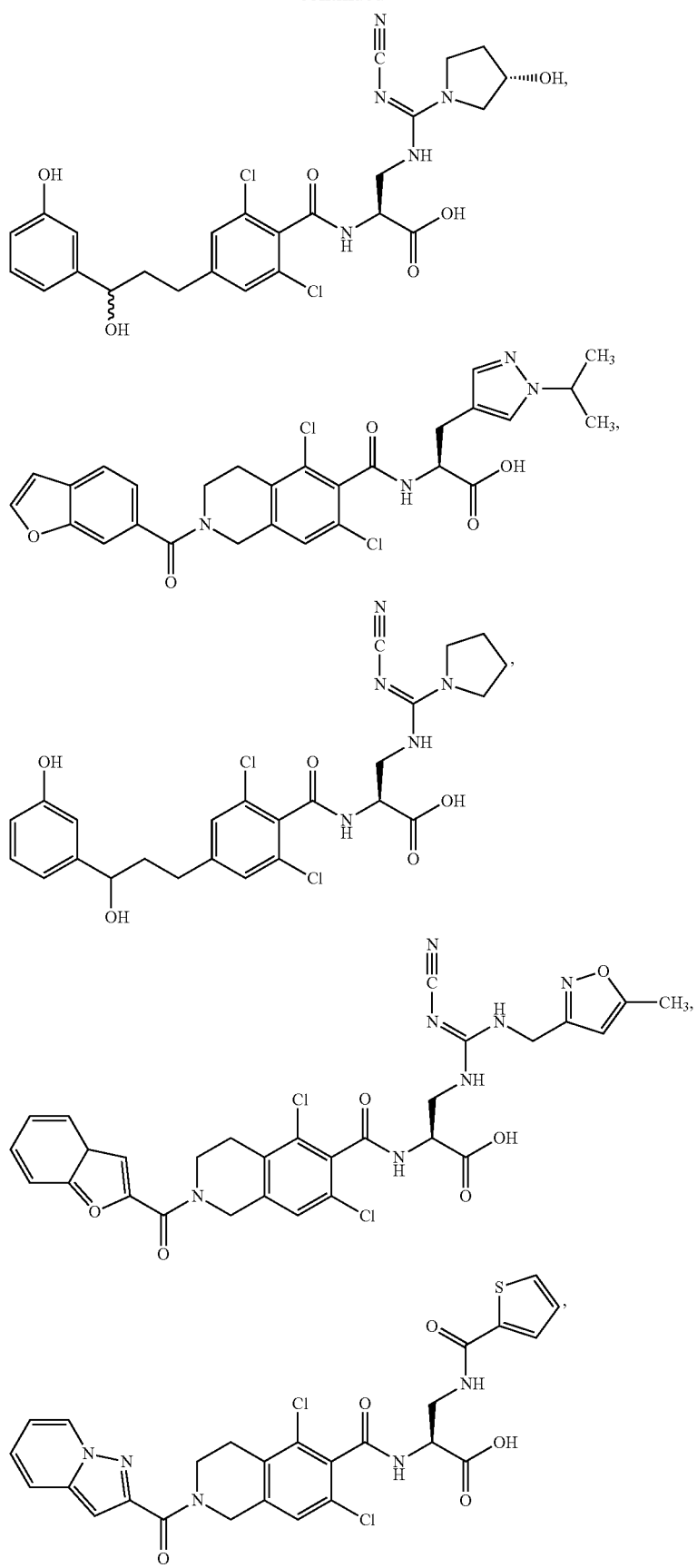

-continued
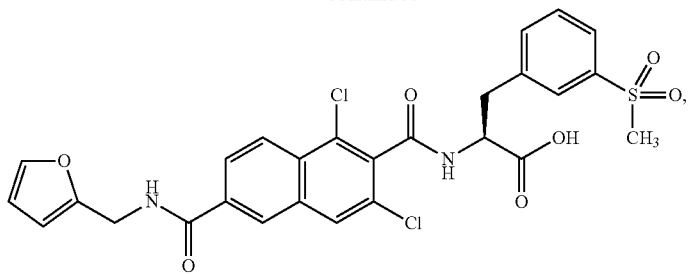
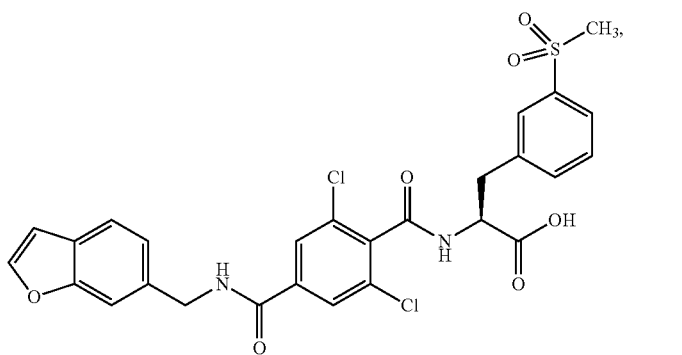
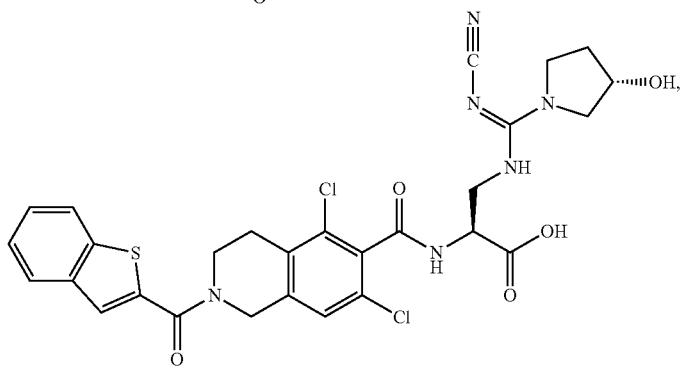
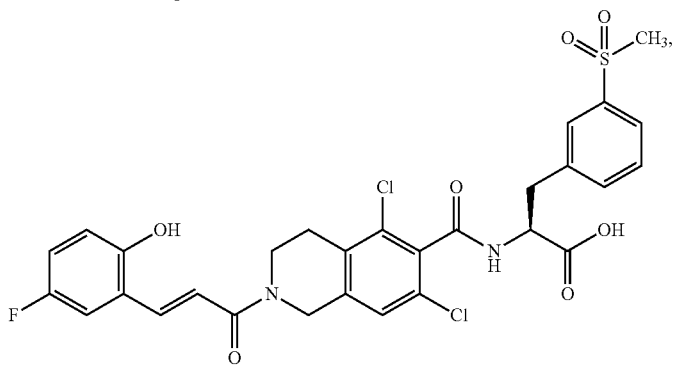
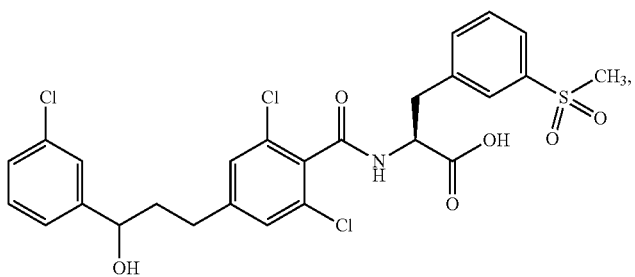

-continued
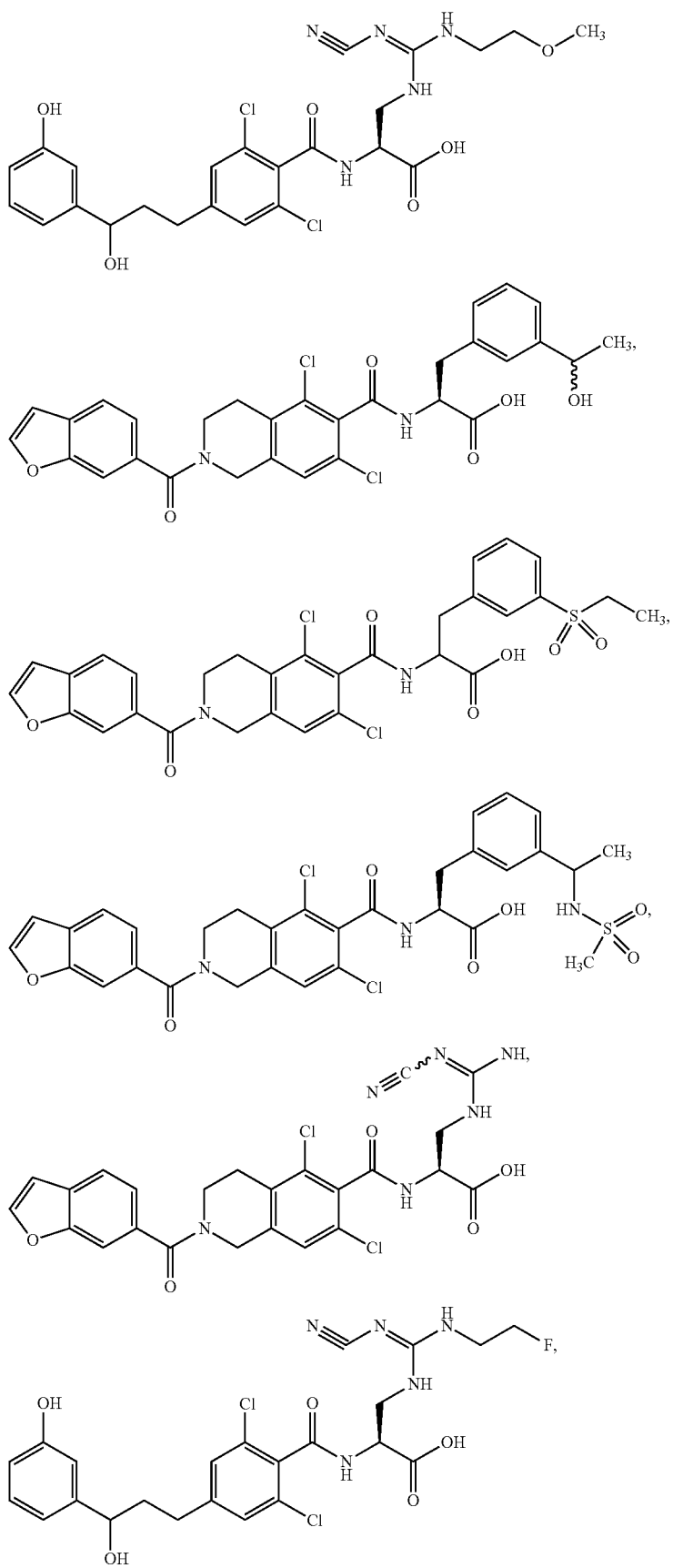

-continued
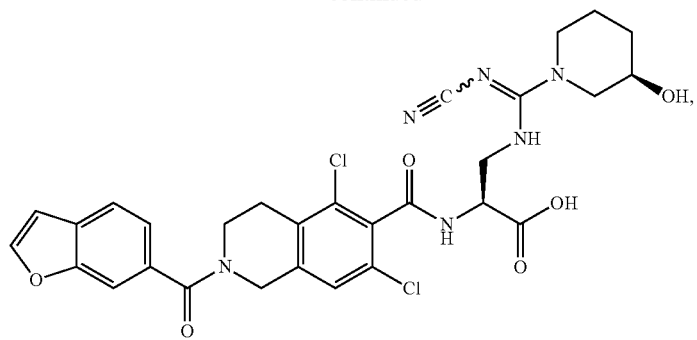
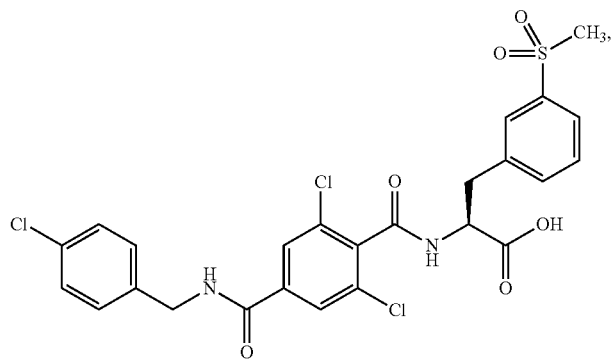
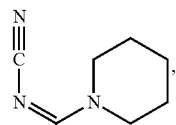
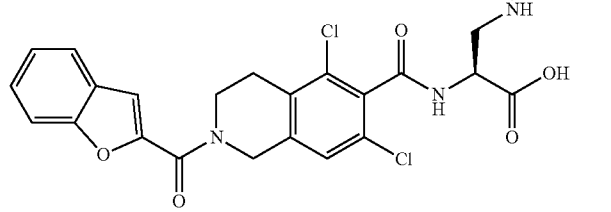
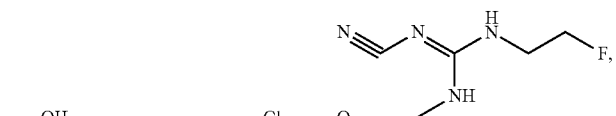
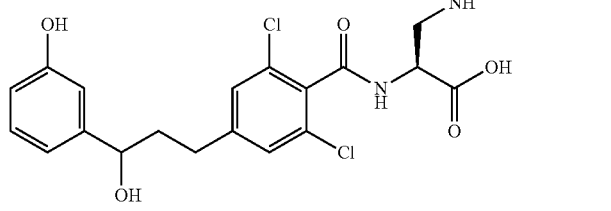
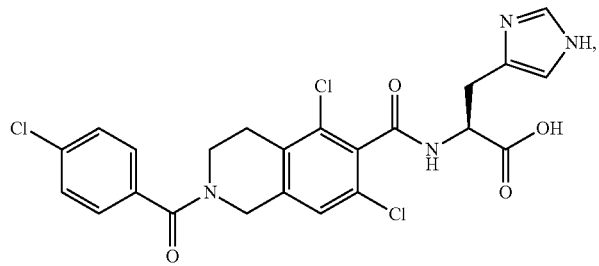

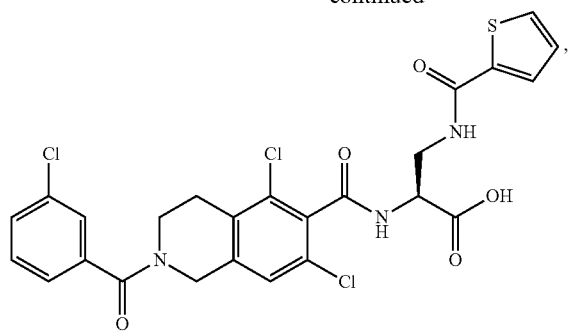
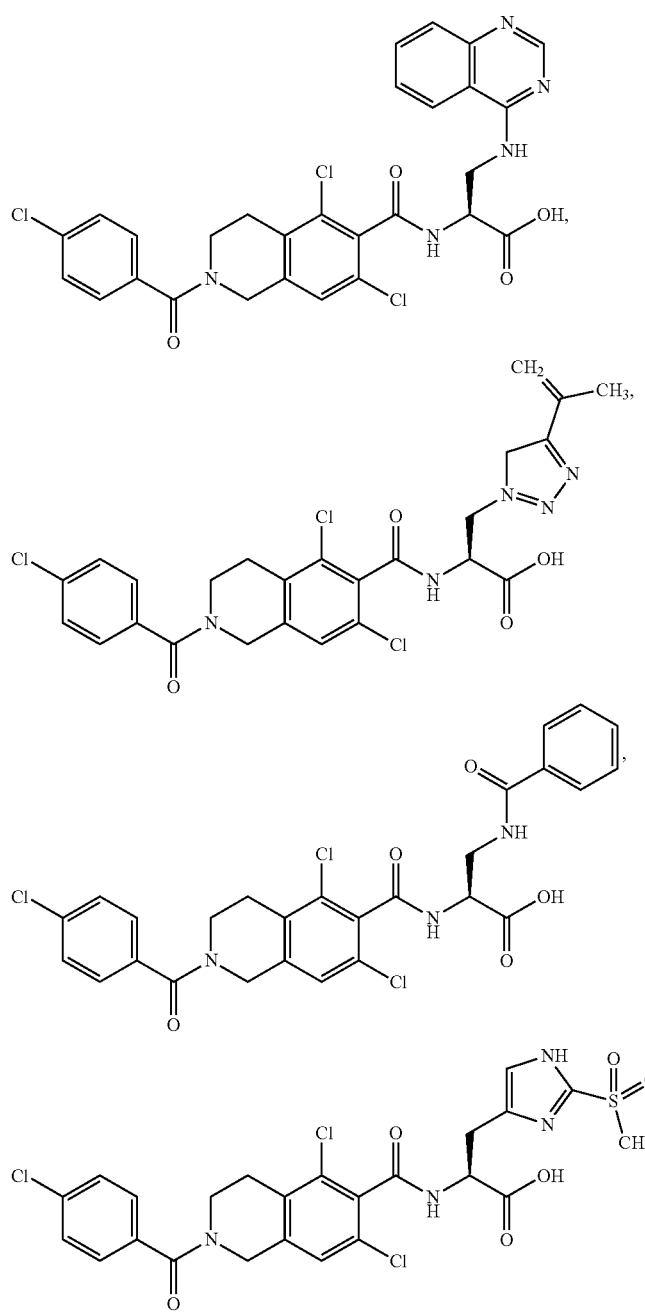

-continued
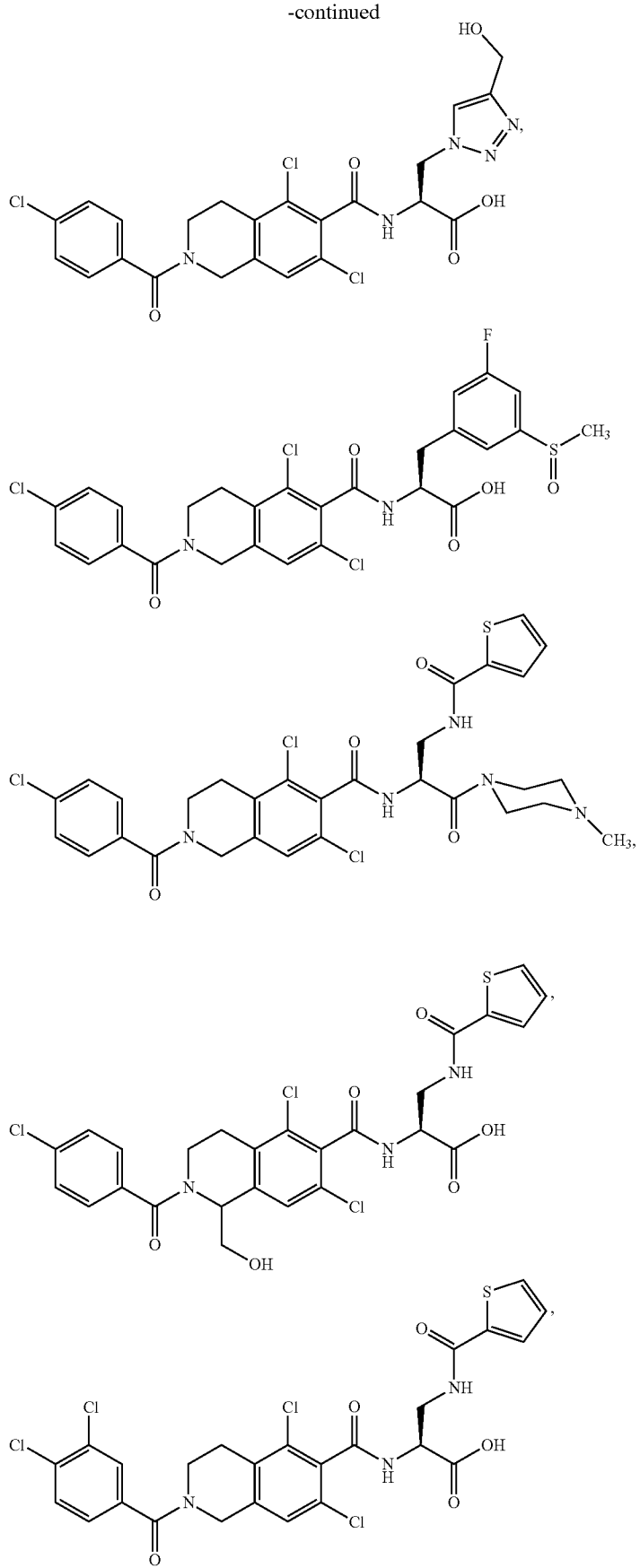

-continued
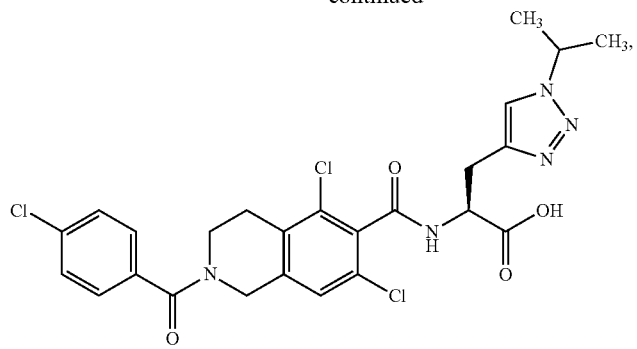
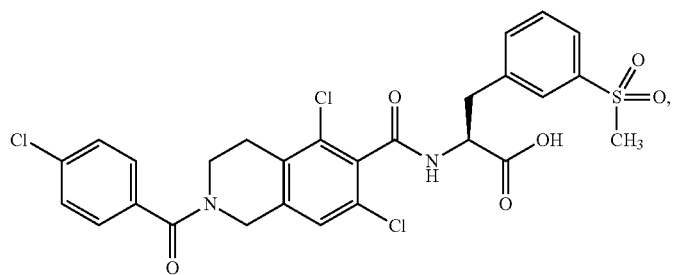
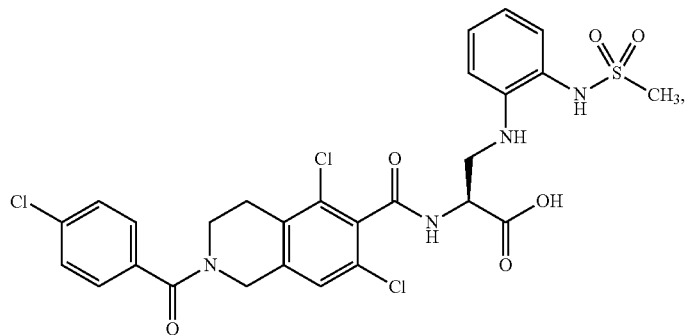
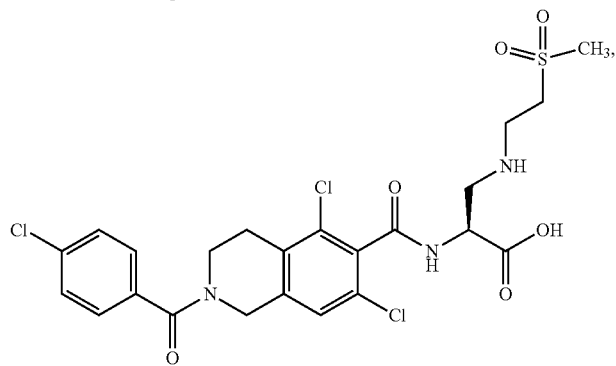
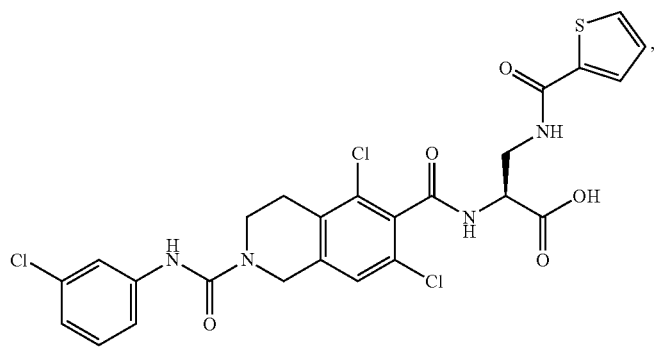

-continued
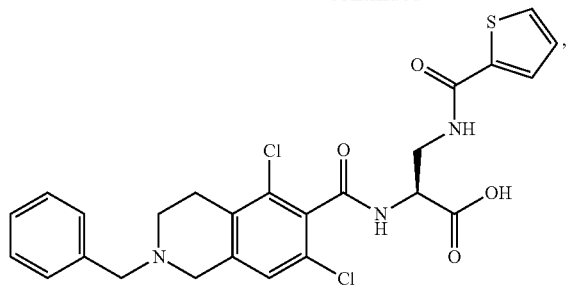
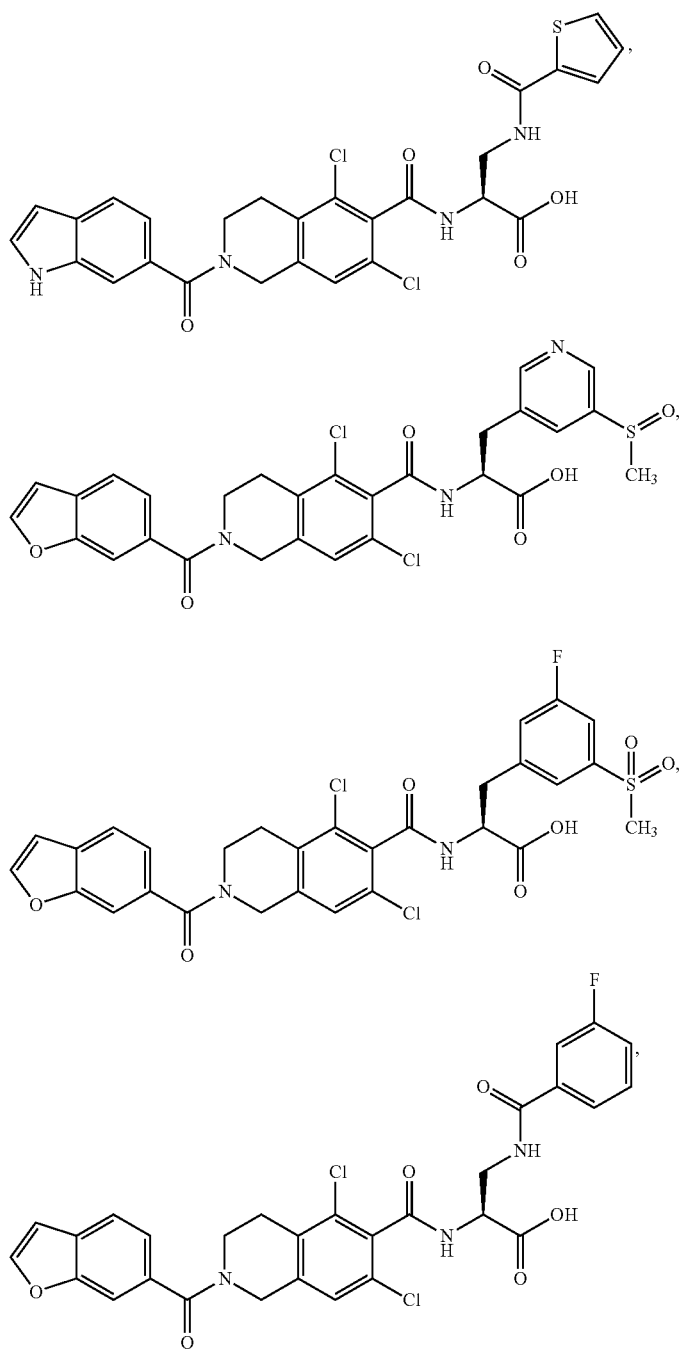

-continued
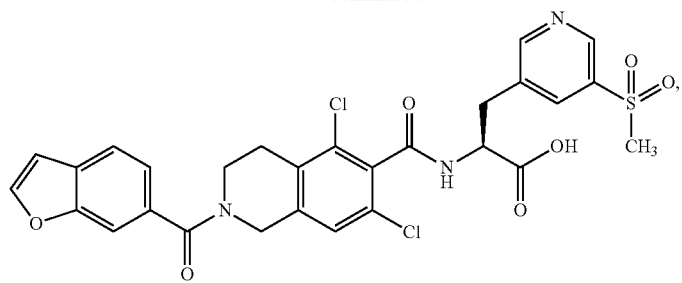
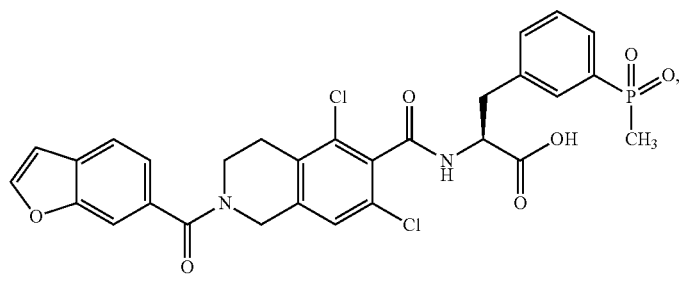
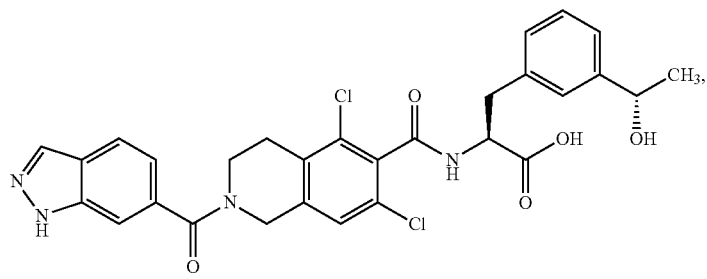
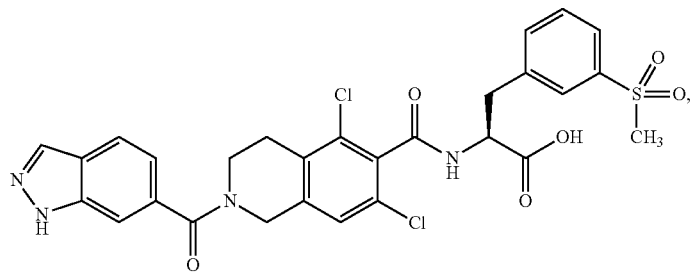
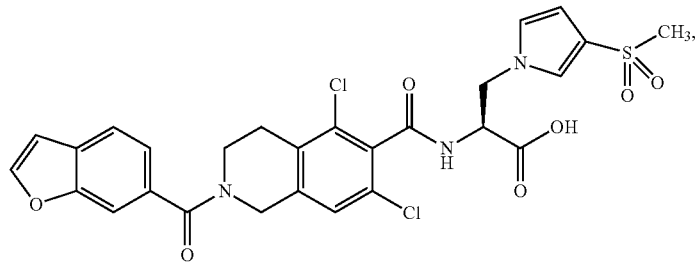
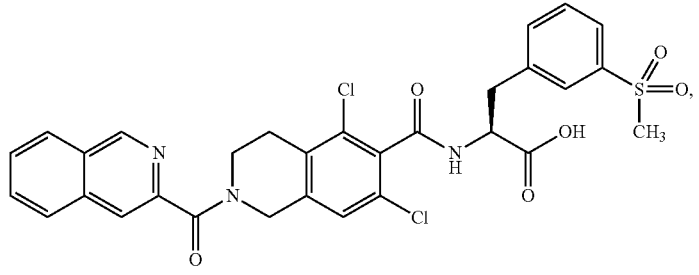

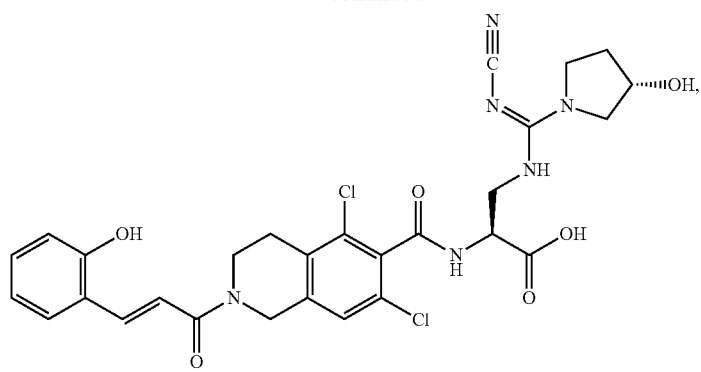
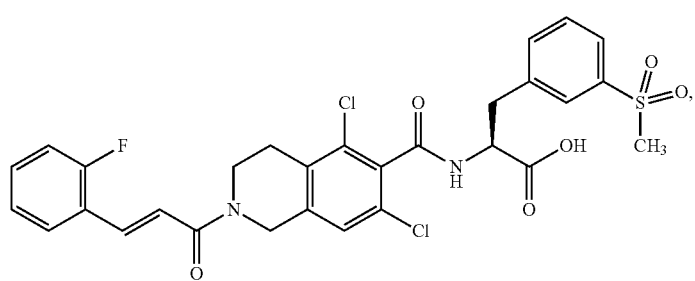
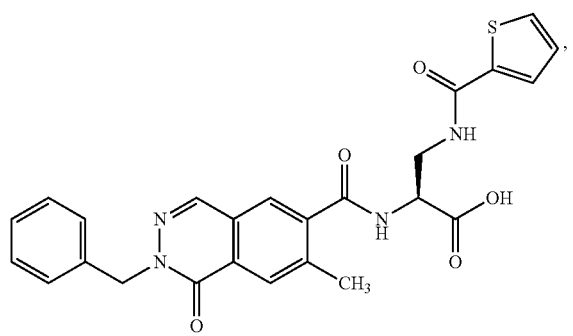
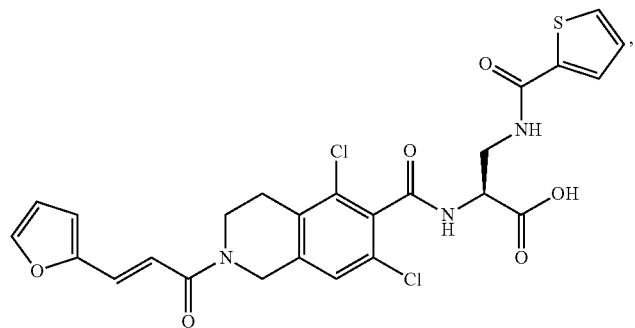
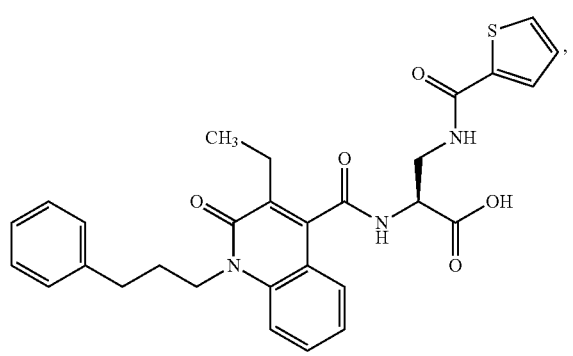

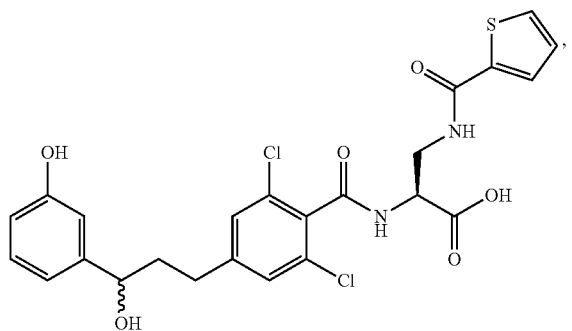
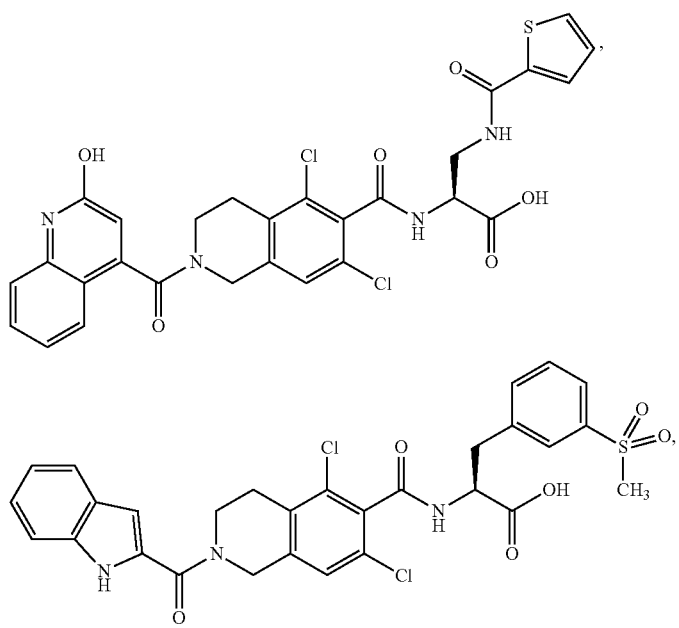
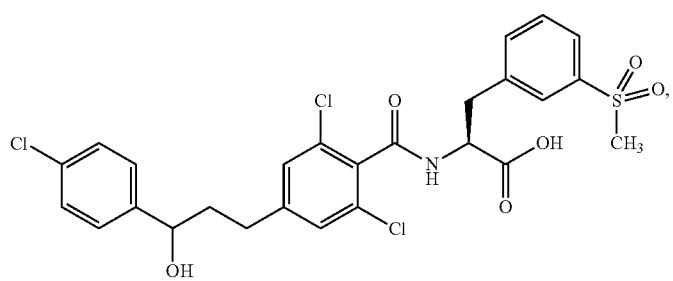
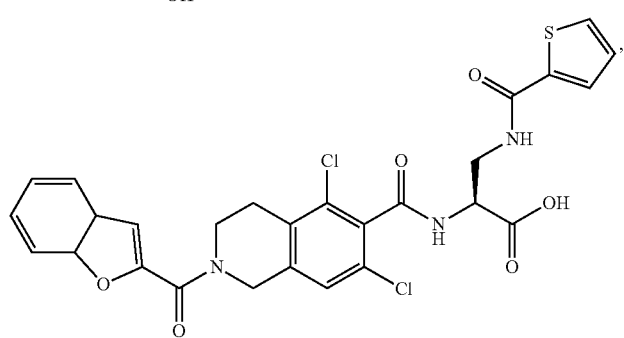

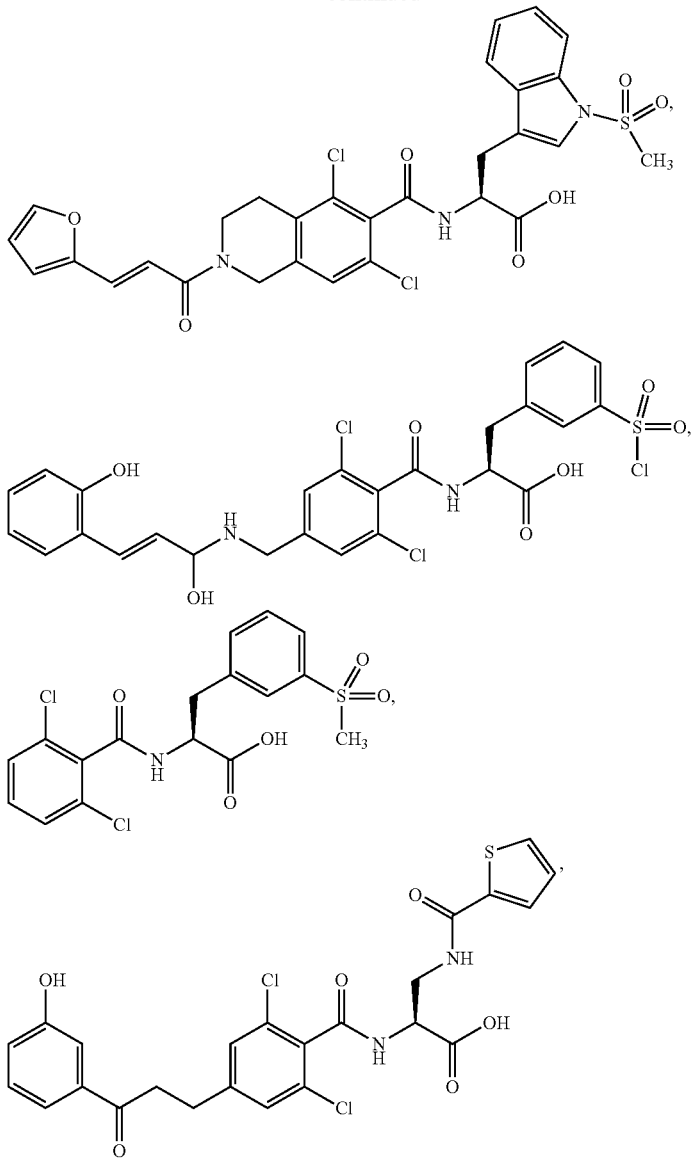

and their pharmaceutically acceptable salts and esters.

and their pharmaceutically acceptable salts and esters.

b. Exemplary Compounds which are Allosteric Antagonists of LFA-1.

i. A family of novel p-arylthio cinnamides can act as allosteric antagonists of LFA-1. See Liu, G.; Link, J. T.; Pei, Z.; Reilly, E. B.; Nguyen, B.; Marsh, K. C.; Okasinski, G. F.; von Geldern, T. W.; Ormes, M.; Fowler, K.; Gallatin, M. 2000 "Discovery of novel p-arylthio cinnamides as antagonists of leukocyte function-associated antigen-1/intracellular adhesion molecule-1 interaction. 1. Identification of an additional binding pocket based on an anilino diaryl sulfide lead." J. Med. Chem. 43, 4015-4030.

Compounds of Formula VII are provided in the present invention which are useful in the methods of the invention, as disclosed in US Patent Application Publication No. 20080234271, wherein:

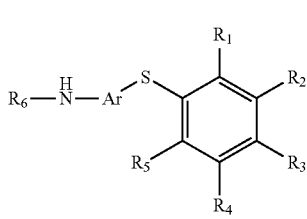

Formula VII and pharmaceutically-acceptable salts and prodrugs thereof, wherein $R_1$, $R_2$, $R_3$, $R_4$, and $R_5$ are each independently hydrogen, alkyl, alkenyl, alkenoxy, alkynyl, aldehyde, alkanoyl, alkoxy, amido, amino, aryl, aryloxy, carboxy, cyano, cycloalkyl, ether, ester, halogen, heterocyclyl, hydroxy, ketone, nitro, oxo, perfluoroalkyl, sulfonyl, sulfonate, thio, or other carbonyl-containing groups, $R_6$ is unsubstituted alkyls, unsubstituted saturated cycloalkyls, unsubstituted carboxyalkyls, or unsubstituted heterocyclylalkyls, wherein the unsubstituted saturated cycloalkyls, unsubstituted carboxyalkyls, and unsubstituted heterocyclylalkyls are bonded to the NH of formula VII through the alkyl group, wherein the unsubstituted carboxyalkyls comprise a branched alkyl chain, with the proviso that at least one of $R_1$ and $R_3$ is selected from:

A. cinnamides selected from cis-cinnamide or trans-cinnamide defined as

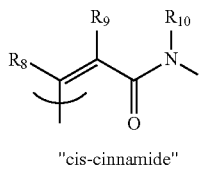
"cis-cinnamide"
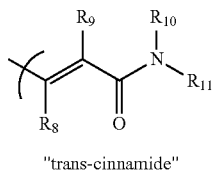
"trans-cinnamide"

wherein $R_8$ and $R_9$ are each independently hydrogen, aldehyde, alkyl, alkenyl, alkynyl, alkoxy, amido, amino, aryl, carboxy, cyano, cycloalkyl, ester, ether, halogen, hydroxy, ketone, nitro, sulfonate, sulfonyl, thio, or other carbonyl-containing groups;

B. substituents of formula VII-a:

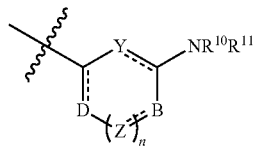

Formula VII-a wherein D, B, Y and Z are each independently $-CR^{31}=$, $-CR^{32}R^{33}-$, $-C(O)-$, $-O-$, $-SO-$, $-S-$, $-N=$, or $-NR^{34}-$;

n is an integer of zero to three; and $R^{31}$, $R^{32}$, $R^{33}$ and $R^{34}$ are each independently hydrogen, alkyl, carboxy, hydroxyalkyl, monoalkylaminocarbonylalkyl, dialkylaminocarbonylalkyl or carboxyalkyl;

C. cyclopropyl derivatives selected from cis-cyclopropanoic acid, trans-cyclopropanoic acid, cis-cyclopropanamide and trans-cyclopropanamide defined as

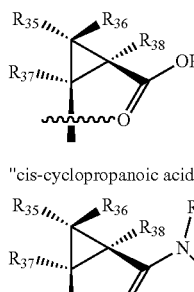
"cis-cyclopropanoic acid"
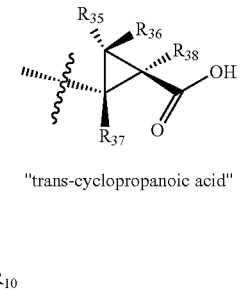
"trans-cyclopropanoic acid"

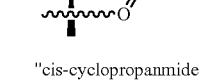
"cis-cyclopropanmide"

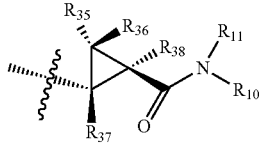
"trans-cyclopropanamide"

wherein $R_{35}$ and $R_{36}$ are each independently hydrogen, alkyl, carboxy, hydroxyalkyl, or carboxyalkyl, and wherein $R_{37}$ and $R_{38}$ are each independently hydrogen, alkyl, carboxyalkyl, monoalkylaminocarbonylalkyl, or dialkylaminocarbonylalkyl;

D. substituents of formula VII-b:

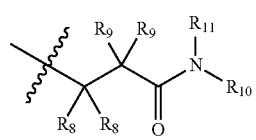

Formula VII-b wherein $R_8$ and $R_9$ are as defined above;
E. cinnamic acids of formula VII-c:

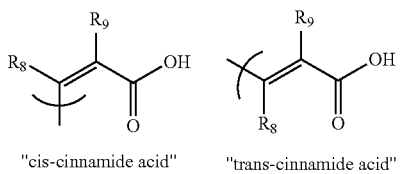

Formula VIII-c

"cis-cinnamide acid"    "trans-cinnamide acid"

wherein $R_8$ and $R_9$ are as defined above;
wherein:

$R_{10}$ and $R_{11}$ are each independently hydrogen, alkanoyl, alkyl, alkenyl, alkynyl, alkoxy, amido, aryl, arylalkyl, carboxy, cyano, cycloalkyl, ester, ether, heterocyclyl, hydroxy, ketone, nitro, sulfonyl thio, or other carbonyl-containing groups, or $R_{10}$ and $R_{11}$ are taken together with N to form a heterocyclyl group comprising at least one substituent which is independently hydrogen, alkyl, alkenyl, alkenoxy, alkynyl, aldehyde, alkanoyl, alkoxy, amido, amino, aryl, aryloxy, carboxy, cyano, cycloalkyl, ether, ester, halogen, heterocyclyl, hydroxy, ketone, nitro, oxo, perfluoroalkyl, sulfonyl, sulfonate, thio, or other carbonyl-containing group, or $R_1$ and $R_2$, and/or $R_4$ and $R_5$ are joined together to form a 5- to 7-membered cycloalkyl, aryl or heterocyclyl ring when $R_3$ is a cinnamide, substituent of formula VII-a, substituent of formula VII-b, or cyclopropyl derivative as defined above; or $R_2$ and $R_3$, and/or $R_3$ and $R_4$, and/or $R_4$ and $R_5$ are joined to form a 5- to 7-membered cycloalkyl, aryl or heterocyclyl ring when $R_1$ is selected from cinnamides, substituents of formula VII-a, substituents of formula VII-b, and cyclopropyl derivatives as defined above; and wherein Ar is substituted aryl or substituted heteroaryl having at least one substituent which independently is hydrogen, alkyl, alkenyl, alkenoxy, alkynyl, aldehyde, alkanoyl, alkoxy, amido, amino, aryl, aryloxy, carboxy, cyano, cycloalkyl, ether, ester, halogen, heterocyclyl, hydroxy, ketone, nitro, oxo, perfluoroalkyl, sulfonyl, sulfonate, thio, or other carbonyl-containing groups.

In some embodiments of the compounds of Formula VII, R6 is not an unsubstituted heterocyclylalkyl of the following structures:

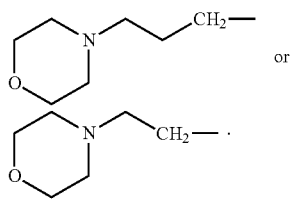

Some exemplary compounds of Formula VII include:

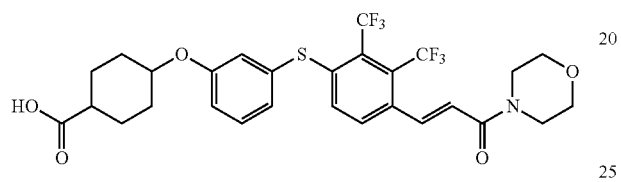

which includes its stereoisomers, for example

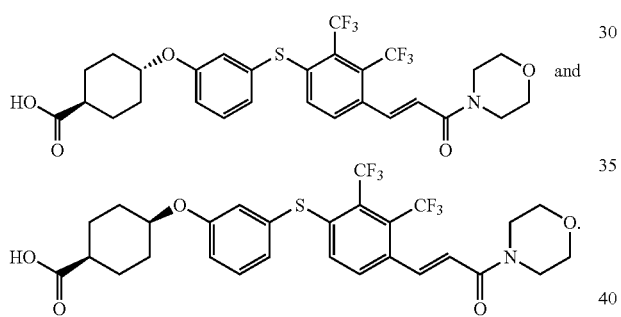

Other compounds of this general class are disclosed in U.S. Patent Application Publication Nos. 20040116518, 20050014746, 20020156314, 20020132807, 2008 0249157, and 20070066585.

ii. Another family of small molecule allosteric antagonists of LFA-1 is disclosed in US Patent Application Publication No 20080108677. The present invention provides compounds of Formula VIII, and their pharmaceutically acceptable salts, which are useful in the methods of the invention described herein.

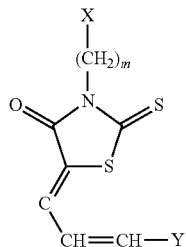

Formula VIII

The compound of Formula VIII, wherein m is 0, 1 or 2; X is H, cycloalkyl or phenyl, which is unsubstituted or substituted with one or more substituents which are lower alkyl, hydroxy or halogen; n is 0 or 1; and Y is phenyl, furanyl, indole or pyrrole, which all may be substituted with one or more substituents which are independently lower alkyl, lower alkoxy, halogen, (3,5-dimethylphenoxy)propoxy, or phenyl, wherein phenyl may be further substituted with one or more halogen atoms, nitro, amino or carboxyl groups.

One exemplary compound of Formula VIII is

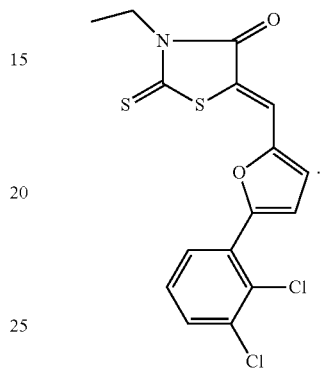

iii. A further family of small molecule allosteric antagonists of LFA-1 is disclosed in US Patent Application Publication No 2008/0242710. In another aspect the present invention provides a 3a,4,5,6-tetrahydro-pyrrolol,2-b]-isothiazole, and its pharmaceutically acceptable salts, wherein the sulphur is in the form of a dioxide which is a compound of Formula IX., which is useful in the methods of the present invention.

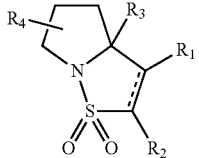

Formula IX such as a compound of Formula IX-a:

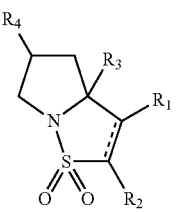

Formula IX-a wherein the dotted line is a bond or is no bond, $R_1$ is hydrogen, optionally substituted alkyl, alkenyl, alkynyl, cycloalkyl, alkoxy, aryl, heterocyclyl, hydroxy, SH, $SR_5$, cyano, halogen or amino, or the dotted line is no bond and $R_1$ is attached to the ring system via a double bond and is oxo, $R_2$ is hydrogen, or optionally substituted cycloalkyl, aryl, or heterocyclyl, $R_3$ is hydrogen, $COOR_6$, or aminocarbonyl, or optionally substituted alkyl, alkenyl, alkynyl, aralkyl, alkoxy, cycloalkyloxy, aryloxy, or heterocycyloxy, $R_4$ is hydrogen, halogen, hydroxy, SH, optionally substituted alkyl, alkenyl, alkynyl, alkoxy or alkylthio, or $R_4$ is a silyl group such as trialkylsilyl or trialkylsilyloxy, e.g. tri($C_{1-6}$)alkylsilyl(oxy), $N_3$, amino, or $R_4$ is heterocyclyl comprising at least one nitrogen atom as a heteroatom and being bound via that nitrogen atom to the compound of formula IX, or $R_4$ is attached to the ring system by a double bond and is oxo; and $R_5$ and $R_6$ independently of each other are alkyl, alkenyl, alkynyl, cycloalkyl, aryl or heterocyclyl, In some embodiments, the compound of Formula IX is:

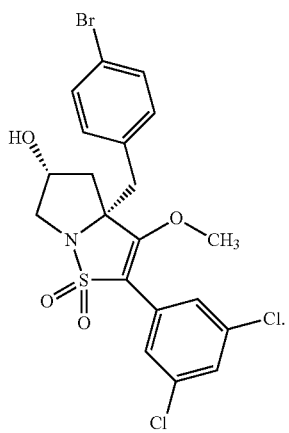 [SMILES: COC1=C(c2cc(Cl)cc(Cl)c2)S(=O)(=O)N2C[C@H](O)C[C@@]12Cc1ccc(Br)cc1]

iv. Allosteric small molecule antagonists include statins which bind to the CD11a domain of LFA-1. See Kallen, J., Welzenbach, K., Ramage, P. Geyl, D. Kriwacki, R., Legge, G., Cottens, S., Weitz-Schmidt, G., and Hommel, U. 1999. "Structural basis for LFA-1 inhibition upon lovastatin binding to the CD11a I-domain", J. Mol. Biol., 292: 1-9; and Weitz-Schmidt, G., Welzenbach, K., Brinkmann, V., Kamata, T., Kallen, J., Bruns, C., Cottens, S., Takada, Y., and Hommel, U. 2001. Statins selectively inhibit leukocyte function antigen-1 by binding to a novel regulatory integrin site, Nature Med., 7: 687-692; and Frenette, P. S. 2001. "locking a leukocyte integrin with statins", N. Engl. J. Med., 345: 1419-1421. Molecules derived from the mevinolin/compactin motif also show activity against LFA-1. See Welzenbach, K., Hommel, U., and Weitz-Schmidt, G. 2002. "Small molecule inhibitors induce conformational changes in the I domain and the I-like domain of Lymphocyte Function-Associated Antigen-1", J. Biol. Chem., 277: 10590-10598, and U.S. Pat. No. 6,630,492.

A family of allosteric LFA-1 antagonists of Formula X are disclosed which are useful in the methods of the present invention. See U.S. Pat. No. 6,818,638.

A compound of Formula X is provided for use in the methods of the invention wherein, Formula X

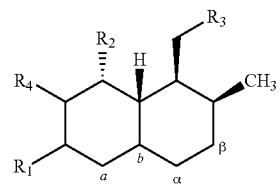

each of a - - - b and α - - - β independently, is either a single bond or a double bond; $R_1$ is ⋯⫼ H, ⋯⫼ $C_{1-4}$ alkyl or ◼ $OR_a$ $R_a$ is H, $C_{1-6}$ alkyl optionally substituted by OH or $C_{1-4}$ alkoxy, $C_{2-6}$ alkenyl or aryl-$C_{1-4}$ alkyl;

$R_2$ is OH; —O—CO—$R_5$;

$R_4$ is H or $OR_{19}$ wherein $R_{19}$ is $C_{1-6}$ alkyl, hydroxy-$C_{1-6}$ alkyl, $C_{1-4}$alkoxy-$C_{1-6}$alkyl, aryl-$C_{1-4}$alkyl or $C_{1-4}$ alkoxy-carbonyl-$C_{1-4}$alkyl;

$R_5$ is $C_{1-8}$ alkyl, $C_{3-7}$cycloalkyl, $C_{3-7}$cycloalkyl-$C_{1-4}$ alkyl, aryl or aryl-$C_{1-4}$alkyl; or $R_5$ is —O—$R_6$ wherein $R_6$ is the residue of an a-amino-acid attached to O through its carbonyl residue; or —$R_5$ is —$CHR_7$—$COR_8$ wherein $R_7$ is H, $C_{1-4}$ alkyl, hetero$C_{1-4}$ alkyl, $C_{3-7}$cycloalkyl, $C_{3-7}$cycloalkyl-$C_{1-4}$alkyl, aryl or aryl-$C_{1-4}$ alkyl and $R_8$ is OH, $C_{1-4}$alkoxy or $NR_9R_{10}$;

each of $R_9$ and $R_{10}$ independently is H or $C_{1-4}$ alkyl, or $R_9$ and $R_{10}$ form together with the nitrogen to which they are bound, a heteroaryl group;

$R_3$ is a lactam of formula X-a:

X-a

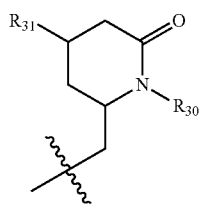

wherein $R_{30}$, is $C_{1-8}$ alkyl, $C_{3-7}$cycloalkyl, aryl, $C_{3-7}$cycloalkyl-$C_{1-4}$ alkyl, aryl-$C_{1-4}$ alkyl, heteroaryl, or heteroaryl-$C_{1-4}$; and $R_{31}$, is OH, $C_{1-4}$alkoxy, $C_{1-4}$ alkyl, $C_{1-4}$ alkoxy-carbonyl-$C_{1-4}$alkyl, hydroxy-$C_{1-5}$alkoxy, $C_{1-4}$alkoxy-$C_{1-5}$ alkoxy, $C_{1-4}$alkoxy-carbonyl-$C_{1-4}$ alkyl, amino-$C_{1-4}$ alkoxy, HOOC—$C_{1-4}$ alkoxy, HOOC—$C_{1-4}$ alkyl, $R_{9a}R_{10a}$N—$C_{1-5}$ alkoxy wherein $R_{9a}$, and $R_{10a}$ are independently $R_9$ or $R_{10}$.

In some embodiments, wherever "aryl" or "aryl-$C_{1-4}$ alkyl" appears in the above definition, it is "phenyl" or "naphthyl" optionally substituted by halogen, OH, $NR_1$, $R_{12}$, COOH, $CF_3$, $C_{1-4}$alkoxy, $C_{1-4}$alkyl, hydroxy-$C_{1-4}$ alkyl, hydroxy-$C_1$ alkoxy, $C_{1-4}$ alkoxy-carbonyl, cyano or $CONR_{11}$, $R_{12}$, each of $R_{11}$ and $R_{12}$ independently being H, $C_{1-4}$ alkyl, phenyl, naphthyl, phenyl-$C_{1-4}$ alkyl or naphthyl-$C_{1-4}$ alkyl or $R_{11}$ and $R_{12}$ together with the nitrogen to which they are bound forming heteroaryl; and wherever "heteroaryl" appears, it is a 5- or 6-membered heteroaryl optionally fused to a benzene ring; in free form or in salt form.

In some embodiments, the compound of Formula X is one of the following compounds:

123

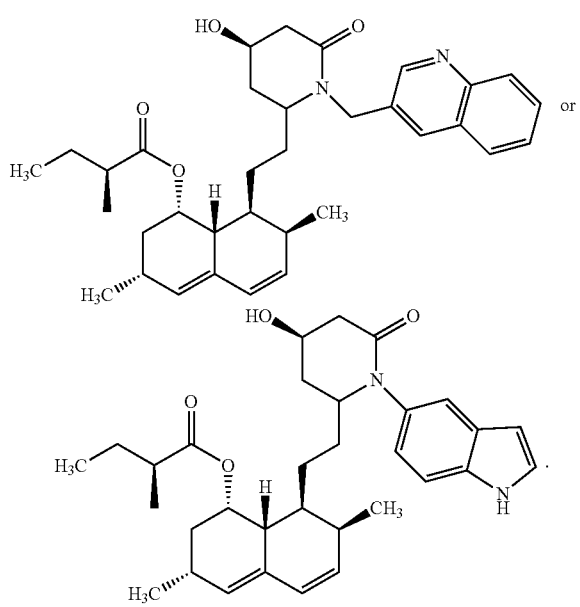

v. A family of hydantoin-based inhibitors can also be used as antagonists. See Kelly, T. A., Jeanfavre, D. D., McNeil, D. W., Woska, J. R. Jr., Reilly, P. L., Mainolfi, E. A., Kishimoto, K. M., Nabozny, G. H., Zinter, R., Bormann, B.-J., and Rothlein, R. 1999. "Cutting edge: a small molecule antagonist of LFA-1-mediated cell adhesion", J. Immunol., 163: 5173-5177. These compounds are believed to be allosteric inhibitors of LFA-1.

A family of such hydantoin-based inhibitors of Formula XI is disclosed in U.S. Patent Application Publication No. 2006/0148836 and are useful in the methods of the present invention.

A compound according to formula XI, is provided for use in the methods of the invention,

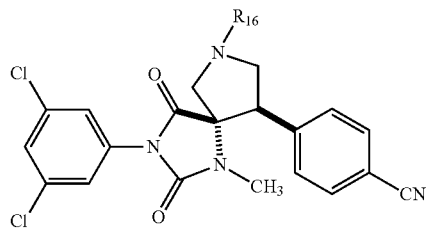

Formula XI and its enantiomers, pharmaceutically-acceptable salts, or solvates, thereof, wherein:

$R_{16}$ is:

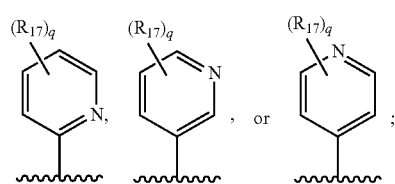

each $R_{17}$ is independently $-OR_{18}$, $-NR_{18}R_{19}$, $-C(=O)R_{18}$, $-CO_2R_{18}$, $-C(=O)NR_{18}R_{19}$, $-NR_{18}C$

124

$(=O)R_{19}$, $-NR_{18}C(=O)OR_{19}$, $-S(O)_pR_{19}$, $-NR_{18}SO_2R_{19}$, or $-SO_2NR_{18}R_{19}$;

$R_{18}$ and $R_{19}$ are independently hydrogen, alkyl, substituted alkyl, cycloalkyl, or substituted cycloalkyl; q is 1, 2, or 3; and p is 1 or 2.

In one embodiment, the compound of Formula XI is:

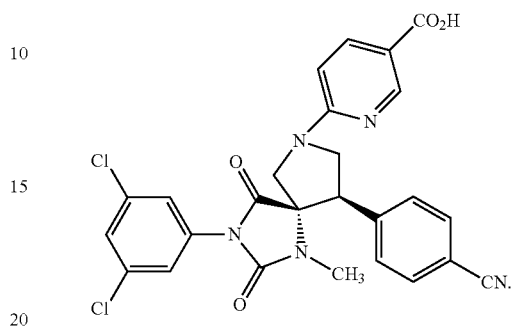

Other compounds of the general class of spiro-hydantoin compounds which may be useful as allosteric antagonists of LFA-1 in the methods of the invention are U.S. Application Publication Nos. 20060142319, 20060074099, 20060052434, 20050119279, 20050004153, 20040259897, 20040248920, 20040009998, and 20020143035.

c. Other Small Molecule Antagonists.

Other families of small molecule inhibitors are disclosed in publications (See Gadek, T. R., Burdick, D. J., McDowell, R. S., Stanley, M. S., Marsters, J. C. Jr., Paris, K. J., Oare, D. A., Reynolds, M. E., Ladner, C., Zioncheck, K. A., Lee, W. P., Gribling, P., Dennis, M. S., Skelton, N. J., Tumas, D. B., Clark, K. R., Keating, S. M., Beresini, M. H., Tilley, J. W., Presta, L. G., and Bodary, S. C. 2002. "Generation of an LFA-1 antagonist by the transfer of the ICAM-1 immunoregulatory epitope to a small molecule" Science, 295: 1086-1089 and online supplementary material.) and in patents, including U.S. Pat. Nos. 6,872,735, 6,667,318, 6,803,384, 6,515,124, 6,331,640, and patent applications, including: U.S. 20020119994. U.S. 20040058968, U.S. 20050080119, WO99/49856, WO00/21920, WO01/58853, WO02/59114, WO05/044817, and others. The contents of all the cited references are incorporated in their entirety by reference.

The compounds of the invention may be prepared by methods well known to those skilled in the art, or disclosed in the references incorporated herein and may be purified in a number of ways, including by crystallization or precipitation under varied conditions to yield one or more polymorphs. Thus, the present invention encompasses the above described inventive compounds, their polymorphs, their pharmaceutically acceptable salts, their pharmaceutically acceptable solvates, and pharmaceutically acceptable compositions containing them.

The above examples of preferred embodiments are meant to illustrate some of the potential therapeutic agents, and are not meant to limit the invention in any way. The method of the invention can be practiced with antibodies, fragments of antibodies, peptides and other synthetic molecules that is a selective, potent and directly competitive inhibitor of the interaction between LFA-1 and ICAM-1, in order to treat the symptoms of diabetic retinopathy.

II. Methods of Treatment.

The term "subject" as used herein includes animals, in particular humans as well as other mammals.

The term "treating" and its grammatical equivalents as used herein includes achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made. The compositions may be administered to a subject to prevent progression of physiological symptoms or of the underlying disorder.

In some embodiments of the invention, methods are provided to administer a therapeutic agent to a subject to treat diabetic retinopathy. In some embodiments of the invention, the therapeutic agent is a LFA-1 antagonist. In some embodiments, the LFA-1 antagonist is a directly competitive antagonist of LFA-1. In some embodiments, the LFA-1 antagonist is a competitive antagonist of LFA-1. In some embodiments, the LFA-1 antagonist is an allosteric antagonist of LFA-1. In some embodiments of the invention, the LFA-1 antagonist can modulate inflammation mediated by leukocytes. Another embodiment of the invention treats a subject by administering a therapeutically effective amount of an antagonist of LFA-1 to modulate inflammation associated with ocular inflammation. An embodiment of the invention treats a subject with symptoms of diabetic retinopathy by administering a therapeutically effective amount of a LFA-1 antagonist. In some embodiments of the invention methods are provided to treat a subject with symptoms of Type II diabetes by administering a therapeutically effective amount of a LFA-1 antagonist. In some embodiments of the invention methods are provided to treat a subject with symptoms of Type I diabetes by administering a therapeutically effective amount of a LFA-1 antagonist. In some embodiments of the invention, methods are provided to treat a subject by administering a therapeutically effective amount of a LFA-1 antagonist to decrease retinal edema in an eye of the subject. In other embodiments of the invention, methods are provided to treat a subject by administering a therapeutically effect amount of a LFA-1 antagonist to decrease macular edema. In other embodiments, methods are provided to treat a subject by administering a therapeutically effective amount of a LFA-1 antagonist to decrease basement membrane thickening in an eye of the subject. In yet other embodiments of the invention, methods are provided to treat a subject by administering a therapeutically effective amount of a LFA-1 antagonist to decrease retinal neovascularization in an eye of the subject. In some embodiments of the invention, methods are provided to treat a subject by administering a therapeutically effective amount of a LFA-1 antagonist to retard the loss of vision due to diabetic retinopathy. In some embodiments, methods are provided to treat a subject by administering a therapeutically effective amount of a LFA-1 antagonist to decrease retinal ischemia in an eye of the subject. In other embodiments, methods are provided to decrease fibrovascular growth over a retina in an eye of a subject suffering from diabetic retinopathy, by administering a therapeutically effective amount of a LFA-1 antagonist. In some embodiments, methods are provided to reduce retinal injury or degeneration due to diabetic retinopathy in an eye of a subject suffering from diabetic retinopathy, by administering a therapeutically effective amount of a LFA-1 antagonist. In other embodiments, methods are provided to limit non-proliferative damage to a retina in an eye of a subject suffering from diabetic retinopathy, by administering a therapeutically effective amount of a LFA-1 antagonist. In other embodiments, methods are provided to slow proliferative damage to a retina in an eye of a subject suffering from diabetic retinopathy, by administering a therapeutically effective amount of a LFA-1 antagonist. In other embodiments, methods are provided to reduce or prevent adhesion of leukocytes to capillary epithelial cells in an eye of a subject in need thereof, by administering a therapeutically effective amount of a LFA-1 antagonist. In some other embodiments, methods are provided to reduce or prevent damage from ischemic reperfusion in an eye of a subject in need thereof, by administering a therapeutically effective amount of a LFA-1 antagonist. In some embodiments of the invention, methods are provided wherein the LFA-1 antagonist which is administered to the subject suffering from diabetic retinopathy, binds to a high affinity binding site in the $\alpha$L subunit of LFA-1 overlapping the ICAM-1 binding site. Some embodiments of the invention utilize compounds that are directly competitive inhibitors of the LFA-1/ICAM-1 interaction. Some of the embodiments of the invention utilize compounds which directly compete for a common high affinity binding site for ICAM-1 on LFA-1. In some embodiments, methods are provided which administer to a subject in need of treatment a therapeutically effective amount of a LFA-1 antagonist which is a compound of Formulas I, II, II', III, III', IV, IV', V, or VI. In some embodiments, methods are provided which administer to a subject in need of treatment a therapeutically effective amount of a LFA-1 antagonist which is a compound of Formulas VII, VIII, IX, X or XI.

In other therapeutic interventions which can be associated with diabetic complications in the eye, vitrectomy procedures may be utilized. Dexamethansone, a glucocorticoid steroid, has been shown to be useful in reducing post-operative inflammation which can be enhanced in diabetic subjects relative to non-diabetic subjects. Thus, it may be desirable to use an LFA-1 antagonist of the invention to reduce inflammation. In some embodiments of the invention, methods are provided to reduce postoperative inflammation in diabetic subjects undergoing vitrectomy procedures by administering an LFA-1 antagonist to the subject in need thereof. Further, in some embodiments, an LFA-1 antagonist of the invention may be administered to a subject prior to a vitrectomy procedure to prophylactically reduce post-operative inflammation.

In other therapeutic interventions which can be associated with diabetic complications in the eye, photodynamic therapy may be utilized to correct occlusion or leakiness, and may cause excessive inflammation in a diabetic subject. Thus, it may be desirable to use an LFA-1 antagonist of the invention to reduce inflammation. In some embodiments of the invention, methods are provided to reduce postoperative inflammation in diabetic subjects undergoing photodynamic therapeutic (PDT) procedures by administering an LFA-1 antagonist to the subject in need thereof. Further, in some embodiments, an LFA-1 antagonist of the invention may be administered to a subject prior to a PDT procedure to prophylactically reduce post-operative inflammation.

In other therapeutic interventions which can be associated with diabetic complications in the eye, laser photocoagulation therapy may be utilized to correct occlusion or leakiness, and may cause excessive inflammation in a diabetic subject, Thus, it may be desirable to use an LFA-1 antagonist of the invention to reduce inflammation. In some embodiments of the invention, methods are provided to reduce postoperative inflammation in diabetic subjects undergoing laser photocoagulation therapeutic procedures by administering an LFA-1 antagonist to the subject in need thereof. Further, in some embodiments, an LFA-1 antagonist of the invention may be administered to a subject prior to a laser photocoagulation therapy procedure to prophylactically reduce post-operative inflammation.

In LASIK treatment of vision defects, diabetic patients are at increased risk of post-operative complications from corneal epithelial inflammation and defects than non-diabetic patients, and anti-inflammatory treatment may be indicated. In some embodiments of the invention, methods are provided to reduce inflammation due to diabetic complications of LASIK treatment in an eye of a subject thereof, by administering a LFA-1 antagonist and thereby reduce such inflammation. Administration is made post-operatively or pre-operatively to prophylactically prevent or reduce such inflammation.

Individuals with DME have higher risk of cataract development which is a frequent cause of vision loss. Diabetic patients have a higher risk of both anterior and posterior segment complications following cataract surgery. One of the most significant of these is neovascularization of the iris as it can progress to neovascular glaucoma. Other anterior chamber complications include pigment dispersion with precipitates on the surface of the newly implanted intraocular lens (IOL), fibrinous exudates or membrane formation (from inflammation) in the anterior chamber. In some embodiments of the invention, methods are provided to reduce anterior or posterior segment complications following cataract surgery in an eye of a subject with DME, by administering a LFA-1 antagonist to a subject in need thereof., In some embodiments, methods are provided to prophylactically administer a LFA-1 antagonist to a subject with DME who is at higher risk of developing cataracts compared to a healthy subject, thereby reducing or preventing developing cataracts.

The methods generally involve the administration of one or more drugs for the treatment of diabetic retinopathy where the drug is delivered to or is distributed subsequent to delivery to the retina or intraocular region of the eye. Combinations of agents can be used to treat diabetic retinopathy or to modulate the side-effects of one or more agents in the combination. Since the pathological events in this disease state are marked by a combination of impaired autoregulation, apoptosis, ischemia, reperfused tissue, neovascularization, and inflammatory stimuli, it may be desirable to administer the LFA-1 antagonists of the invention in combination with other therapeutic agents to additionally or synergistically intervene. In some embodiments, the second therapeutic agent is an antioxidant, antiinflammatory agent, antimicrobial, antiangiogenic agent, and/or anti-apoptotic agent. In some embodiments of the invention, in addition to administering a compound which directly competes for binding to LFA-1, an additional therapeutic agent may be administered which is an allosteric, but not a directly competitive, anatagonist of LFA-1 as discussed above, potentially resulting in synergistic efficacy. An example of such allosteric antagonist is the class of hydantoin inhibitors of LFA-1. Other examples of allosteric antagonists include compounds of Formula VII, VIII, IX, X, or XI.

Another class of therapeutic agents which my be useful to administer in combination with, prior to, after or concomitantly with the LFA-1 antagonists of the invention is an anti-adhesion therapeutic antibody or antibody fragment.

Another class of therapeutic agents which may be useful to administer in combination, prior to, after, or concomitantly with the LFA-1 antagonists of the invention is the group of drugs which inhibit Vascular Endothelial Growth Factor and thus may target another route of initiation of neovascularization. Any VEGF inhibitor may be of use in the compositions of the invention, which include, but are not limited to 1) neutralizing monoclonal antibodies against VEGF or its receptor, 2) small molecule tyrosine kinase inhibitors of VEGF receptors, 3) soluble VEGF receptors which act as decoy receptors for VEGF, 4) ribozymes which specifically target VEGF, and 5) siRNA which specifically targets VEGF signalling proteins. Some examples of antibodies which are active against VEGF are, for example, e.g., Lucentis (ranibizumab), and Avastin (bevacizumab). An example of an oligonucleotide drug is, e.g., Macugen (pegaptanib sodium injection). Small molecule tyrosine kinase inhibitors include, for example, pazopanib, sorafenib, sutent, and the like.

Inflammation is induced by the vascular permeability caused by DR and by the process of leukocyte adhesion and neovascularization. Therefore, other anti-inflammatory agents may be administered in combination, prior to, after, or concomitantly with the LFA-1 antagonists of the invention. The anti-inflammatory agents can be chosen from corticosteroid related drugs including but not limited to dexamethasone, fluorometholone, medrysone, betamethasone, triamcinolone, triamcinolone acetonide; prednisone, prednisolone, hydrocortisone, rimexolone, and pharmaceutically acceptable salts thereof, prednicarbate, deflazacort, halomethasone, tixocortol, prednylidene, prednival, paramethasone, methylprednisolone, meprednisone, mazipredone, isoflupredone, halopredone acetate, halcinonide, formocortal, flurandrenolide, fluprednisolone, fluprednidine acetate, fluperolone acetate, fluocortolone, fluocortin butyl, fluocinonide, fluocinolone acetonide, flunisolide, flumethasone, fludrocortisone, fluclorinide, enoxolone, difluprednate, diflucortolone, diflorasone diacetate, desoximetasone (desoxymethasone), desonide, descinolone, cortivazol, corticosterone, cortisone, cloprednol, clocortolone, clobetasone, clobetasol, chloroprednisone, cafestol, budesonide, beclomethasone, amcinonide, allopregnane acetonide, alclometasone, 21-acetoxypregnenolone, tralonide, diflorasone acetate, deacylcortivazol, RU-26988, budesonide, deacylcortivazol, and the like. Alternatively, the antiinflammatory agents can be chosen from the group of NSAIDs including but not limited to acetaminophen, acemetacin, aceclofenac, alminoprofen, amfenac, bendazac, benoxaprofen, bromfenac, bucloxic acid, butibufen, carprofen, celecoxib, cinmetacin, clopirac, diclofenac, etodolac, etoricoxib, felbinac, fenclozic acid, fenbufen, fenoprofen, fentiazac, flunoxaprofen, flurbiprofen, ibufenac, ibuprofen, indomethacin, isofezolac, isoxicam, isoxepac, indoprofen, ketoprofen, lonazolac, loxoprofen, mefenamic acid, meclofenamic acid, meloxicam, metiazinic acid, mofezolac, miroprofen, naproxen, niflumic, oxaprozin, pirozolac, pirprofen, pranoprofen, protizinic acid, rofecoxib, salicylic acid and its derivatives (i.e. for example, asprin), sulindac, suprofen, suxibuzone, triaprofenic acid, tolmetin, valdecoxib, xenbucin, ximoprofen, zaltoprofen, zomepirac, aspirin, acemetcin, bumadizon, carprofenac, clidanac, diflunisal, enfenamic acid, fendosal, flufenamic acid, flunixin, gentisic acid, ketorolac, mesalamine, prodrugs thereof, and the like.

Another group of therapeutic agents which may be useful to administer in combination, prior to, after, or concomitantly with the LFA-1 antagonists of the invention is the group of drugs which are known to inhibit retinopathy by inhibiting NFKβ. Some of these classes of therapeutics include PARP inhibitors, benfotiamine or other agents which intervene in blockade of AGEs (advanced glycation endproducts), aldose reductase inhibitors, iNOS inhibitors, FasL inhibitors, or angiopoeitin-1.

Oxidative stress may be induced in cells with impaired autoregulatory and ischemic processes induced by DR. Therefore, anti-oxidants may be useful to administer in combination, prior to, after, or concomitantly with the LFA-1 antagonists of the invention. Examples of suitable anti-oxidants useful in the methods of the invention include, but are not limited to, ascorbic acid, tocopherols, tocotrienols, carotinoids, glutathione, alpha-lipoic acid, ubiquinols, bioflavonoids, carnitine, and superoxide dismutase mimetics, such as, for example, 2,2,6,6-tetramethyl-1-piperidinyloxy (TEMPO), DOXYL, PROXYL nitroxide compounds; 4-hydroxy-2,2,6,6-tetramethyl-1-piperidinyloxy (Tempol), M-40401, M-40403, M-40407, M-40419, M-40484, M-40587, M-40588, and the like.

In some stages of diabetic retinopathy, retinal ischemia is a result, causing further cell death. In some embodiments of the invention, methods are provided wherein anti-apoptotic therapeutic agents may be administered in combination, prior to, after, or concomitantly with the LFA-1 antagonists of the invention. Examples of suitable anti-apoptotic agents are, for example, inhibitors of caspases, cathepsins, and TNF-α.

Another class of therapeutic agents which may be useful to administer in combination, prior to, after, or concomitantly with the LFA-1 antagonists of the invention are complement inhibitors. The LFA-1/ICAM binding event is downstream of complement activation of ICAM upregulation in tissue and on vascular/capilary epithelial cells. Administration of both a complement inhibitor and LFA-1 antagonist may permit more complete modulation of LFA-1 expressing leukocytes. One example of a complement inhibitor is Eculizumab. Other complement inhibitors include, but are not limited to U.S. Pat. Nos. 7,166,568, 6,319,897, 5,843,884, 5,135,916, and 5,624,837.

Another class of therapeutic agents which may be useful to administer in combination, prior to, after, or concomitantly with the LFA-1 antagonists of the invention are medications used in the management of glaucoma in patients with background DM, which includes primary, open angle, angle-closure as well as neovascular glaucoma. Some of the therapeutic agents used for glaucoma include but are not limited to prostaglandin analogs such as, for example, latanoprost, bimatoprost, and travaprost; topical beta-adrenergic receptor antagonists such as, for example, timolol, levobunolol, and betaxolol; alpha 2-adrenergic agonist such as, for example, brimonidine; sympathomimetics such as for example, epinephrine or dipivifrin; miotic agents, such as, for example, pilocarpine; carbonic anhydrase inhibitors, such as, for example, dorzolamide, brinzolamide, and acetozolamide; or physostigmine.

Another class of therapeutic agents which may be useful to administer in combination, prior to, after, or concomitantly with the LFA-1 antagonists of the invention are antimicrobial agents. Suitable antimicrobial compounds, include, but are not limited to, penicillins, such as, for example, amoxicillin, ampicillin, azlocillin, carbenicillin, cloxacillin, dicloxacillin, flucloxacillin, mezlocillin, nafcillin, penicillin, piperacillin, ticarcillin, and the like; beta-lactamase inhibitors; carbapenems, such as, for example, ertapenem, imipenem, meropenem, and the like; cephalosporins, such as, for example, cefaclor, cefamandole, cefoxitin, cefprozil, cefuroxime, cefixime, cefdinir, cefditoren, cefoperazone, cefotaxime, cefpodoxime, cefadroxil, ceftazidime, ceftibuten, ceftizoxime, cefftriaxone, cefazolin, cefixime, cephalexin, cefepime, and the like; quinolones, such as, for example, ciprofloxacin, enoxacin, gatifloxacin, levofloxacin, lomefloxacin, morifloxacin, norfloxacin, ofloxacin, trovafloxacin, and the like; macrolides, such as, for example, azithromycin, clarithromycin, dirithromycin, erythromycin, milbemycin, troleandomycin, and the like; monbactams, such as, for example, aztreonam, and the like; tetracyclins, such as, for example, demeclocyclin, doxycycline, minocycline, oxytetracyclin, tetracycline, and the like; aminoglycosides, such as, for example, amikacin, gentamicin, kanamycin, neomycin, netilmicin, paromomycin, streptomycin, tobramycin, and the like; carbacephem, such as, for example, loracarbef, and the like; streptogramins; sulfonamides, such as, for example, mefanide, prontosil, sulfacetamide, sulfamethizole, sulfanilamide, sulfasalazine, sulfisoxazole, trimethoprim, trimethoprim-sultamethoxazole, and the like; and the combination drugs such as for example, sulfamethoxazole and trimethoprim, and the like; and polypeptides, such as, for example, bacitracin, colistin, polymyxin B, and the like.

Examples of other therapeutic agents which may be useful to administer in combination, prior to, after, or concomitantly with the LFA-1 antagonists of the invention are, include, but are not limited to: (a) anti-diabetic agents such as insulin and insulin mimetics, sulfonylureas (e.g., glyburide, meglinatide), biguanides, e.g., metformin (Glucophage™), .alpha.-glucosidase inhibitors (acarbose), insulin sensitizers, e.g., thiazolidinone compounds, rosiglitazone (Avandia™), troglitazone (Rezulin™), ciglitazone, pioglitazone (Actos™) and englitazone; (b) cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acylCoA-cholesterol acyltransferase (ACAT) inhibitors such as melinamide), HMG-CoA synthase inhibitors, squalene epoxidase inhibitors and squalene synthetase inhibitors; and (c) antithrombotic agents, such as thrombolytic agents (e.g., streptokinase, alteplase, anistreplase and reteplase), heparin, hirudin and warfarin derivatives, beta-blockers (e.g., atenolol), beta-adrenergic agonists (e.g., isoproterenol), ACE inhibitors and vasodilators (e.g., sodium nitroprusside, nicardipine hydrochloride, nitroglycerin and enaloprilat).

In some embodiments, the LFA-1 antagonist is present in an amount sufficient to exert a therapeutic effect to reduce symptoms of diabetic retinopathy by an average of at least about 5, 10, 15, 20, 25, 30, 40, 50, 60, 70, 80, 90, more than 90%, or substantially eliminate symptoms of diabetic retinopathy.

In other embodiments, the LFA-1 antagonist is present in an amount sufficient to reduce retinal degeneration in a subject by an average of at least about 5, 10, 15, 20, 25, 30, 40, 50, 60, 70, 80, 90, more than 90%, or substantially eliminate retinal degeneration.

In some embodiments, the LFA-1 antagonist is present in an amount sufficient to decrease retinal edema in a treated eye of a subject by an average of at least about 5, 10, 15, 20, 25, 30, 40, 50, 60, 70, 80, 90, more than 90%, or substantially eliminate retinal edema.

In yet other embodiments, the LFA-1 antagonist is present in an amount sufficient to decrease basement membrane thickening in a treated eye of a subject by an average of at least about 5, 10, 15, 20, 25, 30, 40, 50, 60, 70, 80, 90, more than 90%, or substantially eliminate basement membrane thickening.

In some embodiments, the LFA-1 antagonist is present in an amount sufficient to decrease retinal neovascularization in a treated eye of a subject by an average of at least about 5, 10, 15, 20, 25, 30, 40, 50, 60, 70, 80, 90, more than 90%, or substantially eliminate retinal neovascularization.

In some embodiments, the LFA-1 antagonist is present in an amount sufficient to decrease fibrovascular growth over a retina in a treated eye of a subject by an average of at least about 5, 10, 15, 20, 25, 30, 40, 50, 60, 70, 80, 90, more than 90%, or substantially eliminate fibrovascular growth over the retina.

In some embodiments, the LFA-1 antagonist is present in an amount sufficient to retard loss of vision in a treated eye of a subject by an average of at least about 5, 10, 15, 20, 25, 30, 40, 50, 60, 70, 80, 90, more than 90%, or substantially eliminate further loss of vision.

In some embodiments, the LFA-1 antagonist is present in an amount sufficient to limit non-proliferative damage to a retina of a subject by an average of at least about 5, 10, 15, 20, 25, 30, 40, 50, 60, 70, 80, 90, more than 90%, or substantially eliminate the non-proliferative damage to the retina.

In some embodiments, the LFA-1 antagonist is present in an amount sufficient to slow proliferative damage to a retina of a subject by an average of at least about 5, 10, 15, 20, 25, 30, 40, 50, 60, 70, 80, 90, more than 90%, or substantially eliminate further proliferative damage to the retina.

In some embodiments, an effective amount of the LFA-1 antagonist is a daily dose of about $1\times10^{-11}$, $1\times10^{-10}$, $1\times10^{-9}$, $1\times10^{-8}$, $1\times10^{-7}$, $1\times10^{-6}$, $1\times10^{-5}$, $1\times10^{-4}$, $1\times10^{-3}$, $1\times10^{-2}$, $1\times10^{-1}$, 1, $1\times10^{1}$, $1\times10^{2}$ grams.

Administration of the therapeutic agent may be by any suitable means. In some embodiments, the therapeutic agent is administered by oral administration. In some embodiments, the therapeutic agent is administered by transdermal administration. In some embodiments, the therapeutic agent is administered by instillation. In some embodiments, the therapeutic agent is administered by injection. In some embodiments, the therapeutic agent is administered by slow release intravitreal injection. In some embodiments, the therapeutic agent is administered by slow release intraocular implantation. In some embodiments, the therapeutic agent is administered by periocular implantation. In some embodiments, the therapeutic agent is administered topically. In some embodiments, the therapeutic agent is administered topically, via an eye drop. If combinations of agents are administered as separate compositions, they may be administered by the same route or by different routes. If combinations of agents are administered in a single composition, they may be administered by any suitable route. In some embodiments, combinations of agents are administered as a single composition by oral administration. In some embodiments, combinations of agents are administered as a single composition by transdermal administration. In some embodiments, the combinations of agent are administered as a single composition by injection. In some embodiments, the combinations of agent are administered as a single composition topically.

In some embodiments of the invention, diagnostic procedures will be employed to identify a subject in need of treatment by the method of the invention. An exemplary list of procedures that may be used to diagnose symptoms of diabetic retinopathy, includes, e.g., for example, complete ophthalmic examination (which may include Amsler grid examination and slit lamp examination), fundus photography, fluorescein angiography, optical coherence tomography, non-myriadic photography, and beta scan ultrasound, conventional ocular exam, optical coherence tomography, beta scan ultrasound alone, complete ophthalmic examination with fundus photography and fluorescein angiography.

The antagonist of the method of the invention may be an antibody, fragment of an antibody, peptide or small molecule. In some embodiments, the LFA-1 antagonist used is a peptide which is not an antibody. In other embodiments the, LFA-1 antagonist used is a small molecule.

In some embodiments of the invention, treating or preventing the symptoms of diabetic retinopathy by using LFA-1 antagonists requires chronic therapy; therefore, small molecule inhibitors of the LFA-1/ICAM-1 interaction may be utilized as they have the potential for local administration as ocular drops with a lowered cost of goods. Similarly oral administration offers advantages in lowered cost of goods. Implantable devices, which may be biodegradable or bioabsorbable or biodegradable slow release or sustained release formulations implanted or injected into the eye or near the eye in periocular tissue are used for chronic therapy.

Another embodiment is a method of treating the symptoms of diabetic retinopathy using therapeutic agents which are suitable for formulation and administration as ocular therapeutics.

A cream formulation of the compounds of the invention may be useful in the local delivery of a LFA-1 antagonist to the skin. Compounds useful in this regard include LFA-1 antagonists and their pro-drugs which are transformed into the active drug once within the skin. A skin cream applied to the outer surface of the eyelids thus delivering a LFA-1 antagonist across the eyelid to the inner lining of the eyelid and the intervening conjunctival tissue and accessory lacrimal glands and appear in tear and thus be absorbed into the eye. This form of delivery may be desirable in treating LFA-1 mediated inflammation of the eye, particularly in the treatment of diabetic retinopathy.

III. Administration

The method of the present invention may draw upon many suitable modes of administration to deliver the LFA-1 antagonist of the methods described herein. Such delivery to affected regions of the body may be achieved either via local or systemic administration. Suitable formulations and additional carriers are described in Remington "The Science and Practice of Pharmacy" (20$^{th}$ Ed., Lippincott Williams & Wilkins, Baltimore Md.), the teachings of which are incorporated by reference in their entirety herein.

In some embodiments, the invention provides a pharmaceutical composition for administration to a subject containing: (i) an effective amount of a therapeutic agent; and (ii) a pharmaceutical excipient suitable for oral administration. In some embodiments, the composition further contains: (iii) an effective amount of a second therapeutic agent. A pharmaceutical composition of the invention can comprise any of the molecules disclosed herein.

In order to reduce inflammation in eye disorders, the pharmaceutical composition of the invention is preferably delivered to the retina, intraocular space, ocular surface, interconnecting innervation, conjunctiva, lacrimal glands, or meibomian glands. It is envisioned that effective treatment can encompass administering therapeutic agents of the present invention via oral administration, topical administration, via injection, intranasally, rectally, transdermally, via an impregnated or coated device such as an ocular insert or implant, or iontophoretically, amongst other routes of administration.

For administration via injection, the pharmaceutical composition can be injected intraocularly, periocularly, intramuscularly, intra-arterially, subcutaneously, or intravenously. A pump mechanism may be employed to administer the pharmaceutical composition over a preselected period. For some embodiments of the invention it is desirable to deliver drug locally, thus injections may be made periocularly, intraocularly, intravitreally, subconjunctively, retrobulbarly, into the sclera, or intercamerally. For some embodiments of the invention, systemic delivery is preferred.

For systemic administration, the compounds of the invention can be formulated for and administered orally.

For administration that may result in either regional or systemic distribution of the therapeutic agents, the composition of the invention may be administered intranasally, transdermally, or via some forms of oral administration, e.g. with use of a mouthwash or lozenge incorporating a compound of the invention that is poorly absorbed from the G.I. For administration that may result in regional or local delivery of the composition of the invention, iontophoretic or topical administration may be used.

Additionally, the pharmaceutical compositions of the present invention may be administered to the ocular surface via a pump-catheter system, or released from within a continuous or selective release device such as, e.g., membranes such as, but not limited to, those employed in the Ocusert™ System (Alza Corp, Palo Alto, Calif.). The pharmaceutical compositions can be incorporated within, carried by or attached to contact lenses which are then worn by the subject. The pharmaceutical compositions can be sprayed onto ocular surface.

Alternatively, the pharmaceutical compositions of the present invention may be administered intraocularly or periocularly via a pump-catheter system, or released from within a continuous or selective release device. The pharmaceutical compositions may also comprise biodegradable sustained, slow and/or delayed release formulations such as, for example, PLGA microspheres, microparticles or nanoparticles which may be delivered via a device as described above or injected intraocularly or periocularly.

In some embodiments, the LFA-1 antagonist is administered in a single dose. A single dose of a LFA-1 antagonist may also be used when it is co-administered with another substance (e.g, an analgesic) for treatment of an acute condition.

In some embodiments, the LFA-1 antagonist (by itself or in combination with other drugs) is administered in multiple doses. Dosing may be about once, twice, three times, four times, five times, six times, seven times, eight times, nine times, ten times or more than ten times per day. Dosing may be about once a year, twice a year, every six months, every 4 months, every 3 months, every 60 days, once a month, once every two weeks, once a week, or once every other day. In one embodiment the drug is an analgesic. In another embodiment the LFA-1 antagonist and another therapeutic substance are administered together about once per day to about 10 times per day. In another embodiment the administration of the LFA-1 antagonist and another therapeutic substance continues for less than about 7 days. In yet another embodiment the co-administration continues for more than about 6, 10, 14, 28 days, two months, six months, or one year. In some cases, co-administered dosing is maintained as long as necessary, e.g., dosing for chronic inflammation.

Administration of the compositions of the invention may continue as long as necessary. In some embodiments, a composition of the invention is administered for more than 1, 2, 3, 4, 5, 6, 7, 14, or 28 days. In some embodiments, a composition of the invention is administered for less than 28, 14, 7, 6, 5, 4, 3, 2, or 1 day. In some embodiments, a composition of the invention is administered chronically on an ongoing basis, e.g., for the treatment of chronic pain.

Dosing for the LFA-1 antagonist in the method of the invention may be found by routine experimentation. The daily dose can range from about $1\times10^{-8}$ g to 5000 mg. Daily dose range may depend on the form of LFA-1 antagonist e.g., the esters or salts used, and/or route of administration, as described herein. For example, for systemic administration, typical daily dose ranges are, e.g. about 1-5000 mg, or about 1-3000 mg, or about 1-2000 mg, or about 1-1000 mg, or about 1-500 mg, or about 1-100 mg, or about 10-5000 mg, or about 10-3000 mg, or about 10-2000 mg, or about 10-1000 mg, or about 10-500 mg, or about 10-200 mg, or about 10-100 mg, or about 20-2000 mg or about 20-1500 mg or about 20-1000 mg or about 20-500 mg, or about 20-100 mg, or about 50-5000 mg, or about 50-4000 mg, or about 50-3000 mg, or about 50-2000 mg, or about 50-1000 mg, or about 50-500 mg, or about 50-100 mg, about 100-5000 mg, or about 100-4000 mg, or about 100-3000 mg, or about 100-2000 mg, or about 100-1000 mg, or about 100-500 mg. In some embodiments, the daily dose of LFA-1 antagonist is about 100, 200, 300, 400, 500, 600, 700, 800, 900, or 1000 mg. In some embodiments, the daily dose of the LFA-1 antagonist is 10 mg. In some embodiments, the daily dose of the LFA-1 antagonist is 100 mg. In some embodiments, the daily dose of LFA-1 antagonist is 500 mg. In some embodiments, the daily dose of LFA-1 antagonist is 1000 mg.

For topical delivery to the ocular surface, the typical daily dose ranges are, e.g. about $1\times10^{-8}$ to 5.0 g, or about $1\times10^{-8}$ g to 2.5 g, or about $1\times10^{-8}$ g to 1.00 g, or about $1\times10^{-8}$ g to 0.5 g, or about $1\times10^{-8}$ g to 0.25 g, or about $1\times10^{-8}$ g to 0.1 g, or about $1\times10^{-8}$ g to 0.05 g, or about $1\times10^{-8}$ g to 0.025 g, or about $1\times10^{-8}$ g to $1\times10^{-2}$ g, or about $1\times10^{-8}$ g to $5\times10^{-3}$ g, or about $1\times10^{-8}$ g to $2.5\times10^{-3}$ g, or about $1\times10^{-8}$ g to $1\times10^{-3}$ g, or about $1\times10^{-8}$ g to $5\times10^{-4}$ g, or about $1\times10^{-7}$ g to 5.0 g, or about $1\times10^{-7}$ g to 2.5 g, or about $1\times10^{-7}$ g to 1.00 g, or about $1\times10^{-7}$ g to 0.5 g, or about $1\times10^{-7}$ g to 0.25 g, or about $1\times10^{-7}$ g to 0.1 g, or about $1\times10^{-7}$ g to 0.05 g, or about $1\times10^{-7}$ g to 0.025 g, or about $1\times10^{-7}$ g to $1\times10^{-2}$ g, or about $1\times10^{-7}$ g to $5\times10^{-3}$ g, or about $1\times10^{-7}$ g to $2.5\times10^{-3}$ g, or about $1\times10^{-7}$ g to $1\times10^{-3}$ g, or about $1\times10^{-7}$ g to $5\times10^{-4}$ g, or about $1\times10^{-6}$ g to 5.0 g, or about $1\times10^{-6}$ g to 2.5 g, or about $1\times10^{-6}$ g to 1 g, or about $1\times10^{-6}$ g to 0.5 g, or about $1\times10^{-6}$ g to 0.25 g, or about $1\times10^{-6}$ g to 0.1 g, or about $1\times10^{-6}$ g to $5\times10^{-2}$ g, or about $1\times10^{-6}$ g to $5\times10^{-2}$ g, or about $1\times10^{-6}$ g to $2.5\times10^{-2}$ g, or about $1\times10^{-6}$ g to $1\times10^{-2}$ g, or about $1\times10^{-6}$ g to $5\times10^{-3}$ g, or about $1\times10^{-6}$ g to $2.5\times10^{-3}$ g, or about $1\times10^{-6}$ g to $1\times10^{-3}$ g, or about $1\times10^{-6}$ g to $5\times10^{-4}$ g, or about $1\times10^{-5}$ g to 5 g, or about $1\times10^{-5}$ g to 2.5 g, or about $1\times10^{-5}$ g to 1 g, or about $1\times10^{-5}$ g to 0.5 g, or about $1\times10^{-5}$ g to 0.25 g, or about $1\times10^{-5}$ g to 0.1 g, or about $1\times10^{-5}$ g to 0.05 g, or about $1\times10^{-5}$ g to $2.5\times10^{-2}$ g, or about $1\times10^{-5}$ g to $1\times10^{-2}$ g, or about $1\times10^{-5}$ g to $5\times10^{-3}$ g, or about $1\times10^{-5}$ g to $2.5\times10^{-3}$ g, or about $1\times10^{-5}$ g to $1\times10^{-3}$ g, or about $1\times10^{-5}$ g to $5\times10^{-4}$ g. In some embodiments, the daily dose of LFA-1 antagonist is about $1\times10^{-7}$, $1\times10^{-6}$, $1\times10^{-5}$, $1\times10^{-4}$, $1\times10^{-3}$ g, $1\times10^{2}$ g, $1\times10^{1}$ g, or 1 g. In some embodiments, the daily dose of the LFA-1 antagonist is $1\times10^{-7}$ g. In some embodiments, the daily dose of the LFA-1 antagonist is $1\times10^{-5}$ g. In some embodiments, the daily dose of LFA-1 antagonist is $1\times10^{-3}$ g. In some embodiments, the daily dose of LFA-1 antagonist is $1\times10^{-2}$ g. In some embodiments the subject dose ranges from about $1\times10^{-8}$ g to 5.0 g, or about $1\times10^{-8}$ g to 2.5 g, or about $1\times10^{-8}$ g to 1.00 g, or about $1\times10^{-8}$ g to 0.5 g, or about $1\times10^{-8}$ g to 0.25 g, or about $1\times10^{-8}$ g to 0.1 g, or about $1\times10^{-8}$ g to 0.05 g, or about $1\times10^{-8}$ g to 0.025 g, or about $1\times10^{-8}$ g to $1\times10^{-2}$ g, or about $1\times10^{-8}$ g to $5\times10^{-3}$ g, or about $1\times10^{-8}$ g to $2.5\times10^{-3}$ g, or about $1\times10^{-8}$ g to $1\times10^{-3}$ g, or about $1\times10^{-8}$ g to $5\times10^{-4}$ g, or about $1\times10^{-7}$ g to 5.0 g, or about $1\times10^{-7}$ g to 2.5 g, or about $1\times10^{-7}$ g to 1.00 g, or about $1\times10^{-7}$ g to 0.5 g, or about $1\times10^{-7}$ g to 0.25 g, or about $1\times10^{-7}$ g to 0.1 g, or about $1\times10^{-7}$ g to 0.05 g, or about $1\times10^{-7}$ g to 0.025 g, or about $1\times10^{-7}$ g to $1\times10^{-2}$ g, or about $1\times10^{-7}$ g to $5\times10^{-3}$ g, or about $1\times10^{-7}$ g to $2.5\times10^{-3}$ g, or about $1\times10^{-7}$ g to $1\times10^{-3}$ g, or about $1\times10^{-7}$ g to $5\times10^{-4}$ g, or about $1\times10^{-6}$ g to 5.0 g, or about $1\times10^{-6}$ g to 2.5 g, or about $1\times10^{-6}$ g to 1 g, or about $1\times10^{-6}$ g to 0.5 g, or about $1\times10^{-6}$ g to 0.25 g, or about $1\times10^{-6}$ g to 0.1 g, or about $1\times10^{-6}$ g to $5\times10^{-2}$ g, or about $1\times10^{-6}$ g to $5\times10^{-6}$ g, or about $1\times10^{-6}$ g to $2.5\times10^{-2}$ g, or about $1\times10^{-6}$ g to $1\times10^{-2}$ g, or about $1\times10^{-6}$ g to $5\times10^{-3}$ g, or about $1\times10^{-6}$ g to $2.5\times10^{-3}$ g, or about $1\times10^{-6}$ g to $1\times10^{-3}$ g, or about $1\times10^{-6}$ g to $5\times10^{-4}$ g, or about $1\times10^{-5}$ g to 5 g, or about $1\times10^{-5}$ g to 2.5 g, or about $1\times10^{-5}$ g to 1 g, or about $1\times10^{-5}$ g to 0.5 g, or about $1\times10^{-5}$ g to 0.25 g, or about $1\times10^{-5}$ g to 0.1 g, or about $1\times10^{-5}$ g to 0.05 g, or about $1\times10^{-5}$ g to $2.5\times10^{-2}$ g, or about $1\times10^{-5}$ g to $1\times10^{-2}$ g, or about $1\times10^{-5}$ g to $5\times10^{-3}$ g, or about $1\times10^{-5}$ g to $2.5\times10^{-3}$ g, or about $1\times10^{-5}$ g to $1\times10^{-3}$ g, or about $1\times10^{-5}$ g to $5\times10^{-4}$ g. In some embodiments, the individual dose as described above, is repeated 1, 2, 3, 4, 5, 6, 7, 8, 9, or 10 times per day.

In some embodiments of the invention, the eye drop, cream, lotion or other topical formulations of the invention release sufficient therapeutic agent intraocularly or periocularly to sustain a level of LFA-1 antagonist of at least about 10 nM, about 50 nM, about 100 nM, about 150 nM, about 200 nM, about 250 nM, about 300 nM, about 350 nM, about 500 nM, about 600 nM, about 700 nM, about 800 nM, about 900 nM, about 1 mM, about 2 mM, about 3 mM, about 5 mM, about 6 mM, about 7 mM, about 8 mM, about 9 mM, about 10 mM, about 15 mM, about 20 mM or about 25 mM from dose to dose.

In some embodiments of the invention, an eye drop formulation of the invention release sufficient therapeutic agent intraocularly or periocularly to achieve a level of LFA-1 antagonist in the retina of at least about 10 nM, about 50 nM, about 100 nM, about 150 nM, about 200 nM, about 250 nM, about 300 nM, about 350 nM, about 500 nM, about 600 nM, about 700 nM, about 800 nM, about 900 nM, about 1 mM, about 2 mM, about 3 mM, about 5 mM, about 6 mM, about 7 mM, about 8 mM, about 9 mM, about 10 mM, about 15 mM, about 20 mM or about 25 mM from dose to dose.

For other forms of administration, the daily dosages may range about the range described for systemic administration or may range about the range described for topical administration.

For slow or sustained release intraocular or periocular devices and formulations, in some embodiments, a typical dose range is about 0.1 mg to about 100 mg of LFA-1 antagonist released over the dosing period. In other embodiments, about 1 mg to about 50 mg, about 1 to about 25 mg, about 5 mg to about 100 mg, about 5 to about 50 mg, about 5 to about 25 mg, about 10 mg to about 100 mg, about 10 mg to about 50 mg, about 10 mg to about 25 mg, or about 15 mg to about 50 mg is released over the dosing period. The dosing period for slow release intraocular or periocular devices and formulations, typically range from about 10 days to about 1 year, about 30 days to about 1 year, about 60 days to about 1 year, about 3 months to about 1 year, about 4 months to about 1 year, about 5 months to about 1 year, or about 6 months to about 1 year. In some embodiments, the slow release intraocular or periocular devices and formulations release therapeutic agent over the period of about 1 month to about 9 months, about 1 month to about 8 months, about 1 month to about 7 months, about 1 month, to about 6 months, about 1 month to about 5 months, about 1 month to about 4 months, or about 1 month to about 3 months. In other embodiments the slow release formulations and devices release therapeutic agent for up to 1 month, 2 months, 3 months, 4 months, 5 months, 6 months, 7 months, 8 months, 9 months, 10 months, 12 months, 18 months, 2 years, 30 months, or 3 years.

In some embodiments of the invention, the sustained release formulation and/or implantations release sufficient therapeutic agent intraocularly or periocularly to sustain a level of LFA-1 antagonist of at least about 10 nM, about 50 nM, about 100 nM, about 150 nM, about 200 nM, about 250 nM, about 300 nM, about 350 nM, about 500 nM, about 600 nM, about 700 nM, about 800 nM, about 900 nM, about 1 mM, about 2 mM, about 3 mM, about 5 mM, about 6 mM, about 7 mM, about 8 mM, about 9 mM, about 10 mM, about 15 mM, about 20 mM or about 25 mM across 1 year. In some embodiments of the invention, the sustained release formulation and/or implantations release sufficient therapeutic agent intraocularly or periocularly to sustain a level of LFA-1 antagonist of at least about 10 nM, about 50 nM, about 100 nM, about 150 nM, about 200 nM, about 250 nM, about 300 nM, about 350 nM, about 500 nM, about 600 nM, about 700 nM, about 800 nM, about 900 nM, about 1 mM, about 2 mM, about 3 mM, about 5 mM, about 6 mM, about 7 mM, about 8 mM, about 9 mM, about 10 mM, about 15 mM, about 20 mM or about 25 mM across 6 months.

IV. Formulations

The compounds of the invention may be formulated as a sterile solution or suspension, in suitable vehicles, well known in the art. Suitable formulations and additional carriers are described in Remington "The Science and Practice of Pharmacy" ($20^{th}$ Ed., Lippincott Williams & Wilkins, Baltimore Md.), the teachings of which are incorporated by reference in their entirety herein.

For injectable formulations, the vehicle may be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation may also comprise polymer compositions which are biocompatible, biodegradable, such as poly(lactic-co-glycolic)acid. These materials may be made into micro or nanoparticles, loaded with drug and further coated or derivatized to provide superior sustained release performance. Vehicles suitable for periocular or intraocular injection include, for example, suspensions of therapeutic agent in injection grade water, liposomes and vehicles suitable for lipophilic substances. Other vehicles for periocular or intraocular injection are well known in the art.

The concentration of drug may be adjusted, the pH of the solution buffered and the isotonicity adjusted to be compatible with intravenous injection, as is well known in the art.

Any of the forms of LFA-1 may also be milled to provide more suitable properties for formulation. Milling may provide smaller particle size with greater surface area exposure, which can provide faster solubilization in-vivo or during formulation. Alternatively, milling to a smaller particle size may provide the capacity to pass through biological barriers, such as the skin or gut wall, directly, without initial solubilization, permitting use as a solid in the formulation, which may provide additional benefits of temperature stability, shelf life, ease of transport, and ease of use by the subject.

Oral formulations can be tablets, capsules, troches, pills, wafers, chewing gums, lozenges, aqueous solutions or suspensions, oily suspensions, syrups, elixirs, or dispersible powders or granules, and the like and may be made in any way known in the art. Oral formulations may also contain sweetening, flavoring, coloring and preservative agents. Pharmaceutically acceptable excipients for tablet forms may comprise nontoxic ingredients such as inert diluents, such as calcium carbonate, sodium carbonate, lactose, calcium phosphate, or sodium phosphate, and the like.

In the case of tablets for oral use, carriers which are commonly used include lactose and corn starch, and lubricating agents such as magnesium stearate are commonly added. For oral administration in capsule form, useful carriers include lactose and corn starch. Further nonlimiting examples of carriers and excipients include milk, sugar, certain types of clay, gelatin, stearic acid or salts thereof, calcium stearate, talc, vegetable fats or oils, gums and glycols.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, preferred ionic surfactants include, by way of example: lecithins, lysolecithin, phospholipids, lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE- 20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

Surfactants may be used in any formulation of the invention where its use is not otherwise contradicted. In some embodiments of the invention, the use of no surfactants or limited classes of surfactants are preferred.

Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include methyl and n-propyl p-hydroxybenzoate.

Chelating agents which can be used to form pharmaceutical compositions and dosage forms of the invention include, but are not limited to, ethylene diaminetetraacetic acid (EDTA), EDTA disodium, calcium disodium edetate, EDTA trisodium, albumin, transferrin, desferoxamine, desferal, desferoxamine mesylate, EDTA tetrasodium and EDTA dipotassium, sodium metasilicate or combinations of any of these.

Preservatives which can be used to form pharmaceutical compositions and dosage forms of the invention include, but are not limited to, purite, peroxides, perborates, imidazolidinyl urea, diazolidinyl urea, phenoxyethanol, alkonium chlorides including benzalkonium chlorides, methylparaben, ethylparaben and propylparaben.

Thickening agents which can be used to form pharmaceutical compositions land dosage forms of the invention include, but are not limited to, isopropyl myristate, isopropyl palmitate, isodecyl neopentanoate, squalene, mineral oil, $C_{12}$-$C_{15}$ benzoate and hydrogenated polyisobutene. Particularly preferred are those agents which would not disrupt other compounds of the final product, such as non-ionic thickening agents. The selection of additional thickening agents is well within the skill of one in the art.

Anti-oxidants which can be used to form pharmaceutical compositions and dosage forms of the invention include, but are not limited to, propyl, octyl and dodecyl esters of gallic acid, butylated hydroxyanisole (BHA, usually purchased as a mixture of ortho and meta isomers), green tea extract, uric acid, cysteine, pyruvate, nordihydroguaiaretic acid, ascorbic acid, salts of ascorbic acid such as ascorbyl palmitate and sodium ascorbate, ascorbyl glucosamine, vitamin E (i.e., tocopherols such as a-tocopherol), derivatives of vitamin E (e.g., tocopheryl acetate), retinoids such as retinoic acid, retinol, trans-retinol, cis-retinol, mixtures of trans-retinol and cis-retinol, 3-dehydroretinol and derivatives of vitamin A (e.g., retinyl acetate, retinal and retinyl palmitate, also known as tetinyl palmitate), sodium citrate, sodium, sulfite, lycopene, anthocyanids, bioflavinoids (e.g., hesperitin, naringen, rutin and quercetin), superoxide dismutase, glutathione peroxidase, butylated hydroxytoluene (BHT), indole-3-carbinol, pycnogenol, melatonin, sulforaphane, pregnenolone, lipoic acid and 4-hydroxy-5-methyl-3[2H]-furanone.

When formulating compounds of the invention for oral administration, it may be desirable to utilize gastroretentive formulations to enhance absorption from the gastrointestinal (GI) tract. A formulation which is retained in the stomach for several hours may release compounds of the invention slowly and provide a sustained release that may be preferred in some embodiments of the invention. Disclosure of such gastro-retentive formulations are found in Klausner, E. A.; Lavy, E.; Barta, M.; Cserepes, E.; Friedman, M.; Hoffman, A. 2003 "Novel gastroretentive dosage forms: evaluation of gastroretentivity and its effect on levodopa in humans." Pharm. Res. 20, 1466-73, Hoffman, A.; Stepensky, D.; Lavy, E.; Eyal, S. Klausner, E.; Friedman, M. 2004 "Pharmacokinetic and pharmacodynamic aspects of gastroretentive dosage forms" Int. J. Pharm. 11, 141-53, Streubel, A.; Siepmann, J.; Bodmeier, R.; 2006 "Gastroretentive drug delivery systems" Expert Opin. Drug Deliver. 3, 217-3, and Chavanpatil, M. D.; Jain, P.; Chaudhari, S.; Shear, R.; Vavia, P. R. "Novel sustained release, swellable and bioadhesive gastroretentive drug delivery system for olfoxacin" Int. J. Pharm. 2006 epub March 24. Expandable, floating and bioadhesive techniques may be utilized to maximize absorption of the compounds of the invention.

Intranasal administration may utilize an aerosol suspension of respirable particles comprised of the compounds of the invention, which the subject inhales. The compound of the invention are absorbed into the bloodstream via pulmonary absorption or contact the lacrimal tissues via nasolacrimal ducts, and subsequently be delivered to the retinal tissues in a pharmaceutically effective amount. The respirable particles may be solid or liquid, with suitably sized particles, as is known in the art to be effective for absorption. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

For transdermal administration, any suitable formulation known in the art may be utilized, either as a solution, drop, suspension, gel, powder, cream, oil, solids, dimethylsulfoxide (DMSO)-based solutions or liposomal formulation for use in a patch or other delivery system known in the art. The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For topical administration, all the formulations for topical ocular administration used in the field of ophthalmology (e.g., eye drops, inserts, eye packs, impregnated contact lenses, pump delivery systems, dimethylsulfoxide (DMSO)-based solutions suspensions, liposomes, and eye ointment) and all the formulations for external use in the fields of dermatology and otolaryngology (e.g., ointment, cream, gel, powder, salve, lotion, crystalline forms, foam, and spray) may be utilized as is known in the art. In some embodiments, the extraordinary solubility of some of the LFA-1 antagonists of the invention permit concentrated solution formulations which can then deliver therapeutically relevant doses to regions of the eye. Additionally all suitable formulations for topical administration to skin and mucus membranes of the nasal passages may be utilized to deliver the compounds of the invention. The pharmaceutical compositions of the present invention may be a liposomal formulation for topical or oral administration, any of which are known in the art to be suitable for the purpose of this invention.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

Skin protecting agents are agents that protect the skin against chemical irritants and/or physical irritants, e.g., UV light, including sunscreens, anti-acne additives, anti-wrinkle and anti-skin atrophy agents. Suitable sunscreens as skin protecting agents include 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropy dibenzoylmethane, 3-benzylidene camphor, 3-(4-methylbenzylidene) camphor, anthanilates, ultrafine titanium dioxide, zinc oxide, iron oxide, silica, 4-N,N-(2-ethylhexyl)methylaminobenzoic acid ester of 2,4-dihydroxybenzophenone, 4-N,N-(2-ethylhexyl)-methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone and 4-N,N (2-ethylhexyl)-methylaminobenzoic acid ester of 4-(2-hydroxyethoxy)dibenzoylmethane. Suitable anti-acne agents include salicylic acid; 5-octanoyl salicylic acid; resorcinol; retinoids such as retinoic acid and its derivatives; sulfur-containing D and L amino acids other than cysteine; lipoic acid; antibiotics and antimicrobials such as benzoyl peroxide, octopirox, tetracycline, 2,4,4'-trichloro-2'-hydroxydiphenyl ether, 3,4,4'-trichlorobanilide, azelaic acid, phenoxyethanol, phenoxypropanol, phenoxisopropanol, ethyl acetate, clindamycin and melclocycline; flavonoids; and bile salts such as scymnol sulfate, deoxycholate and cholate. Examples of anti-wrinkle and anti-skin atrophy agents are retinoic acid and its derivatives, retinol, retinyl esters, salicylic acid and its derivatives, sulfur-containing D and L amino acids except cysteine, alpha-hydroxy acids (e.g., glycolic acid and lactic acid), phytic acid, lipoic acid and lysophosphatidic acid.

The formulations may also contain irritation-mitigating additives to minimize or eliminate the possibility of skin irritation or skin damage resulting from the other components of the composition. Suitable irritation-mitigating additives include, for example: -tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; and chloroquine. The irritant-mitigating additive, if present, may be incorporated into the present formulations at a concentration effective to mitigate irritation or skin damage, typically representing not more than about 20 wt. %, more typically not more than about 5 wt. %, of the composition.

A dry-feel modifier is an agent which when added to an emulsion, imparts a "dry feel" to the skin when the emulsion dries. Dry feel modifiers can include talc, kaolin, chalk, zinc oxide, silicone fluids, inorganic salts such as barium sulfate, surface treated silica, precipitated silica, fumed silica such as an Aerosil available from Degussa Inc. of New York, N.Y. U.S.A. Another dry feel modifier is an epichlorohydrin cross-linked glyceryl starch of the type that is disclosed in U.S. Pat. No. 6,488,916.

Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, purite, peroxides, perborates and combinations thereof.

The formulation may also contain an aesthetic agent. Examples of aesthetic agents include fragrances, pigments, colorants, essential oils, skin sensates and astringents. Suitable aesthetic agents include clove oil, menthol, camphor, eucalyptus oil, eugenol, methyl lactate, bisabolol, witch hazel distillate (preferred) and green tea extract (preferred).

Fragrances are aromatic substances which can impart an aesthetically pleasing aroma to the sunscreen composition. Typical fragrances include aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products: One or more fragrances can optionally be included in the sunscreen composition in an amount ranging from about 0.001 to about 5 weight percent, preferably about 0.01 to about 0.5 percent by weight. Additional preservatives may also be used if desired and include well known preservative compositions such as benzyl alcohol, phenyl ethyl alcohol and benzoic acid, diazolydinyl, urea, chlorphenesin, iodopropynyl and butyl carbamate, among others.

It is envisioned additionally, that the compounds of the invention may be attached releasably to biocompatible polymers for use in sustained release formulations on, in or attached to inserts for topical, intraocular, periocular, or systemic administration. The controlled release from a biocompatible polymer may be utilized with a water soluble polymer to form a instillable formulation, as well. The controlled release from a biocompatible polymer, such as for example, PLGA microspheres, microparticles or nanoparticles, may be utilized in a formulation suitable for intra ocular implantation or injection for sustained release administration, as well Any suitable biodegradable and biocompatible polymer or matrix may be used.

Eye drops may be prepared by dissolving the active ingredient in a sterile aqueous solution such as physiological saline, buffering solution, etc., or by combining powder compositions to be dissolved before use. Other vehicles may be chosen, as is known in the art, including but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

The solubility of the components of the present compositions may be enhanced by a surfactant or other appropriate co-solvent in the composition. Such cosolvents include polysorbate 20, 60, and 80, Pluronic F68, F-84 and P-103, cyclodextrin, or other agents known to those skilled in the art. Such co-solvents may be employed at a level of from about 0.01% to 2% by weight.

The composition of the invention can be formulated as a sterile unit dose type containing no preservatives.

The compositions of the invention may be packaged in multidose form. Preservatives may be preferred to prevent microbial contamination during use. Suitable preservatives include: benzalkonium chloride, thimerosal, chlorobutanol, methyl paraben, propyl paraben, phenylethyl alcohol, edetate disodium, sorbic acid, sodium perborate, Onamer M, or other agents known to those skilled in the art. In the prior art ophthalmic products, such preservatives may be employed at a level of from 0.004% to 0.02%. In the compositions of the present application the preservative, preferably benzalkonium chloride, may be employed at a level of from 0.001% to less than 0.01%, e.g. from 0.001% to 0.008%, preferably about 0.005% by weight. It has been found that a concentration of benzalkonium chloride of 0.005% may be sufficient to preserve the compositions of the present invention from microbial attack.

The amount of administration and the number of administrations of the active ingredient used in the present invention vary according to sex, age and body weight of subject, symptoms to be treated, desirable therapeutic effects, administration routes and period of treatment. For eye drops for an adult, the formulations containing the compounds of the invention may range in concentration from about 0.0001 to 10.0 W/V %, about 0.005 to 10.0 W/V %, about 0.01 to 10.0 W/V %, about 0.05 to 10.0 W/V %, about 0.1 to 10.0 W/V %, about 0.5 to 10.0 W/V %, about 1.0 to 10.0 W/V %, about 20 to 10.0 W/V %, about 3.0 to 10.0 W/V %, about 4.0 to 10.0 W/V %, or about 5.0 to 10.0 W/V %. One embodiment of the invention has a formulation of about 1.0 to 10.0 W/V % of the compounds of the invention. One embodiment of the invention has a formulation of about 0.01 to 10.0 W/V % of the compounds of the invention. One embodiment of the invention has a formulation of about 5.0 to 10.0 W/V % of the compounds of the invention. The administration may be administered several times a day per eye, preferably one to ten times, more preferably one to four times, most preferably once a day. The size of the drop administered may be in the range of about 10-100 µl, about 10-90 µl, about 10-80 µl, about 10-70 µl, about 10-60 µl, about 10-50 µl, about 10-40 µl, about 10-30 µl, about 20-100 µl, about 20-90 µl, about 20-80 µl, about 20-70 µl, about 20-60 µl, about 20-50 µl, about 20-40 µl, or about 20-30 µl. One embodiment of the invention administers a drop in the range of about 10 to about 30 µl. One embodiment of the invention administers a drop in the range of about 10 to about 100 µl. One embodiment of the invention administers a drop in the range of about 20 to about 50 µl. One embodiment of the invention administers a drop in the range of about 20 to about 40 µl. One embodiment of the invention administers a drop in the range of about 10 to about 60 µl.

The formulations of the invention may be administered several drops per time, one to four drops, preferably one to three drops, more preferably one to two drops, and most preferably one drop per day. In one embodiment, the formulations of the invention are administered about one drop per time and one time per day.

In formulations for ointment, cream, lotion or spray, the concentration of the compounds of the invention in the formulations may range about 0.0001 10.0 W/V %, about 0.005 to 10.0 W/V %, about 0.01 to 10.0 W/V %, about 0.05 to 10.0 W/V %, about 0.1 to 10.0 W/V %, about 0.5 to 10.0 W/V %, about 1.0 to 10.0 W/V %, about 20 to 10.0 W/V %, about 3.0 to 10.0 W/V %, about 4.0 to 10.0 W/V %, or about 5.0 to 10.0 W/V %. One embodiment of the invention has a formulation of about 1.0 to 10.0 W/V % of the compounds of the invention. One embodiment of the invention has a formulation of about 0.01 to 10.0 W/V % of the compounds of the invention. One embodiment of the invention has a formulation of about 5.0 to 10.0 W/V % of the compounds of the invention. These formulations may be applied or sprayed several times a day, preferably one to six times, more preferably one to four times, and most preferably once a day. The compounding ratio of each ingredient may be suitably increased or decreased based on the degree of inflammations or infections.

The formulations of the invention can further include other pharmacological active ingredients as far as they do not contradict the purpose of the present invention. In a combination of plural active ingredients, their respective contents may be suitably increased or decreased in consideration of their effects and safety.

V. Kits

The invention also provides kits. The kits include a compound of the invention in suitable packaging, and written material that can include instructions for use, discussion of clinical studies, listing of side effects, and the like. The kit may further contain another therapeutic agent that is co-administered with the LFA-1 antagonist of the invention. In some embodiments, the therapeutic agent and the LFA-1 antagonist of the invention are provided as separate compositions in separate containers within the kit. In some embodiments, the therapeutic agent and the LFA-1 antagonist of the invention are provided as a single composition within a container in the kit. Suitable packaging and additional articles for use (e.g., measuring cup for liquid preparations, foil wrapping to minimize exposure to air, dispensers, and the like) are known in the art and may be included in the kit.

VI. EXAMPLES

Example 1: Affinity Measurements

The affinities of the small molecules for LFA-1 were measured using fluorescence polarization (FP) in a competitive format with a small molecule antagonist, compound 1 (FIG. 2), as previously described. All measurements were performed in buffer containing 50 mM Hepes, pH 7.2, 150 mM NaCl, 0.05% n-octyglucoside and 0.05% bovine gamma globulins (BGG) and either 1 mM $MnCl_2$, or 1 mM $CaCl_2$ and 1 mM $MgCl_2$. The affinity of compound 1 for LFA-1 was first measured by addition of 2 nM compound 1 to serial dilutions of LFA-1 starting from 1 µM in buffer containing either $MnCl_2$ or $CaCl_2$ and $MgCl_2$. Competition experiments were performed by addition of serial dilutions of antagonists to 2 nM compound 1 (using either 3 nM LFA-1 (in $MnCl_2$) or 40 nM LFA-1 (in $CaCl_2$ and $MgCl_2$)). In the ICAM-1-Ig competition experiments, the LFA-1 concentrations were reduced to 2 and 20 nM LFA-1 in the two divalent cation buffer conditions to maximize inhibition by ICAM-1-Ig. The different LFA-1 concentrations used in the experiments were taken into account in the affinity calculations (see below). The solutions were incubated in 96-well black HE96 plates (Molecular Devices, Sunnyvale, Calif.) for 2 hours at 37° C. Fluorescence Polarization (FP) measurements were performed on an Analyst platereader (Molecular Devices, Sunnyvale, Calif.) using 485 nm excitation, 530 nm emission and 505 nm dichroic filters. All raw intensity data were corrected for background emissions by subtraction of the intensities measured from the appropriate samples without compound 1. The LFA-1 binding and antagonist competition data were analyzed using a non linear least squares fit of a four-parameter equation with KaleidaGraph software (Synergy Software, Reading, Pa.) to obtain the $EC_{50}$ values for the LFA-1 titration and the $IC_{50}$ values of the antagonists. The equation used to fit the data is $Y=((A-D)/(1+(X/C)^B))+D$, where Y is the assay response, A is Y—value at the upper asymptote, B is the slope factor, C is the $IC_{50}$ or $EC_{50}$ and D is Y—the value at the lower asymptote. In general, the data measured in both the homogeneous FP and heterogeneous ELISA formats described below, contain relatively large signal to background ratios and the error estimates in the fits are typically less than 10% of the final value of the fitted parameter. The equilibrium dissociation constants ($K_d$) of LFA-1 for compound 1 with and without A-286982 were calculated using Klotz and Hill analyses. The affinities ($K_i$) of the antagonists for LFA-1 were calculated using the $IC_{50}$ values, the $K_d$ of compound 1/LFA-1, and the concentrations of compound 1 and LFA-1 in the competition experiments.

Example 2: LFA-1/ICAM-1 and LFA-1/Small Molecule Enzyme-Linked Immunosorbent Assays (ELISAs)

(A) Antagonist Competition: Small molecules and sICAM-1 were assayed for the ability to disrupt binding of ICAM-1-Ig or a fluorescein-labeled small molecule antagonist, compound 2B, to LFA-1 in a competitive format. Compound 2B is similar to compound 1, but with a longer linker between the small molecule and fluorescein to maximize the binding of the anti-fluorescein detection antibody. 96-well plates were coated with 5 µg/ml (33.3 nM) mouse anti-human β2 integrin (a non-function blocking antibody) in phosphate-buffered saline (PBS) overnight at 4° C. The plates were blocked with assay buffer (20 mM Hepes, pH 7.2, 140 mM NaCl, 1 mM $MnCl_2$, 0.5% bovine serum albumin (BSA) and 0.05% Tween-20) for 1 hour at room temperature. After washing in buffer (50 mM Tris-HCl, pH 7.5, 100 mM NaCl, 1 mM $MnCl_2$, and 0.05% Tween-20), 8 nM LFA-1 (LFA-1/ICAM-1 ELISA) or 2 nM LFA-1 (LFA-1/small molecule ELISA) were added, followed by incubation for 1 h at 37° C. The plates were washed, and for the LFA-1/ICAM-1 ELISA, serial dilutions of the small molecule antagonists or sICAM-1 were added to the plates for 30 minutes, followed by addition of 0.89 nM ICAM-1-Ig (final concentration) for 2 hour at 37° C. After an additional wash, goat anti-huIgG (Fc specific)-HRP was added and incubated for one hour at 37° C. In the LFA-1/small molecule ELISA, the diluted antagonists and 25 nM compound 2B were added concurrently to the plates, followed by a 2-hour incubation at 37° C. Sheep anti-fluorescein-HRP was added after a wash and incubated for one hour at 37° C. For both assays, after washing, the bound HRP-conjugated antibodies were detected by addition of tetramethylbenzidine (TMB) followed by measurement of the absorbance of the product at 450 nm after the addition of 1 M $H_3PO_4$ to stop the reaction. The $IC_{50}$ values for each curve were determined by fitting to the four-parameter equation described above using KaleidaGraph software.

(B) Ligand Binding: The LFA-1/ICAM-1 and LFA-1/small molecule ELISAs were performed as described above except that serial dilutions of either ICAM-1-Ig or compound 2B were added to plates either in the presence or absence of antagonist. In all cases the ligand was added concurrently with the antagonist. The plates were incubated for 6 h at 37° C. to approach equilibrium conditions after antagonist and ligand addition, before wash and addition of the detection antibody. The $EC_{50}$ values for each curve were determined by fitting with a four parameter model as described above. The $EC_{50}$ values generated in the presence and absence of antagonist were analyzed by Schild regression. The Schild plots of Log (Conc. ratio −1) vs. antagonist concentration are calculated from, (Conc. ratio −1)=((ligand $EC_{50}$ with antagonist)/(ligand $EC_{50}$ without antagonist))−1. The slopes of the plots of the Log (Conc. ratio −1) vs. Antagonist concentration are calculated by fitting the line to the linear equation, $Y=A+BX$.

Example 3: Crosslinking of a Radiolabeled, Photoactivatable Analogue of Compound 3 to LFA-1

Full length human membrane-associated LFA-1 or BSA (0.35 mg/mL [1.4 and 5.3 µM, respectively] in 20 mM Hepes, 150 mM NaCl, 5 mM $CaCl_2$, 5 mM $MgCl_2$, 1 mM $MnCl_2$, and 1% n-octylglucoside, pH 7.2) was incubated overnight at 37° C. with 4.1 µM compound 5, a tritium-labeled photoactivatable analogue of compound 3, in either the presence or absence of 290 µM compound 3. The molar ratio of compound 5 to LFA-1 was 3:1. A 96-well plate precoated with 1% BSA was used for the incubation. Just prior to crosslinking, excess compound 5 was rapidly removed by gel filtration with a G-25 microspin column in a 96-well format equilibrated with the same buffer. The LFA-1/compound 5 complex was crosslinked by exposure to a high-pressure mercury-vapor lamp (450 watts, Ace glass, Vineland, N.J.). During irradiation, samples were cooled on ice and protected by a 5-mm thick plate of borosilicate glass to minimize protein degradation. Residual unlinked compound 5 was removed by gel filtration (G-25) as above. The crosslinked complex was then denatured in 8 M guanidine hydrochloride (GuHCl) and reduced and alkylated. The treated proteins were subjected to SDS-PAGE followed by Coomassie blue staining. Radiolabeled proteins were visualized by audioradiography.

To identify compound 5 binding sites, the treated αL and β2 subunits were separated by size exclusion chromatography in the presence of 6 M GuHCl, 20 mM Hepes, 10 mM EDTA, pH 6.8 and then chemically cleaved with 2.6 M hydroxylamine in 10% acetic acid with 7 M GuHCl for 4 h at 75° C. The radiolabeled protein fragments were separated by SDS-PAGE and either visualized by autoradiography or transferred onto a polyvinylidene fluoride membrane, stained with Coomassie blue, and then identified by N-terminal protein sequencing.

Example 4: Generation of the αL Construct Lacking the I Domain

The construct used, pLFA.huID.Δp, contains the sequence of the αL gene from the Nar1 restriction site 5' of the I domain to the second PflM1 restriction site 3' of the I domain in which the first PflM1 restriction site 3' of the I domain was abolished (Edwards et al. 1995). In order to generate the mutant lacking the I domain, the following primers were made: the forward primer CACTGTGGCGCCCTGGTTTTCAGGAAGGTAGTG-GATCAGGCACAAGCAAACAGGACCTGACTTC (SEQ ID NO 3), containing the sequence from the Nar1 site to the start of the I domain, a sequence of DNA encoding GSGSG (SEQ ID NO 3) and the 23 bp of the αL sequence after the end of the I domain, and the reverse primer TCTGAGC-CATGTGCTGGTATCGAGGGGC (SEQ ID NO 5), which primes at the second PflM1 restriction site after the I domain. PCR was performed using these primers and the pLFA.huID.Δp linearized with Bgl II, which cut at a site within the I domain. A DNA fragment was amplified that contained the sequence from the Nar 1 site to the second PflM1 site and in which the entire I domain, from C125 through G311, was replaced with a DNA sequence encoding GSGSG. This piece of DNA was purified, digested with Nar1 and PflM1 and inserted into the human αL plasmid (pRKLFAαm) at the corresponding Nar1 and PflM1 sites. Correct insertion of the DNA sequence encoding GSGSG was confirmed by sequence analysis.

Example 5: Binding of LFA-1 Lacking the I Domain to ICAM-1 or Compound 2B 293 cells were transfected with the β2 construct alone (mock) or with either the wild-type αL construct (wt) or the αL construct lacking the I domain (I-less) and allowed to recover for 3 days. The cells were detached and resuspended in adhesion buffer (0.02 M HEPES, pH 7.2, 0.14 M NaCl, 0.2% glucose). Binding to plate bound ICAM-1-Ig was performed as described (Edwards et al. 1998). For binding of compound 2B, $2 \times 10^5$ cells were added per well in a round bottom 96-well plate in adhesion buffer containing 0.5% BGG, 0.1 mM $MnCl_2$, 1 □g/ml anti-β2 activating antibody MEM-48 and 1 µM compound 2B. The cells were incubated for 1 hour at 37° C., washed with cold PBS and fixed with 1% formaldehyde/PBS. The cells were then incubated with a 1:500 dilution of sheep anti-fluorescein-HRP for 1 hour at room temperature, washed with PBS and incubated with TMB for 15 minutes. The reaction was stopped with 1M $H_3PO_4$ and read at 450 nm. In parallel, the transfectants were tested for the structural integrity of the surface-expressed αL/β2 complexes and for the presence or absence of the I domain by FACS analysis using a panel of antibodies with known binding epitopes.

Example 6: Streptozotocin-Induced Rat Diabetic Retinopathy Model 15 adult laboratory rats (Sprague-Dawley) are injected intraperitoneally on day 1 with strepozocin (SZT), 65 mg/kg, to render them hyperglycemic and to induce diabetes. 5 additional rats are treated with a similar volume of saline, to create a non-diabetic control group. Daily thereafter for a total of 6 days, 8 of the diabetic rats receive an instillation of an LFA-1 antagonist in a suitable carrier vehicle in each eye. 7 of the diabetic animals receive similar instillations of the same volume of carrier vehicle alone, according to the same dosage schedule. Animals of the non-diabetic control group receive instillations of carrier vehicle alone, and remain normogylcemic.

On day 14, the eyes of all animals are examined by fluorescein angiography. all animals from the three groups are then sacrificed, and their eyes surgically removed and retinal tissue is isolated from them. The retinal tissue is examined by micropictograph. The extent to which microvasculature abnormalities develops in the corneal tissue of the diabetic control, their inhibition by administration of LFA-1 antagonist in the diabetic treatment group, and comparison to the normoglyemic control group are quantified by standardized morphometric analysis of the photomicrographs.

Example 7: Human T-Cell Adhesion Assay

The T-cell adhesion assay was performed using the human T-lymphoid cell line HuT 78 (ATCC TIB-161). Goat anti-HuIgG(Fc) was diluted to 2 µg/ml in PBS and 96-well plates were coated with 50 µl/well at 37° C. for 1 h. Plates were washed with PBS and blocked for 1 h at room temperature with 1% BSA in PBS. 5 domain ICAM-Ig was diluted to 100 ng/ml in PBS and 50 µl/well was added to the plates 0/N at 4° C. HuT 78 cells were centrifuged at 100 g and the cell pellet was treated with 5 mM EDTA for ~5' at 37° C. in a 5% $CO_2$ incubator. Cells were washed in 0.14 M NaCl, 0.02 M Hepes, 0.2% glucose and 0.1 mM $MnCl_2$ (assay buffer) and centrifuged. The cells were resuspended in assay buffer to $3.0 \times 10^6$ c/ml. Inhibitors were diluted in assay buffer to a 2× final concentration and pre-incubated with HuT78 cells for 30' at room temperature. 100 µl/well of cells and inhibitors were added to the plates and incubated at room temperature for 1 h. 100 µl/well PBS was added and the plates were sealed and centrifuged inverted at 100 g for 5'. Unattached cells were flicked out of the plate and excess PBS was blotted on a paper towel. 60 µl/well p-nitrophenyl n-acetyl-β-D-glucosaminide (0.257 g to 100 ml citrate buffer) was added to the plate and incubated for 1.5 h at 37° C. The enzyme reaction was stopped with 90 µl/well 50 mM glycine/5 mM EDTA and read on a platereader at 405 nM. HUT 78 cell adhesion to 5dICAM-Ig was measured using the p-nitrophenyl n-acetyl-.β-D-glucosaminide method of Landegren, U. (1984). J. Immunol. Methods 57, 379-388. The results are shown in Table 1.

TABLE 1

Adhesion assays results and solubility results for selected directly competitive LFA-1 antagonists of the invention.

| Compound # | Structure | Hut78 ($EC_{50}$) | Solubility |
|---|---|---|---|
| 1 | 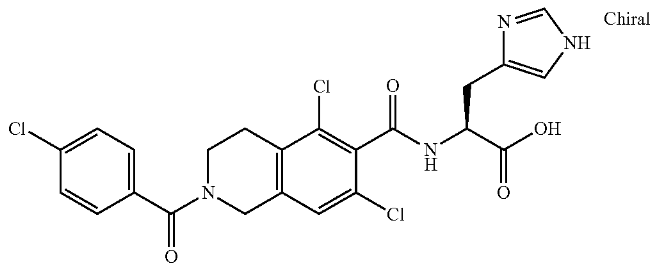 [SMILES: O=C(N[C@@H](Cc1c[nH]cn1)C(=O)O)c1c(Cl)cc2c(c1Cl)CCN(C(=O)c1ccc(Cl)cc1)C2] | ** | |
| 2 | 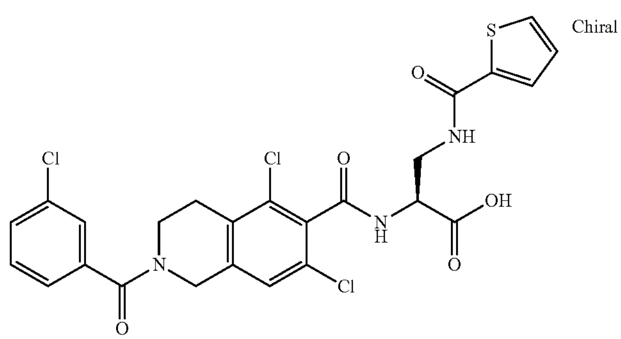 [SMILES: O=C(NC[C@H](NC(=O)c1c(Cl)cc2c(c1Cl)CCN(C(=O)c1cccc(Cl)c1)C2)C(=O)O)c1cccs1] | **** | +++ |
| 3 | 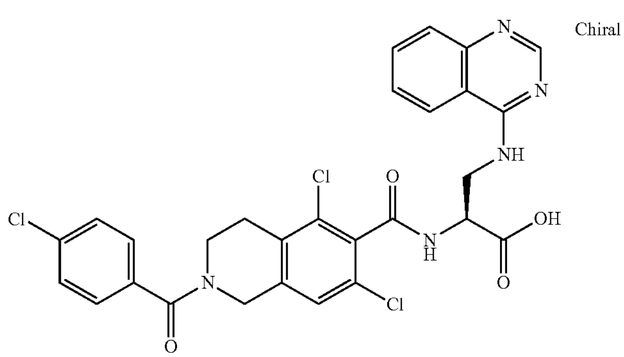 [SMILES: O=C(N[C@@H](CNc1ncnc2ccccc12)C(=O)O)c1c(Cl)cc2c(c1Cl)CCN(C(=O)c1ccc(Cl)cc1)C2] | **** | |

TABLE 1-continued
Adhesion assays results and solubility results for selected directly competitive LFA-1 antagonists of the invention.
| Compound # | Structure | Hut78 (EC$_{50}$) | Solubility |
|---|---|---|---|
| 4 | 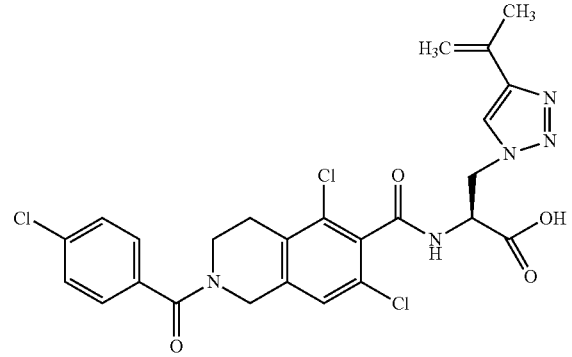 | *** | |
| 5 | 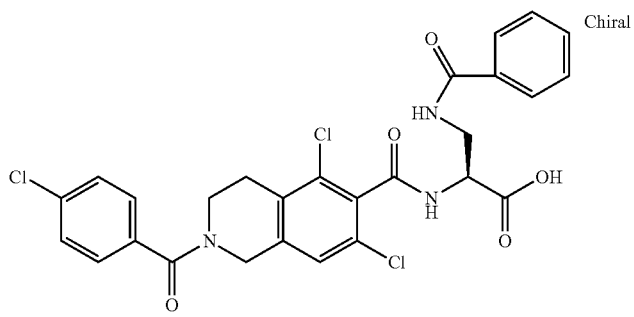 [SMILES: O=C(NC[C@H](NC(=O)c1c(Cl)cc2c(c1Cl)CCN(C(=O)c1ccc(Cl)cc1)C2)C(=O)O)c1ccccc1] | **** | |
| 6 | 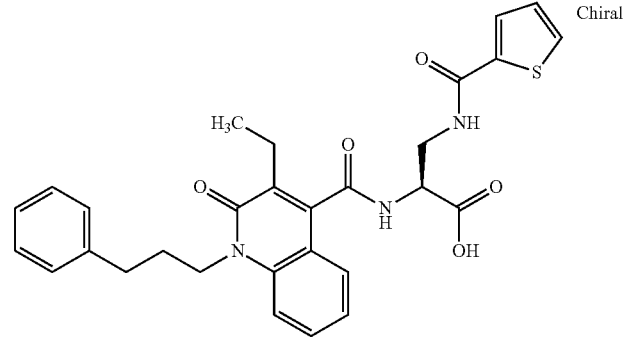 [SMILES: CCc1c(C(=O)N[C@@H](CNC(=O)c2cccs2)C(=O)O)c2ccccc2n(CCCc2ccccc2)c1=O] | **** | +++ |
| 7 | 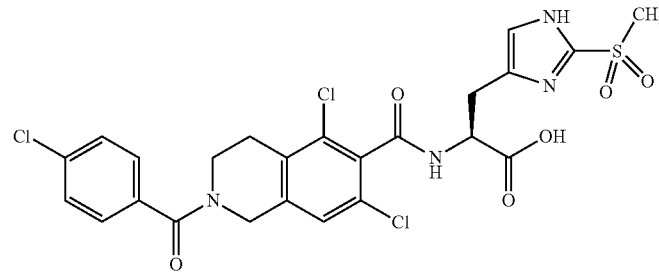 | **** | |

TABLE 1-continued

Adhesion assays results and solubility results for selected directly competitive LFA-1 antagonists of the invention.

| Compound # | Structure | Hut78 (EC$_{50}$) | Solubility |
|---|---|---|---|
| 8 | 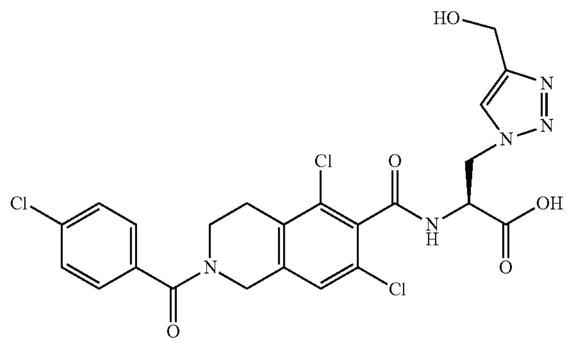 | *** | |
| 9 | 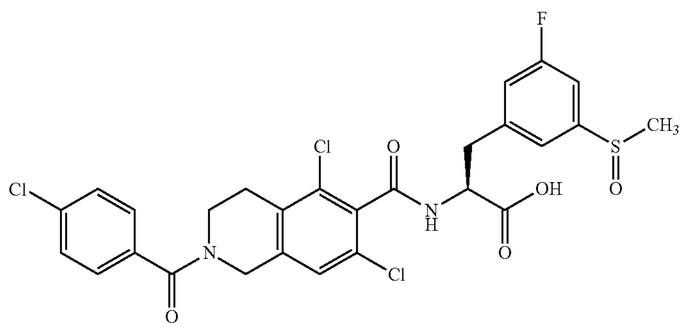 | **** | ++ |
| 10 | 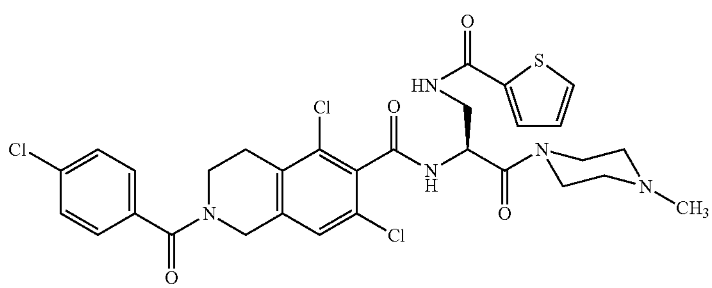 | | +++ |
| 11 | 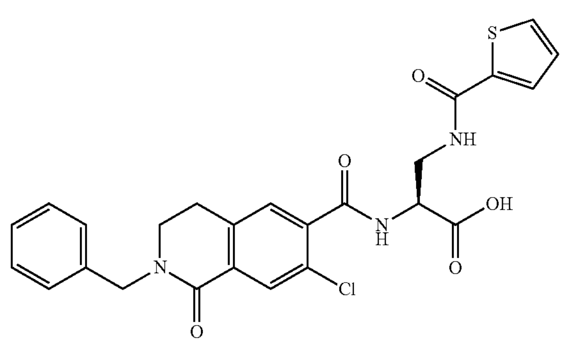 | * | |

TABLE 1-continued

Adhesion assays results and solubility results for selected directly competitive LFA-1 antagonists of the invention.

| Compound # | Structure | Hut78 (EC$_{50}$) | Solubility |
|---|---|---|---|
| 12 | [Chiral structure: benzofuran-carbonyl-tetrahydroisoquinoline (dichloro) carboxamide linked to phenylalanine derivative with 3-(methylsulfonyl)phenyl group and carboxylic acid] | **** | +++ |
| 13 | [Chiral structure: indole-carbonyl-tetrahydroisoquinoline (dichloro) carboxamide linked to diaminopropionic acid derivative with thiophene-2-carboxamide] | **** | |
| 14 | [Chiral structure: benzofuran-carbonyl-tetrahydroisoquinoline (dichloro) carboxamide linked to alanine derivative with 5-(methylsulfinyl)pyridin-3-yl group and carboxylic acid] | **** | |
| 15 | [Chiral structure: indazole-carbonyl-tetrahydroisoquinoline (dichloro) carboxamide linked to phenylalanine derivative with 3-(methylsulfonyl)phenyl group and carboxylic acid] | **** | +++ |
| 16 | [Chiral structure: isoquinoline-3-carbonyl-tetrahydroisoquinoline (dichloro) carboxamide linked to phenylalanine derivative with 3-(methylsulfonyl)phenyl group and carboxylic acid] | **** | +++ |

TABLE 1-continued

Adhesion assays results and solubility results for selected directly competitive LFA-1 antagonists of the invention.

| Compound # | Structure | Hut78 (EC$_{50}$) | Solubility |
|---|---|---|---|
| 17 | 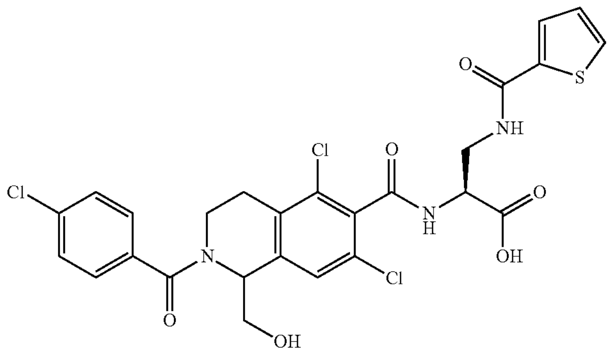 | **** | |
| 18 | 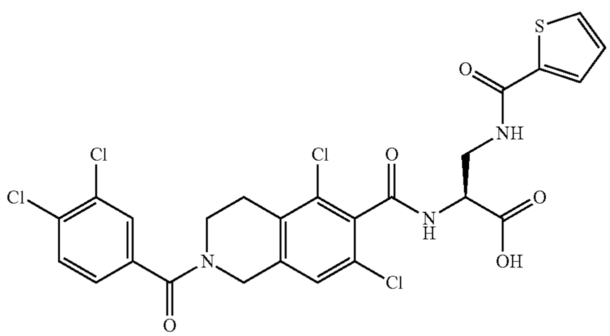 | **** | |
| 19 | 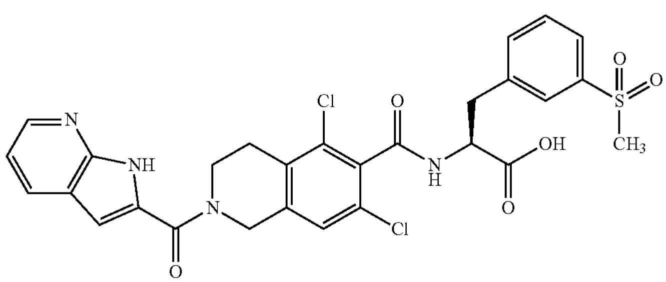 | **** | ++ |
| 20 | 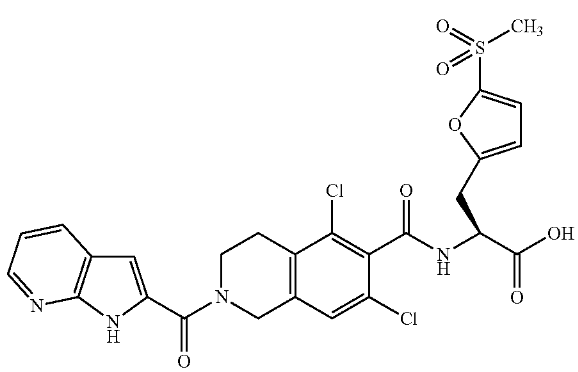 | **** | +++ |

TABLE 1-continued

Adhesion assays results and solubility results for selected directly competitive LFA-1 antagonists of the invention.

| Compound # | Structure | Hut78 (EC$_{50}$) | Solubility |
|---|---|---|---|
| 21 | 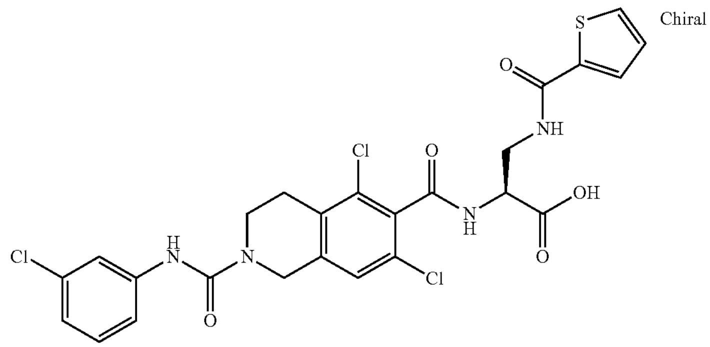 [SMILES: O=C(NC[C@H](NC(=O)c1c(Cl)cc2c(c1Cl)CCN(C(=O)Nc1cccc(Cl)c1)C2)C(=O)O)c1cccs1] | **** | +++ |
| 22 | 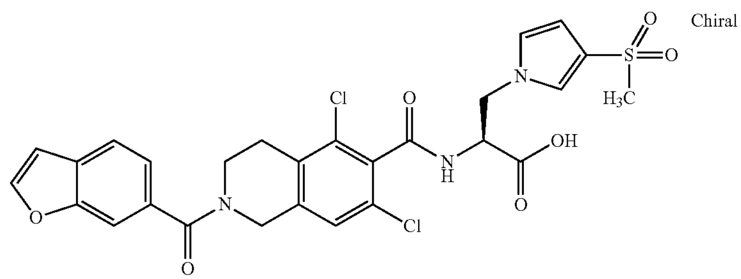 [SMILES: CS(=O)(=O)c1ccn(C[C@H](NC(=O)c2c(Cl)cc3c(c2Cl)CCN(C(=O)c2ccc4ccoc4c2)C3)C(=O)O)c1] | **** | |
| 23 | 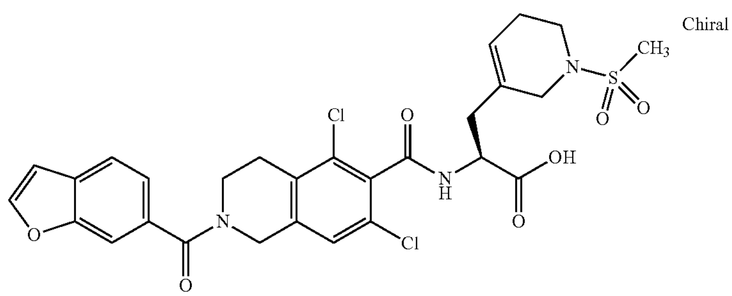 [SMILES: CS(=O)(=O)N1CCC=C(C[C@H](NC(=O)c2c(Cl)cc3c(c2Cl)CCN(C(=O)c2ccc4ccoc4c2)C3)C(=O)O)C1] | **** | |
| 24 | 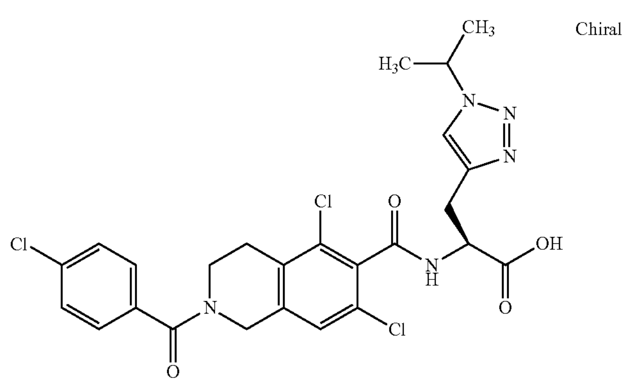 [SMILES: CC(C)n1cc(C[C@H](NC(=O)c2c(Cl)cc3c(c2Cl)CCN(C(=O)c2ccc(Cl)cc2)C3)C(=O)O)nn1] | *** | |

TABLE 1-continued
Adhesion assays results and solubility results for selected directly competitive LFA-1 antagonists of the invention.
| Compound # | Structure | Hut78 (EC$_{50}$) | Solubility |
|---|---|---|---|
| 25 | 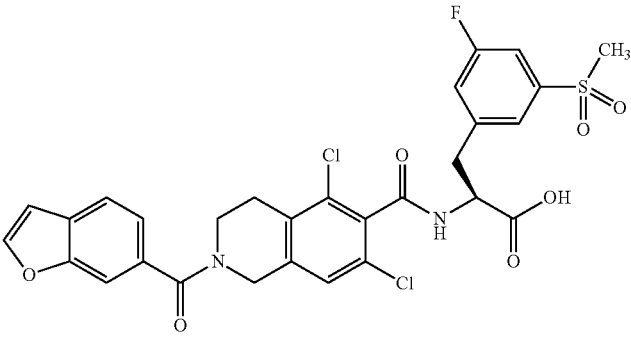 Chiral | **** | +++ |
| 26 | 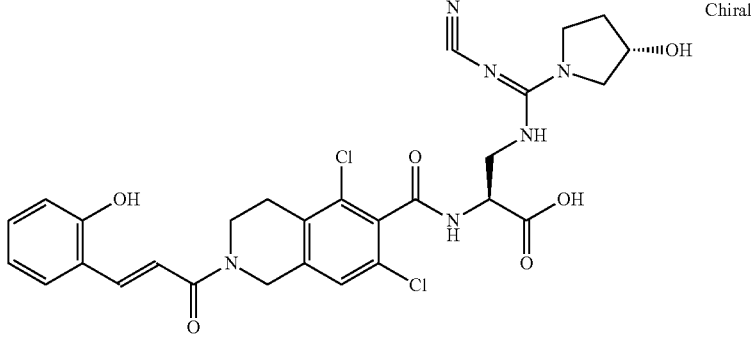 [SMILES: N#CN=C(NC[C@H](NC(=O)c1c(Cl)cc2c(c1Cl)CCN(C(=O)/C=C/c1ccccc1O)C2)C(=O)O)N1CC[C@H](O)C1] Chiral | **** | |
| 27 | 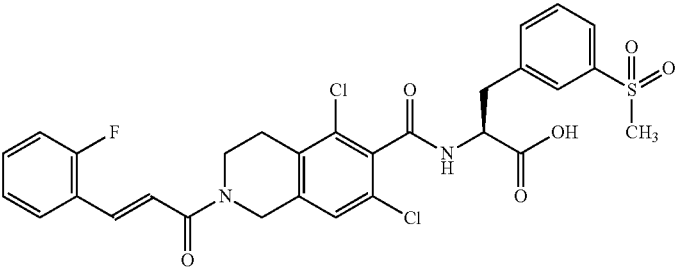 Chiral | **** | +++ |
| 28 | 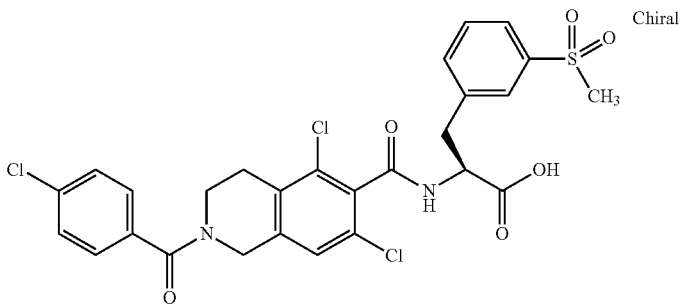 [SMILES: CS(=O)(=O)c1cccc(C[C@H](NC(=O)c2c(Cl)cc3c(c2Cl)CCN(C(=O)c2ccc(Cl)cc2)C3)C(=O)O)c1] Chiral | **** | |

TABLE 1-continued

Adhesion assays results and solubility results for selected directly competitive LFA-1 antagonists of the invention.

| Compound # | Structure | Hut78 (EC$_{50}$) | Solubility |
|---|---|---|---|
| 29 | [Chiral structure: 2-benzyl-7-methyl-1-oxo-phthalazine-6-carboxamide linked to a diaminopropionic acid derivative bearing a thiophene-2-carboxamide] | * | ++ |
| 30 | [Chiral structure: 6-(benzofuran-6-carbonyl)-5,7-dichloro-1,2,3,4-tetrahydroisoquinoline-6-carboxamide linked to an amino acid with a 4-(methylsulfonyl)-5-methylfuran-2-yl substituent] | **** | |
| 31 | [Chiral structure: 6-(benzofuran-6-carbonyl)-5,7-dichloro-1,2,3,4-tetrahydroisoquinoline-6-carboxamide linked to a diaminopropionic acid derivative bearing a 3-fluorobenzamide] | **** | ++ |
| 32 | [Chiral structure: 2,6-dichloro-4-[3-(3-hydroxyphenyl)-3-hydroxypropyl]benzamide linked to a diaminopropionic acid derivative bearing a thiophene-2-carboxamide] | **** | ++ |

TABLE 1-continued

Adhesion assays results and solubility results for selected directly competitive LFA-1 antagonists of the invention.

| Compound # | Structure | | Hut78 (EC$_{50}$) | Solubility |
|---|---|---|---|---|
| 33 | 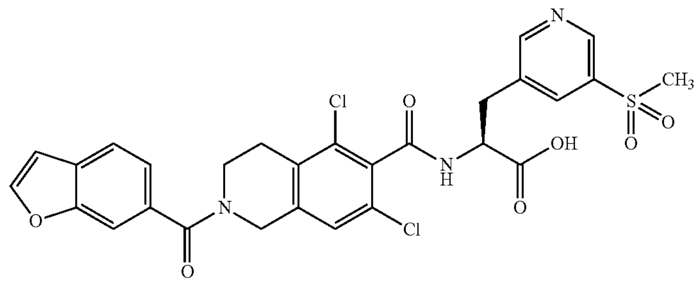 | Chiral | **** | |
| 34 | 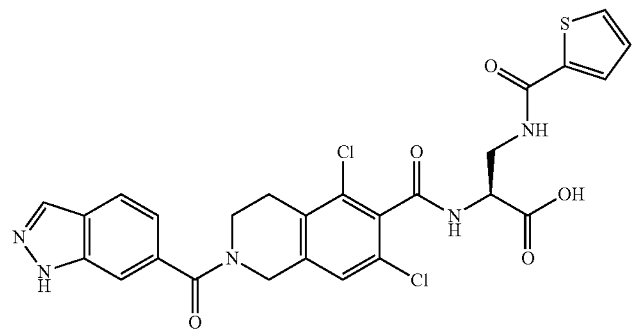 | Chiral | **** | |
| 35 | 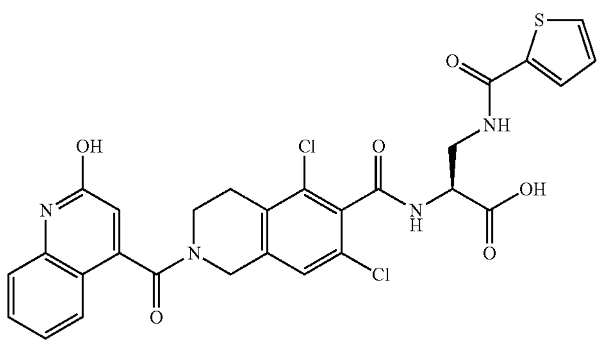 | Chiral | **** | +++ |
| 36 | 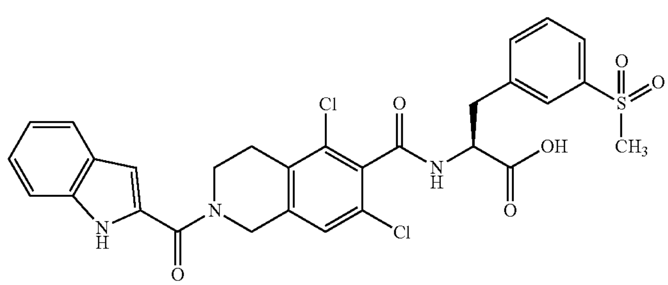 | Chiral | **** | ++ |
| 37 | 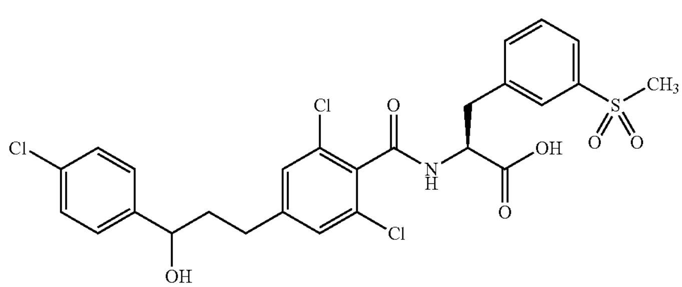 | Chiral | *** | |

TABLE 1-continued

Adhesion assays results and solubility results for selected directly competitive LFA-1 antagonists of the invention.

| Compound # | Structure | Hut78 (EC$_{50}$) | Solubility |
|---|---|---|---|
| 38 | 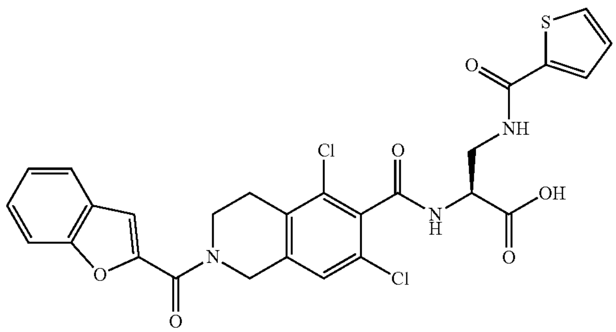 | **** | |
| 39 | 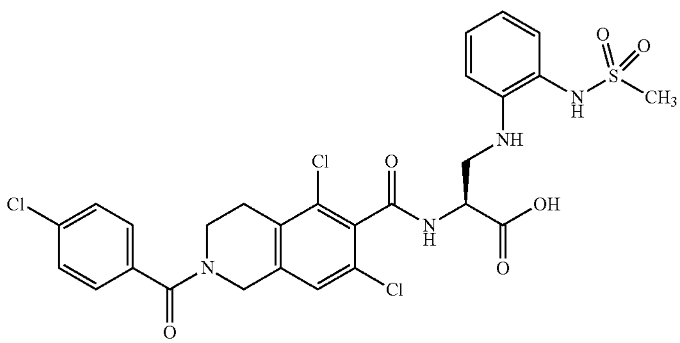 | **** | |
| 40 | 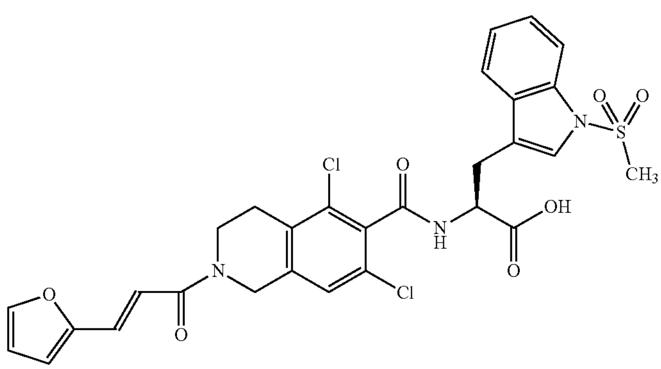 | ** | |
| 41 | 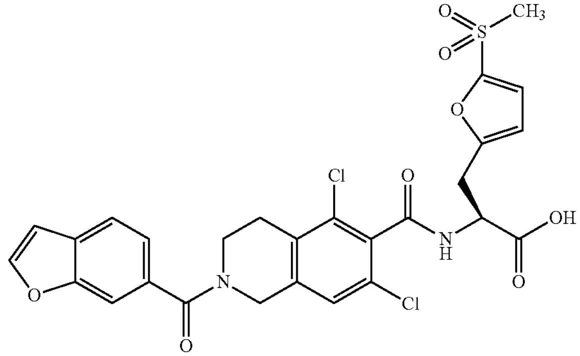 | **** | +++ |

TABLE 1-continued

Adhesion assays results and solubility results for selected directly competitive LFA-1 antagonists of the invention.

| Compound # | Structure | Hut78 (EC$_{50}$) | Solubility |
|---|---|---|---|
| 42 | 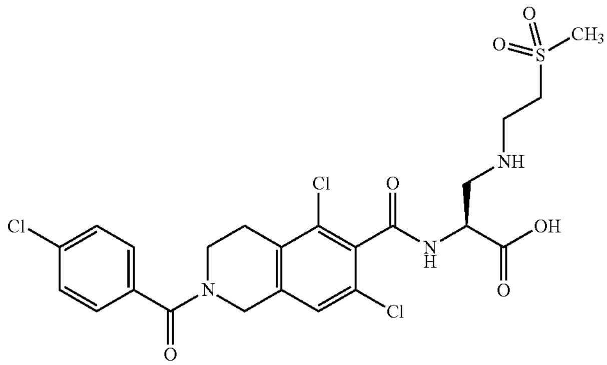 | * | +++ |
| 43 | 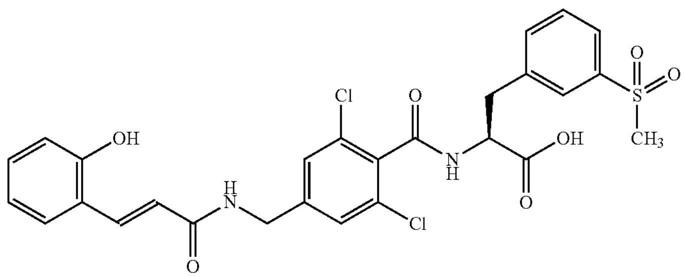 | **** | |
| 44 | 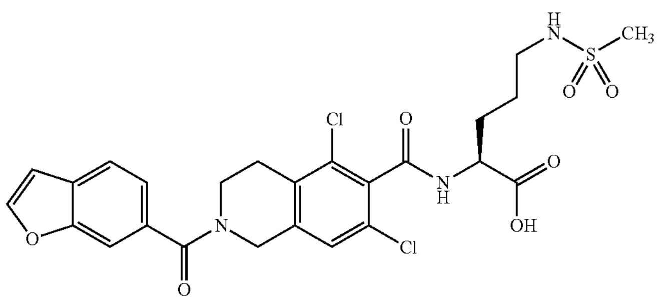 | **** | +++ |
| 45 | 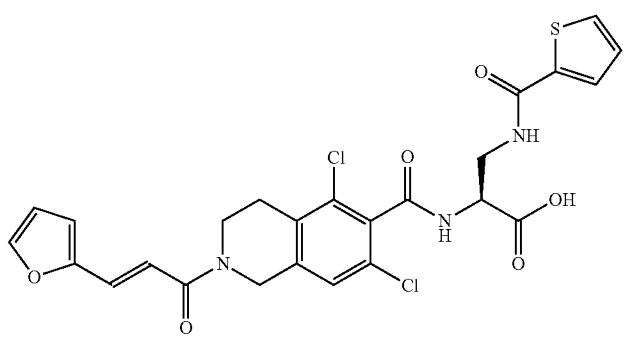 | **** | +++ |
| 46 | 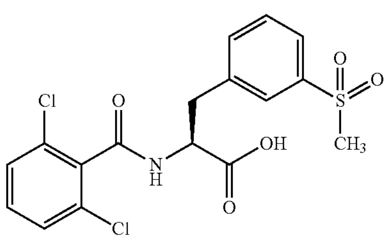 | *** | +++ |

TABLE 1-continued

Adhesion assays results and solubility results for selected directly competitive LFA-1 antagonists of the invention.

| Compound # | Structure | Hut78 (EC$_{50}$) | Solubility |
|---|---|---|---|
| 47 | 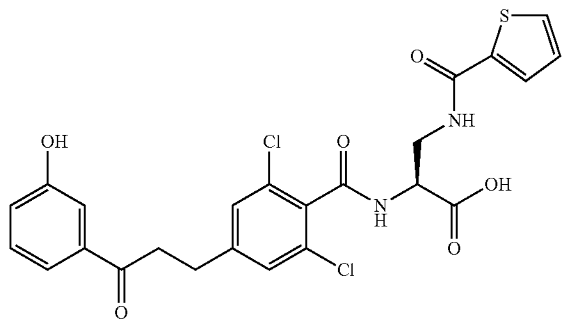 | **** | |
| 48 | 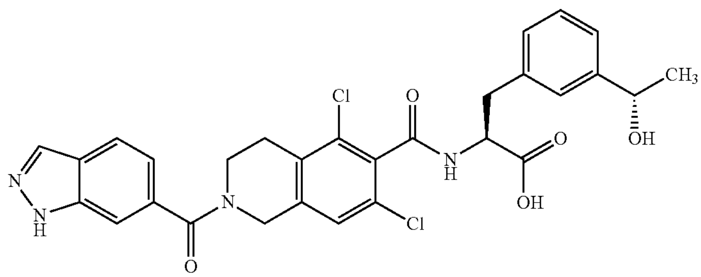 | **** | |
| 49 | 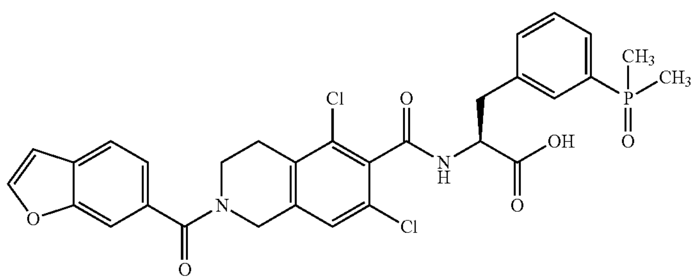 | *** | |

The scale in the table represents EC$_{50}$ values as follows:
* represents 3 µM or less,
** represents 300 nM or less,
*** represents 100 nM or less, and
**** represents 50 nM or less.
The scale in the table represents Solubility values as follows:
+ represents greater than 10 mg/mL,
++ represents greater than 50 mg/mL, and
+++ represents greater than 100 mg/mL.

Example 8: In-Vitro Inhibition of Antigen Stimulated Release of Cytokines From Human Peripheral Blood Monocytes (PBMC)

A directly competitive LFA-1 antagonist of the invention was evaluated for its ability to inhibit release of inflammatory cytokines, in human mononucleocytes (PBMC) stimulated with staphylococcal enterotoxin B (SEB). Stock solutions of antagonist, Rebamipide (a mucosal protective agent), and Cyclosporin A (CsA) were prepared in culture media and dilutions were prepared by addition of culture media to achieve the desired concentration. Negative controls were prepared without SEB stimulation. SEB stimulation with vehicle (0.25% DMSO/media) was used as the positive control.

Human PBMC, frozen in cryopreservation media were thawed, washed with RPMI culture media containing 10% FBS in growth media and seeded onto a 96 well plate at 20,000 cells/well containing 180 µl culture media. Cells were incubated in the presence of antagonist, Rebamipide or CsA at 37 C for 1 hour prior to stimulation with SEB. SEB was added at 1 ng/ml and cell supernatants were harvested at 6, 16, and 48 hours. Cytokine levels in the assay supernatants were determined using a Luminex multiplex assay.

Figure 11:
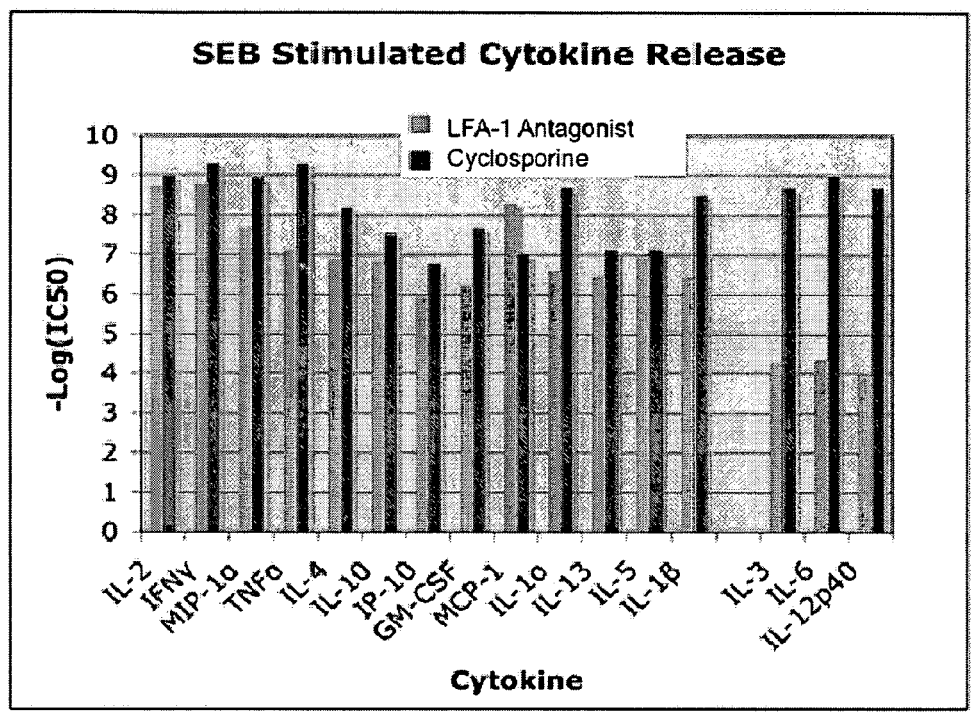
FIG. 11 is a graphical representation of the effect of a directly competitive LFA-1 antagonist of the invention upon the release of inflammatory cytokines, in human mononucleocytes (PBMC) stimulated with staphylococcal enterotoxin B (SEB) as compared to the effect of cyclosporine-A (CsA).

The antagonist demonstrated potent inhibition of the release of inflammatory cytokines, particularly the T-cell regulating cytokines, IL-2 and IL-4, with increasing dose. The results are shown in Tables 2, 3, and 4 and graphically represented in FIG. 11. The pattern of cytokine release inhibited by more than 50% with the directly competitive LFA-1 antagonist is similar to that seen in comparison with CsA. The exceptions to this similarity, IL-3, 11-6, and IL-12p40, have not been shown to be important to T-cell mediated inflammation.

TABLE 2

EC50 Concentrations for Inhibition of IL-2, IFNγ, MIP-1α, and TNF-α.

| | EC50 µM Cytokine Release | | | |
|---|---|---|---|---|
| | IL-2 | IFNγ | MIP-1α | TNF-α |
| LFA-antagonist | 0.0018 | 0.0016 | 0.020 | 0.076 |
| Rebamipide | >1000 | >1000 | >1000 | >1000 |
| Cyclosporine A | 0.00094 | 0.00050 | 0.0011 | 0.00049 |

TABLE 3

EC50 Concentrations for Inhibition of IL-4, IL-10, IP-10, GM-CSF and MCP-1.

| | EC50 µM Cytokine Release | | | | |
|---|---|---|---|---|---|
| | IL-4 | IL-10 | IP-10 | GM-CSF | MCP-1 |
| LFA-1 antagonist | 0.143 | 0.147 | 1.158 | 0.545 | 0.0050 |
| Rebamipide | >1000 | >1000 | >1000 | >1000 | >1000 |
| Cyclosporine A | 0.0063 | 0.0292 | 0.167 | 0.0202 | 0.0926 |

TABLE 4

EC50 Concentrations for Inhibition of IL-1α, IL-1β, IL-3, IL-5, IL-6, IL-12p40, and IL-13.

| | EC50 µM Cytokine Release | | | | | | |
|---|---|---|---|---|---|---|---|
| | IL-1α | IL-1β | IL-3 | IL-5 | IL-6 | IL-12p40 | IL-13 |
| LFA-1 antagonist | 0.24 | 0.36 | 52.23 | 0.11 | 43.51 | >1000 | 0.36 |
| Rebamipide | >1000 | >1000 | >1000 | >1000 | >1000 | >1000 | >1000 |
| Cyclosporine A | 0.002 | 0.003 | 0.002 | 0.073 | 0.001 | 0.002 | 0.074 |

Example 9: Formulations of an LFA-1 Antagonist

A directly competitive LFA-1 antagonist of the invention was formulated in several compositions for administration as gels, lotions, ointments, and solutions, for administration by varying routes, including but not limited to topical, via instillation, aerosol, transdermal patch, via insert, or oral administration.

TABLE 5

Gel Formulations 1 and 2 of LFA-1 Antagonist.

| Formulation 1 (% w/w) | Formulation 2 (% w/w) |
|---|---|
| LFA-1 antagonist | LFA-1 antagonist |
| 15% Dimethyl Isosorbide | 15% Dimethyl Isosorbide |
| 25% Transcutol | 25% Transcutol |
| 12% Hexylene glycol | 12% Hexylene glycol |
| 5% Propylene Glycol | 5% Propylene Glycol |
| 0.15% Methylparaben | 0.15% Methylparaben |
| 0.05% Propylparaben | 0.05% Propylparaben |
| 0.01% EDTA | 0.01% EDTA |
| 0.5% Penmulen TR-1 | 1% Hydroxyethyl Cellulose |
| q.s. pH 6.0 25% Trolamine | q.s. pH 4.5 25% Trolamine |
| q.s. 100 Water | q.s. 100 Water |

TABLE 6

Lotion Formulations 3 and 4 of LFA-1 Antagonist.

| Formulation 3 (% w/w) | Formulation 4 (% w/w) |
|---|---|
| 1% LFA-1 Antagonist | 1% LFA-1 Antagonist |
| 13% Dimethyl Isosorbide | 13% Dimethyl Isosorbide |
| 20% Transcutol | 20% Transcutol |
| 10% Hexylene glycol | 10% Hexylene glycol |
| 4% Propylene Glycol | 4% Propylene Glycol |

TABLE 6-continued

Lotion Formulations 3 and 4 of LFA-1 Antagonist.

| Formulation 3 (% w/w) | Formulation 4 (% w/w) |
|---|---|
| 0.15% Methylparaben | 0.15% Methylparaben |
| 0.05% Propylparaben | 0.05% Propylparaben |
| 0.01% EDTA | 0.01% EDTA |
| 0.5% Carbopol Ultrez 10 | 0.3% Carbopol Ultrez 10 |
| 0.2% Penmulen TR-1 | 0.2% Penmulen TR-1 |
| 3% Isopropyl Myristate | 2% Cetyl Alcohol |
| 5% Olelyl Alcohol | 5.5% Light Mineral Oil |
| 5% White Petrolatum | 5% Oleic Acid |
| 0.02% Butylated Hydroxytoluene | 0.02% Butylated Hydroxytoluene |
| q.s. pH 6.0 25% Trolamine | q.s. pH 6.0 25% Trolamine |
| q.s. 100 Water | q.s. 100 Water |

TABLE 7

Ointment Formulations 5 and 6 of LFA-1 Antagonist.

| Formulation 5 (% w/w) | Formulation 6 (% w/w) |
|---|---|
| 1% LFA-1 Antagonist | 1% LFA-1 Antagonist |
| 15% PEG 400 | 10% Dimethyl Isosorbide |
| 0.02% Butylated Hydroxytoluene | 0.02% Butylated Hydroxytoluene |
| 2% Span 80 | 2% Span 80 |

TABLE 7-continued

Ointment Formulations 5 and 6 of LFA-1 Antagonist.

| Formulation 5 (% w/w) | Formulation 6 (% w/w) |
|---|---|
| 10% White Wax | 10% White Wax |
| 71.98% White Petrolatum | 76.98% White Petrolatum |

TABLE 8

Solution Formulations 7, 8, and 9 of LFA-1 Antagonist.

| Formulation 7 (% w/w) | Formulation 8 (% w/w) | Formulation 9 (% w/w) |
|---|---|---|
| 1% LFA-1 Antagonist | 1% LFA-1 Antagonist | 1% LFA-1 Antagonist |
| 15% Dimethyl Isosorbide | 15% Dimethyl Isosorbide | 99% Dimethyl Sulfoxide |
| 25% Transcutol | 25% Transcutol | |
| 12% Hexylene glycol | 12% Hexylene glycol | |
| 5% Propylene Glycol | 5% Propylene Glycol | |
| q.s. pH 4.5 25% Trolamine | q.s. pH 6.0 25% Trolamine | |
| q.s. 100 Water | q.s. 100 Water | |

TABLE 9

Solution Formulations 10, 11, 12, 13 and 14 of LFA-1 Antagonist.

| W/W % | Formulation 10 | Formulation 11 | Formulation 12 | Formulation 13 | Formulation 14 |
|---|---|---|---|---|---|
| LFA-1 Antagonist | 0.1% | 0.3% | 1% | 3% | 5% |
| Sodium Bicarbonate | 0.015% | 0.046% | 0.15% | 0.46% | 0.77% |
| 0.1% EDTA | | | | | |
| 0.12% Sodium Phosphate, Monobasic | | | | | |
| 0.4% Methylparaben | | | | | |
| 0.02% Propylparaben | | | | | |
| q.s. Osmolality 270, Sodium Chloride | | | | | |
| q.s. pH 7.0 1% Sodium Hydroxide | | | | | |
| q.s. pH 7.0 1% HCl | | | | | |
| q.s. Water | | | | | |

TABLE 10

Solution Formulation 15 of LFA-1 Antagonist.

| Formulation 15 |
|---|
| 1 ml of a solution of LFA-1 Antagonist |
| 10% W/W in water, plus 0.158 mmol sodium bicarbonate |
| Dilute with 9 ml PBS |

Example 10: In-Vitro pPercutaneous Absorption of a Directly Competitive Antagonist of LFA-1 of the Invention Following Topical Application Bioavailability following topical application in-vivo was assessed using in-vito percutaneous absorption test methods, using procedures adapted from Skelly et al., Pharmaceutical Research 1987 4(3): 265-276, "FDA and AAPS Report of the Workshop on Principles and Practices of In-Vitro Percutaneous Penetration Studies: Relevance to Bioavailability and Bioequivalence".

Formulations 1-9 were applied to dermatomed human skin tissue excised from a single donor in a single clinically relevant dose of 5 mg/cm$^2$, which is equivalent to a 30-35 μg dose. The thickness of the tissue ranges form 0.023 to 0.039 inches (0.584 to 0.991 mm) with a mean+/− standard deviation in thickness of 0.030+/−0.004 inches (0.773+/−0.111 mm) and a coefficient of variation of 14.4%. The tissue samples were mounted in Bronaugh flow-through diffusion cells. The cells were maintained at a constant temperature of 32° C. using recirculating water baths. The cells have a nominal diffusion area of 0.64 cm$^2$. PBS, at pH 7.4, with 0.1% sodium azide and 4% Bovine Serum Albumin was used as the receptor phase below the mounted tissue. Fresh receptor phase was continuously pumped under the tissue at a flow rate of nominally 1.0 ml/hr and collected in 6 hour intervals. The receptor phases were collected for analysis.

The tissue samples were exposed to Formulations 1-9 for 24 hours. The excess formulation residing on the strateum corneum at that timepoint was removed by tape-stripping with CuDerm D-Squame stripping discs. The tape strips were discarded. The epidermis and dermis were separated by blunt dissection. Epidermis, dermis and receptor phase were analyzed for content of LFA-1 Antagonist. The results are represented in Table 11.

Tissue permeation levels (the receptor phase) of LFA-1 Antagonist for all formulations except for Formulation 9, which contained 99% DMSO, were below the limits of quantitation, which was 0.54 ng/ml (which is equivalent to 0.013% of the applied dose). Formulation 9, in contrast, provided 1.4% of the applied dose, permeating through all the layers of the skin tissue over the exposure period of 24 hours.

Epidermal deposition of LFA-1 Antagonist over the 24 hour exposure period was very high and consistent with a large percentage of the applied dose being retained in the upper layers of the epidermis. The levels reported in Table 10 were obtained from small volume samples, which could not be re-assayed, and thus are considered underestimates of the amount of drug present in the epidermis.

Analytical data for the dermis fell within the linearity range established for LFA-1 Antagonist, and are quantitative. Dermal deposition of LFA-1 Antagonist following a 24 hour exposure ranged from 0.66% (Formulation 6, 0.258 μg/cm$^2$) to 4.4% (Formulation 7, 34.3 μg/cm$^2$) of the applied dose. The concentration of LFA-1 Antagonist in the dermis is calculated as 6.7 μM (Formulation 6) or greater (i.e., Formulation 7 provides a concentration in the dermis of 54.1 μM) for Formulations 1 to 9 in the dermis. These concentrations are well above the in-vitro EC50 concentration for half maximal effect in inhibiting release of inflammatory cytokines by the class of LFA-1 antagonists shown in Example 7 and corresponding Table 1. These results are therefore predictive for the ability of a variety of formulations, which incorporate 1% W/W LFA-1 Antagonist, to provide therapeutically effective levels of in-vivo inhibition of cytokine release.

TABLE 11

Cumulative Receptor Phase and Tissue Levels of LFA-1 Antagonist After 24 Hours of Topical Exposure.

| Formulation # | | Receptor Phase Content at 24 hours | | Epidermis | | Dermis | | |
|---|---|---|---|---|---|---|---|---|
| | | µg/cm² | % Dose Applied | µg/cm² | % Dose Applied | µg/cm² | µg/ml | % Dose Applied |
| 1 | Mean | <Limit of Quantitation | | 3.93 | 7.48 | 1.14 | 18.8 | 2.15 |
|   | SD[1] | | | 2.92 | 5.50 | 0.91 | 14.9 | 1.73 |
|   | % CV[2] | | | 74 | 74 | 80 | 80 | 80 |
| 2 | Mean | <Limit of Quantitation | | 6.03 | 11.9 | 0.750 | 12.3 | 1.49 |
|   | SD | | | 2.56 | 5.1 | 0.304 | 5.0 | 0.63 |
|   | % CV | | | 43 | 42 | 40 | 40 | 42 |
| 3 | Mean | <Limit of Quantitation | | 6.03 | 12.1 | 1.40 | 23.0 | 2.74 |
|   | SD | | | 2.97 | 6.4 | 0.27 | 4.4 | 0.47 |
|   | % CV | | | 49 | 53 | 19 | 19 | 17 |
| 4 | Mean | <Limit of Quantitation | | 7.92 | 17.0 | 0.975 | 16.0 | 2.10 |
|   | SD | | | 3.41 | 7.2 | 0.350 | 5.8 | 0.75 |
|   | % CV | | | 43 | 42 | 36 | 36 | 36 |
| 5 | Mean | <Limit of Quantitation | | 5.71 | 14.6 | 0.670 | 11.0 | 1.71 |
|   | SD | | | 1.73 | 4.2 | 0.351 | 5.8 | 0.87 |
|   | % CV | | | 30 | 29 | 52 | 52 | 51 |
| 6 | Mean | <Limit of Quantitation | | 6.47 | 16.8 | 0.258 | 4.25 | 0.657 |
|   | SD | | | 1.07 | 2.7 | 0.158 | 2.6 | 0.394 |
|   | % CV | | | 17 | 16 | 61 | 61 | 60 |
| 7 | Mean | <Limit of Quantitation | | 7.22 | 15.0 | 2.08 | 34.3 | 4.35 |
|   | SD | | | 2.15 | 4.5 | 0.84 | 13.7 | 1.83 |
|   | % CV | | | 30 | 30 | 40 | 40 | 42 |
| 8 | Mean | <Limit of Quantitation | | 8.58 | 18.0 | 1.48 | 24.3 | 3.09 |
|   | SD | | | 3.53 | 7.7 | 0.99 | 16.2 | 2.07 |
|   | % CV | | | 41 | 43 | 67 | 67 | 67 |
| 9 | Mean | 0.660 | 1.43 | 5.78 | 13.2 | 1.19 | 19.6 | 2.63 |
|   | SD | 0.253 | 0.49 | 3.18 | 8.3 | 0.49 | 8.1 | 1.15 |
|   | % CV | 38 | 34 | 55 | 63 | 41 | 41 | 44 |

[1]Standard Deviation.
[2]Percent Coefficient of Variation.

Example 11: T-Cell Proliferation Assay

This assay is an in vitro model of lymphocyte proliferation resulting from activation, induced by engagement of the T-cell receptor and LFA-1, upon interaction with antigen presenting cells (Springer, Nature 346: 425 (1990)).

Microtiter plates (Nunc 96 well ELISA certified) are pre-coated overnight at 4° C. with 50 µl of 2 µg/ml of goat anti-human Fc(Caltag H10700) and 50 µl of 0.07 µg/ml monoclonal antibody to CD3 (Immunotech 0178) in sterile PBS. The next day coat solutions are aspirated. Plates are then washed twice with PBS and 100 µl of 17 ng/ml 5d-ICAM-1-IgG is added for 4 hours at 37° C. Plates are washed twice with PBS prior to addition of CD4+ T cells. Lymphocytes from peripheral blood are separated from heparinized whole blood drawn from healthy donors. An alternative method is to obtain whole blood from healthy donors through leukophoresis. Blood is diluted 1:1 with saline, layered and centrifuged at 2500×g for 30 minutes on LSM (6.2 g Ficoll and 9.4 g sodium diztrizoate per 100 ml) (Organon Technica, N.J.). Monocytes are depleted using a myeloid cell depletion reagent method (Myeloclear, Cedarlane Labs, Hornby, Ontario, Canada). PBLs are resuspended in 90% heat-inactivated Fetal Bovine serum and 10% DMSO, aliquoted, and stored in liquid nitrogen. After thawing, cells are resuspended in RPMI 1640 medium (Gibco, Grand Island, N.Y.) supplemented with 10% heat-inactivated Fetal Bovine serum (Intergen, Purchase, N.Y.), 1 mM sodium pyruvate, 3 mM L-glutamine, 1 mM nonessential amino acids, 500 µg/ml penicillin, 50 µg/ml streptomycin, 50 µg/ml gentamycin (Gibco).

Purification of CD4+ T cells are obtained by negative selection method (Human CD4 Cell Recovery Column Kit #CL 110-5 Accurate). 100,000 purified CD4+ T cells (90% purity) per microtiter plate well are cultured for 72 hours at 37° C. in 5% $CO_2$ in 100 ml of culture medium (RPMI 1640 (Gibco) supplemented with 10% heat inactivated FBS (Intergen), 0.1 mM non-essential amino acids, 1 nM Sodium Pyruvate, 100 units/ml Penicillin, 100 µg/ml Streptomycin, 50 µg/ml Gentamicin, 10 mM Hepes and 2 mM Glutamine). Inhibitors are added to the plate at the initiation of culture. Proliferative responses in these cultures are measured by addition of 1 µCi/well titrated thymidine during the last 6 hours before harvesting of cells. Incorporation of radioactive label is measured by liquid scintillation counting (Packard 96 well harvester and counter). Results are expressed in counts per minute (cpm).

Example 12: In Vitro Mixed Lymphocyte Culture Model

The mixed lymphocyte culture model, which is an in vitro model of transplantation (A. J. Cunningham, "Understanding Immunology, Transplantation Immunology" pages 157-159 (1978) examines the effects of various LFA-1 antagonists in both the proliferative and effector arms of the human mixed lymphocyte response.

Isolation of Cells: Mononuclear cells from peripheral blood (PBMC) are separated from heparanized whole blood drawn from healthy donors. Blood is diluted 1:1 with saline, layered, and centrifuged at 2500×g for 30 minutes on LSM (6.2 g Ficoll and 9.4 g sodium diztrizoate per 100 ml) (Organon Technica, N.J.). An alternative method is to obtain whole blood from healthy donors through leukophoresis. PBMCs are separated as above, resuspended in 90% heat inactivated Fetal Bovine serum and 10% DMSO, aliquoted and stored in liquid nitrogen. After thawing, cells are resuspended in RPMI 1640 medium (Gibco, Grand Island, N.Y.) supplemented with 10% heat-inactivated Fetal Bovine serum (Intergen, Purchase, N.Y.), 1 mM sodium pyruvate, 3 mM L-glutamine, 1 mM nonessential amino acids, 500 µg/ml penicillin, 50 µg/ml streptomycin, 50 µg/ml gentamycin (Gibco).

Mixed Lymphocyte Response (MLR): One way human mixed lymphocyte cultures are established are in 96-well flat-bottomed microtiter plates. $1.5 \times 10^5$ responder PBMCs are co-cultured with an equal number of allogeneic irradiated (3000 rads for 3 minutes, 52 seconds stimulator PBMSc in 200 µl of complete medium. LFA-1 antagonists are added at the initiation of cultures. Cultures are incubated at 37° C. in 5% $CO_2$ for 6 days, then pulsed with 1 µCi/well of 3H-thymidine (6.7 Ci/mmol, NEN, Boston, Mass.) for 6 hours. Cultures are harvested on a Packard cell harvester (Packard, Canberra, Canada). [$^3$H] TdR incorporation is measured by liquid scintillation counting. Results are expressed as counts per minute (cpm).

Example 13: T-Cell Adhesion Assay Using Jurkat Cells

The purpose of this study is to evaluate the anti-adhesive properties of LFA-1 Antagonists on the attachment of Jurkat cells to ICAM-1 following in vitro exposure.

Stock solutions of LFA-1 Antagonist and positive control are prepared in DMSO/water (1:1) and diluted into assay media and subsequent dilutions are prepared by addition of assay media to achieve the desired concentration. A reported LFA-1 antagonist is used as the positive control.

Jurkat cells are labeled with an 8 µM solution of BCECF-AM (2',7'-bis-(2-carboxyethyl)-5-(and -6)-carboxyfluorescein) in growth media at room temperature for 15 minutes. Labeled cells are incubated in 70 µL of assay media in each well of a 96 well plate at 500,000 cells per well with 70 µL of LFA-1 Antagonist or positive control in assay media at 37° C. for 30 minutes. A 100 µL aliquot of this fluorescently labeled Jurkat cell suspension is allowed to settle in the presence of LFA-1 antagonist or the positive control in wells of a 96 well plate coated with recombinant human ICAM-1 expressed as an Fc chimera at 37° C. for 1 hour. Non-adherent cells are removed by washing and centrifugation at 100 g for 1 minute. Adherent cells are determined as adherent fluorescent units on a fluorescent plate reader.

Example 14: Dermal Delivery of a Directly Competitive LFA-1 Antagonist of the Invention Via Topical Application to the Bloodstream A study is performed to determine delivery of a directly competitive LFA-1 antagonist of the invention via topical application on the skin, to the bloodstream. Gel (formulated as in Formulation #1, Table 5), lotion (formulated as in Formulation #3, Table 6), ointment (formulated as in Formulation #5, Table 6) and 1% DMSO solution (Control) formulations are evaluated in male Sprague Dawley rats, as shown in Table 12.

Dose Administration.

Animals are not fasted for this study. All single and multiple doses are given on a fixed basis (200 µL formulation/animal/dose). Loaded and empty dose apparatus weights are recorded for determination of actual formulation weights administered.

Dermal.

For dermal administration in Groups 1 through 4 (Group 1(Gel); Group 2(Ointment); Group 3 (Lotion); Group 4(DMSO) single day study, data not shown), each animal receives a single topical application to the dorsal skin on Day 1. For dermal administration in Groups 6 through 9 (Group 6 (Gel); Group 7 (Ointment); Group 8 (Lotion); Group 9(DMSO, Dermal)), each animal receives 3 topical applications given daily (approximately 4 hours apart) to the dorsal skin for 7 consecutive days.

Intradermal.

For each animal in Group 5 (DMSO, Intradermal), the single 200-µL intradermal dose is administered on Day 1 as two, 100-µL injections given sequentially via a syringe and needle in a shaved area of the subscapular region.

Sample Collection: Blood (All Groups).

For the final dose administration as applicable based on study group, blood is collected from each animal predose and at 0.25, 0.5, 1, 2, and 4 hours postdose.

Sample Collection: Application Sites (Dermal Groups Only).

Following sacrifice for the terminal blood sample, the section of skin exposed to the test article formulation is excised. The stratum corneum and any unabsorbed test article formulation remaining on the surface of the skin is removed by tape stripping. The strips were combined into one sample vial for each animal, and the remaining skin section was placed into a second sample vial. Sample weights were recorded.

TABLE 12

Doses Administered to Male Sprague Dawley Rats give Dermal or Intradermal Doses of a Directly Competitive LFA-1 Antagonist of the Invention in Various Formulations (Groups 5 through 9).

| Animal Number | Antagonist Formulation | Dose Route | Dose Concentration (mg/g) | Target Dose Level (mg/animal) | Nominal Dose Administered | | |
|---|---|---|---|---|---|---|---|
| | | | | | (g/animal)$^a$ | (mg/animal) | (mg/kg) |
| B11704 | Gel 1% | Dermal | 10 | 2 | 0.2088 | 2.09 | 6.76 |
| B11705 | Gel 1% | Dermal | 10 | 2 | 0.2080 | 2.08 | 6.69 |
| B11706 | Gel 1% | Dermal | 10 | 2 | 0.2079 | 2.08 | 6.79 |
| B11707 | Ointment 1% | Dermal | 10 | 2 | 0.1669 | 1.67 | 5.06 |
| B11708 | Ointment 1% | Dermal | 10 | 2 | 0.1722 | 1.72 | 5.63 |
| B11709 | Ointment 1% | Dermal | 10 | 2 | 0.1744 | 1.74 | 5.64 |
| B11710 | Lotion 1% | Dermal | 10 | 2 | 0.2075 | 2.08 | 6.69 |
| B11711 | Lotion 1% | Dermal | 10 | 2 | 0.2003 | 2.00 | 6.34 |
| B11712 | Lotion 1% | Dermal | 10 | 2 | 0.2063 | 2.06 | 6.92 |
| B11713 | DMSO 1% | Dermal | 10 | 2 | 0.2195 | 2.20 | 7.13 |

TABLE 12-continued

Doses Administered to Male Sprague Dawley Rats give Dermal or Intradermal Doses of a Directly Competitive LFA-1 Antagonist of the Invention in Various Formulations (Groups 5 through 9).

| Animal Number | Antagonist Formulation | Dose Route | Dose Concentration (mg/g) | Target Dose Level (mg/animal) | Nominal Dose Administered (g/animal)[a] | (mg/animal) | (mg/kg) |
|---|---|---|---|---|---|---|---|
| B11714 | DMSO 1% | Dermal | 10 | 2 | 0.2180 | 2.18 | 6.96 |
| B11715 | DMSO 1% | Dermal | 10 | 2 | 0.2201 | 2.20 | 6.94 |
| B11716 | DMSO 1% | Intradermal | 10 | 2 | 0.2209 | 2.21 | 6.97 |
| B11717 | DMSO 1% | Intradermal | 10 | 2 | 0.2201 | 2.20 | 7.01 |
| B11718 | DMSO 1% | Intradermal | 10 | 2 | 0.2248 | 2.25 | 7.54 |

[a]Formulation weight administered.

Results: Data in Table 13 demonstrates that appreciable drug penetrated the skin in the test formulations and was detected circulating in plasma after absorption from capillaries in the dermis and epidermis.

TABLE 13

Concentration of a Directly Competitive LFA-1 Antagonist in Blood via Delivery in Various Formulations after 7 Days (Dermal) or 1 Day (Intradermal).

| Animal # | Timepoint | Group | Dose Route | Conc. (ng/mL) |
|---|---|---|---|---|
| B11704 | Predose | Gel 1% | Dermal | <0.500 |
| B11704 | 4 Hr | Gel 1% | Dermal | <0.500 |
| B11705 | Predose | Gel 1% | Dermal | <2.00~ |
| B11705 | 4 Hr | Gel 1% | Dermal | <0.500 |
| B11706 | Predose | Gel 1% | Dermal | NR |
| B11706 | 4 Hr | Gel 1% | Dermal | <0.500 |
| B11707 | Predose | Ointment 1% | Dermal | <0.500 |
| B11707 | 4 Hr | Ointment 1% | Dermal | <0.500 |
| B11708 | Predose | Ointment 1% | Dermal | <0.500 |
| B11708 | 4 Hr | Ointment 1% | Dermal | <0.500 |
| B11709 | Predose | Ointment 1% | Dermal | <0.500 |
| B11709 | 4 Hr | Ointment 1% | Dermal | <0.500 |
| B11710 | Predose | Lotion 1% | Dermal | <2.00~ |
| B11710 | 4 Hr | Lotion 1% | Dermal | <0.500 |
| B11711 | Predose | Lotion 1% | Dermal | <2.00~ |
| B11711 | 4 Hr | Lotion 1% | Dermal | <0.500 |
| B11712 | Predose | Lotion 1% | Dermal | <2.00~ |
| B11712 | 4 Hr | Lotion 1% | Dermal | <0.500 |
| B11713 | Predose | DMSO 1% | Dermal | <2.00~ |
| B11713 | 4 Hr | DMSO 1% | Dermal | 2.08 |
| B11714 | Predose | DMSO 1% | Dermal | <0.500 |
| B11714 | 4 Hr | DMSO 1% | Dermal | 2.81 |
| B11715 | Predose | DMSO 1% | Dermal | <2.00~ |
| B11715 | 4 Hr | DMSO 1% | Dermal | 2.22 |
| B11716 | Predose | DMSO 1% | Intra-Dermal | <2.00~ |
| B11716 | 4 Hr | DMSO 1% | Intra-Dermal | 93.9 |
| B11717 | Predose | DMSO 1% | Intra-Dermal | <2.00~ |
| B11717 | 4 Hr | DMSO 1% | Intra-Dermal | 214 |
| B11718 | Predose | DMSO 1% | Intra-Dermal | <0.500 |
| B11718 | 4 Hr | DMSO 1% | Intra-Dermal | 136 |

<0.500 = Below the Limit of Quantitation (BLQ).
<2.00 = Below the Limit of Quantitation (BLQ) due to a 4.00-fold dilution.
NR = Low internal standard response. Insufficient sample volume for reanalysis.

Example 15: Rat Ocular Pharmacokinetics

Figure 12:
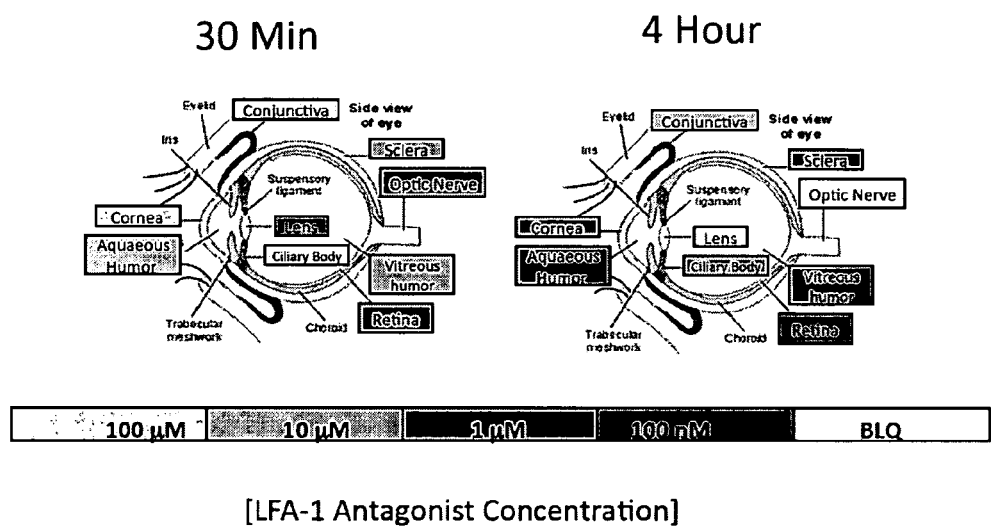
FIG. 12 is a graphical representation of the distribution into the eye via topical application of a $^{14}C$ labeled directly competitive LFA-1 antagonist of the invention at a 30 minute timepoint and a 4 hour timepoint after administration, as measured by detection of the radiolabel.

A rat model is used to measure distribution of a directly competitive LFA-1 antagonist to tissues in the eye, particularly to retina. (See S. P. Ayalasomayajula, and U. B. Kompella, European Journal of Pharmacology, (2003) "Celecoxib, a selective cyclooxygenase-2 inhibitor, inhibits retinal vascular endothelial growth factor expression and vascular leakage in a streptozotocin-induced diabetic rat model", 458: 283-289.) A single drop of a 1% solution formulation of a $^{14}C$ radiolabeled LFA-1 antagonist of the invention (Formulation 12, Table 9 or Formulation 15, Table 10) is administered to the eye of rats, and radioactivity followed over time. Data for t 30 min. and t=4 hours, is graphically represented in FIG. 12. In FIG. 12, the concentration of radiolabeled antagonist measured in each anatomical region is indicated by the increasing grayscale of the box corresponding to the anatomical region as labeled. Numerical values for this data are shown in Table 14 and is given in nanogram equivalents of radiolabelled—LFA-1 antagonist per gram tissue.

TABLE 14

LFA-1 Antagonist Concentration, ng Equivalents [$^{14}C$]-LFA-1 Antagonist/g tissue.

| Physical region | 0.5 hour after administration | 4.0 hours after administration |
|---|---|---|
| Aqueous humor | 1770 | 116 |
| Conjunctiva (bulbar) | 31500 | 4480 |
| Conjunctiva (palpebral) | 26300 | 21830 |
| Cornea | 17150 | 1346 |
| Iris-ciliary body | 17550 | 500 |
| Lens | 38.8 | 9.69 |
| Optic Nerve | 796 | 0 |
| Retina and Choroid (with RPE) | 510 | 46.7 |
| Sclera | 2750 | 387 |
| Vitreous Humor | 1330 | 183 |

The results show that therapeutic levels of LFA-1 antagonist are achieved in the retina, extending to the four hour timepoint after administration, where a 50 ng/g concentration of drug is seen in the retina. This is well above the expected threshold of 10 nM required for inhibition of leukocyte adhesion and function in Diabetic Macular Edema/Diabetic Retinopathy, for an antagonist with an $IC_{50}$ in the HuT78 cell adhesion assay of about 2 to 6 nM.

Example 16: Phase 1 Human Study

Healthy subjects are enrolled. A randomized, controlled, dose escalation trial of both single and multiple administrations of LFA-1 antagonist is conducted. Cohorts of 7 subjects each (5 treatment, 2 placebo) are treated at each of 6-8 dose levels of LFA-1 antagonists formulated as sterile, neutral, isotonic, buffered aqueous solutions. Subjects receive a single instillation on Day 1. Samples are obtained for pharmacokinetic and pharmacodynamic. assessments over the subsequent week. Starting Day 8, subjects receive the same dose of LFA-1 antagonist daily for a total of 14 days. PK/PD assessments, safety laboratory studies, ophthalmic exams, corneal staining and fluorescein angiographies are assessed.

Example 17: Phase II Human Study

Adult subjects with diabetic retinopathy in two groups segregated into those with and those without diabetic macular edema as defined by key inclusion/exclusion criteria are enrolled. A randomized, controlled dose finding trial of LFA-1 antagonists is conducted. Three groups of subjects receive instillations of either carrier vehicle alone, or, one of two dose levels of LFA-1 antagonist, formulated as a neutral, buffered, isotonic aqueous solution, daily for twelve weeks. Subjects are followed for safety and for evidence of improvement in fluorescein angiography, fundus photography, and overall visual acuity examinations for a follow up period of three months.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating diabetic retinopathy in a subject in need thereof comprising:
   identifying a subject in need of treatment for diabetic retinopathy; and
   administering to the subject an effective amount of a composition comprising a compound of formula:

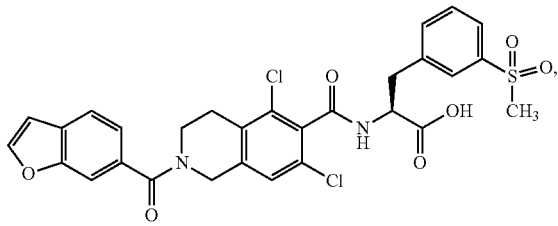 [SMILES: CS(=O)(=O)c1cccc(C[C@H](NC(=O)c2c(Cl)cc3c(c2Cl)CCN(C(=O)c2ccc4ccoc4c2)C3)C(=O)O)c1]

or a pharmaceutically acceptable salt thereof, wherein the administering is by topical administration.

2. The method of claim 1 wherein the composition is administered in a carrier vehicle which is liquid drops, liquid wash, nebulized liquid, gel, ointment, aerosol, spray, polymer micro and nanoparticles, solution, suspension, solid, biodegradable matrix, powder, crystals, foam, or liposomes.

3. The method of claim 1, wherein the composition is administered topically and said topical administration comprises infusion of said compound to said eyes via a device selected from the group consisting of a pump-catheter system, an insert, a continuous or selective release device, a bioabsorbable implant, a continuous or sustained release formulation, and a contact lens.

4. The method of claim 1, wherein said administration is accomplished by administering an intra-ocular instillation of a gel, cream, powder, foam, crystals, liposomes, spray, polymer micro or nanoparticles, or liquid suspension form of said composition.

5. The method of claim 1, wherein said composition is administered to said subject in an amount sufficient to achieve intraocular or retinal concentrations of from about $1 \times 10^{-8}$ to about $1 \times 10^{-1}$ moles/liter.

6. The method of claim 1 wherein said composition is administered at least once a year.

7. The method of claim 1 wherein said composition is administered at least once a day.

8. The method of claim 1 wherein said composition is administered at least once a week.

9. The method of claim 1 wherein said composition is administered at least once a month.

10. The method of claim 1, wherein the compound has an EC50 of 300 nm or less.

11. The method of claim 1, wherein the compound has an EC50 of about 100 nM or less.

12. The method of claim 1, wherein the compound has an EC50 of about 50 nM or less.

13. The method of claim 1, wherein the compound has a solubility of greater than about 10 mg/mL.

14. The method of claim 1, wherein the compound has a solubility of greater than 50 mg/mL.

15. The method of claim 1, wherein the compound has a solubility of greater than 100 mg/mL.

16. The method of claim 1, wherein the diabetic retinopathy causes macular edema.

17. The method of claim 1, wherein the composition comprises:
   0.1% w/w to about 5% w/w of the compound;
   0.1% w/w EDTA;
   0.12% w/w sodium phosphate;
   0.4% w/w methylparaben; and
   0.02% propylparaben.

18. The method of claim 1, wherein the composition comprises:
   10% w/w of the compound; and
   0.158 mmol of sodium bicarbonate.

* * * * *